(12) United States Patent
Bauer et al.

(10) Patent No.: US 10,035,993 B2
(45) Date of Patent: Jul. 31, 2018

(54) DNA POLYMERASES AND RELATED METHODS

(71) Applicant: Roche Molecular Systems, Inc., Pleasanton, CA (US)

(72) Inventors: Keith A. Bauer, San Rafael, CA (US); Ellen Fiss, Albany, CA (US); David Harrow Gelfand, Oakland, CA (US); Edward S. Smith, San Francisco, CA (US); Shawn Suko, El Sobrante, CA (US); Thomas W. Myers, Los Altos, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 0 days.

(21) Appl. No.: 15/642,934

(22) Filed: Jul. 6, 2017

(65) Prior Publication Data

US 2017/0369856 A1    Dec. 28, 2017

Related U.S. Application Data

(62) Division of application No. 14/601,168, filed on Jan. 20, 2015, now Pat. No. 9,738,876, which is a division of application No. 11/873,896, filed on Oct. 17, 2007, now Pat. No. 8,962,293.

(60) Provisional application No. 60/852,882, filed on Oct. 18, 2006.

(51) Int. Cl.
*C12N 9/12*  (2006.01)
*C12P 19/34*  (2006.01)

(52) U.S. Cl.
CPC ......... *C12N 9/1252* (2013.01); *C12N 9/1276* (2013.01); *C12P 19/34* (2013.01)

(58) Field of Classification Search
None
See application file for complete search history.

(56) References Cited

U.S. PATENT DOCUMENTS

| | | | |
|---|---|---|---|
| 5,314,809 A | 5/1994 | Erlich et al. |
| 5,466,591 A | 11/1995 | Abramson et al. |
| 5,501,963 A | 3/1996 | Burckhardt |
| 7,417,133 B2 | 8/2008 | Jestin et al. |
| 7,919,249 B2 | 4/2011 | Gelfand et al. |
| 8,962,293 B2 | 2/2015 | Bauer et al. |
| 9,102,924 B2 | 8/2015 | Bauer et al. |
| 2005/0191635 A1 | 9/2005 | Jestin et al. |
| 2007/0154914 A1 | 7/2007 | Gelfand et al. |
| 2007/0219361 A1 | 9/2007 | Bodepudi et al. |
| 2009/0148891 A1 | 6/2009 | Bauer et al. |
| 2009/0280539 A1 | 11/2009 | Bauer et al. |
| 2011/0294168 A1 | 12/2011 | Bauer et al. |
| 2016/0024548 A1 | 1/2016 | Bauer et al. |

FOREIGN PATENT DOCUMENTS

| | | |
|---|---|---|
| EP | 745675 A2 | 12/1996 |
| EP | 745675 A3 | 12/1996 |
| EP | 1152062 A2 | 11/2001 |
| EP | 1152062 A3 | 9/2002 |
| EP | 1350841 A2 | 10/2003 |
| JP | 2003304870 A | 10/2003 |
| WO | 0151621 A2 | 7/2001 |
| WO | 0151621 A3 | 1/2002 |
| WO | 2005045015 A2 | 5/2005 |
| WO | 2005045015 A3 | 12/2005 |

OTHER PUBLICATIONS

U.S. Appl. No. 12/425,303 , "Advisory Action", dated Nov. 19, 2012, 3 pages.
U.S. Appl. No. 12/425,303 , "Advisory Action", dated Apr. 24, 2012, 4 pages.
U.S. Appl. No. 12/425,303 , "Final Office Action", dated Sep. 20, 2012, 10 pages.
U.S. Appl. No. 12/425,303 , "Final Office Action", dated Jan. 21, 2015, 12 pages.
U.S. Appl. No. 12/425,303 , "Final Office Action", dated Feb. 23, 2012, 8 pages.
U.S. Appl. No. 12/425,303 , "Non-Final Office Action", dated Jun. 23, 2014, 12 pages.
U.S. Appl. No. 12/425,303 , "Non-Final Office Action", dated Oct. 28, 2011, 14 pages.
U.S. Appl. No. 12/425,303 , "Non-Final Office Action", dated May 31, 2012, 9 pages.
U.S. Appl. No. 12/425,303 , "Notice of Allowance", dated Mar. 31, 2015, 10 pages.
U.S. Appl. No. 12/425,303 , "Notice of Allowance", dated Apr. 16, 2015, 4 pages.
U.S. Appl. No. 12/425,303 , "Restriction Requirement", dated Aug. 4, 2011, 8 pages.
U.S. Appl. No. 13/088,049 , "Advisory Action", dated Dec. 5, 2013, 4 pages.
U.S. Appl. No. 13/088,049 , "Advisory Action", dated Feb. 10, 2014, 4 pages.
U.S. Appl. No. 13/088,049 , "Advisory Action", dated May 5, 2015, 4 pages.
U.S. Appl. No. 13/088,049 , "Final Office Action", dated Feb. 26, 2015, 10 pages.
U.S. Appl. No. 13/088,049 , "Final Office Action", dated Aug. 15, 2013, 11 pages.
U.S. Appl. No. 13/088,049 , "Non-Final Office Action", dated Mar. 1, 2013, 15 pages.
U.S. Appl. No. 13/088,049 , "Non-Final Office Action", dated Oct. 27, 2014, 17 pages.
U.S. Appl. No. 13/088,049 , "Restriction Requirement", dated Jan. 9, 2013, 8 pages.

(Continued)

*Primary Examiner* — Richard G Hutson
(74) *Attorney, Agent, or Firm* — Kilpatrick Townsend and Stockton LLP

(57) ABSTRACT

Disclosed are mutant DNA polymerases having improved extension rates relative to a corresponding, unmodified polymerase. The mutant polymerases are useful in a variety of disclosed primer extension methods. Also disclosed are related compositions, including recombinant nucleic acids, vectors, and host cells, which are useful, e.g., for production of the mutant DNA polymerases.

4 Claims, 34 Drawing Sheets

(56) References Cited

OTHER PUBLICATIONS

U.S. Appl. No. 14/810,290, filed Jul. 27, 2015, titled: "DNA Polymerases and Related Methods", 124 pages.
Kranaster et al., "One-step RNA pathogen detection with reverse transcriptase activity of a mutated thermostable Thennus aquaticus DNA", Biotechnol. J., 2010, vol. 5, pp. 224-231.
Ngo et al., "Computational Complexity, Protein Structure Prediction, and the Levinthal Paradox", The Protein Folding Problem and Tertiary Structure Prediction, Merz et al. (ed.), Birkhauser, Boston, MA, 1994, pp. 433 and 492-495.
Ong et al., "Directed Evolution of DNA Polymerase, RNA Polymerase and Reverse Transcriptase Activity in a Single Polypeptide", J. Mol. Biol. 361, 2006, pp. 537-550.
PCT/EP2007/009033 , "International Search Report", dated Mar. 4, 2008, 4 pages.
Price et al., "The presence of melanin in genomic DNA isolated from pigmented cell lines interferes with successful polymerase chain reaction: a solution.", Melanoma Res., vol. 9, No. 1, Feb. 1999, pp. 5-9.
Sauter et al., "Evolving Thermostable Reverse Transcriptase Activity in a DNA polymerase Scaffold", Angew Chem Int. Ed. vol. 45, 2006, pp. 7633-7635.
Vichier-Guerre et al., "Population of Thermostable Reverse Transcriptases Evolved from Thennus aquaticus DNA Polymerase I by Phage Display", Angew, Chem. Int. Ed., vol. 45, 2006, pp. 6133-6137.

FIG. 1

```
  1  MKAMLPLPFP KGRVLLVDGH HLAYRTFFAL KGLTTSRGEP VQAVYGFAKS
 51  LLKALKEDGY KAVFVVFDAK APSFRHEAYE AYKAGRAPTP EDFPRQIALI
101  KELVDLLGFT RLEVPGFEAD DVLATLAKKA EREGYEVRIL TADRDLYQLV
151  SDRVAVLHPE GHLITPEWLW EKYGLKPEQW VDFRALVGDP SDNLPGVKGI
201  GEKTALKLLK EWGSLENILK NLDRVKPESV RERIKAHLED LKLSLELSRV
251  RSDLPLEVDF ARRREPDREG LRAFLERLEF GSLLHEFGLL ESSEPVGYRI
301  VKDLVEFEKL IEKLRESPSF AIDLETSSLD PFDCDIVGIS VSFKPKEAYY
351  IPLHHRNAQN LDEKEVLKKL KEILEDPGAK IVGQNLKFDY KVLMVKGVEP
401  VPPYFDTMIA AYLLEPNEKK FNLDDLALKF LGYKMTSYQE LMSFSFPLFG
451  FSFADVPVEK AANYSCEDAD ITYRLYKTLS LKLHEADLEN VFYKIEMPLV
501  NVLARMELNG VYVDTEFLKK LSEEYGKKLE ELAEEIYRIA GEPFNINSPK
551  QVSRILFEKL GIKPRGKTTK TGDYSTRIEV LEELAGEHEI IPLILEYRKI
601  QKLKSTYIDA LPKMVNPKTG RIHASFNQTG TATGRLSSSD PNLQNLPTKS
651  EEGKEIRKAI VPQDPNWWIV SADYSQIELR ILAHLSGDEN LLRAFEEGID
701  VHTLTASRIF NVKPEEVTEE MRRAGKMVNF SIIYGVTPYG LSVRLGVPVK
751  EAEKMIVNYF VLYPKVRDYI QRVVSEAKEK GYVRTLFGRK RDIPQLMARD
801  RNTQAEGERI AINTPIQGTA ADIIKLAMIE IDRELKERKM RSKMIIQVHD
851  ELVFEVPNEE KDALVELVKD RMTNVVKLSV PLEVDVTIGK TWS (SEQ ID NO: 18)
```

FIG. 2A

```
1   ATGAAAGCTA TGTTACCATT ATTCGAACCC AAAGGCCGGG TCCTCCTGGT
51  GGACGGCCAC CACCTGGCCT ACCGCACCTT CTTCGCCCTG AAGGGCCTCA
101 CCACGAGCCG GGGCGAACCG GTGCAGGCGG TTTACGGCTT CGCCAAGAGC
151 CTCCTCAAGG CCCTGAAGGA GGACGGGTAC AAGGCCGTCT TCGTGGTCTT
201 TGACGCCAAG GCCCCTTCCT TCCGCCACGA GGCCTACGAG GCCTACAAGG
251 CAGGCCGCGC CCCGACCCCC GAGGACTTCC CCCGGCAGCT CGCCCTCATC
301 AAGGAGCTGG TGGACCTCCT GGGGTTTACT CGCCTCGAGG TTCCGGGCTT
351 TGAGGCGGAC GACGTCCTCG CCACCCTGGC CAAGAAGGCG GAAAGGGAGG
401 GGTACGAGGT GCGCATCCTC ACCGCCGACC GGGACCTTTA CCAGCTCGTC
451 TCCGACCGCG TCGCCGTCCT CCACCCCGAG GGCCACCTCA TCACCCCGGA
501 GTGGCTTTGG GAGAAGTACG GCCTAAGCC GGAGCAGTGG GTGGACTTCC
551 GCGCCCTCGT GGGGGACCCC TCCGACAACC TCCCCGGGGT CAAGGGCATC
601 GGGGAGAAGA CCGCCCTCAA GCTCCTCAAG GAGTGGGGAA GCCTGGAAAA
651 TATCCTCAAG AACCTGGACC GGGTGAAGCC GGAAAGCGTC CGGGAAAGGA
701 TCAAGGCCCA CCTGGAAGAC CTTAAGCTCT CCTTGGAGCT TTCCCGGGTG
751 CGCTCGGACC TCCCCCTGGA GGTGGACTTC GCCCGGAGGC GGGAGCCTGA
801 CCGGGAAGGG CTTCGGGCCT TTTTGGAGCG CTTGGAGTTC GGCAGCCTCC
851 TCCACGAGTT CGGCCTTCTA GAGGAGTCCG AACCCGTTGG GTACCGTATA
901 GTTAAAGACC TGGTTGAATT TGAAAAACTC ATAGAGAAAC TGAGAGAATC
```

FIG. 2B

```
 951  TCCTTCGTTC GCTATCGATT TGGAAACTAG TTCCCTCGAT CCTTTCGACT
1001  GCGACATTGT CGGTATCTCT GTGTCTTTCA AACCAAAGGA AGCGTACTAC
1051  ATACCACTCC ATCATAGAAA CGCCCAGAAC CTGGACGAAA AAGAGGTTCT
1101  GAAAAAGCTC AAAGAAATTC TGGAGGACCC CGGAGCAAAG ATCGTTGGTC
1151  AGAATTTGAA ATTCGATTAC AAGGTGTTGA TGGTGAAGGG TGTTGAACCT
1201  GTTCCTCCTT ACTTCGACAC GATGATAGCG GCTTACCTTC TTGAGCCGAA
1251  CGAAAAGAAG TTCAATCTGG ACGATCTCGC ATTGAAATTT CTTGGATACA
1301  AAATGACATC TTACCAAGAG CTCATGTCCT TCTCTTTTCC GCTGTTTGGT
1351  TTCAGTTTTG CCGATGTTCC TGTAGAAAAA GCAGCGAACT ACTCCTGTGA
1401  AGATGCAGAC ATCACCTACA GACTTTACAA GACCCTGAGC TTAAAACTCC
1451  ACGAGGCAGA TCTGGAAAAC GTGTTCTACA AGATAGAAAT GCCCCTTGTG
1501  AACGTGCTTG CACGGATGGA ACTGAACGGT GTGTATGTGG ACACAGAGTT
1551  CCTGAAGAAA CTCTCAGAAG AGTACGGAAA AAAACTCGAA GAACTGGCAG
1601  AGGAAATATA CAGGATAGCT GGAGAGCCGT CAACATAAA CTCACCGAAG
1651  CAGGTTTCAA GGATCCTTTT TGAAAAACTC GGCATAAAAC CACGTGGTAA
1701  AACGACGAAA ACGGGAGACT ATTCAACACG CATAGAAGTC CTCGAGGAAC
1751  TTGCCGGTGA ACACGAAATC ATTCCTCTGA TTCTTGAATA CAGAAAGATA
1801  CAGAAATTGA AATCAACCTA CATAGACGCT CTTCCCAAGA TGGTCAACCC
1851  AAAGACCGGA AGGATTCATG CTTCTTTCAA TCAAACGGGG ACTGCCACTG
```

FIG. 2B (continued)

```
1901 GAAGACTTAG CAGCAGCGAT CCCAATCTTC AGAACCTCCC GACGAAAAGT

1951 GAAGAGGGAA AAGAAATCAG GAAAGCGATA GTTCCTCAGG ATCCAAACTG

2001 GTGGATCGTC AGTGCCGACT ACTCCCAAAT AGAACTGAGG ATCCTCGCCC

2051 ATCTCAGTGG TGATGAGAAT CTTTTGAGGG CATTCGAAGA GGGCATCGAC

2101 GTCCACACTC TAACAGCTTC CAGAATATTC AACGTGAAAC CCGAAGAAGT

2151 AACCGAAGAA ATGCGCCGCG CTGGTAAAAT GGTTAATTTT TCCATCATAT

2201 ACGGTGTAAC ACCTTACGGT CTGTCTGTGA GGCTTGGAGT ACCTGTGAAA

2251 GAAGCAGAAA AGATGATCGT CAACTACTTC GTCCTCTACC CAAAGGTGCG

2301 CGATTACATT CAGAGGGTCG TATCGGAAGC GAAAGAAAAA GGCTATGTTA

2351 GAACGCTGTT TGGAAGAAAA AGAGACATAC CACAGCTCAT GGCCCGGGAC

2401 AGGAACACAC AGGCTGAAGG AGAACGAATT GCCATAAACA CTCCCATACA

2451 GGGTACAGCA GCGGATATAA TAAAGCTGGC TATGATAGAA ATAGACAGGG

2501 AACTGAAAGA AAGAAAAATG AGATCGAAGA TGATCATACA GGTCCACGAC

2551 GAACTGGTTT TTGAAGTGCC CAATGAGGAA AAGGACGCGC TCGTCGAGCT

2601 GGTGAAAGAC AGAATGACGA ATGTGGTAAA GCTTTCAGTG CCGCTCGAAG

2651 TGGATGTAAC CATCGGCAAA ACATGGTCGT GA    (SEQ ID NO: 20)
```

FIG. 2B (continued)

```
  1  MKAMLPLFEP KGRVLLVDGH HLAYRTFFAL KGLTTSRGEP VQAVYGFAKS
 51  LLKALKEDGY KAVPVVFDAK APSFRHEAYE AYKAGRAPTP EDPPRQLALI
101  KELVDLLGFT ELEVPGFEAD DVLATLAKKA EREGYEVRIL TADRDLYQLV
151  SDEVAVLHPE GHLITPEWLW EKYGLKPEQW VDFRALVGDP SDNLPGVKGI
201  GEKTALKLLK EWGSLENILK NLDRVKPESV RERIKAHLED LKLSLELSRV
251  RSDLPLEVDF ARRREPDREG LRAFLERLEF GSLLHEFGLL EESEPVGYRI
301  VKDLVEFEKL IEKLRESPSF AIALATSSLD PFDCDIVGIS VSPKPKEAYY
351  IPLHHRNAQN LDKEVLKKL KEILEDPQAK IVGQNLKFDY KVLMVKGVEP
401  VPPYFDTMIA AYLLEPNEKK FNLDDLALKF LGYKMTSYQE LMSFSFPLFG
451  FSFADVPVEK AANYSCEDAD ITYRLYKTLS LKLHEADLEN VFYKIEMPLV
501  NVLARMELNG VYVDTEFLKK LSEEYGKKLE ELAEEIYRIA GEPFNINSPK
551  QVSRILFEKL GIKPRGKTTK TGDYSTRIEV LEELAGEHEI IPLILEYRKI
601  QKLKSTYIDA LPKMVNPKTG RIHASFNQTG TATGRLSSSD PNLQNLPTKS
651  EEGKEIRKAI VPQDPNWWIV SADYSQIELR ILAHLSGDEN LLRAFEEGID
701  VHTLTASRIF NVKPEEVTEE MRRAGKMVNF SIIYGVTPYG LSVRLGVPVK
751  EAEKMIVNYF VLYPKVRDYI QRVVSEAKEK GYVRTLFGRK RDIPQLMARD
801  RNTQAEGERI AINTPIQGTA ADIIKLAMIE IDRELKERKM RSKMIIQVHD
852  ELVFEVPNEE KDALVELVKD RMTNVVKLSV PLEVDVTIGK TWS (SEQ ID NO: 19)
```

FIG. 3A

```
  1  ATGAAAGCTA TGTTACCATT ATTCGAACCC AAAGGCCGGG TCCTCCTGGT
 51  GGACGGCCAC CACCTGGCCT ACCGCACCTT CTTCGCCCTG AAGGGCCTCA
101  CCACGAGCCG GGGCGAACCG GTGCAGGCGG TTTACGGCTT CGCCAAGAGC
151  CTCCTCAAGG CCCTGAAGGA GGACGGGTAC AAGGCCGTCT TCGTGGTCTT
201  TGACGCCAAG GCCCCTTCCT TCCGCCACGA GGCCTACGAG GCCTACAAGG
251  CAGGCCGCGC CCCGACCCCC GAGGACTTCC CCCGGCAGCT CGCCCTCATC
301  AAGGAGCTGG TGGACCTCCT GGGGTTTACT CGCCTCGAGG TTCCGGGCTT
351  TGAGGCGGAC GACGTCCTCG CCACCCTGGC CAAGAAGGCG GAAAGGGAGG
401  GGTACGAGGT GCGCATCCTC ACCGCCGACC GGGACCTTTA CCAGCTCGTC
451  TCCGACCGCG TCGCCGTCCT CCACCCCGAG GGCCACCTCA TCACCCCGGA
501  GTGGCTTTGG GAGAAGTACG GCCTTAAGCC GGAGCAGTGG GTGGACTTCC
551  GCGCCCTCGT GGGGGACCCC TCCGACAACC TCCCCGGGGT CAAGGGCATC
601  GGGGAGAAGA CCGCCCTCAA GCTCCTCAAG GAGTGGGGAA GCCTGGAAAA
651  TATCCTCAAG AACCTGGACC GGGTGAAGCC GGAAAGCGTC CGGGAAAGGA
701  TCAAGGCCCA CCTGGAAGAC CTTAAGCTCT CCTTGGAGCT TTCCCGGGTG
751  CGCTCGGACC TCCCCCTGGA GGTGGACTTC GCCCGGAGGC GGGAGCCTGA
801  CCGGGAAGGG CTTCGGGCCT TTTTGGAGCG CTTGGAGTTC GGCAGCCTCC
851  TCCACGAGTT CGGCCTTCTA GAGGAGTCCG AACCCGTTGG GTACCGTATA
901  GTTAAAGACC TGGTTGAATT TGAAAAACTC ATAGAGAAAC TGAGAGAATC
```

FIG. 3B

```
 951  TCCTTCGTTC GCGATCGCTC TTGCGACTAG TTCCCTCGAT CCTTTCGACT
1001  GCGACATTGT CGGTATCTCT GTGTCTTTCA AACCAAAGGA AGCGTACTAC
1051  ATACCACTCC ATCATAGAAA CGCCCAGAAC CTGGACGAAA AAGAGGTTCT
1101  GAAAAAGCTC AAAGAAATTC TGGAGGACCC CGGAGCAAAG ATCGTTGGTC
1151  AGAATTTGAA ATTCGATTAC AAGGTGTTGA TGGTGAAGGG TGTTGAACCT
1201  GTTCCTCCTT ACTTCGACAC GATGATAGCG GCTTACCTTC TTGAGCCGAA
1251  CGAAAAGAAG TTCAATCTGG ACGATCTCGC ATTGAAATTT CTTGGATACA
1301  AAATGACATC TTACCAAGAG CTCATGTCCT TCTCTTTTCC GCTGTTTGGT
1351  TTCAGTTTTG CCGATGTTCC TGTAGAAAAA GCAGCGAACT ACTCCTGTGA
1401  AGATGCAGAC ATCACCTACA GACTTTACAA GACCCTGAGC TTAAAACTCC
1451  ACGAGGCAGA TCTGGAAAAC GTGTTCTACA AGATAGAAAT GCCCCTTGTG
1501  AACGTGCTTG CACGGATGGA ACTGAACGGT GTGTATGTGG ACACAGAGTT
1551  CCTGAAGAAA CTCTCAGAAG AGTACGGAAA AAAACTCGAA GAACTGGCAG
1601  AGGAAATATA CAGGATAGCT GGAGAGCCGT TCAACATAAA CTCACCGAAG
1651  CAGGTTTCAA GGATCCTTTT TGAAAAACTC GGCATAAAAC CACGTGGTAA
1701  AACGACGAAA ACGGGAGACT ATTCAACACG CATAGAAGTC CTCGAGGAAC
1751  TTGCCGGTGA ACACGAAATC ATTCCTCTGA TTCTTGAATA CAGAAAGATA
1801  CAGAAATTGA AATCAACCTA CATAGACGCT CTTCCCAAGA TGGTCAACCC
1851  AAAGACCGGA AGGATTCATG CTTCTTTCAA TCAAACGGGG ACTGCCACTG
```

FIG. 3B (continued)

```
1901 GAAGACTTAG CAGCAGCGAT CCCAATCTTC AGAACCTCCC GACGAAAAGT
1951 GAAGAGGGAA AAGAAATCAG GAAAGCGATA GTTCCTCAGG ATCCAAACTG
2001 GTGGATCGTC AGTGCCGACT ACTCCCAAAT AGAACTGAGG ATCCTCGCCC
2051 ATCTCAGTGG TGATGAGAAT CTTTTGAGGG CATTCGAAGA GGGCATCGAC
2101 GTCCACACTC TAACAGCTTC CAGAATATTC AACGTGAAAC CCGAAGAAGT
2151 AACCGAAGAA ATGCGCCGCG CTGGTAAAAT GGTTAATTTT TCCATCATAT
2201 ACGGTGTAAC ACCTTACGGT CTGTCTGTGA GGCTTGGAGT ACCTGTGAAA
2251 GAAGCAGAAA AGATGATCGT CAACTACTTC GTCCTCTACC CAAAGGTGCG
2301 CGATTACATT CAGAGGGTCG TATCGGAAGC GAAAGAAAAA GGCTATGTTA
2351 GAACGCTGTT TGGAAGAAAA AGAGACATAC CACAGCTCAT GGCCCGGGAC
2401 AGGAACACAC AGGCTGAAGG AGAACGAATT GCCATAAACA CTCCCATACA
2451 GGGTACAGCA GCGGATATAA TAAAGCTGGC TATGATAGAA ATAGACAGGG
2501 AACTGAAAGA AAGAAAAATG AGATCGAAGA TGATCATACA GGTCCACGAC
2551 GAACTGGTTT TTGAAGTGCC CAATGAGGAA AAGGACGCGC TCGTCGAGCT
2601 GGTGAAAGAC AGAATGACGA ATGTGGTAAA GCTTTCAGTG CCGCTCGAAG
2651 TGGATGTAAC CATCGGCAAA ACATGGTCGT GA   (SEQ ID NO: 21)
```

FIG. 3B (continued)

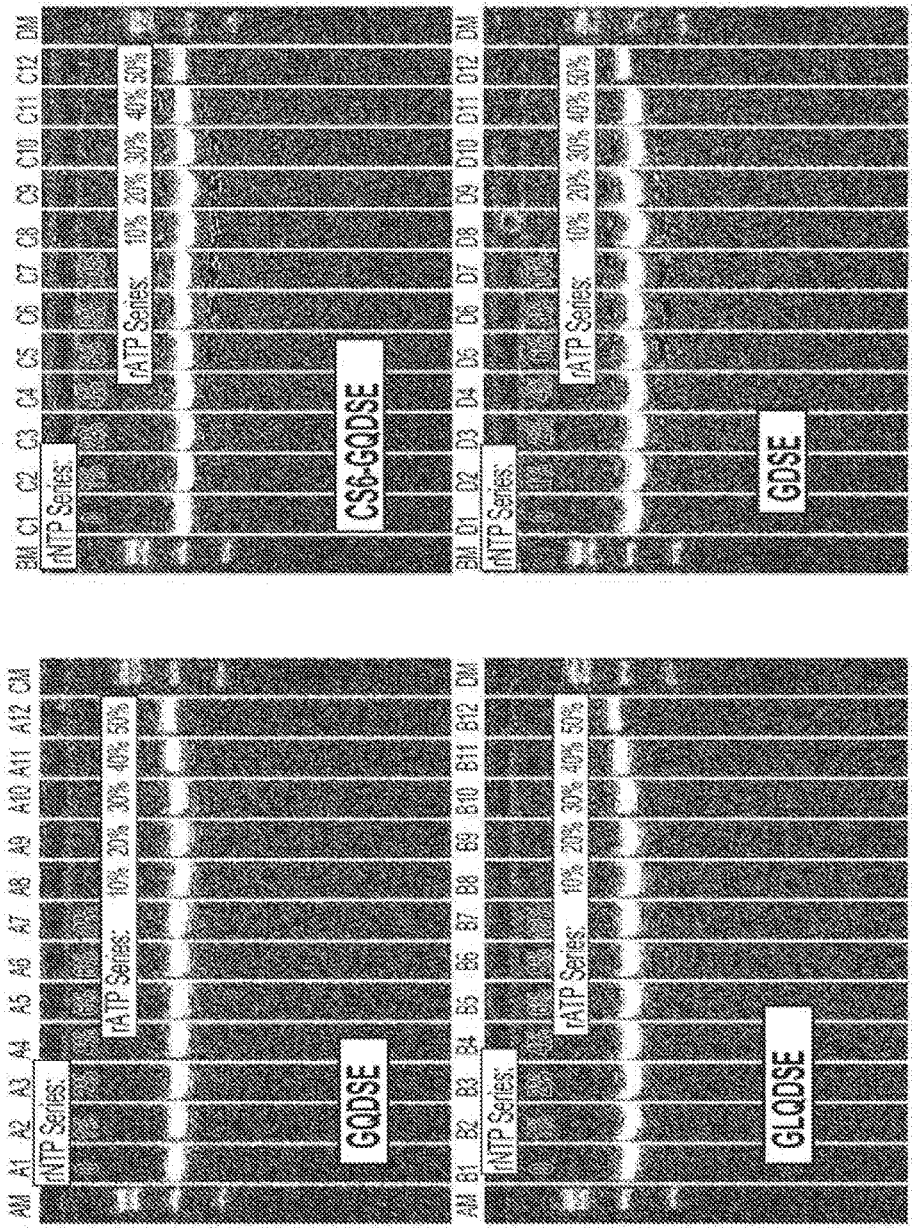
FIG. 13A  Effect of ribonucleotides on amplification of a 1kb PCR product

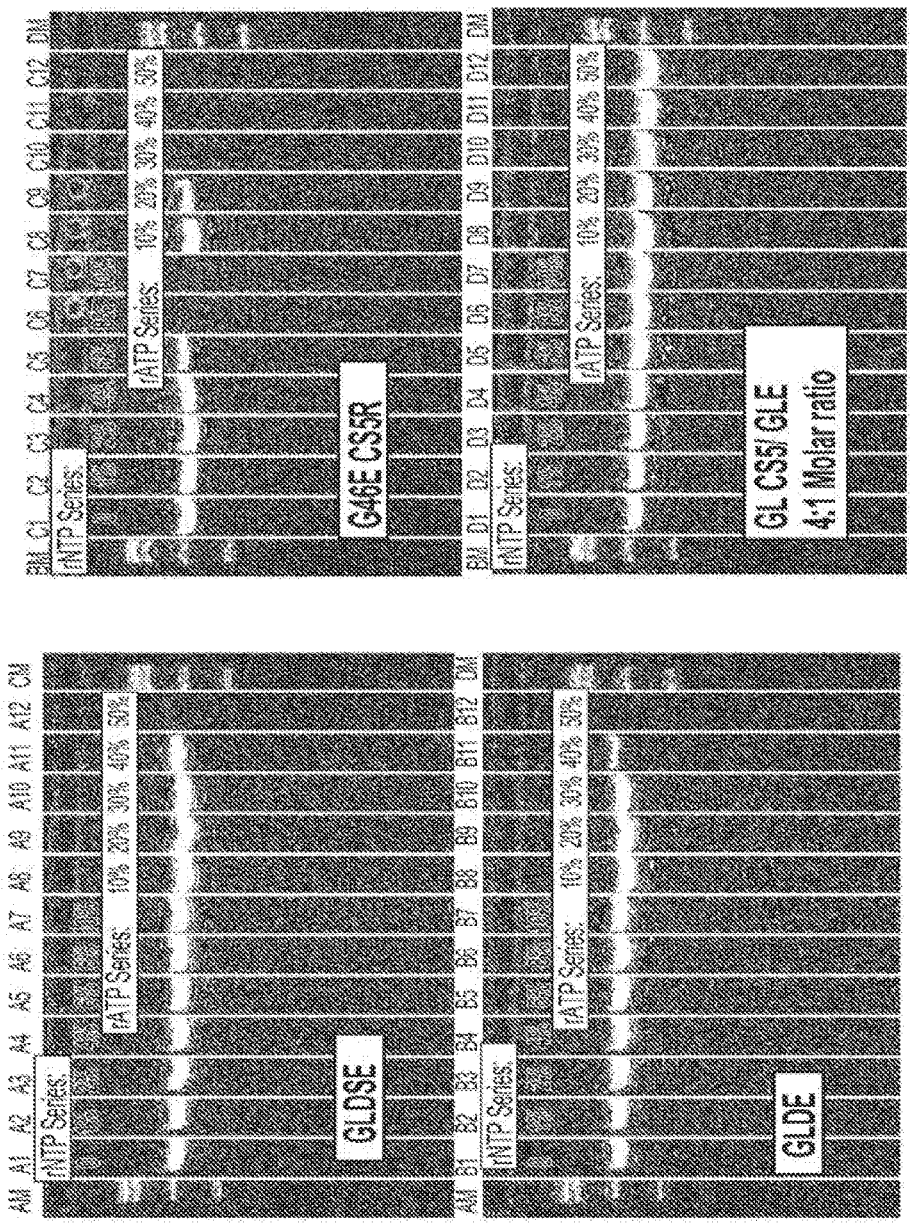

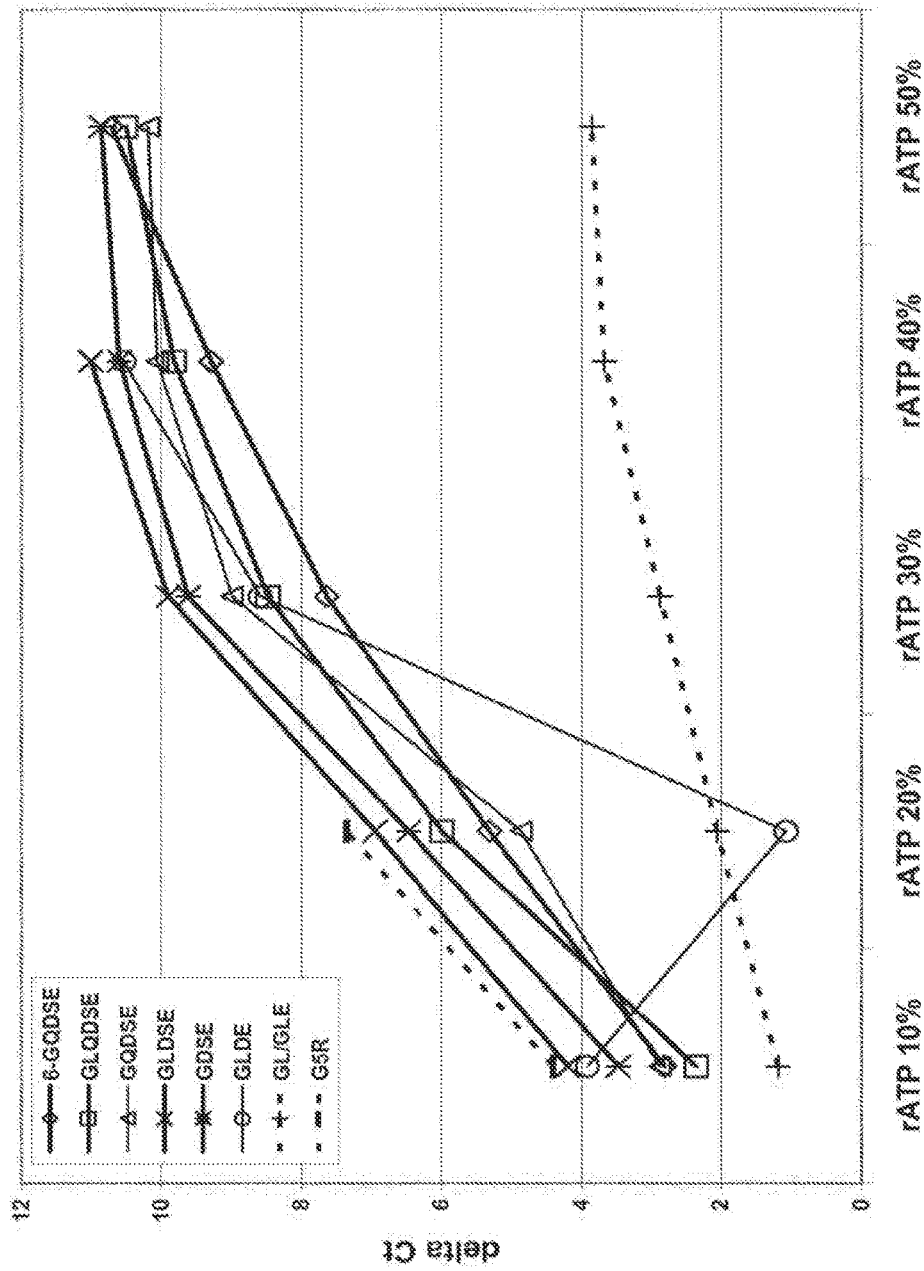
FIG. 14A: delta Ct vs % rATP

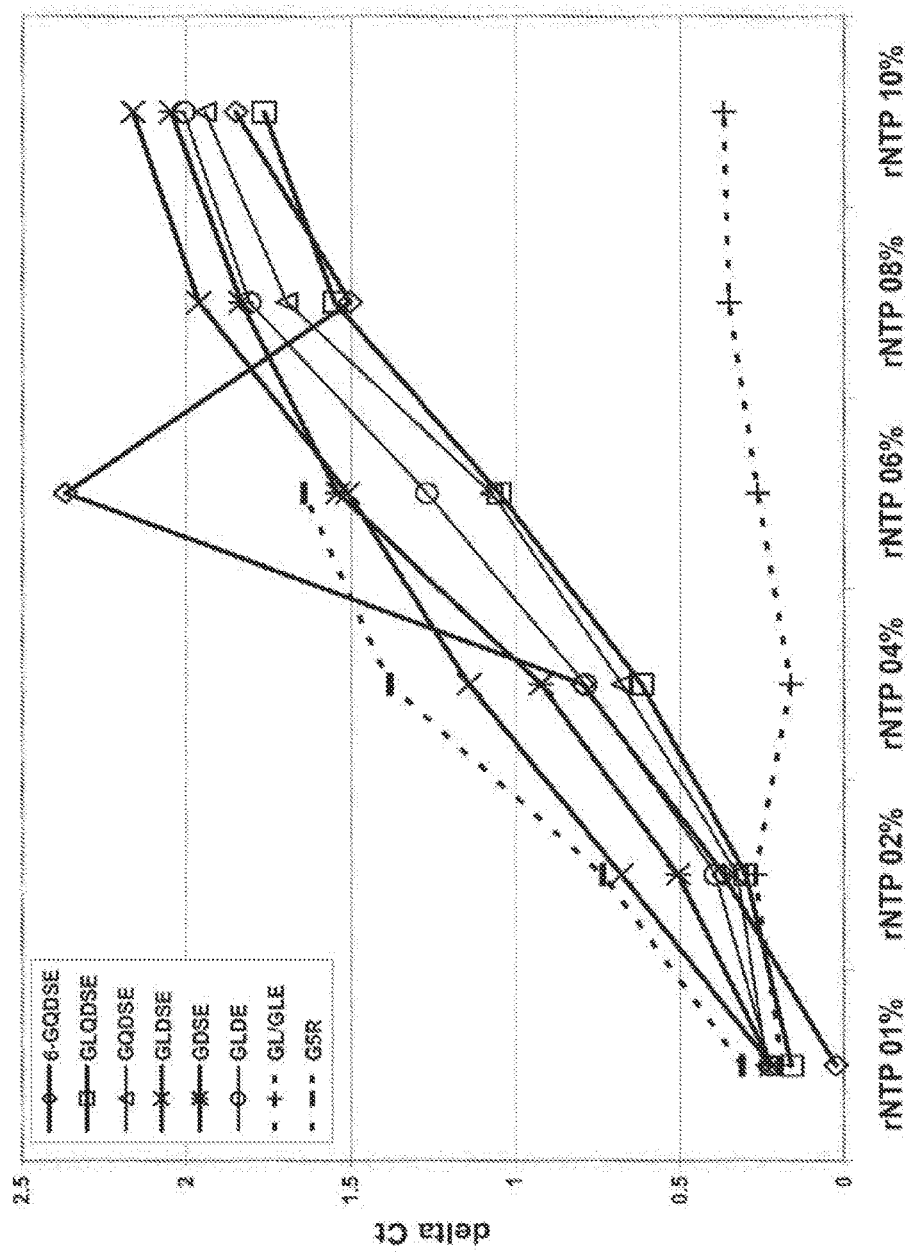
FIG. 14B : delta Ct vs % rATP

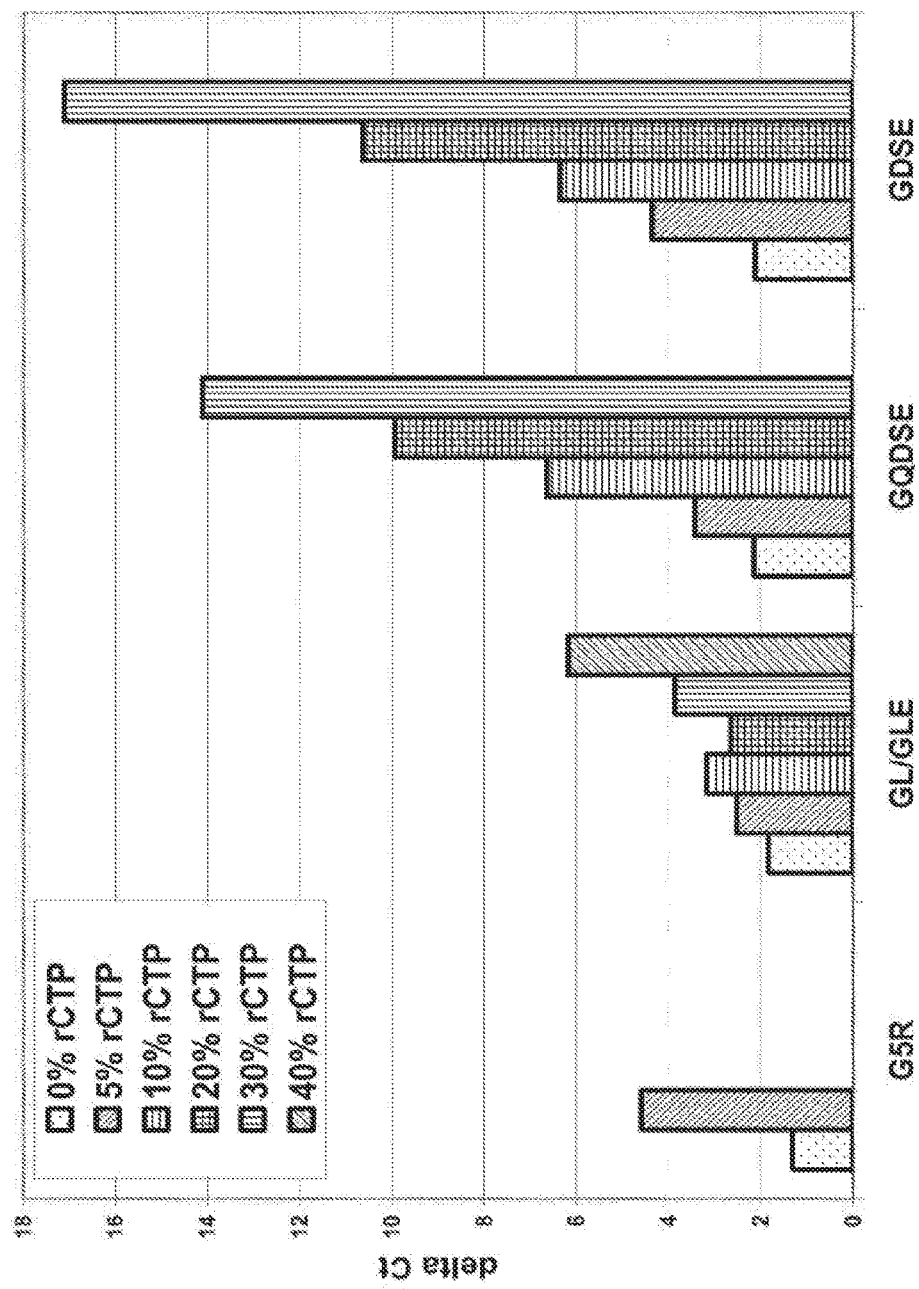

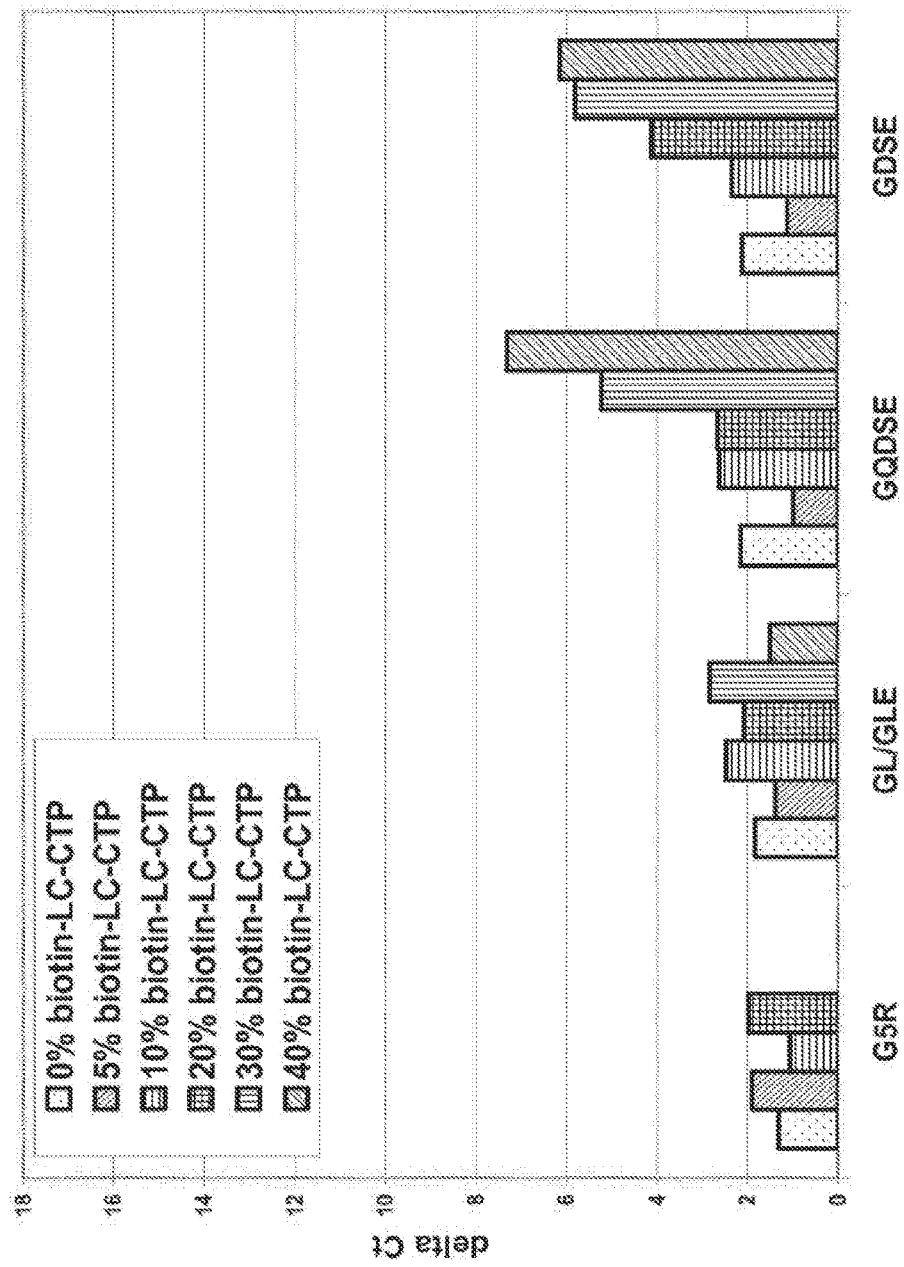
FIG 16B : Delta Ct due to Fragmentation

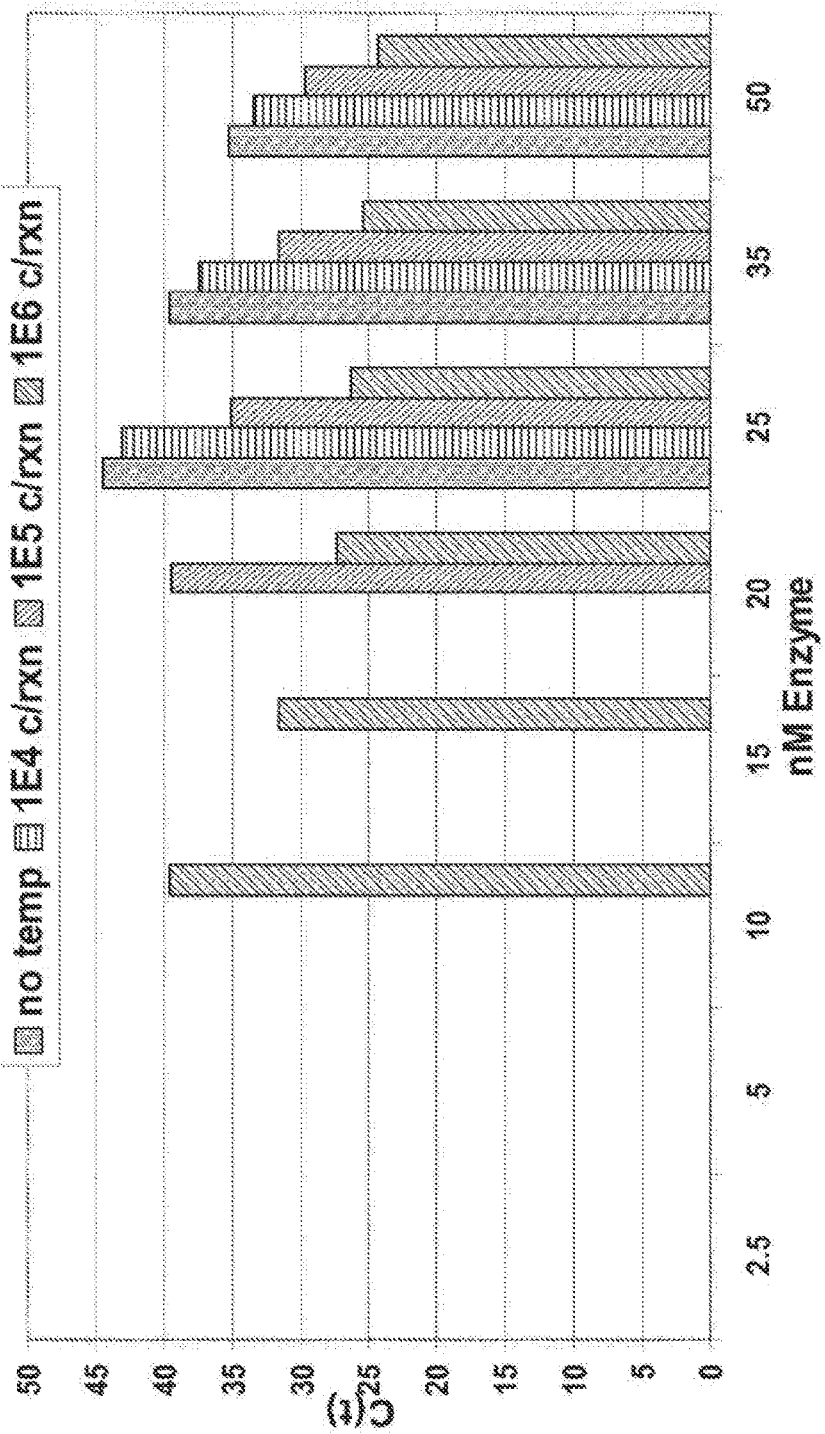

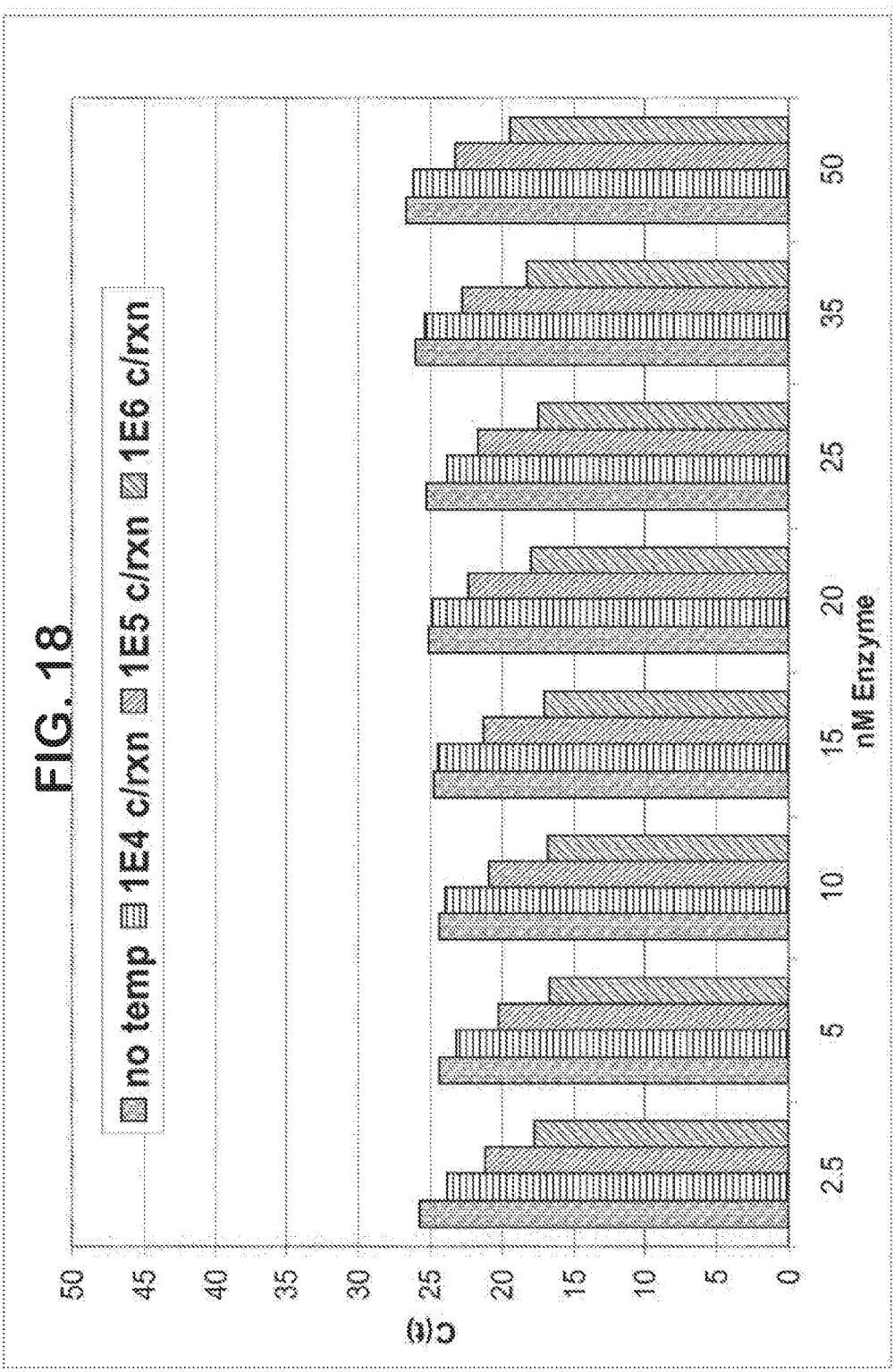

SEQUENCE LISTING

<160> NUMBER OF SEQ ID NOS: 85

<210> SEQ ID NO 1
<211> LENGTH: 16
<212> TYPE: PRT
<213> ORGANISM: Artificial
<220> FEATURE:
<223> OTHER INFORMATION: improved DNA polymerase modified motif a
<220> FEATURE:
<221> NAME/KEY: MOD_RES
<222> LOCATION: (1)
<223> OTHER INFORMATION: Xaa = Ile or Leu
<220> FEATURE:
<221> NAME/KEY: MOD_RES
<222> LOCATION: (2)
<223> OTHER INFORMATION: Xaa = Leu or Gln

```
<220> FEATURE:
<221> NAME/KEY: MOD_RES
<222> LOCATION: (3)
<223> OTHER INFORMATION: Xaa = Gln, His or Glu
<220> FEATURE:
<221> NAME/KEY: MOD_RES
<222> LOCATION: (4)
<223> OTHER INFORMATION: Xaa = Tyr, His or Phe
<220> FEATURE:
<221> NAME/KEY: MOD_RES
<222> LOCATION: (6)
<223> OTHER INFORMATION: Xaa = Glu, Gln or Lys
<220> FEATURE:
<221> NAME/KEY: MOD_RES
<222> LOCATION: (7)
<223> OTHER INFORMATION: Xaa = Ile, Leu or Tyr
<220> FEATURE:
<221> NAME/KEY: MOD_RES
<222> LOCATION: (8)
<223> OTHER INFORMATION: Xaa = any amino acid other than Gln, Thr, Met,
      Gly or Leu
<220> FEATURE:
<221> NAME/KEY: MOD_RES
<222> LOCATION: (11)
<223> OTHER INFORMATION: Xaa = Lys or Gln
<220> FEATURE:
<221> NAME/KEY: MOD_RES
<222> LOCATION: (12)
<223> OTHER INFORMATION: Xaa = Ser or Asn
<220> FEATURE:
<221> NAME/KEY: MOD_RES
<222> LOCATION: (15)
<223> OTHER INFORMATION: Xaa = Ile or Val
<220> FEATURE:
<221> NAME/KEY: MOD_RES
<222> LOCATION: (16)
<223> OTHER INFORMATION: Xaa = Glu or Asp

<400> SEQUENCE: 1

Xaa Xaa Xaa Xaa Arg Xaa Xaa Xaa Lys Leu Xaa Xaa Thr Tyr Xaa Xaa
1               5                   10                  15

<210> SEQ ID NO 2
<211> LENGTH: 13
<212> TYPE: PRT
<213> ORGANISM: Artificial
<220> FEATURE:
<223> OTHER INFORMATION: improved DNA polymerase modified motif b
<220> FEATURE:
<221> NAME/KEY: MOD_RES
<222> LOCATION: (7)
<223> OTHER INFORMATION: Xaa = Ser or Thr
<220> FEATURE:
<221> NAME/KEY: MOD_RES
<222> LOCATION: (8)
<223> OTHER INFORMATION: Xaa = any amino acid other than Asp, Glu or Asn

<400> SEQUENCE: 2

Thr Gly Arg Leu Ser Ser Xaa Xaa Pro Asn Leu Gln Asn
1               5                   10

<210> SEQ ID NO 3
<211> LENGTH: 15
<212> TYPE: PRT
<213> ORGANISM: Artificial
<220> FEATURE:
<223> OTHER INFORMATION: improved DNA polymerase modified motif c
<220> FEATURE:
<221> NAME/KEY: MOD_RES
<222> LOCATION: (1)
<223> OTHER INFORMATION: Xaa = Gly, Asn or Asp
<220> FEATURE:
<221> NAME/KEY: MOD_RES
<222> LOCATION: (2)
<223> OTHER INFORMATION: Xaa = Trp or His
```

-continued

```
<220> FEATURE:
<221> NAME/KEY: MOD_RES
<222> LOCATION: (3)
<223> OTHER INFORMATION: Xaa = Trp, Ala, Leu or Val
<220> FEATURE:
<221> NAME/KEY: MOD_RES
<222> LOCATION: (4)
<223> OTHER INFORMATION: Xaa = any amino acid other than Ile or Leu
<220> FEATURE:
<221> NAME/KEY: MOD_RES
<222> LOCATION: (5)
<223> OTHER INFORMATION: Xaa = Val, Phe or Leu
<220> FEATURE:
<221> NAME/KEY: MOD_RES
<222> LOCATION: (6)
<223> OTHER INFORMATION: Xaa = any amino acid other than Ser, Ala, Val
      or Gly
<220> FEATURE:
<221> NAME/KEY: MOD_RES
<222> LOCATION: (7)
<223> OTHER INFORMATION: Xaa = Ala or Leu

<400> SEQUENCE: 3

Xaa Xaa Xaa Xaa Xaa Xaa Xaa Asp Tyr Ser Gln Ile Glu Leu Arg
1               5                   10                  15

<210> SEQ ID NO 4
<211> LENGTH: 91
<212> TYPE: PRT
<213> ORGANISM: Artificial
<220> FEATURE:
<223> OTHER INFORMATION: active site region from polymerase domain of
      thermostable Family A type DNA-dependent DNA
      polymerase of Thermus thermophilus (Tth)

<400> SEQUENCE: 4

Ile Val Glu Lys Ile Leu Gln His Arg Glu Leu Thr Lys Leu Lys Asn
1               5                   10                  15

Thr Tyr Val Asp Pro Leu Pro Ser Leu Val His Pro Arg Thr Gly Arg
            20                  25                  30

Leu His Thr Arg Phe Asn Gln Thr Ala Thr Ala Thr Gly Arg Leu Ser
        35                  40                  45

Ser Ser Asp Pro Asn Leu Gln Asn Ile Pro Val Arg Thr Pro Leu Gly
    50                  55                  60

Gln Arg Ile Arg Arg Ala Phe Val Ala Glu Ala Gly Trp Ala Leu Val
65                  70                  75                  80

Ala Leu Asp Tyr Ser Gln Ile Glu Leu Arg Val
            85                  90

<210> SEQ ID NO 5
<211> LENGTH: 91
<212> TYPE: PRT
<213> ORGANISM: Artificial
<220> FEATURE:
<223> OTHER INFORMATION: active site region from polymerase domain of
      thermostable Family A type DNA-dependent DNA
      polymerase of Thermus caldophilus (Tca)

<400> SEQUENCE: 5

Ile Val Glu Lys Ile Leu Gln His Arg Glu Leu Thr Lys Leu Lys Asn
1               5                   10                  15

Thr Tyr Val Asp Pro Leu Pro Ser Leu Val His Pro Asn Thr Gly Arg
            20                  25                  30

Leu His Thr Arg Phe Asn Gln Thr Ala Thr Ala Thr Gly Arg Leu Ser
        35                  40                  45
```

Ser Ser Asp Pro Asn Leu Gln Asn Ile Pro Val Arg Thr Pro Leu Gly
    50                  55                  60

Gln Arg Ile Arg Arg Ala Phe Val Ala Glu Ala Gly Trp Ala Leu Val
65                  70                  75                  80

Ala Leu Asp Tyr Ser Gln Ile Glu Leu Arg Val
                85                  90

<210> SEQ ID NO 6
<211> LENGTH: 91
<212> TYPE: PRT
<213> ORGANISM: Artificial
<220> FEATURE:
<223> OTHER INFORMATION: active site region from polymerase domain of
      thermostable Family A type DNA-dependent DNA
      polymerase of Thermus species Z05 (Z05)

<400> SEQUENCE: 6

Ile Val Glu Lys Ile Leu Gln His Arg Glu Leu Thr Lys Leu Lys Asn
1               5                   10                  15

Thr Tyr Val Asp Pro Leu Pro Gly Leu Val His Pro Arg Thr Gly Arg
                20                  25                  30

Leu His Thr Arg Phe Asn Gln Thr Ala Thr Ala Thr Gly Arg Leu Ser
            35                  40                  45

Ser Ser Asp Pro Asn Leu Gln Asn Ile Pro Ile Arg Thr Pro Leu Gly
    50                  55                  60

Gln Arg Ile Arg Arg Ala Phe Val Ala Glu Ala Gly Trp Ala Leu Val
65                  70                  75                  80

Ala Leu Asp Tyr Ser Gln Ile Glu Leu Arg Val
                85                  90

<210> SEQ ID NO 7
<211> LENGTH: 91
<212> TYPE: PRT
<213> ORGANISM: Artificial
<220> FEATURE:
<223> OTHER INFORMATION: active site region from polymerase domain of
      thermostable Family A type DNA-dependent DNA
      polymerase of Thermus aquaticus (Taq)

<400> SEQUENCE: 7

Ile Val Glu Lys Ile Leu Gln Tyr Arg Glu Leu Thr Lys Leu Lys Ser
1               5                   10                  15

Thr Tyr Ile Asp Pro Leu Pro Asp Leu Ile His Pro Arg Thr Gly Arg
                20                  25                  30

Leu His Thr Arg Phe Asn Gln Thr Ala Thr Ala Thr Gly Arg Leu Ser
            35                  40                  45

Ser Ser Asp Pro Asn Leu Gln Asn Ile Pro Val Arg Thr Pro Leu Gly
    50                  55                  60

Gln Arg Ile Arg Arg Ala Phe Ile Ala Glu Glu Gly Trp Leu Leu Val
65                  70                  75                  80

Ala Leu Asp Tyr Ser Gln Ile Glu Leu Arg Val
                85                  90

<210> SEQ ID NO 8
<211> LENGTH: 91
<212> TYPE: PRT
<213> ORGANISM: Artificial
<220> FEATURE:
<223> OTHER INFORMATION: active site region from polymerase domain of
      thermostable Family A type DNA-dependent DNA
      polymerase of Thermus flavus (Tfl)

```
<400> SEQUENCE: 8

Ile Val Asp Arg Ile Leu Gln Tyr Arg Glu Leu Thr Lys Leu Lys Asn
1               5                   10                  15

Thr Tyr Ile Asp Pro Leu Pro Ala Leu Val His Pro Lys Thr Gly Arg
            20                  25                  30

Leu His Thr Arg Phe Asn Gln Thr Ala Thr Ala Thr Gly Arg Leu Ser
        35                  40                  45

Ser Ser Asp Pro Asn Leu Gln Asn Ile Pro Val Arg Thr Pro Leu Gly
    50                  55                  60

Gln Arg Ile Arg Arg Ala Phe Val Ala Glu Glu Gly Trp Val Leu Val
65                  70                  75                  80

Val Leu Asp Tyr Ser Gln Ile Glu Leu Arg Val
                85                  90

<210> SEQ ID NO 9
<211> LENGTH: 91
<212> TYPE: PRT
<213> ORGANISM: Artificial
<220> FEATURE:
<223> OTHER INFORMATION: active site region from polymerase domain of
      thermostable Family A type DNA-dependent DNA
      polymerase of Thermus filiformis (Tfi)

<400> SEQUENCE: 9

Ile Val Gly Arg Ile Leu Glu Tyr Arg Glu Leu Met Lys Leu Lys Ser
1               5                   10                  15

Thr Tyr Ile Asp Pro Leu Pro Arg Leu Val His Pro Lys Thr Gly Arg
            20                  25                  30

Leu His Thr Arg Phe Asn Gln Thr Ala Thr Ala Thr Gly Arg Leu Ser
        35                  40                  45

Ser Ser Asp Pro Asn Leu Gln Asn Ile Pro Val Arg Thr Pro Leu Gly
    50                  55                  60

Gln Arg Ile Arg Lys Ala Phe Ile Ala Glu Glu Gly His Leu Leu Val
65                  70                  75                  80

Ala Leu Asp Tyr Ser Gln Ile Glu Leu Arg Val
                85                  90

<210> SEQ ID NO 10
<211> LENGTH: 91
<212> TYPE: PRT
<213> ORGANISM: Artificial
<220> FEATURE:
<223> OTHER INFORMATION: active site region from polymerase domain of
      thermostable Family A type DNA-dependent DNA
      polymerase of Thermus species sps17 (Sps17)

<400> SEQUENCE: 10

Ile Val Gly Arg Ile Leu Glu Tyr Arg Glu Leu Met Lys Leu Lys Ser
1               5                   10                  15

Thr Tyr Ile Asp Pro Leu Pro Arg Leu Val His Pro Lys Thr Gly Arg
            20                  25                  30

Leu His Thr Arg Phe Asn Gln Thr Ala Thr Ala Thr Gly Arg Leu Ser
        35                  40                  45

Ser Ser Asp Pro Asn Leu Gln Asn Ile Pro Val Arg Thr Pro Leu Gly
    50                  55                  60

Gln Arg Ile Arg Lys Ala Phe Ile Ala Glu Glu Gly His Leu Leu Val
65                  70                  75                  80

Ala Leu Asp Tyr Ser Gln Ile Glu Leu Arg Val
                85                  90
```

<210> SEQ ID NO 11
<211> LENGTH: 92
<212> TYPE: PRT
<213> ORGANISM: Artificial
<220> FEATURE:
<223> OTHER INFORMATION: active site region from polymerase domain of
      thermostable Family A type DNA-dependent DNA
      polymerase of Thermotoga maritima (Tma)

<400> SEQUENCE: 11

Ile Ile Pro Leu Ile Leu Glu Tyr Arg Lys Ile Gln Lys Leu Lys Ser
1               5                   10                  15

Thr Tyr Ile Asp Ala Leu Pro Lys Met Val Asn Pro Lys Thr Gly Arg
            20                  25                  30

Ile His Ala Ser Phe Asn Gln Thr Gly Thr Ala Thr Gly Arg Leu Ser
        35                  40                  45

Ser Ser Asp Pro Asn Leu Gln Asn Leu Pro Thr Lys Ser Glu Glu Gly
    50                  55                  60

Lys Glu Ile Arg Lys Ala Ile Val Pro Gln Asp Pro Asn Trp Trp Ile
65                  70                  75                  80

Val Ser Ala Asp Tyr Ser Gln Ile Glu Leu Arg Ile
            85                  90

<210> SEQ ID NO 12
<211> LENGTH: 92
<212> TYPE: PRT
<213> ORGANISM: Artificial
<220> FEATURE:
<223> OTHER INFORMATION: active site region from polymerase domain of
      thermostable Family A type DNA-dependent DNA
      polymerase of Thermotoga neapolitana (Tne)

<400> SEQUENCE: 12

Ile Val Pro Leu Ile Leu Glu Phe Arg Lys Ile Leu Lys Leu Lys Ser
1               5                   10                  15

Thr Tyr Ile Asp Thr Leu Pro Lys Leu Val Asn Pro Lys Thr Gly Arg
            20                  25                  30

Phe His Ala Ser Phe His Gln Thr Gly Thr Ala Thr Gly Arg Leu Ser
        35                  40                  45

Ser Ser Asp Pro Asn Leu Gln Asn Leu Pro Thr Lys Ser Glu Glu Gly
    50                  55                  60

Lys Glu Ile Arg Lys Ala Ile Val Pro Gln Asp Pro Asp Trp Trp Ile
65                  70                  75                  80

Val Ser Ala Asp Tyr Ser Gln Ile Glu Leu Arg Ile
            85                  90

<210> SEQ ID NO 13
<211> LENGTH: 92
<212> TYPE: PRT
<213> ORGANISM: Artificial
<220> FEATURE:
<223> OTHER INFORMATION: active site region from polymerase domain of
      thermostable Family A type DNA-dependent DNA
      polymerase of Thermosipho africanus (Taf)

<400> SEQUENCE: 13

Ile Ala Lys Leu Leu Leu Glu Tyr Arg Lys Tyr Gln Lys Leu Lys Ser
1               5                   10                  15

Thr Tyr Ile Asp Ser Ile Pro Leu Ser Ile Asn Arg Lys Thr Asn Arg
            20                  25                  30

Val His Thr Thr Phe His Gln Thr Gly Thr Ser Thr Gly Arg Leu Ser
        35                  40                  45

Ser Ser Asn Pro Asn Leu Gln Asn Leu Pro Thr Arg Ser Glu Glu Gly
    50                  55                  60

Lys Glu Ile Arg Lys Ala Val Arg Pro Gln Arg Gln Asp Trp Trp Ile
65                  70                  75                  80

Leu Gly Ala Asp Tyr Ser Gln Ile Glu Leu Arg Val
                85                  90

<210> SEQ ID NO 14
<211> LENGTH: 92
<212> TYPE: PRT
<213> ORGANISM: Artificial
<220> FEATURE:
<223> OTHER INFORMATION: active site region from polymerase domain of
      thermostable Family A type DNA-dependent DNA
      polymerase of Bacillus caldotenax (Bca)

<400> SEQUENCE: 14

Val Glu Asn Ile Leu Gln His Tyr Arg Gln Leu Gly Lys Leu Gln Ser
1               5                   10                  15

Thr Tyr Ile Glu Gly Leu Leu Lys Val Val Arg Pro Asp Thr Lys Lys
                20                  25                  30

Val His Thr Ile Phe Asn Gln Ala Leu Thr Gln Thr Gly Arg Leu Ser
            35                  40                  45

Ser Thr Glu Pro Asn Leu Gln Asn Ile Pro Ile Arg Leu Glu Glu Gly
    50                  55                  60

Arg Lys Ile Arg Gln Ala Phe Val Pro Ser Glu Ser Asp Trp Leu Ile
65                  70                  75                  80

Phe Ala Ala Asp Tyr Ser Gln Ile Glu Leu Arg Val
                85                  90

<210> SEQ ID NO 15
<211> LENGTH: 92
<212> TYPE: PRT
<213> ORGANISM: Artificial
<220> FEATURE:
<223> OTHER INFORMATION: active site region from polymerase domain of
      chimeric thermostable DNA-dependent DNA polymerase CS5

<400> SEQUENCE: 15

Ile Ile Pro Leu Ile Leu Glu Tyr Arg Lys Ile Gln Lys Leu Lys Ser
1               5                   10                  15

Thr Tyr Ile Asp Ala Leu Pro Lys Met Val Asn Pro Lys Thr Gly Arg
                20                  25                  30

Ile His Ala Ser Phe Asn Gln Thr Gly Thr Ala Thr Gly Arg Leu Ser
            35                  40                  45

Ser Ser Asp Pro Asn Leu Gln Asn Leu Pro Thr Lys Ser Glu Glu Gly
    50                  55                  60

Lys Glu Ile Arg Lys Ala Ile Val Pro Gln Asp Pro Asn Trp Trp Ile
65                  70                  75                  80

Val Ser Ala Asp Tyr Ser Gln Ile Glu Leu Arg Ile
                85                  90

<210> SEQ ID NO 16
<211> LENGTH: 92
<212> TYPE: PRT
<213> ORGANISM: Artificial
<220> FEATURE:
<223> OTHER INFORMATION: active site region from polymerase domain of
      chimeric thermostable DNA-dependent DNA polymerase CS6

-continued

<400> SEQUENCE: 16

Ile Ile Pro Leu Ile Leu Glu Tyr Arg Lys Ile Gln Lys Leu Lys Ser
1               5                   10                  15

Thr Tyr Ile Asp Ala Leu Pro Lys Met Val Asn Pro Lys Thr Gly Arg
            20                  25                  30

Ile His Ala Ser Phe Asn Gln Thr Gly Thr Ala Thr Gly Arg Leu Ser
            35                  40                  45

Ser Ser Asp Pro Asn Leu Gln Asn Leu Pro Thr Lys Ser Glu Glu Gly
        50                  55                  60

Lys Glu Ile Arg Lys Ala Ile Val Pro Gln Asp Pro Asn Trp Trp Ile
65                  70                  75                  80

Val Ser Ala Asp Tyr Ser Gln Ile Glu Leu Arg Ile
                85                  90

<210> SEQ ID NO 17
<211> LENGTH: 92
<212> TYPE: PRT
<213> ORGANISM: Artificial
<220> FEATURE:
<223> OTHER INFORMATION: polymerase domain active site region consensus
      sequence (Cons) of thermostable DNA-dependent DNA polymerases
<220> FEATURE:
<221> NAME/KEY: MOD_RES
<222> LOCATION: (2)
<223> OTHER INFORMATION: Xaa = Val, Ile, Ala or Glu
<220> FEATURE:
<221> NAME/KEY: MOD_RES
<222> LOCATION: (3)
<223> OTHER INFORMATION: Xaa = Glu, Pro, Gly, Asp, Lys or Asn
<220> FEATURE:
<221> NAME/KEY: MOD_RES
<222> LOCATION: (4)
<223> OTHER INFORMATION: Xaa = Leu, Lys, Arg or Ile
<220> FEATURE:
<221> NAME/KEY: MOD_RES
<222> LOCATION: (5)
<223> OTHER INFORMATION: Xaa = Ile or Leu
<220> FEATURE:
<221> NAME/KEY: MOD_RES
<222> LOCATION: (6)
<223> OTHER INFORMATION: Xaa = Leu or Gln
<220> FEATURE:
<221> NAME/KEY: MOD_RES
<222> LOCATION: (7)
<223> OTHER INFORMATION: Xaa = Gln, His or Glu
<220> FEATURE:
<221> NAME/KEY: MOD_RES
<222> LOCATION: (8)
<223> OTHER INFORMATION: Xaa = Tyr, His or Phe
<220> FEATURE:
<221> NAME/KEY: MOD_RES
<222> LOCATION: (10)
<223> OTHER INFORMATION: Xaa = Glu, Gln or Lys
<220> FEATURE:
<221> NAME/KEY: MOD_RES
<222> LOCATION: (11)
<223> OTHER INFORMATION: Xaa = Ile, Leu or Tyr
<220> FEATURE:
<221> NAME/KEY: MOD_RES
<222> LOCATION: (12)
<223> OTHER INFORMATION: Xaa = Gln, Thr, Met, Gly or Leu
<220> FEATURE:
<221> NAME/KEY: MOD_RES
<222> LOCATION: (15)
<223> OTHER INFORMATION: Xaa = Lys or Gln
<220> FEATURE:
<221> NAME/KEY: MOD_RES
<222> LOCATION: (16)
<223> OTHER INFORMATION: Xaa = Ser or Asn

```
<220> FEATURE:
<221> NAME/KEY: MOD_RES
<222> LOCATION: (19)
<223> OTHER INFORMATION: Xaa = Ile or Val
<220> FEATURE:
<221> NAME/KEY: MOD_RES
<222> LOCATION: (20)
<223> OTHER INFORMATION: Xaa = Glu or Asp
<220> FEATURE:
<221> NAME/KEY: MOD_RES
<222> LOCATION: (21)
<223> OTHER INFORMATION: Xaa = Pro, Ala, Thr, Ser or Gly
<220> FEATURE:
<221> NAME/KEY: MOD_RES
<222> LOCATION: (22)
<223> OTHER INFORMATION: Xaa = Leu or Ile
<220> FEATURE:
<221> NAME/KEY: MOD_RES
<222> LOCATION: (24)
<223> OTHER INFORMATION: Xaa = Lys, Arg, Ser, Leu, Ala or Asp
<220> FEATURE:
<221> NAME/KEY: MOD_RES
<222> LOCATION: (25)
<223> OTHER INFORMATION: Xaa = Leu, Met, Val or Ser
<220> FEATURE:
<221> NAME/KEY: MOD_RES
<222> LOCATION: (26)
<223> OTHER INFORMATION: Xaa = Val or Ile
<220> FEATURE:
<221> NAME/KEY: MOD_RES
<222> LOCATION: (27)
<223> OTHER INFORMATION: Xaa = His, Asn or Arg
<220> FEATURE:
<221> NAME/KEY: MOD_RES
<222> LOCATION: (28)
<223> OTHER INFORMATION: Xaa = Pro or Arg
<220> FEATURE:
<221> NAME/KEY: MOD_RES
<222> LOCATION: (29)
<223> OTHER INFORMATION: Xaa = Lys, Arg, Asn or Asp
<220> FEATURE:
<221> NAME/KEY: MOD_RES
<222> LOCATION: (31)
<223> OTHER INFORMATION: Xaa = Gly, Lys or Asn
<220> FEATURE:
<221> NAME/KEY: MOD_RES
<222> LOCATION: (32)
<223> OTHER INFORMATION: Xaa = Arg or Lys
<220> FEATURE:
<221> NAME/KEY: MOD_RES
<222> LOCATION: (33)
<223> OTHER INFORMATION: Xaa = Leu, Ile, Val or Phe
<220> FEATURE:
<221> NAME/KEY: MOD_RES
<222> LOCATION: (35)
<223> OTHER INFORMATION: Xaa = Thr or Ala
<220> FEATURE:
<221> NAME/KEY: MOD_RES
<222> LOCATION: (36)
<223> OTHER INFORMATION: Xaa = Arg, Ser, Thr or Ile
<220> FEATURE:
<221> NAME/KEY: MOD_RES
<222> LOCATION: (38)
<223> OTHER INFORMATION: Xaa = Asn or His
<220> FEATURE:
<221> NAME/KEY: MOD_RES
<222> LOCATION: (40)
<223> OTHER INFORMATION: Xaa = Thr or Ala
<220> FEATURE:
<221> NAME/KEY: MOD_RES
<222> LOCATION: (41)
<223> OTHER INFORMATION: Xaa = Ala, Gly or Leu
<220> FEATURE:
<221> NAME/KEY: MOD_RES
<222> LOCATION: (43)
<223> OTHER INFORMATION: Xaa = Ala, Ser or Gln
```

```
<220> FEATURE:
<221> NAME/KEY: MOD_RES
<222> LOCATION: (50)
<223> OTHER INFORMATION: Xaa = Ser or Thr
<220> FEATURE:
<221> NAME/KEY: MOD_RES
<222> LOCATION: (51)
<223> OTHER INFORMATION: Xaa = Asp, Glu or Asn
<220> FEATURE:
<221> NAME/KEY: MOD_RES
<222> LOCATION: (57)
<223> OTHER INFORMATION: Xaa = Ile or Leu
<220> FEATURE:
<221> NAME/KEY: MOD_RES
<222> LOCATION: (59)
<223> OTHER INFORMATION: Xaa = Val, Thr or Ile
<220> FEATURE:
<221> NAME/KEY: MOD_RES
<222> LOCATION: (60)
<223> OTHER INFORMATION: Xaa = Arg or Lys
<220> FEATURE:
<221> NAME/KEY: MOD_RES
<222> LOCATION: (61)
<223> OTHER INFORMATION: Xaa = Thr, Ser or Leu
<220> FEATURE:
<221> NAME/KEY: MOD_RES
<222> LOCATION: (62)
<223> OTHER INFORMATION: Xaa = Pro or Glu
<220> FEATURE:
<221> NAME/KEY: MOD_RES
<222> LOCATION: (63)
<223> OTHER INFORMATION: Xaa = Leu or Glu
<220> FEATURE:
<221> NAME/KEY: MOD_RES
<222> LOCATION: (65)
<223> OTHER INFORMATION: Xaa = Gln, Lys or Arg
<220> FEATURE:
<221> NAME/KEY: MOD_RES
<222> LOCATION: (66)
<223> OTHER INFORMATION: Xaa = Arg, Glu or Lys
<220> FEATURE:
<221> NAME/KEY: MOD_RES
<222> LOCATION: (69)
<223> OTHER INFORMATION: Xaa = Lys, Arg or Gln
<220> FEATURE:
<221> NAME/KEY: MOD_RES
<222> LOCATION: (71)
<223> OTHER INFORMATION: Xaa = Phe, Ile or Val
<220> FEATURE:
<221> NAME/KEY: MOD_RES
<222> LOCATION: (72)
<223> OTHER INFORMATION: Xaa = Val, Ile or Arg
<220> FEATURE:
<221> NAME/KEY: MOD_RES
<222> LOCATION: (73)
<223> OTHER INFORMATION: Xaa = Ala or Pro
<220> FEATURE:
<221> NAME/KEY: MOD_RES
<222> LOCATION: (74)
<223> OTHER INFORMATION: Xaa = Gln or absent
<220> FEATURE:
<221> NAME/KEY: MOD_RES
<222> LOCATION: (75)
<223> OTHER INFORMATION: Xaa = Glu, Asp or Arg
<220> FEATURE:
<221> NAME/KEY: MOD_RES
<222> LOCATION: (76)
<223> OTHER INFORMATION: Xaa = Pro, Glu, Ala, Ser or Asp
<220> FEATURE:
<221> NAME/KEY: MOD_RES
<222> LOCATION: (77)
<223> OTHER INFORMATION: Xaa = Gly, Asp or Asn
<220> FEATURE:
<221> NAME/KEY: MOD_RES
<222> LOCATION: (78)
<223> OTHER INFORMATION: Xaa = Trp or His
```

-continued

```
<220> FEATURE:
<221> NAME/KEY: MOD_RES
<222> LOCATION: (79)
<223> OTHER INFORMATION: Xaa = Trp, Leu, Ala or Val
<220> FEATURE:
<221> NAME/KEY: MOD_RES
<222> LOCATION: (80)
<223> OTHER INFORMATION: Xaa = Leu or Ile
<220> FEATURE:
<221> NAME/KEY: MOD_RES
<222> LOCATION: (81)
<223> OTHER INFORMATION: Xaa = Val, Leu or Phe
<220> FEATURE:
<221> NAME/KEY: MOD_RES
<222> LOCATION: (82)
<223> OTHER INFORMATION: Xaa = Ala, Ser, Gly or Val
<220> FEATURE:
<221> NAME/KEY: MOD_RES
<222> LOCATION: (83)
<223> OTHER INFORMATION: Xaa = Leu or Ala
<220> FEATURE:
<221> NAME/KEY: MOD_RES
<222> LOCATION: (92)
<223> OTHER INFORMATION: Xaa = Val or Ile

<400> SEQUENCE: 17

Ile Xaa Xaa Xaa Xaa Xaa Xaa Arg Xaa Xaa Xaa Lys Leu Xaa Xaa
1               5                   10                  15

Thr Tyr Xaa Xaa Xaa Xaa Pro Xaa Xaa Xaa Xaa Xaa Thr Xaa Xaa
            20                  25                  30

Xaa His Xaa Xaa Phe Xaa Gln Xaa Xaa Thr Xaa Thr Gly Arg Leu Ser
        35                  40                  45

Ser Xaa Xaa Pro Asn Leu Gln Asn Xaa Pro Xaa Xaa Xaa Xaa Gly
    50                  55                  60

Xaa Xaa Ile Arg Xaa Ala Xaa Xaa Xaa Xaa Xaa Xaa Xaa Xaa
65                  70                  75                  80

Xaa Xaa Xaa Asp Tyr Ser Gln Ile Glu Leu Arg Xaa
                85                  90

<210> SEQ ID NO 18
<211> LENGTH: 893
<212> TYPE: PRT
<213> ORGANISM: Artificial
<220> FEATURE:
<223> OTHER INFORMATION: chimeric thermostable DNA-dependent DNA
      polymerase CS5

<400> SEQUENCE: 18

Met Lys Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
                100                 105                 110

Glu Val Pro Gly Phe Glu Ala Asp Asp Val Leu Ala Thr Leu Ala Lys
                115                 120                 125
```

```
Lys Ala Glu Arg Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Lys
                165                 170                 175

Pro Glu Gln Trp Val Asp Phe Arg Ala Leu Val Gly Asp Pro Ser Asp
                180                 185                 190

Asn Leu Pro Gly Val Lys Gly Ile Gly Glu Lys Thr Ala Leu Lys Leu
                195                 200                 205

Leu Lys Glu Trp Gly Ser Leu Glu Asn Ile Leu Lys Asn Leu Asp Arg
    210                 215                 220

Val Lys Pro Glu Ser Val Arg Glu Arg Ile Lys Ala His Leu Glu Asp
225                 230                 235                 240

Leu Lys Leu Ser Leu Glu Leu Ser Arg Val Arg Ser Asp Leu Pro Leu
                245                 250                 255

Glu Val Asp Phe Ala Arg Arg Arg Glu Pro Asp Arg Glu Gly Leu Arg
                260                 265                 270

Ala Phe Leu Glu Arg Leu Glu Phe Gly Ser Leu Leu His Glu Phe Gly
            275                 280                 285

Leu Leu Glu Glu Ser Glu Pro Val Gly Tyr Arg Ile Val Lys Asp Leu
    290                 295                 300

Val Glu Phe Glu Lys Leu Ile Glu Lys Leu Arg Glu Ser Pro Ser Phe
305                 310                 315                 320

Ala Ile Asp Leu Glu Thr Ser Ser Leu Asp Pro Phe Asp Cys Asp Ile
                325                 330                 335

Val Gly Ile Ser Val Ser Phe Lys Pro Lys Glu Ala Tyr Tyr Ile Pro
                340                 345                 350

Leu His His Arg Asn Ala Gln Asn Leu Asp Glu Lys Glu Val Leu Lys
            355                 360                 365

Lys Leu Lys Glu Ile Leu Glu Asp Pro Gly Ala Lys Ile Val Gly Gln
    370                 375                 380

Asn Leu Lys Phe Asp Tyr Lys Val Leu Met Val Lys Gly Val Glu Pro
385                 390                 395                 400

Val Pro Pro Tyr Phe Asp Thr Met Ile Ala Ala Tyr Leu Leu Glu Pro
                405                 410                 415

Asn Glu Lys Lys Phe Asn Leu Asp Leu Ala Leu Lys Phe Leu Gly
                420                 425                 430

Tyr Lys Met Thr Ser Tyr Gln Glu Leu Met Ser Phe Ser Phe Pro Leu
            435                 440                 445

Phe Gly Phe Ser Phe Ala Asp Val Pro Val Glu Lys Ala Ala Asn Tyr
    450                 455                 460

Ser Cys Glu Asp Ala Asp Ile Thr Tyr Arg Leu Tyr Lys Thr Leu Ser
465                 470                 475                 480

Leu Lys Leu His Glu Ala Asp Leu Glu Asn Val Phe Tyr Lys Ile Glu
                485                 490                 495

Met Pro Leu Val Asn Val Leu Ala Arg Met Glu Leu Asn Gly Val Tyr
                500                 505                 510

Val Asp Thr Glu Phe Leu Lys Lys Leu Ser Glu Glu Tyr Gly Lys Lys
            515                 520                 525

Leu Glu Glu Leu Ala Glu Glu Ile Tyr Arg Ile Ala Gly Glu Pro Phe
    530                 535                 540
```

```
Asn Ile Asn Ser Pro Lys Gln Val Ser Arg Ile Leu Phe Glu Lys Leu
545                 550                 555                 560

Gly Ile Lys Pro Arg Gly Lys Thr Thr Lys Thr Gly Asp Tyr Ser Thr
                565                 570                 575

Arg Ile Glu Val Leu Glu Glu Leu Ala Gly Glu His Glu Ile Ile Pro
            580                 585                 590

Leu Ile Leu Glu Tyr Arg Lys Ile Gln Lys Leu Lys Ser Thr Tyr Ile
        595                 600                 605

Asp Ala Leu Pro Lys Met Val Asn Pro Lys Thr Gly Arg Ile His Ala
610                 615                 620

Ser Phe Asn Gln Thr Gly Thr Ala Thr Gly Arg Leu Ser Ser Ser Asp
625                 630                 635                 640

Pro Asn Leu Gln Asn Leu Pro Thr Lys Ser Glu Glu Gly Lys Glu Ile
                645                 650                 655

Arg Lys Ala Ile Val Pro Gln Asp Pro Asn Trp Trp Ile Val Ser Ala
                660                 665                 670

Asp Tyr Ser Gln Ile Glu Leu Arg Ile Leu Ala His Leu Ser Gly Asp
        675                 680                 685

Glu Asn Leu Leu Arg Ala Phe Glu Glu Gly Ile Asp Val His Thr Leu
690                 695                 700

Thr Ala Ser Arg Ile Phe Asn Val Lys Pro Glu Glu Val Thr Glu Glu
705                 710                 715                 720

Met Arg Arg Ala Gly Lys Met Val Asn Phe Ser Ile Ile Tyr Gly Val
                725                 730                 735

Thr Pro Tyr Gly Leu Ser Val Arg Leu Gly Val Pro Val Lys Glu Ala
                740                 745                 750

Glu Lys Met Ile Val Asn Tyr Phe Val Leu Tyr Pro Lys Val Arg Asp
        755                 760                 765

Tyr Ile Gln Arg Val Val Ser Glu Ala Lys Glu Lys Gly Tyr Val Arg
770                 775                 780

Thr Leu Phe Gly Arg Lys Arg Asp Ile Pro Gln Leu Met Ala Arg Asp
785                 790                 795                 800

Arg Asn Thr Gln Ala Glu Gly Glu Arg Ile Ala Ile Asn Thr Pro Ile
                805                 810                 815

Gln Gly Thr Ala Ala Asp Ile Ile Lys Leu Ala Met Ile Glu Ile Asp
                820                 825                 830

Arg Glu Leu Lys Glu Arg Lys Met Arg Ser Lys Met Ile Ile Gln Val
        835                 840                 845

His Asp Glu Leu Val Phe Glu Val Pro Asn Glu Glu Lys Asp Ala Leu
850                 855                 860

Val Glu Leu Val Lys Asp Arg Met Thr Asn Val Val Lys Leu Ser Val
865                 870                 875                 880

Pro Leu Glu Val Asp Val Thr Ile Gly Lys Thr Trp Ser
                885                 890

<210> SEQ ID NO 19
<211> LENGTH: 893
<212> TYPE: PRT
<213> ORGANISM: Artificial
<220> FEATURE:
<223> OTHER INFORMATION: chimeric thermostable DNA-dependent DNA
      polymerase CS6
```

<400> SEQUENCE: 19

```
Met Lys Ala Met Leu Pro Leu Phe Glu Pro Lys Gly Arg Val Leu Leu
1               5                   10                  15
Val Asp Gly His His Leu Ala Tyr Arg Thr Phe Phe Ala Leu Lys Gly
            20                  25                  30
Leu Thr Thr Ser Arg Gly Glu Pro Val Gln Ala Val Tyr Gly Phe Ala
        35                  40                  45
Lys Ser Leu Leu Lys Ala Leu Lys Glu Asp Gly Tyr Lys Ala Val Phe
    50                  55                  60
Val Val Phe Asp Ala Lys Ala Pro Ser Phe Arg His Glu Ala Tyr Glu
65                  70                  75                  80
Ala Tyr Lys Ala Gly Arg Ala Pro Thr Pro Glu Asp Phe Pro Arg Gln
                85                  90                  95
Leu Ala Leu Ile Lys Glu Leu Val Asp Leu Leu Gly Phe Thr Arg Leu
            100                 105                 110
Glu Val Pro Gly Phe Glu Ala Asp Asp Val Leu Ala Thr Leu Ala Lys
        115                 120                 125
Lys Ala Glu Arg Glu Gly Tyr Glu Val Arg Ile Leu Thr Ala Asp Arg
    130                 135                 140
Asp Leu Tyr Gln Leu Val Ser Asp Arg Val Ala Val Leu His Pro Glu
145                 150                 155                 160
Gly His Leu Ile Thr Pro Glu Trp Leu Trp Glu Lys Tyr Gly Leu Lys
                165                 170                 175
Pro Glu Gln Trp Val Asp Phe Arg Ala Leu Val Gly Asp Pro Ser Asp
            180                 185                 190
Asn Leu Pro Gly Val Lys Gly Ile Gly Glu Lys Thr Ala Leu Lys Leu
        195                 200                 205
Leu Lys Glu Trp Gly Ser Leu Glu Asn Ile Leu Lys Asn Leu Asp Arg
    210                 215                 220
Val Lys Pro Glu Ser Val Arg Glu Arg Ile Lys Ala His Leu Glu Asp
225                 230                 235                 240
Leu Lys Leu Ser Leu Glu Leu Ser Arg Val Arg Ser Asp Leu Pro Leu
                245                 250                 255
Glu Val Asp Phe Ala Arg Arg Arg Glu Pro Asp Arg Glu Gly Leu Arg
            260                 265                 270
Ala Phe Leu Glu Arg Leu Glu Phe Gly Ser Leu Leu His Glu Phe Gly
        275                 280                 285
Leu Leu Glu Glu Ser Glu Pro Val Gly Tyr Arg Ile Val Lys Asp Leu
    290                 295                 300
Val Glu Phe Glu Lys Leu Ile Glu Lys Leu Arg Glu Ser Pro Ser Phe
305                 310                 315                 320
Ala Ile Ala Leu Ala Thr Ser Ser Leu Asp Pro Phe Asp Cys Asp Ile
                325                 330                 335
Val Gly Ile Ser Val Ser Phe Lys Pro Lys Glu Ala Tyr Tyr Ile Pro
            340                 345                 350
Leu His His Arg Asn Ala Gln Asn Leu Asp Glu Lys Glu Val Leu Lys
        355                 360                 365
Lys Leu Lys Glu Ile Leu Glu Asp Pro Gly Ala Lys Ile Val Gly Gln
    370                 375                 380
Asn Leu Lys Phe Asp Tyr Lys Val Leu Met Val Lys Gly Val Glu Pro
385                 390                 395                 400
Val Pro Pro Tyr Phe Asp Thr Met Ile Ala Ala Tyr Leu Leu Glu Pro
                405                 410                 415
```

```
Asn Glu Lys Lys Phe Asn Leu Asp Asp Leu Ala Leu Lys Phe Leu Gly
                420                 425                 430

Tyr Lys Met Thr Ser Tyr Gln Glu Leu Met Ser Phe Ser Phe Pro Leu
            435                 440                 445

Phe Gly Phe Ser Phe Ala Asp Val Pro Val Glu Lys Ala Ala Asn Tyr
        450                 455                 460

Ser Cys Glu Asp Ala Asp Ile Thr Tyr Arg Leu Tyr Lys Thr Leu Ser
465                 470                 475                 480

Leu Lys Leu His Glu Ala Asp Leu Glu Asn Val Phe Tyr Lys Ile Glu
                485                 490                 495

Met Pro Leu Val Asn Val Leu Ala Arg Met Glu Leu Asn Gly Val Tyr
            500                 505                 510

Val Asp Thr Glu Phe Leu Lys Lys Leu Ser Glu Glu Tyr Gly Lys Lys
        515                 520                 525

Leu Glu Glu Leu Ala Glu Glu Ile Tyr Arg Ile Ala Gly Glu Pro Phe
530                 535                 540

Asn Ile Asn Ser Pro Lys Gln Val Ser Arg Ile Leu Phe Glu Lys Leu
545                 550                 555                 560

Gly Ile Lys Pro Arg Gly Lys Thr Thr Lys Thr Gly Asp Tyr Ser Thr
                565                 570                 575

Arg Ile Glu Val Leu Glu Glu Leu Ala Gly Glu His Glu Ile Ile Pro
            580                 585                 590

Leu Ile Leu Glu Tyr Arg Lys Ile Gln Lys Leu Lys Ser Thr Tyr Ile
        595                 600                 605

Asp Ala Leu Pro Lys Met Val Asn Pro Lys Thr Gly Arg Ile His Ala
610                 615                 620

Ser Phe Asn Gln Thr Gly Thr Ala Thr Gly Arg Leu Ser Ser Ser Asp
625                 630                 635                 640

Pro Asn Leu Gln Asn Leu Pro Thr Lys Ser Glu Glu Gly Lys Glu Ile
                645                 650                 655

Arg Lys Ala Ile Val Pro Gln Asp Pro Asn Trp Trp Ile Val Ser Ala
            660                 665                 670

Asp Tyr Ser Gln Ile Glu Leu Arg Ile Leu Ala His Leu Ser Gly Asp
        675                 680                 685

Glu Asn Leu Leu Arg Ala Phe Glu Glu Gly Ile Asp Val His Thr Leu
690                 695                 700

Thr Ala Ser Arg Ile Phe Asn Val Lys Pro Glu Glu Val Thr Glu Glu
705                 710                 715                 720

Met Arg Arg Ala Gly Lys Met Val Asn Phe Ser Ile Ile Tyr Gly Val
                725                 730                 735

Thr Pro Tyr Gly Leu Ser Val Arg Leu Gly Val Pro Val Lys Glu Ala
            740                 745                 750

Glu Lys Met Ile Val Asn Tyr Phe Val Leu Tyr Pro Lys Val Arg Asp
        755                 760                 765

Tyr Ile Gln Arg Val Val Ser Glu Ala Lys Glu Lys Gly Tyr Val Arg
770                 775                 780

Thr Leu Phe Gly Arg Lys Arg Asp Ile Pro Gln Leu Met Ala Arg Asp
785                 790                 795                 800

Arg Asn Thr Gln Ala Glu Gly Glu Arg Ile Ala Ile Asn Thr Pro Ile
                805                 810                 815

Gln Gly Thr Ala Ala Asp Ile Ile Lys Leu Ala Met Ile Glu Ile Asp
            820                 825                 830
```

```
Arg Glu Leu Lys Glu Arg Lys Met Arg Ser Lys Met Ile Ile Gln Val
        835                 840                 845

His Asp Glu Leu Val Phe Glu Val Pro Asn Glu Lys Asp Ala Leu
        850                 855                 860

Val Glu Leu Val Lys Asp Arg Met Thr Asn Val Val Lys Leu Ser Val
865                 870                 875                 880

Pro Leu Glu Val Asp Val Thr Ile Gly Lys Thr Trp Ser
                885                 890

<210> SEQ ID NO 20
<211> LENGTH: 2682
<212> TYPE: DNA
<213> ORGANISM: Artificial
<220> FEATURE:
<223> OTHER INFORMATION: chimeric thermostable DNA-dependent DNA
      polymerase CS5

<400> SEQUENCE: 20
```

| | | | |
|---|---|---|---|
| atgaaagcta tgttaccatt attcgaaccc aaaggccggg tcctcctggt ggacggccac | | | 60 |
| cacctggcct accgcacctt cttcgccctg aagggcctca ccacgagccg ggcgaaccg | | | 120 |
| gtgcaggcgg tttacggctt cgccaagagc ctcctcaagg ccctgaagga ggacgggtac | | | 180 |
| aaggccgtct tcgtggtctt tgacgccaag gccccttcct tccgccacga ggcctacgag | | | 240 |
| gcctacaagg caggccgcgc cccgaccccc gaggacttcc cccggcagct cgccctcatc | | | 300 |
| aaggagctgg tggacctcct ggggtttact cgcctcgagg ttccgggctt tgaggcggac | | | 360 |
| gacgtcctcg ccaccctggc caagaaggcg aaaggagg gtacgaggt gcgcatcctc | | | 420 |
| accgccgacc gggacctta ccagctcgtc tccgaccgcg tcgccgtcct ccacccgag | | | 480 |
| ggccacctca tcaccccgga gtggctttgg gagaagtacg ccttaagcc ggagcagtgg | | | 540 |
| gtggacttcc gcgccctcgt gggggacccc tccgacaacc tccccggggt caagggcatc | | | 600 |
| ggggagaaga ccgccctcaa gctcctcaag gagtggggaa gcctggaaaa tatcctcaag | | | 660 |
| aacctggacc gggtgaagcc ggaaagcgtc cgggaaagga tcaaggccca cctggaagac | | | 720 |
| cttaagctct ccttggagct ttcccgggtg cgctcggacc tcccctgga ggtggacttc | | | 780 |
| gcccggaggc gggagcctga ccgggaaggg cttcgggcct ttttggagcg cttggagttc | | | 840 |
| ggcagcctcc tccacgagtt cggccttcta gaggagtccg aacccgttgg gtaccgtata | | | 900 |
| gttaaagacc tggttgaatt tgaaaaactc atagagaaac tgagagaatc tccttcgttc | | | 960 |
| gctatcgatt tggaaactag ttccctcgat cctttcgact cgacattgt cggtatctct | | | 1020 |
| gtgtctttca aaccaaagga agcgtactac ataccactcc atcatagaaa cgcccagaac | | | 1080 |
| ctggacgaaa aagaggttct gaaaagctc aagaaattc tggaggaccc cggagcaaag | | | 1140 |
| atcgttggtc agaatttgaa attcgattac aaggtgttga tggtgaaggg tgttgaacct | | | 1200 |
| gttcctcctt acttcgacac gatgatagcg gcttaccttc ttgagccgaa cgaaaagaag | | | 1260 |
| ttcaatctgg acgatctcgc attgaaattt cttggataca aaatgacatc ttaccaagag | | | 1320 |
| ctcatgtcct tctcttttcc gctgtttggt ttcagttttg ccgatgttcc tgtagaaaaa | | | 1380 |
| gcagcgaact actcctgtga agatgcagac atcacctaca actttacaa gaccctgagc | | | 1440 |
| ttaaaactcc acgaggcaga tctggaaaac gtgttctaca gatagaaat gccccttgtg | | | 1500 |
| aacgtgcttg cacggatgga actgaacggt gtgtatgtgg acacagagtt cctgaagaaa | | | 1560 |
| ctctcagaag agtacggaaa aaactcgaa gaactggcag aggaaatata caggatagct | | | 1620 |
| ggagagccgt tcaacataaa ctcaccgaag caggtttcaa ggatcctttt tgaaaaactc | | | 1680 |

| | |
|---|---|
| ggcataaaac cacgtggtaa aacgacgaaa acgggagact attcaacacg catagaagtc | 1740 |
| ctcgaggaac ttgccggtga acacgaaatc attcctctga ttcttgaata cagaaagata | 1800 |
| cagaaattga aatcaaccta catagacgct cttcccaaga tggtcaaccc aaagaccgga | 1860 |
| aggattcatg cttctttcaa tcaaacgggg actgccactg gaagacttag cagcagcgat | 1920 |
| cccaatcttc agaacctccc gacgaaaagt gaagagggaa aagaaatcag gaaagcgata | 1980 |
| gttcctcagg atccaaactg gtggatcgtc agtgccgact actcccaaat gaactgagg | 2040 |
| atcctcgccc atctcagtgg tgatgagaat cttttgaggg cattcgaaga gggcatcgac | 2100 |
| gtccacactc taacagcttc cagaatattc aacgtgaaac ccgaagaagt aaccgaagaa | 2160 |
| atgcgccgcg ctggtaaaat ggttaatttt tccatcatat acggtgtaac accttacggt | 2220 |
| ctgtctgtga ggcttggagt acctgtgaaa gaagcagaaa agatgatcgt caactacttc | 2280 |
| gtcctctacc caaaggtgcg cgattacatt cagagggtcg tatcggaagc gaaagaaaaa | 2340 |
| ggctatgtta gaacgctgtt tggaagaaaa agagacatac cacagctcat ggcccgggac | 2400 |
| aggaacacac aggctgaagg agaacgaatt gccataaaca ctcccataca gggtacagca | 2460 |
| gcggatataa taaagctggc tatgatagaa atagacaggg aactgaaaga aagaaaaatg | 2520 |
| agatcgaaga tgatcataca ggtccacgac gaactggttt ttgaagtgcc caatgaggaa | 2580 |
| aaggacgcgc tcgtcgagct ggtgaaagac agaatgacga atgtggtaaa gctttcagtg | 2640 |
| ccgctcgaag tggatgtaac catcggcaaa acatggtcgt ga | 2682 |

<210> SEQ ID NO 21
<211> LENGTH: 2682
<212> TYPE: DNA
<213> ORGANISM: Artificial
<220> FEATURE:
<223> OTHER INFORMATION: chimeric thermostable DNA-dependent DNA
      polymerase CS6

<400> SEQUENCE: 21

| | |
|---|---|
| atgaaagcta tgttaccatt attcgaaccc aaaggccggg tcctcctggt ggacggccac | 60 |
| cacctggcct accgcacctt cttcgccctg aagggcctca ccacgagccg ggcgaaccg | 120 |
| gtgcaggcgt tttacggctt cgccaagagc ctcctcaagg ccctgaagga ggacgggtac | 180 |
| aaggccgtct tcgtggtctt tgacgccaag gccccttcct tccgccacga ggcctacgag | 240 |
| gcctacaagg caggccgcgc cccgaccccc gaggacttcc ccggcagct cgccctcatc | 300 |
| aaggagctgg tggacctcct ggggtttact cgcctcgagg ttccgggctt tgaggcggac | 360 |
| gacgtcctcg ccacccctggc caagaaggcg gaaagggagg ggtacgaggt gcgcatcctc | 420 |
| accgccgacc gggaccttta ccagctcgtc tccgaccgcg tcgccgtcct ccaccccgag | 480 |
| ggccacctca tcacccccgga gtggctttgg gagaagtacg gccttaagcc ggagcagtgg | 540 |
| gtggacttcc gcgccctcgt gggggacccc tccgacaacc tccccgggggt caagggcatc | 600 |
| ggggagaaga ccgccctcaa gctcctcaag gagtggggaa gcctggaaaa tatcctcaag | 660 |
| aacctggacc gggtgaagcc ggaaagcgtc cgggaaagga tcaaggccca cctggaagac | 720 |
| cttaagctct ccttggagct ttcccggggtg cgctcggacc tccccctgga ggtgacttc | 780 |
| gcccggaggc gggagcctga ccgggaaggg cttcggggcct ttttggagcg cttggagttc | 840 |
| ggcagcctcc tccacgagtt cggccttcta gaggagtccg aacccgttgg gtaccgtata | 900 |
| gttaaagacc tggttgaatt tgaaaaactc atagagaaac tgagagaatc tccttcgttc | 960 |
| gcgatcgctc ttgcgactag ttccctcgat cctttcgact gcgacattgt cggtatctct | 1020 |

```
gtgtctttca aaccaaagga agcgtactac ataccactcc atcatagaaa cgcccagaac   1080
ctggacgaaa aagaggttct gaaaaagctc aaagaaattc tggaggaccc cggagcaaag   1140
atcgttggtc agaatttgaa attcgattac aaggtgttga tggtgaaggg tgttgaacct   1200
gttcctcctt acttcgacac gatgatagcg gcttaccttc ttgagccgaa cgaaaagaag   1260
ttcaatctgg acgatctcgc attgaaattt cttggataca aaatgacatc ttaccaagag   1320
ctcatgtcct tctcttttcc gctgtttggt ttcagttttg ccgatgttcc tgtagaaaaa   1380
gcagcgaact actcctgtga agatgcagac atcacctaca gactttacaa gaccctgagc   1440
ttaaaactcc acgaggcaga tctgaaaaac gtgttctaca gatagaaat gccccttgtg    1500 aacgtgcttg cacggatgga actgaacggt gtgtatgtgg acacagagtt cctgaagaaa   1560
ctctcagaag agtacggaaa aaaactcgaa gaactggcag aggaaatata caggatagct   1620
ggagagccgt tcaacataaa ctcaccgaag caggtttcaa ggatcctttt tgaaaaactc   1680
ggcataaaac cacgtggtaa aacgacgaaa acgggagact attcaacacg catagaagtc   1740
ctcgaggaac ttgccggtga acacgaaatc attcctctga ttcttgaata cagaaagata   1800
cagaaattga aatcaaccta catagacgct cttcccaaga tggtcaaccc aaagaccgga   1860
aggattcatg cttcttttcaa tcaaacgggg actgccactg gaagacttag cagcagcgat   1920
cccaatcttc agaacctccc gacgaaaagt gaagagggaa aagaaatcag gaaagcgata   1980
gttcctcagg atccaaactg gtggatcgtc agtgccgact actcccaaat gaactgagg    2040 atcctcgccc atctcagtgg tgatgagaat cttttgaggg cattcgaaga gggcatcgac   2100
gtccacactc taacagcttc cagaatattc aacgtgaaac ccgaagaagt aaccgaagaa   2160
atgcgccgcg ctggtaaaat ggttaatttt tccatcatat acggtgtaac accttacggt   2220
ctgtctgtga ggcttggagt acctgtgaaa gaagcagaaa agatgatcgt caactacttc   2280
gtcctctacc caaaggtgcg cgattacatt cagagggtcg tatcggaagc gaaagaaaaa   2340
ggctatgtta gaacgctgtt tggaagaaaa agagacatac cacagctcat ggcccgggac   2400
aggaacacac aggctgaagg agaacgaatt gccataaaca ctcccataca gggtacagca   2460
gcggatataa taaagctggc tatgatagaa atagacaggg aactgaaaga agaaaaatg    2520 agatcgaaga tgatcataca ggtccacgac gaactggttt ttgaagtgcc caatgaggaa   2580
aaggacgcgc tcgtcgagct ggtgaaagac agaatgacga atgtggtaaa gctttcagtg   2640
ccgctcgaag tggatgtaac catcggcaaa acatggtcgt ga                       2682
```

<210> SEQ ID NO 22
<211> LENGTH: 8
<212> TYPE: PRT
<213> ORGANISM: Artificial
<220> FEATURE:
<223> OTHER INFORMATION: DNA polymerase active site conserved motif A

<400> SEQUENCE: 22

Asp Tyr Ser Gln Ile Glu Leu Arg
1               5

<210> SEQ ID NO 23
<211> LENGTH: 91
<212> TYPE: PRT
<213> ORGANISM: Artificial
<220> FEATURE:
<223> OTHER INFORMATION: active site region from exemplary unmodified
      reference polymerase domain of thermostable Family A type
      DNA-dependent DNA polymerase Thermus species Z05 (Z05)

-continued

```
<220> FEATURE:
<221> NAME/KEY: MOD_RES
<222> LOCATION: (5)
<223> OTHER INFORMATION: Xaa = Ile or Leu
<220> FEATURE:
<221> NAME/KEY: MOD_RES
<222> LOCATION: (6)
<223> OTHER INFORMATION: Xaa = Leu or Gln
<220> FEATURE:
<221> NAME/KEY: MOD_RES
<222> LOCATION: (7)
<223> OTHER INFORMATION: Xaa = Gln, His or Glu
<220> FEATURE:
<221> NAME/KEY: MOD_RES
<222> LOCATION: (8)
<223> OTHER INFORMATION: Xaa = Tyr, His or Phe
<220> FEATURE:
<221> NAME/KEY: MOD_RES
<222> LOCATION: (10)
<223> OTHER INFORMATION: Xaa = Glu, Gln or Lys
<220> FEATURE:
<221> NAME/KEY: MOD_RES
<222> LOCATION: (11)
<223> OTHER INFORMATION: Xaa = Ile, Leu or Tyr
<220> FEATURE:
<221> NAME/KEY: MOD_RES
<222> LOCATION: (12)
<223> OTHER INFORMATION: Xaa = Gln, Thr, Met, Gly or Leu
<220> FEATURE:
<221> NAME/KEY: MOD_RES
<222> LOCATION: (15)
<223> OTHER INFORMATION: Xaa = Lys or Gln
<220> FEATURE:
<221> NAME/KEY: MOD_RES
<222> LOCATION: (16)
<223> OTHER INFORMATION: Xaa = Ser or Asn
<220> FEATURE:
<221> NAME/KEY: MOD_RES
<222> LOCATION: (19)
<223> OTHER INFORMATION: Xaa = Ile or Val
<220> FEATURE:
<221> NAME/KEY: MOD_RES
<222> LOCATION: (20)
<223> OTHER INFORMATION: Xaa = Glu or Asp
<220> FEATURE:
<221> NAME/KEY: MOD_RES
<222> LOCATION: (50)
<223> OTHER INFORMATION: Xaa = Ser or Thr
<220> FEATURE:
<221> NAME/KEY: MOD_RES
<222> LOCATION: (51)
<223> OTHER INFORMATION: Xaa = Asp, Glu or Asn
<220> FEATURE:
<221> NAME/KEY: MOD_RES
<222> LOCATION: (76)
<223> OTHER INFORMATION: Xaa = Gly, Asn or Asp
<220> FEATURE:
<221> NAME/KEY: MOD_RES
<222> LOCATION: (77)
<223> OTHER INFORMATION: Xaa = Trp or His
<220> FEATURE:
<221> NAME/KEY: MOD_RES
<222> LOCATION: (78)
<223> OTHER INFORMATION: Xaa = Trp, Ala, Leu or Val
<220> FEATURE:
<221> NAME/KEY: MOD_RES
<222> LOCATION: (79)
<223> OTHER INFORMATION: Xaa = Ile or Leu
<220> FEATURE:
<221> NAME/KEY: MOD_RES
<222> LOCATION: (80)
<223> OTHER INFORMATION: Xaa = Val, Phe or Leu
<220> FEATURE:
<221> NAME/KEY: MOD_RES
<222> LOCATION: (81)
<223> OTHER INFORMATION: Xaa = Ser, Ala, Val or Gly
```

```
<220> FEATURE:
<221> NAME/KEY: MOD_RES
<222> LOCATION: (82)
<223> OTHER INFORMATION: Xaa = Ala or Leu

<400> SEQUENCE: 23

Ile Val Glu Lys Xaa Xaa Xaa Arg Xaa Xaa Lys Leu Xaa Xaa
1               5                   10                  15

Thr Tyr Xaa Xaa Pro Leu Pro Gly Leu Val His Pro Arg Thr Gly Arg
            20                  25                  30

Leu His Thr Arg Phe Asn Gln Thr Ala Thr Ala Thr Gly Arg Leu Ser
            35                  40                  45

Ser Xaa Xaa Pro Asn Leu Gln Asn Ile Pro Ile Arg Thr Pro Leu Gly
        50                  55                  60

Gln Arg Ile Arg Arg Ala Phe Val Ala Glu Ala Xaa Xaa Xaa Xaa Xaa
65                  70                  75                  80

Xaa Xaa Asp Tyr Ser Gln Ile Glu Leu Arg Val
                85                  90

<210> SEQ ID NO 24
<211> LENGTH: 92
<212> TYPE: PRT
<213> ORGANISM: Artificial
<220> FEATURE:
<223> OTHER INFORMATION: active site region from exemplary unmodified
      reference polymerase domain of chimeric thermostable
      DNA-dependent DNA polymerase CS5 or CS6
<220> FEATURE:
<221> NAME/KEY: MOD_RES
<222> LOCATION: (5)
<223> OTHER INFORMATION: Xaa = Ile or Leu
<220> FEATURE:
<221> NAME/KEY: MOD_RES
<222> LOCATION: (6)
<223> OTHER INFORMATION: Xaa = Leu or Gln
<220> FEATURE:
<221> NAME/KEY: MOD_RES
<222> LOCATION: (7)
<223> OTHER INFORMATION: Xaa = Gln, His or Glu
<220> FEATURE:
<221> NAME/KEY: MOD_RES
<222> LOCATION: (8)
<223> OTHER INFORMATION: Xaa = Tyr, His or Phe
<220> FEATURE:
<221> NAME/KEY: MOD_RES
<222> LOCATION: (10)
<223> OTHER INFORMATION: Xaa = Glu, Gln or Lys
<220> FEATURE:
<221> NAME/KEY: MOD_RES
<222> LOCATION: (11)
<223> OTHER INFORMATION: Xaa = Ile, Leu or Tyr
<220> FEATURE:
<221> NAME/KEY: MOD_RES
<222> LOCATION: (12)
<223> OTHER INFORMATION: Xaa = Gln, Thr, Met, Gly or Leu
<220> FEATURE:
<221> NAME/KEY: MOD_RES
<222> LOCATION: (15)
<223> OTHER INFORMATION: Xaa = Lys or Gln
<220> FEATURE:
<221> NAME/KEY: MOD_RES
<222> LOCATION: (16)
<223> OTHER INFORMATION: Xaa = Ser or Asn
<220> FEATURE:
<221> NAME/KEY: MOD_RES
<222> LOCATION: (19)
<223> OTHER INFORMATION: Xaa = Ile or Val
<220> FEATURE:
<221> NAME/KEY: MOD_RES
<222> LOCATION: (20)
<223> OTHER INFORMATION: Xaa = Glu or Asp
```

```
<220> FEATURE:
<221> NAME/KEY: MOD_RES
<222> LOCATION: (50)
<223> OTHER INFORMATION: Xaa = Ser or Thr
<220> FEATURE:
<221> NAME/KEY: MOD_RES
<222> LOCATION: (51)
<223> OTHER INFORMATION: Xaa = Asp, Glu or Asn
<220> FEATURE:
<221> NAME/KEY: MOD_RES
<222> LOCATION: (77)
<223> OTHER INFORMATION: Xaa = Gly, Asn or Asp
<220> FEATURE:
<221> NAME/KEY: MOD_RES
<222> LOCATION: (78)
<223> OTHER INFORMATION: Xaa = Trp or His
<220> FEATURE:
<221> NAME/KEY: MOD_RES
<222> LOCATION: (79)
<223> OTHER INFORMATION: Xaa = Trp, Ala, Leu or Val
<220> FEATURE:
<221> NAME/KEY: MOD_RES
<222> LOCATION: (80)
<223> OTHER INFORMATION: Xaa = Ile or Leu
<220> FEATURE:
<221> NAME/KEY: MOD_RES
<222> LOCATION: (81)
<223> OTHER INFORMATION: Xaa = Val, Phe or Leu
<220> FEATURE:
<221> NAME/KEY: MOD_RES
<222> LOCATION: (82)
<223> OTHER INFORMATION: Xaa = Ser, Ala, Val or Gly
<220> FEATURE:
<221> NAME/KEY: MOD_RES
<222> LOCATION: (83)
<223> OTHER INFORMATION: Xaa = Ala or Leu

<400> SEQUENCE: 24

Ile Ile Pro Leu Xaa Xaa Xaa Xaa Arg Xaa Xaa Xaa Lys Leu Xaa Xaa
1               5                   10                  15

Thr Tyr Xaa Xaa Ala Leu Pro Lys Met Val Asn Pro Lys Thr Gly Arg
            20                  25                  30

Ile His Ala Ser Phe Asn Gln Thr Gly Thr Ala Thr Gly Arg Leu Ser
        35                  40                  45

Ser Xaa Xaa Pro Asn Leu Gln Asn Leu Pro Thr Lys Ser Glu Glu Gly
50                  55                  60

Lys Glu Ile Arg Lys Ala Ile Val Pro Gln Asp Pro Xaa Xaa Xaa Xaa
65                  70                  75                  80

Xaa Xaa Xaa Asp Tyr Ser Gln Ile Glu Leu Arg Ile
                85                  90

<210> SEQ ID NO 25
<211> LENGTH: 91
<212> TYPE: PRT
<213> ORGANISM: Artificial
<220> FEATURE:
<223> OTHER INFORMATION: active site region from exemplary unmodified
      reference polymerase domain of thermostable Family A type
      DNA-dependent DNA polymerase Thermus species Z05 (Z05)
<220> FEATURE:
<221> NAME/KEY: MOD_RES
<222> LOCATION: (50)
<223> OTHER INFORMATION: Xaa = Ser or Thr
<220> FEATURE:
<221> NAME/KEY: MOD_RES
<222> LOCATION: (51)
<223> OTHER INFORMATION: Xaa = Asp, Glu or Asn
```

<400> SEQUENCE: 25

```
Ile Val Glu Lys Ile Leu Gln His Arg Glu Leu Thr Lys Leu Lys Asn
1               5                   10                  15

Thr Tyr Val Asp Pro Leu Pro Ser Leu Val His Pro Asn Thr Gly Arg
                20                  25                  30

Leu His Thr Arg Phe Asn Gln Thr Ala Thr Ala Thr Gly Arg Leu Ser
            35                  40                  45

Ser Xaa Xaa Pro Asn Leu Gln Asn Ile Pro Val Arg Thr Pro Leu Gly
        50                  55                  60

Gln Arg Ile Arg Arg Ala Phe Val Ala Glu Ala Gly Trp Ala Leu Val
65                  70                  75                  80

Ala Leu Asp Tyr Ser Gln Ile Glu Leu Arg Val
                85                  90
```

<210> SEQ ID NO 26
<211> LENGTH: 92
<212> TYPE: PRT
<213> ORGANISM: Artificial
<220> FEATURE:
<223> OTHER INFORMATION: active site region from exemplary unmodified
      reference polymerase domain of chimeric thermostable
      DNA-dependent DNA polymerase CS5 or CS6
<220> FEATURE:
<221> NAME/KEY: MOD_RES
<222> LOCATION: (50)
<223> OTHER INFORMATION: Xaa = Ser or Thr
<220> FEATURE:
<221> NAME/KEY: MOD_RES
<222> LOCATION: (51)
<223> OTHER INFORMATION: Xaa = Asp, Glu or Asn

<400> SEQUENCE: 26

```
Ile Ile Pro Leu Ile Leu Glu Tyr Arg Lys Ile Gln Lys Leu Lys Ser
1               5                   10                  15

Thr Tyr Ile Asp Ala Leu Pro Lys Met Val Asn Pro Lys Thr Gly Arg
                20                  25                  30

Ile His Ala Ser Phe Asn Gln Thr Gly Thr Ala Thr Gly Arg Leu Ser
            35                  40                  45

Ser Xaa Xaa Pro Asn Leu Gln Asn Leu Pro Thr Lys Ser Glu Glu Gly
        50                  55                  60

Lys Glu Ile Arg Lys Ala Ile Val Pro Gln Asp Pro Asn Trp Trp Ile
65                  70                  75                  80

Val Ser Ala Asp Tyr Ser Gln Ile Glu Leu Arg Ile
                85                  90
```

<210> SEQ ID NO 27
<211> LENGTH: 16
<212> TYPE: PRT
<213> ORGANISM: Artificial
<220> FEATURE:
<223> OTHER INFORMATION: improved DNA polymerase modified motif a
<220> FEATURE:
<221> NAME/KEY: MOD_RES
<222> LOCATION: (1)
<223> OTHER INFORMATION: Xaa = Ile or Leu
<220> FEATURE:
<221> NAME/KEY: MOD_RES
<222> LOCATION: (2)
<223> OTHER INFORMATION: Xaa = Leu or Gln
<220> FEATURE:
<221> NAME/KEY: MOD_RES
<222> LOCATION: (3)
<223> OTHER INFORMATION: Xaa = Gln, His or Glu

```
<220> FEATURE:
<221> NAME/KEY: MOD_RES
<222> LOCATION: (4)
<223> OTHER INFORMATION: Xaa = Tyr, His or Phe
<220> FEATURE:
<221> NAME/KEY: MOD_RES
<222> LOCATION: (6)
<223> OTHER INFORMATION: Xaa = Glu, Gln or Lys
<220> FEATURE:
<221> NAME/KEY: MOD_RES
<222> LOCATION: (7)
<223> OTHER INFORMATION: Xaa = Ile, Leu or Tyr
<220> FEATURE:
<221> NAME/KEY: MOD_RES
<222> LOCATION: (8)
<223> OTHER INFORMATION: Xaa = D- or L- Ala, Cys, Asp, Glu, Phe, His,
     Ile, Lys, Asn, Pro, Arg, Ser, Val, Trp or Tyr
<220> FEATURE:
<221> NAME/KEY: MOD_RES
<222> LOCATION: (11)
<223> OTHER INFORMATION: Xaa = Lys or Gln
<220> FEATURE:
<221> NAME/KEY: MOD_RES
<222> LOCATION: (12)
<223> OTHER INFORMATION: Xaa = Ser or Asn
<220> FEATURE:
<221> NAME/KEY: MOD_RES
<222> LOCATION: (15)
<223> OTHER INFORMATION: Xaa = Ile or Val
<220> FEATURE:
<221> NAME/KEY: MOD_RES
<222> LOCATION: (16)
<223> OTHER INFORMATION: Xaa = Glu or Asp

<400> SEQUENCE: 27

Xaa Xaa Xaa Xaa Arg Xaa Xaa Xaa Lys Leu Xaa Xaa Thr Tyr Xaa Xaa
1               5                   10                  15

<210> SEQ ID NO 28
<211> LENGTH: 16
<212> TYPE: PRT
<213> ORGANISM: Artificial
<220> FEATURE:
<223> OTHER INFORMATION: improved DNA polymerase modified motif a
<220> FEATURE:
<221> NAME/KEY: MOD_RES
<222> LOCATION: (1)
<223> OTHER INFORMATION: Xaa = Ile or Leu
<220> FEATURE:
<221> NAME/KEY: MOD_RES
<222> LOCATION: (2)
<223> OTHER INFORMATION: Xaa = Leu or Gln
<220> FEATURE:
<221> NAME/KEY: MOD_RES
<222> LOCATION: (3)
<223> OTHER INFORMATION: Xaa = Gln, His or Glu
<220> FEATURE:
<221> NAME/KEY: MOD_RES
<222> LOCATION: (4)
<223> OTHER INFORMATION: Xaa = Tyr, His or Phe
<220> FEATURE:
<221> NAME/KEY: MOD_RES
<222> LOCATION: (6)
<223> OTHER INFORMATION: Xaa = Glu, Gln or Lys
<220> FEATURE:
<221> NAME/KEY: MOD_RES
<222> LOCATION: (7)
<223> OTHER INFORMATION: Xaa = Ile, Leu or Tyr
<220> FEATURE:
<221> NAME/KEY: MOD_RES
<222> LOCATION: (8)
<223> OTHER INFORMATION: Xaa = Arg, Lys or Asn
<220> FEATURE:
<221> NAME/KEY: MOD_RES
<222> LOCATION: (11)
<223> OTHER INFORMATION: Xaa = Lys or Gln
```

-continued

```
<220> FEATURE:
<221> NAME/KEY: MOD_RES
<222> LOCATION: (12)
<223> OTHER INFORMATION: Xaa = Ser or Asn
<220> FEATURE:
<221> NAME/KEY: MOD_RES
<222> LOCATION: (15)
<223> OTHER INFORMATION: Xaa = Ile or Val
<220> FEATURE:
<221> NAME/KEY: MOD_RES
<222> LOCATION: (16)
<223> OTHER INFORMATION: Xaa = Glu or Asp

<400> SEQUENCE: 28

Xaa Xaa Xaa Xaa Arg Xaa Xaa Xaa Lys Leu Xaa Xaa Thr Tyr Xaa Xaa
1               5                   10                  15

<210> SEQ ID NO 29
<211> LENGTH: 16
<212> TYPE: PRT
<213> ORGANISM: Artificial
<220> FEATURE:
<223> OTHER INFORMATION: improved DNA polymerase modified motif a
<220> FEATURE:
<221> NAME/KEY: MOD_RES
<222> LOCATION: (1)
<223> OTHER INFORMATION: Xaa = Ile or Leu
<220> FEATURE:
<221> NAME/KEY: MOD_RES
<222> LOCATION: (2)
<223> OTHER INFORMATION: Xaa = Leu or Gln
<220> FEATURE:
<221> NAME/KEY: MOD_RES
<222> LOCATION: (3)
<223> OTHER INFORMATION: Xaa = Gln, His or Glu
<220> FEATURE:
<221> NAME/KEY: MOD_RES
<222> LOCATION: (4)
<223> OTHER INFORMATION: Xaa = Tyr, His or Phe
<220> FEATURE:
<221> NAME/KEY: MOD_RES
<222> LOCATION: (6)
<223> OTHER INFORMATION: Xaa = Glu, Gln or Lys
<220> FEATURE:
<221> NAME/KEY: MOD_RES
<222> LOCATION: (7)
<223> OTHER INFORMATION: Xaa = Ile, Leu or Tyr
<220> FEATURE:
<221> NAME/KEY: MOD_RES
<222> LOCATION: (11)
<223> OTHER INFORMATION: Xaa = Lys or Gln
<220> FEATURE:
<221> NAME/KEY: MOD_RES
<222> LOCATION: (12)
<223> OTHER INFORMATION: Xaa = Ser or Asn
<220> FEATURE:
<221> NAME/KEY: MOD_RES
<222> LOCATION: (15)
<223> OTHER INFORMATION: Xaa = Ile or Val
<220> FEATURE:
<221> NAME/KEY: MOD_RES
<222> LOCATION: (16)
<223> OTHER INFORMATION: Xaa = Glu or Asp

<400> SEQUENCE: 29

Xaa Xaa Xaa Xaa Arg Xaa Xaa Arg Lys Leu Xaa Xaa Thr Tyr Xaa Xaa
1               5                   10                  15

<210> SEQ ID NO 30
<211> LENGTH: 13
<212> TYPE: PRT
<213> ORGANISM: Artificial
<220> FEATURE:
<223> OTHER INFORMATION: improved DNA polymerase modified motif b
```

```
<220> FEATURE:
<221> NAME/KEY: MOD_RES
<222> LOCATION: (7)
<223> OTHER INFORMATION: Xaa = Ser or Thr
<220> FEATURE:
<221> NAME/KEY: MOD_RES
<222> LOCATION: (8)
<223> OTHER INFORMATION: Xaa = D- or L- Ala, Cys, Phe, Gly, His, Ile,
      Lys, Leu, Met, Pro, Gln, Arg, Ser, Thr, Val, Trp or Tyr

<400> SEQUENCE: 30

Thr Gly Arg Leu Ser Ser Xaa Xaa Pro Asn Leu Gln Asn
1               5                   10

<210> SEQ ID NO 31
<211> LENGTH: 13
<212> TYPE: PRT
<213> ORGANISM: Artificial
<220> FEATURE:
<223> OTHER INFORMATION: improved DNA polymerase modified motif b
<220> FEATURE:
<221> NAME/KEY: MOD_RES
<222> LOCATION: (7)
<223> OTHER INFORMATION: Xaa = Ser or Thr
<220> FEATURE:
<221> NAME/KEY: MOD_RES
<222> LOCATION: (8)
<223> OTHER INFORMATION: Xaa = Gly, Ala, Ser, Thr, Arg, Lys, Gln, Leu,
      Val or Ile

<400> SEQUENCE: 31

Thr Gly Arg Leu Ser Ser Xaa Xaa Pro Asn Leu Gln Asn
1               5                   10

<210> SEQ ID NO 32
<211> LENGTH: 13
<212> TYPE: PRT
<213> ORGANISM: Artificial
<220> FEATURE:
<223> OTHER INFORMATION: improved DNA polymerase modified motif b
<220> FEATURE:
<221> NAME/KEY: MOD_RES
<222> LOCATION: (7)
<223> OTHER INFORMATION: Xaa = Ser or Thr
<220> FEATURE:
<221> NAME/KEY: MOD_RES
<222> LOCATION: (8)
<223> OTHER INFORMATION: Xaa = Gly, Thr, Arg, Lys or Leu

<400> SEQUENCE: 32

Thr Gly Arg Leu Ser Ser Xaa Xaa Pro Asn Leu Gln Asn
1               5                   10

<210> SEQ ID NO 33
<211> LENGTH: 15
<212> TYPE: PRT
<213> ORGANISM: Artificial
<220> FEATURE:
<223> OTHER INFORMATION: improved DNA polymerase modified motif c
<220> FEATURE:
<221> NAME/KEY: MOD_RES
<222> LOCATION: (1)
<223> OTHER INFORMATION: Xaa = Gly, Asn or Asp
<220> FEATURE:
<221> NAME/KEY: MOD_RES
<222> LOCATION: (2)
<223> OTHER INFORMATION: Xaa = Trp or His
<220> FEATURE:
<221> NAME/KEY: MOD_RES
<222> LOCATION: (3)
<223> OTHER INFORMATION: Xaa = Trp, Ala, Leu or Val
```

```
<220> FEATURE:
<221> NAME/KEY: MOD_RES
<222> LOCATION: (4)
<223> OTHER INFORMATION: Xaa = D- or L- Ala, Cys, Asp, Glu, Phe, Gly,
      His, Lys, Met, Asn, Pro, Gln, Arg, Ser, Thr, Val, Trp or Tyr
<220> FEATURE:
<221> NAME/KEY: MOD_RES
<222> LOCATION: (5)
<223> OTHER INFORMATION: Xaa = Val, Phe or Leu
<220> FEATURE:
<221> NAME/KEY: MOD_RES
<222> LOCATION: (6)
<223> OTHER INFORMATION: Xaa = any amino acid other than Ser, Ala, Val
      or Gly
<220> FEATURE:
<221> NAME/KEY: MOD_RES
<222> LOCATION: (7)
<223> OTHER INFORMATION: Xaa = Ala or Leu

<400> SEQUENCE: 33

Xaa Xaa Xaa Xaa Xaa Xaa Xaa Asp Tyr Ser Gln Ile Glu Leu Arg
1               5                   10                  15

<210> SEQ ID NO 34
<211> LENGTH: 15
<212> TYPE: PRT
<213> ORGANISM: Artificial
<220> FEATURE:
<223> OTHER INFORMATION: improved DNA polymerase modified motif c
<220> FEATURE:
<221> NAME/KEY: MOD_RES
<222> LOCATION: (1)
<223> OTHER INFORMATION: Xaa = Gly, Asn or Asp
<220> FEATURE:
<221> NAME/KEY: MOD_RES
<222> LOCATION: (2)
<223> OTHER INFORMATION: Xaa = Trp or His
<220> FEATURE:
<221> NAME/KEY: MOD_RES
<222> LOCATION: (3)
<223> OTHER INFORMATION: Xaa = Trp, Ala, Leu or Val
<220> FEATURE:
<221> NAME/KEY: MOD_RES
<222> LOCATION: (4)
<223> OTHER INFORMATION: Xaa = Phe or Tyr
<220> FEATURE:
<221> NAME/KEY: MOD_RES
<222> LOCATION: (5)
<223> OTHER INFORMATION: Xaa = Val, Phe or Leu
<220> FEATURE:
<221> NAME/KEY: MOD_RES
<222> LOCATION: (6)
<223> OTHER INFORMATION: Xaa = any amino acid other than Ser, Ala, Val
      or Gly
<220> FEATURE:
<221> NAME/KEY: MOD_RES
<222> LOCATION: (7)
<223> OTHER INFORMATION: Xaa = Ala or Leu

<400> SEQUENCE: 34

Xaa Xaa Xaa Xaa Xaa Xaa Xaa Asp Tyr Ser Gln Ile Glu Leu Arg
1               5                   10                  15

<210> SEQ ID NO 35
<211> LENGTH: 15
<212> TYPE: PRT
<213> ORGANISM: Artificial
<220> FEATURE:
<223> OTHER INFORMATION: improved DNA polymerase modified motif c
<220> FEATURE:
<221> NAME/KEY: MOD_RES
<222> LOCATION: (1)
<223> OTHER INFORMATION: Xaa = Gly, Asn or Asp
```

```
<220> FEATURE:
<221> NAME/KEY: MOD_RES
<222> LOCATION: (2)
<223> OTHER INFORMATION: Xaa = Trp or His
<220> FEATURE:
<221> NAME/KEY: MOD_RES
<222> LOCATION: (3)
<223> OTHER INFORMATION: Xaa = Trp, Ala, Leu or Val
<220> FEATURE:
<221> NAME/KEY: MOD_RES
<222> LOCATION: (5)
<223> OTHER INFORMATION: Xaa = Val, Phe or Leu
<220> FEATURE:
<221> NAME/KEY: MOD_RES
<222> LOCATION: (6)
<223> OTHER INFORMATION: Xaa = any amino acid other than Ser, Ala, Val
      or Gly
<220> FEATURE:
<221> NAME/KEY: MOD_RES
<222> LOCATION: (7)
<223> OTHER INFORMATION: Xaa = Ala or Leu

<400> SEQUENCE: 35

Xaa Xaa Xaa Phe Xaa Xaa Xaa Asp Tyr Ser Gln Ile Glu Leu Arg
1               5                   10                  15

<210> SEQ ID NO 36
<211> LENGTH: 15
<212> TYPE: PRT
<213> ORGANISM: Artificial
<220> FEATURE:
<223> OTHER INFORMATION: improved DNA polymerase modified motif c
<220> FEATURE:
<221> NAME/KEY: MOD_RES
<222> LOCATION: (1)
<223> OTHER INFORMATION: Xaa = Gly, Asn or Asp
<220> FEATURE:
<221> NAME/KEY: MOD_RES
<222> LOCATION: (2)
<223> OTHER INFORMATION: Xaa = Trp or His
<220> FEATURE:
<221> NAME/KEY: MOD_RES
<222> LOCATION: (3)
<223> OTHER INFORMATION: Xaa = Trp, Ala, Leu or Val
<220> FEATURE:
<221> NAME/KEY: MOD_RES
<222> LOCATION: (4)
<223> OTHER INFORMATION: Xaa = any amino acid other than Ile or Leu
<220> FEATURE:
<221> NAME/KEY: MOD_RES
<222> LOCATION: (5)
<223> OTHER INFORMATION: Xaa = Val, Phe or Leu
<220> FEATURE:
<221> NAME/KEY: MOD_RES
<222> LOCATION: (6)
<223> OTHER INFORMATION: Xaa = Cys, Asp, Glu, Phe, His, Ile, Lys, Leu,
      Met, Asn, Pro, Gln, Arg, Thr, Trp or Tyr
<220> FEATURE:
<221> NAME/KEY: MOD_RES
<222> LOCATION: (7)
<223> OTHER INFORMATION: Xaa = Ala or Leu

<400> SEQUENCE: 36

Xaa Xaa Xaa Xaa Xaa Xaa Xaa Asp Tyr Ser Gln Ile Glu Leu Arg
1               5                   10                  15

<210> SEQ ID NO 37
<211> LENGTH: 15
<212> TYPE: PRT
<213> ORGANISM: Artificial
<220> FEATURE:
<223> OTHER INFORMATION: improved DNA polymerase modified motif c
```

```
<220> FEATURE:
<221> NAME/KEY: MOD_RES
<222> LOCATION: (1)
<223> OTHER INFORMATION: Xaa = Gly, Asn or Asp
<220> FEATURE:
<221> NAME/KEY: MOD_RES
<222> LOCATION: (2)
<223> OTHER INFORMATION: Xaa = Trp or His
<220> FEATURE:
<221> NAME/KEY: MOD_RES
<222> LOCATION: (3)
<223> OTHER INFORMATION: Xaa = Trp, Ala, Leu or Val
<220> FEATURE:
<221> NAME/KEY: MOD_RES
<222> LOCATION: (4)
<223> OTHER INFORMATION: Xaa = any amino acid other than Ile or Leu
<220> FEATURE:
<221> NAME/KEY: MOD_RES
<222> LOCATION: (5)
<223> OTHER INFORMATION: Xaa = Val, Phe or Leu
<220> FEATURE:
<221> NAME/KEY: MOD_RES
<222> LOCATION: (6)
<223> OTHER INFORMATION: Xaa = Phe or Tyr
<220> FEATURE:
<221> NAME/KEY: MOD_RES
<222> LOCATION: (7)
<223> OTHER INFORMATION: Xaa = Ala or Leu

<400> SEQUENCE: 37

Xaa Xaa Xaa Xaa Xaa Xaa Xaa Asp Tyr Ser Gln Ile Glu Leu Arg
1               5                   10                  15

<210> SEQ ID NO 38
<211> LENGTH: 15
<212> TYPE: PRT
<213> ORGANISM: Artificial
<220> FEATURE:
<223> OTHER INFORMATION: improved DNA polymerase modified motif c
<220> FEATURE:
<221> NAME/KEY: MOD_RES
<222> LOCATION: (1)
<223> OTHER INFORMATION: Xaa = Gly, Asn or Asp
<220> FEATURE:
<221> NAME/KEY: MOD_RES
<222> LOCATION: (2)
<223> OTHER INFORMATION: Xaa = Trp or His
<220> FEATURE:
<221> NAME/KEY: MOD_RES
<222> LOCATION: (3)
<223> OTHER INFORMATION: Xaa = Trp, Ala, Leu or Val
<220> FEATURE:
<221> NAME/KEY: MOD_RES
<222> LOCATION: (4)
<223> OTHER INFORMATION: Xaa = any amino acid other than Ile or Leu
<220> FEATURE:
<221> NAME/KEY: MOD_RES
<222> LOCATION: (5)
<223> OTHER INFORMATION: Xaa = Val, Phe or Leu
<220> FEATURE:
<221> NAME/KEY: MOD_RES
<222> LOCATION: (7)
<223> OTHER INFORMATION: Xaa = Ala or Leu

<400> SEQUENCE: 38

Xaa Xaa Xaa Xaa Xaa Phe Xaa Asp Tyr Ser Gln Ile Glu Leu Arg
1               5                   10                  15

<210> SEQ ID NO 39
<211> LENGTH: 91
<212> TYPE: PRT
<213> ORGANISM: Artificial
```

-continued

```
<220> FEATURE:
<223> OTHER INFORMATION: active site region from improved mutated
      polymerase domain of thermostable Family A type DNA-dependent DNA
      polymerase of Thermus species Z05 (Z05)

<400> SEQUENCE: 39

Ile Val Glu Lys Ile Leu Gln His Arg Glu Leu Arg Lys Leu Lys Asn
1               5                   10                  15

Thr Tyr Val Asp Pro Leu Pro Gly Leu Val His Pro Arg Thr Gly Arg
                20                  25                  30

Leu His Thr Arg Phe Asn Gln Thr Ala Thr Ala Thr Gly Arg Leu Ser
            35                  40                  45

Ser Ser Asp Pro Asn Leu Gln Asn Ile Pro Ile Arg Thr Pro Leu Gly
        50                  55                  60

Gln Arg Ile Arg Arg Ala Phe Val Ala Glu Ala Gly Trp Ala Leu Val
65                  70                  75                  80

Ala Leu Asp Tyr Ser Gln Ile Glu Leu Arg Val
                85                  90

<210> SEQ ID NO 40
<211> LENGTH: 91
<212> TYPE: PRT
<213> ORGANISM: Artificial
<220> FEATURE:
<223> OTHER INFORMATION: active site region from improved mutated
      polymerase domain of thermostable Family A type DNA-dependent DNA
      polymerase of Thermus species Z05 (Z05)

<400> SEQUENCE: 40

Ile Val Glu Lys Ile Leu Gln His Arg Glu Leu Thr Lys Leu Lys Asn
1               5                   10                  15

Thr Tyr Val Asp Pro Leu Pro Gly Leu Val His Pro Arg Thr Gly Arg
                20                  25                  30

Leu His Thr Arg Phe Asn Gln Thr Ala Thr Ala Thr Gly Arg Leu Ser
            35                  40                  45

Ser Ser Gly Pro Asn Leu Gln Asn Ile Pro Ile Arg Thr Pro Leu Gly
        50                  55                  60

Gln Arg Ile Arg Arg Ala Phe Val Ala Glu Ala Gly Trp Ala Leu Val
65                  70                  75                  80

Ala Leu Asp Tyr Ser Gln Ile Glu Leu Arg Val
                85                  90

<210> SEQ ID NO 41
<211> LENGTH: 91
<212> TYPE: PRT
<213> ORGANISM: Artificial
<220> FEATURE:
<223> OTHER INFORMATION: active site region from improved mutated
      polymerase domain of thermostable Family A type DNA-dependent DNA
      polymerase of Thermus species Z05 (Z05)

<400> SEQUENCE: 41

Ile Val Glu Lys Ile Leu Gln His Arg Glu Leu Thr Lys Leu Lys Asn
1               5                   10                  15

Thr Tyr Val Asp Pro Leu Pro Gly Leu Val His Pro Arg Thr Gly Arg
                20                  25                  30

Leu His Thr Arg Phe Asn Gln Thr Ala Thr Ala Thr Gly Arg Leu Ser
            35                  40                  45

Ser Ser Asp Pro Asn Leu Gln Asn Ile Pro Ile Arg Thr Pro Leu Gly
        50                  55                  60
```

```
Gln Arg Ile Arg Arg Ala Phe Val Ala Glu Ala Gly Trp Ala Phe Val
 65                  70                  75                  80

Ala Leu Asp Tyr Ser Gln Ile Glu Leu Arg Val
                 85                  90

<210> SEQ ID NO 42
<211> LENGTH: 91
<212> TYPE: PRT
<213> ORGANISM: Artificial
<220> FEATURE:
<223> OTHER INFORMATION: active site region from improved mutated
      polymerase domain of thermostable Family A type DNA-dependent DNA
      polymerase of Thermus species Z05 (Z05)

<400> SEQUENCE: 42

Ile Val Glu Lys Ile Leu Gln His Arg Glu Leu Thr Lys Leu Lys Asn
  1               5                  10                  15

Thr Tyr Val Asp Pro Leu Pro Gly Leu Val His Pro Arg Thr Gly Arg
                 20                  25                  30

Leu His Thr Arg Phe Asn Gln Thr Ala Thr Ala Thr Gly Arg Leu Ser
             35                  40                  45

Ser Ser Asp Pro Asn Leu Gln Asn Ile Pro Ile Arg Thr Pro Leu Gly
 50                  55                  60

Gln Arg Ile Arg Arg Ala Phe Val Ala Glu Ala Gly Trp Ala Leu Val
 65                  70                  75                  80

Phe Leu Asp Tyr Ser Gln Ile Glu Leu Arg Val
                 85                  90

<210> SEQ ID NO 43
<211> LENGTH: 91
<212> TYPE: PRT
<213> ORGANISM: Artificial
<220> FEATURE:
<223> OTHER INFORMATION: active site region from improved mutated
      polymerase domain of thermostable Family A type DNA-dependent DNA
      polymerase of Thermus species Z05 (Z05)

<400> SEQUENCE: 43

Ile Val Glu Lys Ile Leu Gln His Arg Glu Leu Arg Lys Leu Lys Asn
  1               5                  10                  15

Thr Tyr Val Asp Pro Leu Pro Gly Leu Val His Pro Arg Thr Gly Arg
                 20                  25                  30

Leu His Thr Arg Phe Asn Gln Thr Ala Thr Ala Thr Gly Arg Leu Ser
             35                  40                  45

Ser Ser Gly Pro Asn Leu Gln Asn Ile Pro Ile Arg Thr Pro Leu Gly
 50                  55                  60

Gln Arg Ile Arg Arg Ala Phe Val Ala Glu Ala Gly Trp Ala Leu Val
 65                  70                  75                  80

Ala Leu Asp Tyr Ser Gln Ile Glu Leu Arg Val
                 85                  90

<210> SEQ ID NO 44
<211> LENGTH: 91
<212> TYPE: PRT
<213> ORGANISM: Artificial
<220> FEATURE:
<223> OTHER INFORMATION: active site region from improved mutated
      polymerase domain of thermostable Family A type DNA-dependent DNA
      polymerase of Thermus species Z05 (Z05)
```

-continued

```
<400> SEQUENCE: 44

Ile Val Glu Lys Ile Leu Gln His Arg Glu Leu Arg Lys Leu Lys Asn
1               5                   10                  15

Thr Tyr Val Asp Pro Leu Pro Gly Leu Val His Pro Arg Thr Gly Arg
                20                  25                  30

Leu His Thr Arg Phe Asn Gln Thr Ala Thr Ala Thr Gly Arg Leu Ser
            35                  40                  45

Ser Ser Asp Pro Asn Leu Gln Asn Ile Pro Ile Arg Thr Pro Leu Gly
        50                  55                  60

Gln Arg Ile Arg Arg Ala Phe Val Ala Glu Ala Gly Trp Ala Phe Val
65                  70                  75                  80

Ala Leu Asp Tyr Ser Gln Ile Glu Leu Arg Val
                85                  90

<210> SEQ ID NO 45
<211> LENGTH: 91
<212> TYPE: PRT
<213> ORGANISM: Artificial
<220> FEATURE:
<223> OTHER INFORMATION: active site region from improved mutated
      polymerase domain of thermostable Family A type DNA-dependent DNA
      polymerase of Thermus species Z05 (Z05)

<400> SEQUENCE: 45

Ile Val Glu Lys Ile Leu Gln His Arg Glu Leu Arg Lys Leu Lys Asn
1               5                   10                  15

Thr Tyr Val Asp Pro Leu Pro Gly Leu Val His Pro Arg Thr Gly Arg
                20                  25                  30

Leu His Thr Arg Phe Asn Gln Thr Ala Thr Ala Thr Gly Arg Leu Ser
            35                  40                  45

Ser Ser Asp Pro Asn Leu Gln Asn Ile Pro Ile Arg Thr Pro Leu Gly
        50                  55                  60

Gln Arg Ile Arg Arg Ala Phe Val Ala Glu Ala Gly Trp Ala Leu Val
65                  70                  75                  80

Phe Leu Asp Tyr Ser Gln Ile Glu Leu Arg Val
                85                  90

<210> SEQ ID NO 46
<211> LENGTH: 91
<212> TYPE: PRT
<213> ORGANISM: Artificial
<220> FEATURE:
<223> OTHER INFORMATION: active site region from improved mutated
      polymerase domain of thermostable Family A type DNA-dependent DNA
      polymerase of Thermus species Z05 (Z05)

<400> SEQUENCE: 46

Ile Val Glu Lys Ile Leu Gln His Arg Glu Leu Thr Lys Leu Lys Asn
1               5                   10                  15

Thr Tyr Val Asp Pro Leu Pro Gly Leu Val His Pro Arg Thr Gly Arg
                20                  25                  30

Leu His Thr Arg Phe Asn Gln Thr Ala Thr Ala Thr Gly Arg Leu Ser
            35                  40                  45

Ser Ser Gly Pro Asn Leu Gln Asn Ile Pro Ile Arg Thr Pro Leu Gly
        50                  55                  60

Gln Arg Ile Arg Arg Ala Phe Val Ala Glu Ala Gly Trp Ala Phe Val
65                  70                  75                  80

Ala Leu Asp Tyr Ser Gln Ile Glu Leu Arg Val
                85                  90
```

```
<210> SEQ ID NO 47
<211> LENGTH: 91
<212> TYPE: PRT
<213> ORGANISM: Artificial
<220> FEATURE:
<223> OTHER INFORMATION: active site region from improved mutated
      polymerase domain of thermostable Family A type DNA-dependent DNA
      polymerase of Thermus species Z05 (Z05)

<400> SEQUENCE: 47

Ile Val Glu Lys Ile Leu Gln His Arg Glu Leu Thr Lys Leu Lys Asn
1               5                  10                  15

Thr Tyr Val Asp Pro Leu Pro Gly Leu Val His Pro Arg Thr Gly Arg
            20                  25                  30

Leu His Thr Arg Phe Asn Gln Thr Ala Thr Ala Thr Gly Arg Leu Ser
        35                  40                  45

Ser Ser Gly Pro Asn Leu Gln Asn Ile Pro Ile Arg Thr Pro Leu Gly
    50                  55                  60

Gln Arg Ile Arg Arg Ala Phe Val Ala Glu Ala Gly Trp Ala Leu Val
65                  70                  75                  80

Phe Leu Asp Tyr Ser Gln Ile Glu Leu Arg Val
                85                  90

<210> SEQ ID NO 48
<211> LENGTH: 91
<212> TYPE: PRT
<213> ORGANISM: Artificial
<220> FEATURE:
<223> OTHER INFORMATION: active site region from improved mutated
      polymerase domain of thermostable Family A type DNA-dependent DNA
      polymerase of Thermus species Z05 (Z05)

<400> SEQUENCE: 48

Ile Val Glu Lys Ile Leu Gln His Arg Glu Leu Thr Lys Leu Lys Asn
1               5                  10                  15

Thr Tyr Val Asp Pro Leu Pro Gly Leu Val His Pro Arg Thr Gly Arg
            20                  25                  30

Leu His Thr Arg Phe Asn Gln Thr Ala Thr Ala Thr Gly Arg Leu Ser
        35                  40                  45

Ser Ser Asp Pro Asn Leu Gln Asn Ile Pro Ile Arg Thr Pro Leu Gly
    50                  55                  60

Gln Arg Ile Arg Arg Ala Phe Val Ala Glu Ala Gly Trp Ala Phe Val
65                  70                  75                  80

Phe Leu Asp Tyr Ser Gln Ile Glu Leu Arg Val
                85                  90

<210> SEQ ID NO 49
<211> LENGTH: 91
<212> TYPE: PRT
<213> ORGANISM: Artificial
<220> FEATURE:
<223> OTHER INFORMATION: active site region from improved mutated
      polymerase domain of thermostable Family A type DNA-dependent DNA
      polymerase of Thermus species Z05 (Z05)

<400> SEQUENCE: 49

Ile Val Glu Lys Ile Leu Gln His Arg Glu Leu Arg Lys Leu Lys Asn
1               5                  10                  15

Thr Tyr Val Asp Pro Leu Pro Gly Leu Val His Pro Arg Thr Gly Arg
            20                  25                  30

Leu His Thr Arg Phe Asn Gln Thr Ala Thr Ala Thr Gly Arg Leu Ser
        35                  40                  45
```

```
Ser Ser Gly Pro Asn Leu Gln Asn Ile Pro Ile Arg Thr Pro Leu Gly
    50                  55                  60

Gln Arg Ile Arg Arg Ala Phe Val Ala Glu Ala Gly Trp Ala Phe Val
65                  70                  75                  80

Ala Leu Asp Tyr Ser Gln Ile Glu Leu Arg Val
                85                  90

<210> SEQ ID NO 50
<211> LENGTH: 91
<212> TYPE: PRT
<213> ORGANISM: Artificial
<220> FEATURE:
<223> OTHER INFORMATION: active site region from improved mutated
      polymerase domain of thermostable Family A type DNA-dependent DNA
      polymerase of Thermus species Z05 (Z05)

<400> SEQUENCE: 50

Ile Val Glu Lys Ile Leu Gln His Arg Glu Leu Arg Lys Leu Lys Asn
1               5                   10                  15

Thr Tyr Val Asp Pro Leu Pro Gly Leu Val His Pro Arg Thr Gly Arg
                20                  25                  30

Leu His Thr Arg Phe Asn Gln Thr Ala Thr Ala Thr Gly Arg Leu Ser
            35                  40                  45

Ser Ser Gly Pro Asn Leu Gln Asn Ile Pro Ile Arg Thr Pro Leu Gly
    50                  55                  60

Gln Arg Ile Arg Arg Ala Phe Val Ala Glu Ala Gly Trp Ala Leu Val
65                  70                  75                  80

Phe Leu Asp Tyr Ser Gln Ile Glu Leu Arg Val
                85                  90

<210> SEQ ID NO 51
<211> LENGTH: 91
<212> TYPE: PRT
<213> ORGANISM: Artificial
<220> FEATURE:
<223> OTHER INFORMATION: active site region from improved mutated
      polymerase domain of thermostable Family A type DNA-dependent DNA
      polymerase of Thermus species Z05 (Z05)

<400> SEQUENCE: 51

Ile Val Glu Lys Ile Leu Gln His Arg Glu Leu Arg Lys Leu Lys Asn
1               5                   10                  15

Thr Tyr Val Asp Pro Leu Pro Gly Leu Val His Pro Arg Thr Gly Arg
                20                  25                  30

Leu His Thr Arg Phe Asn Gln Thr Ala Thr Ala Thr Gly Arg Leu Ser
            35                  40                  45

Ser Ser Asp Pro Asn Leu Gln Asn Ile Pro Ile Arg Thr Pro Leu Gly
    50                  55                  60

Gln Arg Ile Arg Arg Ala Phe Val Ala Glu Ala Gly Trp Ala Phe Val
65                  70                  75                  80

Phe Leu Asp Tyr Ser Gln Ile Glu Leu Arg Val
                85                  90

<210> SEQ ID NO 52
<211> LENGTH: 91
<212> TYPE: PRT
<213> ORGANISM: Artificial
<220> FEATURE:
<223> OTHER INFORMATION: active site region from improved mutated
      polymerase domain of thermostable Family A type DNA-dependent DNA
      polymerase of Thermus species Z05 (Z05)
```

```
<400> SEQUENCE: 52

Ile Val Glu Lys Ile Leu Gln His Arg Glu Leu Thr Lys Leu Lys Asn
1               5                   10                  15

Thr Tyr Val Asp Pro Leu Pro Gly Leu Val His Pro Arg Thr Gly Arg
                20                  25                  30

Leu His Thr Arg Phe Asn Gln Thr Ala Thr Ala Thr Gly Arg Leu Ser
            35                  40                  45

Ser Ser Gly Pro Asn Leu Gln Asn Ile Pro Ile Arg Thr Pro Leu Gly
        50                  55                  60

Gln Arg Ile Arg Arg Ala Phe Val Ala Glu Ala Gly Trp Ala Phe Val
65                  70                  75                  80

Phe Leu Asp Tyr Ser Gln Ile Glu Leu Arg Val
                85                  90

<210> SEQ ID NO 53
<211> LENGTH: 91
<212> TYPE: PRT
<213> ORGANISM: Artificial
<220> FEATURE:
<223> OTHER INFORMATION: active site region from improved mutated
      polymerase domain of thermostable Family A type DNA-dependent DNA
      polymerase of Thermus species Z05 (Z05)

<400> SEQUENCE: 53

Ile Val Glu Lys Ile Leu Gln His Arg Glu Leu Arg Lys Leu Lys Asn
1               5                   10                  15

Thr Tyr Val Asp Pro Leu Pro Gly Leu Val His Pro Arg Thr Gly Arg
                20                  25                  30

Leu His Thr Arg Phe Asn Gln Thr Ala Thr Ala Thr Gly Arg Leu Ser
            35                  40                  45

Ser Ser Gly Pro Asn Leu Gln Asn Ile Pro Ile Arg Thr Pro Leu Gly
        50                  55                  60

Gln Arg Ile Arg Arg Ala Phe Val Ala Glu Ala Gly Trp Ala Phe Val
65                  70                  75                  80

Phe Leu Asp Tyr Ser Gln Ile Glu Leu Arg Val
                85                  90

<210> SEQ ID NO 54
<211> LENGTH: 92
<212> TYPE: PRT
<213> ORGANISM: Artificial
<220> FEATURE:
<223> OTHER INFORMATION: active site region from improved mutated
      polymerase domain of chimeric thermostable DNA-dependent DNA
      polymerase CS5 or CS6

<400> SEQUENCE: 54

Ile Ile Pro Leu Ile Leu Glu Tyr Arg Lys Ile Arg Lys Leu Lys Ser
1               5                   10                  15

Thr Tyr Ile Asp Ala Leu Pro Lys Met Val Asn Pro Lys Thr Gly Arg
                20                  25                  30

Ile His Ala Ser Phe Asn Gln Thr Gly Thr Ala Thr Gly Arg Leu Ser
            35                  40                  45

Ser Ser Asp Pro Asn Leu Gln Asn Leu Pro Thr Lys Ser Glu Glu Gly
        50                  55                  60

Lys Glu Ile Arg Lys Ala Ile Val Pro Gln Asp Pro Asn Trp Trp Ile
65                  70                  75                  80

Val Ser Ala Asp Tyr Ser Gln Ile Glu Leu Arg Ile
                85                  90
```

-continued

```
<210> SEQ ID NO 55
<211> LENGTH: 92
<212> TYPE: PRT
<213> ORGANISM: Artificial
<220> FEATURE:
<223> OTHER INFORMATION: active site region from improved mutated
      polymerase domain of chimeric thermostable DNA-dependent DNA
      polymerase CS5 or CS6

<400> SEQUENCE: 55

Ile Ile Pro Leu Ile Leu Glu Tyr Arg Lys Ile Gln Lys Leu Lys Ser
1               5                   10                  15

Thr Tyr Ile Asp Ala Leu Pro Lys Met Val Asn Pro Lys Thr Gly Arg
            20                  25                  30

Ile His Ala Ser Phe Asn Gln Thr Gly Thr Ala Thr Gly Arg Leu Ser
        35                  40                  45

Ser Ser Gly Pro Asn Leu Gln Asn Leu Pro Thr Lys Ser Glu Glu Gly
    50                  55                  60

Lys Glu Ile Arg Lys Ala Ile Val Pro Gln Asp Pro Asn Trp Trp Ile
65                  70                  75                  80

Val Ser Ala Asp Tyr Ser Gln Ile Glu Leu Arg Ile
                85                  90

<210> SEQ ID NO 56
<211> LENGTH: 92
<212> TYPE: PRT
<213> ORGANISM: Artificial
<220> FEATURE:
<223> OTHER INFORMATION: active site region from improved mutated
      polymerase domain of chimeric thermostable DNA-dependent DNA
      polymerase CS5 or CS6

<400> SEQUENCE: 56

Ile Ile Pro Leu Ile Leu Glu Tyr Arg Lys Ile Gln Lys Leu Lys Ser
1               5                   10                  15

Thr Tyr Ile Asp Ala Leu Pro Lys Met Val Asn Pro Lys Thr Gly Arg
            20                  25                  30

Ile His Ala Ser Phe Asn Gln Thr Gly Thr Ala Thr Gly Arg Leu Ser
        35                  40                  45

Ser Ser Asp Pro Asn Leu Gln Asn Leu Pro Thr Lys Ser Glu Glu Gly
    50                  55                  60

Lys Glu Ile Arg Lys Ala Ile Val Pro Gln Asp Pro Asn Trp Trp Phe
65                  70                  75                  80

Val Ser Ala Asp Tyr Ser Gln Ile Glu Leu Arg Ile
                85                  90

<210> SEQ ID NO 57
<211> LENGTH: 92
<212> TYPE: PRT
<213> ORGANISM: Artificial
<220> FEATURE:
<223> OTHER INFORMATION: active site region from improved mutated
      polymerase domain of chimeric thermostable DNA-dependent DNA
      polymerase CS5 or CS6

<400> SEQUENCE: 57

Ile Ile Pro Leu Ile Leu Glu Tyr Arg Lys Ile Gln Lys Leu Lys Ser
1               5                   10                  15

Thr Tyr Ile Asp Ala Leu Pro Lys Met Val Asn Pro Lys Thr Gly Arg
            20                  25                  30

Ile His Ala Ser Phe Asn Gln Thr Gly Thr Ala Thr Gly Arg Leu Ser
        35                  40                  45
```

Ser Ser Asp Pro Asn Leu Gln Asn Leu Pro Thr Lys Ser Glu Glu Gly
            50                  55                  60

Lys Glu Ile Arg Lys Ala Ile Val Pro Gln Asp Pro Asn Trp Trp Ile
 65                  70                  75                  80

Val Phe Ala Asp Tyr Ser Gln Ile Glu Leu Arg Ile
                85                  90

<210> SEQ ID NO 58
<211> LENGTH: 92
<212> TYPE: PRT
<213> ORGANISM: Artificial
<220> FEATURE:
<223> OTHER INFORMATION: active site region from improved mutated
      polymerase domain of chimeric thermostable DNA-dependent DNA
      polymerase CS5 or CS6

<400> SEQUENCE: 58

Ile Ile Pro Leu Ile Leu Glu Tyr Arg Lys Ile Arg Lys Leu Lys Ser
 1               5                  10                  15

Thr Tyr Ile Asp Ala Leu Pro Lys Met Val Asn Pro Lys Thr Gly Arg
                20                  25                  30

Ile His Ala Ser Phe Asn Gln Thr Gly Thr Ala Thr Gly Arg Leu Ser
            35                  40                  45

Ser Ser Gly Pro Asn Leu Gln Asn Leu Pro Thr Lys Ser Glu Glu Gly
        50                  55                  60

Lys Glu Ile Arg Lys Ala Ile Val Pro Gln Asp Pro Asn Trp Trp Ile
 65                  70                  75                  80

Val Ser Ala Asp Tyr Ser Gln Ile Glu Leu Arg Ile
                85                  90

<210> SEQ ID NO 59
<211> LENGTH: 92
<212> TYPE: PRT
<213> ORGANISM: Artificial
<220> FEATURE:
<223> OTHER INFORMATION: active site region from improved mutated
      polymerase domain of chimeric thermostable DNA-dependent DNA
      polymerase CS5 or CS6

<400> SEQUENCE: 59

Ile Ile Pro Leu Ile Leu Glu Tyr Arg Lys Ile Arg Lys Leu Lys Ser
 1               5                  10                  15

Thr Tyr Ile Asp Ala Leu Pro Lys Met Val Asn Pro Lys Thr Gly Arg
                20                  25                  30

Ile His Ala Ser Phe Asn Gln Thr Gly Thr Ala Thr Gly Arg Leu Ser
            35                  40                  45

Ser Ser Asp Pro Asn Leu Gln Asn Leu Pro Thr Lys Ser Glu Glu Gly
        50                  55                  60

Lys Glu Ile Arg Lys Ala Ile Val Pro Gln Asp Pro Asn Trp Trp Phe
 65                  70                  75                  80

Val Ser Ala Asp Tyr Ser Gln Ile Glu Leu Arg Ile
                85                  90

<210> SEQ ID NO 60
<211> LENGTH: 92
<212> TYPE: PRT
<213> ORGANISM: Artificial
<220> FEATURE:
<223> OTHER INFORMATION: active site region from improved mutated
      polymerase domain of chimeric thermostable DNA-dependent DNA
      polymerase CS5 or CS6

<400> SEQUENCE: 60

Ile Ile Pro Leu Ile Leu Glu Tyr Arg Lys Ile Arg Lys Leu Lys Ser
1               5                   10                  15

Thr Tyr Ile Asp Ala Leu Pro Lys Met Val Asn Pro Lys Thr Gly Arg
            20                  25                  30

Ile His Ala Ser Phe Asn Gln Thr Gly Thr Ala Thr Gly Arg Leu Ser
        35                  40                  45

Ser Ser Asp Pro Asn Leu Gln Asn Leu Pro Thr Lys Ser Glu Glu Gly
    50                  55                  60

Lys Glu Ile Arg Lys Ala Ile Val Pro Gln Asp Pro Asn Trp Trp Ile
65                  70                  75                  80

Val Phe Ala Asp Tyr Ser Gln Ile Glu Leu Arg Ile
                85                  90

<210> SEQ ID NO 61
<211> LENGTH: 92
<212> TYPE: PRT
<213> ORGANISM: Artificial
<220> FEATURE:
<223> OTHER INFORMATION: active site region from improved mutated
      polymerase domain of chimeric thermostable DNA-dependent DNA
      polymerase CS5 or CS6

<400> SEQUENCE: 61

Ile Ile Pro Leu Ile Leu Glu Tyr Arg Lys Ile Gln Lys Leu Lys Ser
1               5                   10                  15

Thr Tyr Ile Asp Ala Leu Pro Lys Met Val Asn Pro Lys Thr Gly Arg
            20                  25                  30

Ile His Ala Ser Phe Asn Gln Thr Gly Thr Ala Thr Gly Arg Leu Ser
        35                  40                  45

Ser Ser Gly Pro Asn Leu Gln Asn Leu Pro Thr Lys Ser Glu Glu Gly
    50                  55                  60

Lys Glu Ile Arg Lys Ala Ile Val Pro Gln Asp Pro Asn Trp Trp Phe
65                  70                  75                  80

Val Ser Ala Asp Tyr Ser Gln Ile Glu Leu Arg Ile
                85                  90

<210> SEQ ID NO 62
<211> LENGTH: 92
<212> TYPE: PRT
<213> ORGANISM: Artificial
<220> FEATURE:
<223> OTHER INFORMATION: active site region from improved mutated
      polymerase domain of chimeric thermostable DNA-dependent DNA
      polymerase CS5 or CS6

<400> SEQUENCE: 62

Ile Ile Pro Leu Ile Leu Glu Tyr Arg Lys Ile Gln Lys Leu Lys Ser
1               5                   10                  15

Thr Tyr Ile Asp Ala Leu Pro Lys Met Val Asn Pro Lys Thr Gly Arg
            20                  25                  30

Ile His Ala Ser Phe Asn Gln Thr Gly Thr Ala Thr Gly Arg Leu Ser
        35                  40                  45

Ser Ser Gly Pro Asn Leu Gln Asn Leu Pro Thr Lys Ser Glu Glu Gly
    50                  55                  60

Lys Glu Ile Arg Lys Ala Ile Val Pro Gln Asp Pro Asn Trp Trp Ile
65                  70                  75                  80

Val Phe Ala Asp Tyr Ser Gln Ile Glu Leu Arg Ile
                85                  90

```
<210> SEQ ID NO 63
<211> LENGTH: 92
<212> TYPE: PRT
<213> ORGANISM: Artificial
<220> FEATURE:
<223> OTHER INFORMATION: active site region from improved mutated
      polymerase domain of chimeric thermostable DNA-dependent DNA
      polymerase CS5 or CS6

<400> SEQUENCE: 63

Ile Ile Pro Leu Ile Leu Glu Tyr Arg Lys Ile Gln Lys Leu Lys Ser
1               5                   10                  15

Thr Tyr Ile Asp Ala Leu Pro Lys Met Val Asn Pro Lys Thr Gly Arg
            20                  25                  30

Ile His Ala Ser Phe Asn Gln Thr Gly Thr Ala Thr Gly Arg Leu Ser
        35                  40                  45

Ser Ser Asp Pro Asn Leu Gln Asn Leu Pro Thr Lys Ser Glu Glu Gly
    50                  55                  60

Lys Glu Ile Arg Lys Ala Ile Val Pro Gln Asp Pro Asn Trp Trp Phe
65                  70                  75                  80

Val Phe Ala Asp Tyr Ser Gln Ile Glu Leu Arg Ile
                85                  90

<210> SEQ ID NO 64
<211> LENGTH: 92
<212> TYPE: PRT
<213> ORGANISM: Artificial
<220> FEATURE:
<223> OTHER INFORMATION: active site region from improved mutated
      polymerase domain of chimeric thermostable DNA-dependent DNA
      polymerase CS5 or CS6

<400> SEQUENCE: 64

Ile Ile Pro Leu Ile Leu Glu Tyr Arg Lys Ile Arg Lys Leu Lys Ser
1               5                   10                  15

Thr Tyr Ile Asp Ala Leu Pro Lys Met Val Asn Pro Lys Thr Gly Arg
            20                  25                  30

Ile His Ala Ser Phe Asn Gln Thr Gly Thr Ala Thr Gly Arg Leu Ser
        35                  40                  45

Ser Ser Gly Pro Asn Leu Gln Asn Leu Pro Thr Lys Ser Glu Glu Gly
    50                  55                  60

Lys Glu Ile Arg Lys Ala Ile Val Pro Gln Asp Pro Asn Trp Trp Phe
65                  70                  75                  80

Val Ser Ala Asp Tyr Ser Gln Ile Glu Leu Arg Ile
                85                  90

<210> SEQ ID NO 65
<211> LENGTH: 92
<212> TYPE: PRT
<213> ORGANISM: Artificial
<220> FEATURE:
<223> OTHER INFORMATION: active site region from improved mutated
      polymerase domain of chimeric thermostable DNA-dependent DNA
      polymerase CS5 or CS6

<400> SEQUENCE: 65

Ile Ile Pro Leu Ile Leu Glu Tyr Arg Lys Ile Arg Lys Leu Lys Ser
1               5                   10                  15

Thr Tyr Ile Asp Ala Leu Pro Lys Met Val Asn Pro Lys Thr Gly Arg
            20                  25                  30

Ile His Ala Ser Phe Asn Gln Thr Gly Thr Ala Thr Gly Arg Leu Ser
        35                  40                  45
```

Ser Ser Gly Pro Asn Leu Gln Asn Leu Pro Thr Lys Ser Glu Glu Gly
    50                  55                  60

Lys Glu Ile Arg Lys Ala Ile Val Pro Gln Asp Pro Asn Trp Trp Ile
65                  70                  75                  80

Val Phe Ala Asp Tyr Ser Gln Ile Glu Leu Arg Ile
                85                  90

<210> SEQ ID NO 66
<211> LENGTH: 92
<212> TYPE: PRT
<213> ORGANISM: Artificial
<220> FEATURE:
<223> OTHER INFORMATION: active site region from improved mutated
      polymerase domain of chimeric thermostable DNA-dependent DNA
      polymerase CS5 or CS6

<400> SEQUENCE: 66

Ile Ile Pro Leu Ile Leu Glu Tyr Arg Lys Ile Arg Lys Leu Lys Ser
1               5                   10                  15

Thr Tyr Ile Asp Ala Leu Pro Lys Met Val Asn Pro Lys Thr Gly Arg
                20                  25                  30

Ile His Ala Ser Phe Asn Gln Thr Gly Thr Ala Thr Gly Arg Leu Ser
            35                  40                  45

Ser Ser Asp Pro Asn Leu Gln Asn Leu Pro Thr Lys Ser Glu Glu Gly
    50                  55                  60

Lys Glu Ile Arg Lys Ala Ile Val Pro Gln Asp Pro Asn Trp Trp Phe
65                  70                  75                  80

Val Phe Ala Asp Tyr Ser Gln Ile Glu Leu Arg Ile
                85                  90

<210> SEQ ID NO 67
<211> LENGTH: 92
<212> TYPE: PRT
<213> ORGANISM: Artificial
<220> FEATURE:
<223> OTHER INFORMATION: active site region from improved mutated
      polymerase domain of chimeric thermostable DNA-dependent DNA
      polymerase CS5 or CS6

<400> SEQUENCE: 67

Ile Ile Pro Leu Ile Leu Glu Tyr Arg Lys Ile Gln Lys Leu Lys Ser
1               5                   10                  15

Thr Tyr Ile Asp Ala Leu Pro Lys Met Val Asn Pro Lys Thr Gly Arg
                20                  25                  30

Ile His Ala Ser Phe Asn Gln Thr Gly Thr Ala Thr Gly Arg Leu Ser
            35                  40                  45

Ser Ser Gly Pro Asn Leu Gln Asn Leu Pro Thr Lys Ser Glu Glu Gly
    50                  55                  60

Lys Glu Ile Arg Lys Ala Ile Val Pro Gln Asp Pro Asn Trp Trp Phe
65                  70                  75                  80

Val Phe Ala Asp Tyr Ser Gln Ile Glu Leu Arg Ile
                85                  90

<210> SEQ ID NO 68
<211> LENGTH: 92
<212> TYPE: PRT
<213> ORGANISM: Artificial
<220> FEATURE:
<223> OTHER INFORMATION: active site region from improved mutated
      polymerase domain of chimeric thermostable DNA-dependent DNA
      polymerase CS5 or CS6

<400> SEQUENCE: 68

```
Ile Ile Pro Leu Ile Leu Glu Tyr Arg Lys Ile Arg Lys Leu Lys Ser
1               5                   10                  15

Thr Tyr Ile Asp Ala Leu Pro Lys Met Val Asn Pro Lys Thr Gly Arg
            20                  25                  30

Ile His Ala Ser Phe Asn Gln Thr Gly Thr Ala Thr Gly Arg Leu Ser
        35                  40                  45

Ser Ser Gly Pro Asn Leu Gln Asn Leu Pro Thr Lys Ser Glu Glu Gly
    50                  55                  60

Lys Glu Ile Arg Lys Ala Ile Val Pro Gln Asp Pro Asn Trp Trp Phe
65                  70                  75                  80

Val Phe Ala Asp Tyr Ser Gln Ile Glu Leu Arg Ile
                85                  90
```

<210> SEQ ID NO 69
<211> LENGTH: 16
<212> TYPE: PRT
<213> ORGANISM: Artificial
<220> FEATURE:
<223> OTHER INFORMATION: DNA polymerase unmodified motif a
<220> FEATURE:
<221> NAME/KEY: MOD_RES
<222> LOCATION: (1)
<223> OTHER INFORMATION: Xaa = Ile or Leu
<220> FEATURE:
<221> NAME/KEY: MOD_RES
<222> LOCATION: (2)
<223> OTHER INFORMATION: Xaa = Leu or Gln
<220> FEATURE:
<221> NAME/KEY: MOD_RES
<222> LOCATION: (3)
<223> OTHER INFORMATION: Xaa = Gln, His or Glu
<220> FEATURE:
<221> NAME/KEY: MOD_RES
<222> LOCATION: (4)
<223> OTHER INFORMATION: Xaa = Tyr, His or Phe
<220> FEATURE:
<221> NAME/KEY: MOD_RES
<222> LOCATION: (6)
<223> OTHER INFORMATION: Xaa = Glu, Gln or Lys
<220> FEATURE:
<221> NAME/KEY: MOD_RES
<222> LOCATION: (7)
<223> OTHER INFORMATION: Xaa = Ile, Leu or Tyr
<220> FEATURE:
<221> NAME/KEY: MOD_RES
<222> LOCATION: (8)
<223> OTHER INFORMATION: Xaa = Gln, Thr, Met, Gly or Leu
<220> FEATURE:
<221> NAME/KEY: MOD_RES
<222> LOCATION: (11)
<223> OTHER INFORMATION: Xaa = Lys or Gln
<220> FEATURE:
<221> NAME/KEY: MOD_RES
<222> LOCATION: (12)
<223> OTHER INFORMATION: Xaa = Ser or Asn
<220> FEATURE:
<221> NAME/KEY: MOD_RES
<222> LOCATION: (15)
<223> OTHER INFORMATION: Xaa = Ile or Val
<220> FEATURE:
<221> NAME/KEY: MOD_RES
<222> LOCATION: (16)
<223> OTHER INFORMATION: Xaa = Glu or Asp

<400> SEQUENCE: 69

```
Xaa Xaa Xaa Xaa Arg Xaa Xaa Xaa Lys Leu Xaa Xaa Thr Tyr Xaa Xaa
1               5                   10                  15
```

```
<210> SEQ ID NO 70
<211> LENGTH: 13
<212> TYPE: PRT
<213> ORGANISM: Artificial
<220> FEATURE:
<223> OTHER INFORMATION: DNA polymerase unmodified motif b
<220> FEATURE:
<221> NAME/KEY: MOD_RES
<222> LOCATION: (7)
<223> OTHER INFORMATION: Xaa = Ser or Thr
<220> FEATURE:
<221> NAME/KEY: MOD_RES
<222> LOCATION: (8)
<223> OTHER INFORMATION: Xaa = Asp, Glu or Asn

<400> SEQUENCE: 70

Thr Gly Arg Leu Ser Ser Xaa Xaa Pro Asn Leu Gln Asn
1               5                   10

<210> SEQ ID NO 71
<211> LENGTH: 15
<212> TYPE: PRT
<213> ORGANISM: Artificial
<220> FEATURE:
<223> OTHER INFORMATION: DNA polymerase unmodified motif c
<220> FEATURE:
<221> NAME/KEY: MOD_RES
<222> LOCATION: (1)
<223> OTHER INFORMATION: Xaa = Gly, Asn or Asp
<220> FEATURE:
<221> NAME/KEY: MOD_RES
<222> LOCATION: (2)
<223> OTHER INFORMATION: Xaa = Trp or His
<220> FEATURE:
<221> NAME/KEY: MOD_RES
<222> LOCATION: (3)
<223> OTHER INFORMATION: Xaa = Trp, Ala, Leu or Val
<220> FEATURE:
<221> NAME/KEY: MOD_RES
<222> LOCATION: (4)
<223> OTHER INFORMATION: Xaa = Ile or Leu
<220> FEATURE:
<221> NAME/KEY: MOD_RES
<222> LOCATION: (5)
<223> OTHER INFORMATION: Xaa = Val, Phe or Leu
<220> FEATURE:
<221> NAME/KEY: MOD_RES
<222> LOCATION: (6)
<223> OTHER INFORMATION: Xaa = Ser, Ala, Val or Gly
<220> FEATURE:
<221> NAME/KEY: MOD_RES
<222> LOCATION: (7)
<223> OTHER INFORMATION: Xaa = Ala or Leu

<400> SEQUENCE: 71

Xaa Xaa Xaa Xaa Xaa Xaa Xaa Asp Tyr Ser Gln Ile Glu Leu Arg
1               5                   10                  15

<210> SEQ ID NO 72
<211> LENGTH: 30
<212> TYPE: DNA
<213> ORGANISM: Artificial
<220> FEATURE:
<223> OTHER INFORMATION: synthetic M13mp18 single-stranded DNA template
      primer

<400> SEQUENCE: 72
gggaagggcg atcggtgcgg gcctcttcgc                                    30

<210> SEQ ID NO 73
<211> LENGTH: 27
<212> TYPE: DNA
<213> ORGANISM: Artificial
```

```
<220> FEATURE:
<223> OTHER INFORMATION: synthetic oligonucleotide Primer QX
<220> FEATURE:
<221> NAME/KEY: modified_base
<222> LOCATION: (15)
<223> OTHER INFORMATION: n = a modified by quenching dye (Q) Black Hole
      Quencher (BHQ)

<400> SEQUENCE: 73
gcaagcaccc tatcnggcag taccaca                                            27

<210> SEQ ID NO 74
<211> LENGTH: 28
<212> TYPE: DNA
<213> ORGANISM: Artificial
<220> FEATURE:
<223> OTHER INFORMATION: synthetic complementary oligonucleotide R1
<220> FEATURE:
<221> NAME/KEY: modified_base
<222> LOCATION: (28)
<223> OTHER INFORMATION: n = c modified by 3' phosphate

<400> SEQUENCE: 74
ttgtggtact gcctgatagg gtgcttgn                                           28

<210> SEQ ID NO 75
<211> LENGTH: 27
<212> TYPE: DNA
<213> ORGANISM: Artificial
<220> FEATURE:
<223> OTHER INFORMATION: synthetic fluorescein-labeled Primer FAM-QX
<220> FEATURE:
<221> NAME/KEY: modified_base
<222> LOCATION: (15)
<223> OTHER INFORMATION: n = a modified by quenching dye (Q) Black Hole
      Quencher (BHQ)
<220> FEATURE:
<221> NAME/KEY: modified_base
<222> LOCATION: (27)
<223> OTHER INFORMATION: n = fluorescein-labeled a modified by 2'
      phosphate, fluorescein-labeled deoxyadenine tetraphosphate (dA4P),
      fluorescein-labeled 2'-terminator nucleotide

<400> SEQUENCE: 75
gcaagcaccc tatcnggcag taccacn                                            27

<210> SEQ ID NO 76
<211> LENGTH: 25
<212> TYPE: DNA
<213> ORGANISM: Artificial
<220> FEATURE:
<223> OTHER INFORMATION: synthetic Primer HC2

<400> SEQUENCE: 76
gcagaaagcg tctagccatg gctta                                              25

<210> SEQ ID NO 77
<211> LENGTH: 893
<212> TYPE: PRT
<213> ORGANISM: Thermotoga maritima
<220> FEATURE:
<223> OTHER INFORMATION: DNA polymerase

<400> SEQUENCE: 77

Met Ala Arg Leu Phe Leu Phe Asp Gly Thr Ala Leu Ala Tyr Arg Ala
1               5                   10                  15

Tyr Tyr Ala Leu Asp Arg Ser Leu Ser Thr Ser Thr Gly Ile Pro Thr
            20                  25                  30
```

```
Asn Ala Thr Tyr Gly Val Ala Arg Met Leu Val Arg Phe Ile Lys Asp
            35                  40                  45

His Ile Ile Val Gly Lys Asp Tyr Val Ala Val Ala Phe Asp Lys Lys
 50                  55                  60

Ala Ala Thr Phe Arg His Lys Leu Leu Glu Thr Tyr Lys Ala Gln Arg
 65                  70                  75                  80

Pro Lys Thr Pro Asp Leu Leu Ile Gln Gln Leu Pro Tyr Ile Lys Lys
                 85                  90                  95

Leu Val Glu Ala Leu Gly Met Lys Val Leu Val Glu Gly Tyr Glu
                100                 105                 110

Ala Asp Asp Ile Ile Ala Thr Leu Ala Val Lys Gly Leu Pro Leu Phe
                115                 120                 125

Asp Glu Ile Phe Ile Val Thr Gly Asp Lys Asp Met Leu Gln Leu Val
        130                 135                 140

Asn Glu Lys Ile Lys Val Trp Arg Ile Val Lys Gly Ile Ser Asp Leu
145                 150                 155                 160

Glu Leu Tyr Asp Ala Gln Lys Val Lys Glu Lys Tyr Gly Val Glu Pro
                165                 170                 175

Gln Gln Ile Pro Asp Leu Leu Ala Leu Thr Gly Asp Glu Ile Asp Asn
                180                 185                 190

Ile Pro Gly Val Thr Gly Ile Gly Glu Lys Thr Ala Val Gln Leu Leu
                195                 200                 205

Glu Lys Tyr Lys Asp Leu Glu Asp Ile Leu Asn His Val Arg Glu Leu
        210                 215                 220

Pro Gln Lys Val Arg Lys Ala Leu Leu Arg Asp Arg Glu Asn Ala Ile
225                 230                 235                 240

Leu Ser Lys Lys Leu Ala Ile Leu Glu Thr Asn Val Pro Ile Glu Ile
                245                 250                 255

Asn Trp Glu Glu Leu Arg Tyr Gln Gly Tyr Asp Arg Glu Lys Leu Leu
                260                 265                 270

Pro Leu Leu Lys Glu Leu Glu Phe Ala Ser Ile Met Lys Glu Leu Gln
        275                 280                 285

Leu Tyr Glu Glu Ser Glu Pro Val Gly Tyr Arg Ile Val Lys Asp Leu
        290                 295                 300

Val Glu Phe Glu Lys Leu Ile Glu Lys Leu Arg Glu Ser Pro Ser Phe
305                 310                 315                 320

Ala Ile Asp Leu Glu Thr Ser Ser Leu Asp Pro Phe Asp Cys Asp Ile
                325                 330                 335

Val Gly Ile Ser Val Ser Phe Lys Pro Lys Glu Ala Tyr Tyr Ile Pro
                340                 345                 350

Leu His His Arg Asn Ala Gln Asn Leu Asp Glu Lys Glu Val Leu Lys
        355                 360                 365

Lys Leu Lys Glu Ile Leu Glu Asp Pro Gly Ala Lys Ile Val Gly Gln
        370                 375                 380

Asn Leu Lys Phe Asp Tyr Lys Val Leu Met Val Lys Gly Val Glu Pro
385                 390                 395                 400

Val Pro Pro Tyr Phe Asp Thr Met Ile Ala Ala Tyr Leu Leu Glu Pro
                405                 410                 415

Asn Glu Lys Lys Phe Asn Leu Asp Asp Leu Ala Leu Lys Phe Leu Gly
                420                 425                 430

Tyr Lys Met Thr Ser Tyr Gln Glu Leu Met Ser Phe Ser Phe Pro Leu
        435                 440                 445
```

-continued

Phe Gly Phe Ser Phe Ala Asp Val Pro Val Glu Lys Ala Ala Asn Tyr
            450                 455                 460

Ser Cys Glu Asp Ala Asp Ile Thr Tyr Arg Leu Tyr Lys Thr Leu Ser
465                 470                 475                 480

Leu Lys Leu His Glu Ala Asp Leu Glu Asn Val Phe Tyr Lys Ile Glu
                485                 490                 495

Met Pro Leu Val Asn Val Leu Ala Arg Met Glu Leu Asn Gly Val Tyr
            500                 505                 510

Val Asp Thr Glu Phe Leu Lys Lys Leu Ser Glu Tyr Gly Lys Lys
                515                 520                 525

Leu Glu Glu Leu Ala Glu Ile Tyr Arg Ile Ala Gly Glu Pro Phe
530                 535                 540

Asn Ile Asn Ser Pro Lys Gln Val Ser Arg Ile Leu Phe Glu Lys Leu
545                 550                 555                 560

Gly Ile Lys Pro Arg Gly Lys Thr Thr Lys Thr Gly Asp Tyr Ser Thr
                565                 570                 575

Arg Ile Glu Val Leu Glu Leu Ala Gly His Glu Ile Ile Pro
            580                 585                 590

Leu Ile Leu Glu Tyr Arg Lys Ile Gln Lys Leu Lys Ser Thr Tyr Ile
                595                 600                 605

Asp Ala Leu Pro Lys Met Val Asn Pro Lys Thr Gly Arg Ile His Ala
610                 615                 620

Ser Phe Asn Gln Thr Gly Thr Ala Thr Gly Arg Leu Ser Ser Ser Asp
625                 630                 635                 640

Pro Asn Leu Gln Asn Leu Pro Thr Lys Ser Glu Glu Gly Lys Glu Ile
                645                 650                 655

Arg Lys Ala Ile Val Pro Gln Asp Pro Asn Trp Trp Ile Val Ser Ala
            660                 665                 670

Asp Tyr Ser Gln Ile Glu Leu Arg Ile Leu Ala His Leu Ser Gly Asp
                675                 680                 685

Glu Asn Leu Leu Arg Ala Phe Glu Glu Gly Ile Asp Val His Thr Leu
690                 695                 700

Thr Ala Ser Arg Ile Phe Asn Val Lys Pro Glu Glu Val Thr Glu Glu
705                 710                 715                 720

Met Arg Arg Ala Gly Lys Met Val Asn Phe Ser Ile Ile Tyr Gly Val
                725                 730                 735

Thr Pro Tyr Gly Leu Ser Val Arg Leu Gly Val Pro Val Lys Glu Ala
            740                 745                 750

Glu Lys Met Ile Val Asn Tyr Phe Val Leu Tyr Pro Lys Val Arg Asp
            755                 760                 765

Tyr Ile Gln Arg Val Val Ser Glu Ala Lys Glu Lys Gly Tyr Val Arg
            770                 775                 780

Thr Leu Phe Gly Arg Lys Arg Asp Ile Pro Gln Leu Met Ala Arg Asp
785                 790                 795                 800

Arg Asn Thr Gln Ala Glu Gly Glu Arg Ile Ala Ile Asn Thr Pro Ile
                805                 810                 815

Gln Gly Thr Ala Ala Asp Ile Ile Lys Leu Ala Met Ile Glu Ile Asp
            820                 825                 830

Arg Glu Leu Lys Glu Arg Lys Met Arg Ser Lys Met Ile Ile Gln Val
                835                 840                 845

His Asp Glu Leu Val Phe Glu Val Pro Asn Glu Glu Lys Asp Ala Leu
850                 855                 860

Val Glu Leu Val Lys Asp Arg Met Thr Asn Val Lys Leu Ser Val
865                 870                 875                 880

Pro Leu Glu Val Asp Val Thr Ile Gly Lys Thr Trp Ser
            885                 890

<210> SEQ ID NO 78
<211> LENGTH: 832
<212> TYPE: PRT
<213> ORGANISM: Thermus aquaticus
<220> FEATURE:
<223> OTHER INFORMATION: DNA polymerase

<400> SEQUENCE: 78

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
            355                 360                 365

Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
            405                 410                 415

Trp Gly Arg Leu Glu Gly Glu Arg Leu Leu Trp Leu Tyr Arg Glu
            420                 425                 430

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
            450                 455                 460

Glu Glu Ile Ala Arg Leu Glu Ala Glu Val Phe Arg Leu Ala Glu His
465                 470                 475                 480

Pro Phe Asn Leu Asn Ser Arg Asp Gln Leu Glu Arg Val Leu Phe Asp
            485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
            515                 520                 525

Val Glu Lys Ile Leu Gln Tyr Arg Glu Leu Thr Lys Leu Lys Ser Thr
            530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
            565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
            595                 600                 605

Leu Asp Tyr Ser Gln Ile Glu Leu Arg Val Leu Ala His Leu Ser Gly
            610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
            645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
            675                 680                 685

Ala Gln Ala Phe Ile Glu Arg Tyr Phe Gln Ser Phe Pro Lys Val Arg
            690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
            725                 730                 735

Val Lys Ser Val Arg Glu Ala Ala Glu Arg Met Ala Phe Asn Met Pro
            740                 745                 750

```
Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
                820                 825                 830

<210> SEQ ID NO 79
<211> LENGTH: 834
<212> TYPE: PRT
<213> ORGANISM: Thermus thermophilus
<220> FEATURE:
<223> OTHER INFORMATION: DNA polymerase

<400> SEQUENCE: 79

Met Glu Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Tyr Glu Ala Asp Asp Val Leu Ala Thr Leu Ala Lys
        115                 120                 125

Lys Ala Glu Lys Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Arg
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Leu Leu Lys Asn Leu Asp Arg
    210                 215                 220

Val Lys Pro Glu Asn Val Arg Glu Lys Ile Lys Ala His Leu Glu Asp
225                 230                 235                 240

Leu Arg Leu Ser Leu Glu Leu Ser Arg Val Arg Thr Asp Leu Pro Leu
                245                 250                 255

Glu Val Asp Leu Ala Gln Gly Arg Glu Pro Asp Arg Glu Gly Leu Arg
            260                 265                 270

Ala Phe Leu Glu Arg Leu Glu Phe Gly Ser Leu Leu His Glu Phe Gly
        275                 280                 285
```

```
Leu Leu Glu Ala Pro Ala Pro Leu Glu Glu Ala Pro Trp Pro Pro
    290                 295                 300

Glu Gly Ala Phe Val Gly Phe Val Leu Ser Arg Pro Glu Pro Met Trp
305                 310                 315                 320

Ala Glu Leu Lys Ala Leu Ala Ala Cys Arg Asp Gly Arg Val His Arg
                325                 330                 335

Ala Ala Asp Pro Leu Ala Gly Leu Lys Asp Leu Lys Glu Val Arg Gly
            340                 345                 350

Leu Leu Ala Lys Asp Leu Ala Val Leu Ala Ser Arg Glu Gly Leu Asp
        355                 360                 365

Leu Val Pro Gly Asp Asp Pro Met Leu Leu Ala Tyr Leu Leu Asp Pro
370                 375                 380

Ser Asn Thr Thr Pro Glu Gly Val Ala Arg Arg Tyr Gly Gly Glu Trp
385                 390                 395                 400

Thr Glu Asp Ala Ala His Arg Ala Leu Leu Ser Glu Arg Leu His Arg
                405                 410                 415

Asn Leu Leu Lys Arg Leu Glu Gly Glu Lys Leu Leu Trp Leu Tyr
                420                 425                 430

His Glu Val Glu Lys Pro Leu Ser Arg Val Leu Ala His Met Glu Ala
            435                 440                 445

Thr Gly Val Arg Leu Asp Val Ala Tyr Leu Gln Ala Leu Ser Leu Glu
        450                 455                 460

Leu Ala Glu Glu Ile Arg Arg Leu Glu Glu Val Phe Arg Leu Ala
465                 470                 475                 480

Gly His Pro Phe Asn Leu Asn Ser Arg Asp Gln Leu Glu Arg Val Leu
                485                 490                 495

Phe Asp Glu Leu Arg Leu Pro Ala Leu Gly Lys Thr Gln Lys Thr Gly
            500                 505                 510

Lys Arg Ser Thr Ser Ala Ala Val Leu Glu Ala Leu Arg Glu Ala His
        515                 520                 525

Pro Ile Val Glu Lys Ile Leu Gln His Arg Glu Leu Thr Lys Leu Lys
530                 535                 540

Asn Thr Tyr Val Asp Pro Leu Pro Ser Leu Val His Pro Arg Thr Gly
545                 550                 555                 560

Arg Leu His Thr Arg Phe Asn Gln Thr Ala Thr Ala Thr Gly Arg Leu
                565                 570                 575

Ser Ser Ser Asp Pro Asn Leu Gln Asn Ile Pro Val Arg Thr Pro Leu
            580                 585                 590

Gly Gln Arg Ile Arg Arg Ala Phe Val Ala Glu Ala Gly Trp Ala Leu
        595                 600                 605

Val Ala Leu Asp Tyr Ser Gln Ile Glu Leu Arg Val Leu Ala His Leu
610                 615                 620

Ser Gly Asp Glu Asn Leu Ile Arg Val Phe Gln Glu Gly Lys Asp Ile
625                 630                 635                 640

His Thr Gln Thr Ala Ser Trp Met Phe Gly Val Pro Pro Glu Ala Val
                645                 650                 655

Asp Pro Leu Met Arg Arg Ala Ala Lys Thr Val Asn Phe Gly Val Leu
            660                 665                 670

Tyr Gly Met Ser Ala His Arg Leu Ser Gln Glu Leu Ala Ile Pro Tyr
        675                 680                 685

Glu Glu Ala Val Ala Phe Ile Glu Arg Tyr Phe Gln Ser Phe Pro Lys
690                 695                 700
```

```
Val Arg Ala Trp Ile Glu Lys Thr Leu Glu Glu Gly Arg Lys Arg Gly
705                 710                 715                 720

Tyr Val Glu Thr Leu Phe Gly Arg Arg Arg Tyr Val Pro Asp Leu Asn
            725                 730                 735

Ala Arg Val Lys Ser Val Arg Glu Ala Ala Glu Arg Met Ala Phe Asn
            740                 745                 750

Met Pro Val Gln Gly Thr Ala Ala Asp Leu Met Lys Leu Ala Met Val
            755                 760                 765

Lys Leu Phe Pro Arg Leu Arg Glu Met Gly Ala Arg Met Leu Leu Gln
            770                 775                 780

Val His Asp Glu Leu Leu Leu Glu Ala Pro Gln Ala Arg Ala Glu Glu
785                 790                 795                 800

Val Ala Ala Leu Ala Lys Glu Ala Met Glu Lys Ala Tyr Pro Leu Ala
            805                 810                 815

Val Pro Leu Glu Val Glu Val Gly Met Gly Glu Asp Trp Leu Ser Ala
            820                 825                 830

Lys Gly

<210> SEQ ID NO 80
<211> LENGTH: 831
<212> TYPE: PRT
<213> ORGANISM: Thermus flavus
<220> FEATURE:
<223> OTHER INFORMATION: DNA polymerase

<400> SEQUENCE: 80

Met Ala Met Leu Pro Leu Phe Glu Pro Lys Gly Arg Val Leu Leu Val
1               5                   10                  15

Asp Gly His His Leu Ala Tyr Arg Thr Phe Phe Ala Leu Lys Gly Leu
            20                  25                  30

Thr Thr Ser Arg Gly Glu Pro Val Gln Ala Val Tyr Gly Phe Ala Lys
            35                  40                  45

Ser Leu Leu Lys Ala Leu Lys Glu Asp Gly Asp Val Val Val Val
    50                  55                  60

Phe Asp Ala Lys Ala Pro Ser Phe Arg His Glu Ala Tyr Glu Ala Tyr
65                  70                  75                  80

Lys Ala Gly Arg Ala Pro Thr Pro Glu Asp Phe Pro Arg Gln Leu Ala
            85                  90                  95

Leu Ile Lys Glu Leu Val Asp Leu Leu Gly Leu Val Arg Leu Glu Val
            100                 105                 110

Pro Gly Phe Glu Ala Asp Asp Val Leu Ala Thr Leu Ala Lys Arg Ala
            115                 120                 125

Glu Lys Glu Gly Tyr Glu Val Arg Ile Leu Thr Ala Asp Arg Asp Leu
            130                 135                 140

Tyr Gln Leu Leu Ser Glu Arg Ile Ala Ile Leu His Pro Glu Gly Tyr
145                 150                 155                 160

Leu Ile Thr Pro Ala Trp Leu Tyr Glu Lys Tyr Gly Leu Arg Pro Glu
            165                 170                 175

Gln Trp Val Asp Tyr Arg Ala Leu Ala Gly Asp Pro Ser Asp Asn Ile
            180                 185                 190

Pro Gly Val Lys Gly Ile Gly Glu Lys Thr Ala Gln Arg Leu Ile Arg
            195                 200                 205

Glu Trp Gly Ser Leu Glu Asn Leu Phe Gln His Leu Asp Gln Val Lys
            210                 215                 220
```

```
Pro Ser Leu Arg Glu Lys Leu Gln Ala Gly Met Glu Ala Leu Ala Leu
225                 230                 235                 240

Ser Arg Lys Leu Ser Gln Val His Thr Asp Leu Pro Leu Glu Val Asp
        245                 250                 255

Phe Gly Arg Arg Thr Pro Asn Leu Glu Gly Leu Arg Ala Phe Leu
            260                 265                 270

Glu Arg Leu Glu Phe Gly Ser Leu Leu His Glu Phe Gly Leu Leu Glu
        275                 280                 285

Gly Pro Lys Ala Ala Glu Ala Pro Trp Pro Pro Glu Gly Ala
    290                 295                 300

Phe Leu Gly Phe Ser Phe Ser Arg Pro Glu Pro Met Trp Ala Glu Leu
305                 310                 315                 320

Leu Ala Leu Ala Gly Ala Trp Glu Gly Arg Leu His Arg Ala Gln Asp
            325                 330                 335

Pro Leu Arg Gly Leu Arg Asp Leu Lys Gly Val Arg Gly Ile Leu Ala
            340                 345                 350

Lys Asp Leu Ala Val Leu Ala Leu Arg Glu Gly Leu Asp Leu Phe Pro
        355                 360                 365

Glu Asp Asp Pro Met Leu Leu Ala Tyr Leu Leu Asp Pro Ser Asn Thr
370                 375                 380

Thr Pro Glu Gly Val Ala Arg Arg Tyr Gly Gly Glu Trp Thr Glu Asp
385                 390                 395                 400

Ala Gly Glu Arg Ala Leu Leu Ala Glu Arg Leu Phe Gln Thr Leu Lys
            405                 410                 415

Glu Arg Leu Lys Gly Glu Glu Arg Leu Leu Trp Leu Tyr Glu Glu Val
        420                 425                 430

Glu Lys Pro Leu Ser Arg Val Leu Ala Arg Met Glu Ala Thr Gly Val
        435                 440                 445

Arg Leu Asp Val Ala Tyr Leu Gln Ala Leu Ser Leu Glu Val Glu Ala
450                 455                 460

Glu Val Arg Gln Leu Glu Glu Glu Val Phe Arg Leu Ala Gly His Pro
465                 470                 475                 480

Phe Asn Leu Asn Ser Arg Asp Gln Leu Glu Arg Val Leu Phe Asp Glu
            485                 490                 495

Leu Gly Leu Pro Ala Ile Gly Lys Thr Glu Lys Thr Gly Lys Arg Ser
            500                 505                 510

Thr Ser Ala Ala Val Leu Glu Ala Leu Arg Glu Ala His Pro Ile Val
            515                 520                 525

Asp Arg Ile Leu Gln Tyr Arg Glu Leu Thr Lys Leu Lys Asn Thr Tyr
530                 535                 540

Ile Asp Pro Leu Pro Ala Leu Val His Pro Lys Thr Gly Arg Leu His
545                 550                 555                 560

Thr Arg Phe Asn Gln Thr Ala Thr Ala Thr Gly Arg Leu Ser Ser Ser
            565                 570                 575

Asp Pro Asn Leu Gln Asn Ile Pro Val Arg Thr Pro Leu Gly Gln Arg
            580                 585                 590

Ile Arg Arg Ala Phe Val Ala Glu Gly Trp Val Leu Val Val Leu
        595                 600                 605

Asp Tyr Ser Gln Ile Glu Leu Arg Val Leu Ala His Leu Ser Gly Asp
        610                 615                 620

Glu Asn Leu Ile Arg Val Phe Gln Glu Gly Arg Asp Ile His Thr Gln
625                 630                 635                 640
```

```
Thr Ala Ser Trp Met Phe Gly Val Ser Pro Glu Gly Val Asp Pro Leu
                645                 650                 655

Met Arg Arg Ala Ala Lys Thr Ile Asn Phe Gly Val Leu Tyr Gly Met
            660                 665                 670

Ser Ala His Arg Leu Ser Gly Glu Leu Ser Ile Pro Tyr Glu Glu Ala
        675                 680                 685

Val Ala Phe Ile Glu Arg Tyr Phe Gln Ser Tyr Pro Lys Val Arg Ala
    690                 695                 700

Trp Ile Glu Gly Thr Leu Glu Glu Gly Arg Arg Gly Tyr Val Glu
705                 710                 715                 720

Thr Leu Phe Gly Arg Arg Tyr Val Pro Asp Leu Asn Ala Arg Val
                725                 730                 735

Lys Ser Val Arg Glu Ala Ala Glu Arg Met Ala Phe Asn Met Pro Val
            740                 745                 750

Gln Gly Thr Ala Ala Asp Leu Met Lys Leu Ala Met Val Arg Leu Phe
        755                 760                 765

Pro Arg Leu Gln Glu Leu Gly Ala Arg Met Leu Leu Gln Val His Asp
    770                 775                 780

Glu Leu Val Leu Glu Ala Pro Lys Asp Arg Ala Glu Arg Val Ala Ala
785                 790                 795                 800

Leu Ala Lys Glu Val Met Glu Gly Val Trp Pro Leu Gln Val Pro Leu
                805                 810                 815

Glu Val Glu Val Gly Leu Gly Glu Asp Trp Leu Ser Ala Lys Glu
            820                 825                 830

<210> SEQ ID NO 81
<211> LENGTH: 830
<212> TYPE: PRT
<213> ORGANISM: Thermus sp.
<220> FEATURE:
<223> OTHER INFORMATION: Thermus sp. sps17 DNA polymerase

<400> SEQUENCE: 81

Met Leu Pro Leu Phe Glu Pro Lys Gly Arg Val Leu Leu Val Asp Gly
1               5                   10                  15

His His Leu Ala Tyr Arg Thr Phe Phe Ala Leu Lys Gly Leu Thr Thr
            20                  25                  30

Ser Arg Gly Glu Pro Val Gln Ala Val Tyr Gly Phe Ala Lys Ser Leu
        35                  40                  45

Leu Lys Ala Leu Lys Glu Asp Gly Glu Val Ala Ile Val Val Phe Asp
    50                  55                  60

Ala Lys Ala Pro Ser Phe Arg His Glu Ala Tyr Glu Ala Tyr Lys Ala
65                  70                  75                  80

Gly Arg Ala Pro Thr Pro Glu Asp Phe Pro Arg Gln Leu Ala Leu Ile
                85                  90                  95

Lys Glu Leu Val Asp Leu Leu Gly Leu Val Arg Leu Glu Val Pro Gly
            100                 105                 110

Phe Glu Ala Asp Asp Val Leu Ala Thr Leu Ala Lys Lys Ala Glu Arg
        115                 120                 125

Glu Gly Tyr Glu Val Arg Ile Leu Ser Ala Asp Arg Asp Leu Tyr Gln
    130                 135                 140

Leu Leu Ser Asp Arg Ile His Leu Leu His Pro Glu Gly Glu Val Leu
145                 150                 155                 160

Thr Pro Gly Trp Leu Gln Glu Arg Tyr Gly Leu Ser Pro Glu Arg Trp
                165                 170                 175
```

```
Val Glu Tyr Arg Ala Leu Val Gly Asp Pro Ser Asp Asn Leu Pro Gly
                180                 185                 190

Val Pro Gly Ile Gly Glu Lys Thr Ala Leu Lys Leu Leu Lys Glu Trp
            195                 200                 205

Gly Ser Leu Glu Ala Ile Leu Lys Asn Leu Asp Gln Val Lys Pro Glu
        210                 215                 220

Arg Val Arg Glu Ala Ile Arg Asn Asn Leu Asp Lys Leu Gln Met Ser
225                 230                 235                 240

Leu Glu Leu Ser Arg Leu Arg Thr Asp Leu Pro Leu Glu Val Asp Phe
                245                 250                 255

Ala Lys Arg Arg Glu Pro Asp Trp Glu Gly Leu Lys Ala Phe Leu Glu
            260                 265                 270

Arg Leu Glu Phe Gly Ser Leu Leu His Glu Phe Gly Leu Leu Glu Ala
        275                 280                 285

Pro Lys Glu Ala Glu Glu Ala Pro Trp Pro Pro Gly Gly Ala Phe
290                 295                 300

Leu Gly Phe Leu Leu Ser Arg Pro Glu Pro Met Trp Ala Glu Leu Leu
305                 310                 315                 320

Ala Leu Ala Gly Ala Lys Glu Gly Arg Val His Arg Ala Glu Asp Pro
                325                 330                 335

Val Gly Ala Leu Lys Asp Leu Lys Glu Ile Arg Gly Leu Leu Ala Lys
            340                 345                 350

Asp Leu Ser Val Leu Ala Leu Arg Glu Gly Arg Glu Ile Pro Pro Gly
        355                 360                 365

Asp Asp Pro Met Leu Leu Ala Tyr Leu Leu Asp Pro Gly Asn Thr Asn
370                 375                 380

Pro Glu Gly Val Ala Arg Arg Tyr Gly Gly Glu Trp Lys Glu Asp Ala
385                 390                 395                 400

Ala Ala Arg Ala Leu Leu Ser Glu Arg Leu Trp Gln Ala Leu Tyr Pro
                405                 410                 415

Arg Val Ala Glu Glu Arg Leu Leu Trp Leu Tyr Arg Glu Val Glu
            420                 425                 430

Arg Pro Leu Ala Gln Val Leu Ala His Met Glu Ala Thr Gly Val Arg
        435                 440                 445

Leu Asp Val Pro Tyr Leu Glu Ala Leu Ser Gln Glu Val Ala Phe Glu
450                 455                 460

Leu Glu Arg Leu Glu Ala Glu Val His Arg Leu Ala Gly His Pro Phe
465                 470                 475                 480

Asn Leu Asn Ser Arg Asp Gln Leu Glu Arg Val Leu Phe Asp Glu Leu
                485                 490                 495

Gly Leu Pro Pro Ile Gly Lys Thr Glu Lys Thr Gly Lys Arg Ser Thr
            500                 505                 510

Ser Ala Ala Val Leu Glu Leu Arg Glu Ala His Pro Ile Val Gly
        515                 520                 525

Arg Ile Leu Glu Tyr Arg Glu Leu Met Lys Leu Lys Ser Thr Tyr Ile
530                 535                 540

Asp Pro Leu Pro Arg Leu Val His Pro Lys Thr Gly Arg Leu His Thr
545                 550                 555                 560

Arg Phe Asn Gln Thr Ala Thr Ala Thr Gly Arg Leu Ser Ser Ser Asp
                565                 570                 575

Pro Asn Leu Gln Asn Ile Pro Val Arg Thr Pro Leu Gly Gln Arg Ile
            580                 585                 590
```

```
Arg Lys Ala Phe Ile Ala Glu Glu Gly His Leu Leu Val Ala Leu Asp
            595                 600                 605
Tyr Ser Gln Ile Glu Leu Arg Val Leu Ala His Leu Ser Gly Asp Glu
        610                 615                 620
Asn Leu Ile Arg Val Phe Arg Glu Gly Lys Asp Ile His Thr Glu Thr
625                 630                 635                 640
Ala Ala Trp Met Phe Gly Val Pro Pro Glu Gly Val Asp Gly Ala Met
                645                 650                 655
Arg Arg Ala Ala Lys Thr Val Asn Phe Gly Val Leu Tyr Gly Met Ser
            660                 665                 670
Ala His Arg Leu Ser Gln Glu Leu Ser Ile Pro Tyr Glu Glu Ala Ala
        675                 680                 685
Ala Phe Ile Glu Arg Tyr Phe Gln Ser Phe Pro Lys Val Arg Ala Trp
    690                 695                 700
Ile Ala Lys Thr Leu Glu Glu Gly Arg Lys Lys Gly Tyr Val Glu Thr
705                 710                 715                 720
Leu Phe Gly Arg Arg Arg Tyr Val Pro Asp Leu Asn Ala Arg Val Lys
                725                 730                 735
Ser Val Arg Glu Ala Ala Glu Arg Met Ala Phe Asn Met Pro Val Gln
            740                 745                 750
Gly Thr Ala Ala Asp Leu Met Lys Leu Ala Met Val Lys Leu Phe Pro
        755                 760                 765
Arg Leu Arg Pro Leu Gly Val Arg Ile Leu Leu Gln Val His Asp Glu
    770                 775                 780
Leu Val Leu Glu Ala Pro Lys Ala Arg Ala Glu Glu Ala Ala Gln Leu
785                 790                 795                 800
Ala Lys Glu Thr Met Glu Gly Val Tyr Pro Leu Ser Val Pro Leu Glu
                805                 810                 815
Val Glu Val Gly Met Gly Glu Asp Trp Leu Ser Ala Lys Ala
            820                 825                 830

<210> SEQ ID NO 82
<211> LENGTH: 832
<212> TYPE: PRT
<213> ORGANISM: Thermus sp.
<220> FEATURE:
<223> OTHER INFORMATION: Thermus sp. Z05 DNA polymerase

<400> SEQUENCE: 82

Met Lys Ala Met Leu Pro Leu Phe Glu Pro Lys Gly Arg Val Leu Leu
1               5                   10                  15
Val Asp Gly His His Leu Ala Tyr Arg Thr Phe Phe Ala Leu Lys Gly
            20                  25                  30
Leu Thr Thr Ser Arg Gly Glu Pro Val Gln Ala Val Tyr Gly Phe Ala
        35                  40                  45
Lys Ser Leu Leu Lys Ala Leu Lys Glu Asp Gly Tyr Lys Ala Val Phe
    50                  55                  60
Val Val Phe Asp Ala Lys Ala Pro Ser Phe Arg His Glu Ala Tyr Glu
65                  70                  75                  80
Ala Tyr Lys Ala Gly Arg Ala Pro Thr Pro Glu Asp Phe Pro Arg Gln
                85                  90                  95
Leu Ala Leu Ile Lys Glu Leu Val Asp Leu Leu Gly Phe Thr Arg Leu
            100                 105                 110
Glu Val Pro Gly Phe Glu Ala Asp Asp Val Leu Ala Thr Leu Ala Lys
        115                 120                 125
```

```
Lys Ala Glu Arg Glu Gly Tyr Glu Val Arg Ile Leu Thr Ala Asp Arg
        130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Lys
                165                 170                 175

Pro Glu Gln Trp Val Asp Phe Arg Ala Leu Val Gly Asp Pro Ser Asp
                180                 185                 190

Asn Leu Pro Gly Val Lys Gly Ile Gly Glu Lys Thr Ala Leu Lys Leu
            195                 200                 205

Leu Lys Glu Trp Gly Ser Leu Glu Asn Ile Leu Lys Asn Leu Asp Arg
210                 215                 220

Val Lys Pro Glu Ser Val Arg Glu Arg Ile Lys Ala His Leu Glu Asp
225                 230                 235                 240

Leu Lys Leu Ser Leu Glu Leu Ser Arg Val Arg Ser Asp Leu Pro Leu
                245                 250                 255

Glu Val Asp Phe Ala Arg Arg Arg Glu Pro Asp Arg Glu Gly Leu Arg
                260                 265                 270

Ala Phe Leu Glu Arg Leu Glu Phe Gly Ser Leu Leu His Glu Phe Gly
        275                 280                 285

Leu Leu Glu Ala Pro Ala Pro Leu Glu Glu Ala Pro Trp Pro Pro Pro
290                 295                 300

Glu Gly Ala Phe Val Gly Phe Val Leu Ser Arg Pro Glu Pro Met Trp
305                 310                 315                 320

Ala Glu Leu Lys Ala Leu Ala Ala Cys Lys Glu Gly Arg Val His Arg
                325                 330                 335

Ala Lys Asp Pro Leu Ala Gly Leu Lys Asp Leu Lys Glu Val Arg Gly
            340                 345                 350

Leu Leu Ala Lys Asp Leu Ala Val Leu Ala Leu Arg Glu Gly Leu Asp
                355                 360                 365

Leu Ala Pro Ser Asp Asp Pro Met Leu Leu Ala Tyr Leu Leu Asp Pro
370                 375                 380

Ser Asn Thr Thr Pro Glu Gly Val Ala Arg Arg Tyr Gly Gly Glu Trp
385                 390                 395                 400

Thr Glu Asp Ala Ala His Arg Ala Leu Leu Ala Glu Arg Leu Gln Gln
                405                 410                 415

Asn Leu Leu Glu Arg Leu Lys Gly Glu Glu Lys Leu Leu Trp Leu Tyr
            420                 425                 430

Gln Glu Val Glu Lys Pro Leu Ser Arg Val Leu Ala His Met Glu Ala
        435                 440                 445

Thr Gly Val Arg Leu Asp Val Ala Tyr Leu Lys Ala Leu Ser Leu Glu
    450                 455                 460

Leu Ala Glu Glu Ile Arg Arg Leu Glu Glu Val Phe Arg Leu Ala
465                 470                 475                 480

Gly His Pro Phe Asn Leu Asn Ser Arg Asp Gln Leu Glu Arg Val Leu
                485                 490                 495

Phe Asp Glu Leu Arg Leu Pro Ala Leu Gly Lys Thr Gln Lys Thr Gly
            500                 505                 510

Lys Arg Ser Thr Ser Ala Ala Val Leu Glu Ala Leu Arg Glu Ala His
        515                 520                 525

Pro Ile Val Glu Lys Ile Leu Gln His Arg Glu Leu Thr Lys Leu Lys
530                 535                 540
```

Asn Thr Tyr Val Asp Pro Leu Pro Gly Leu Val His Pro Arg Thr Gly
545                 550                 555                 560

Arg Leu His Thr Arg Phe Asn Gln Thr Ala Thr Ala Thr Gly Arg Leu
                565                 570                 575

Ser Ser Ser Asp Pro Asn Leu Gln Asn Ile Pro Ile Arg Thr Pro Leu
            580                 585                 590

Gly Gln Arg Ile Arg Arg Ala Phe Val Ala Glu Ala Gly Trp Ala Leu
        595                 600                 605

Val Ala Leu Asp Tyr Ser Gln Ile Glu Leu Arg Val Leu Ala His Leu
    610                 615                 620

Ser Gly Asp Glu Asn Leu Ile Arg Val Phe Gln Glu Gly Lys Asp Ile
625                 630                 635                 640

His Thr Gln Thr Ala Ser Trp Met Phe Gly Val Ser Pro Glu Ala Val
                645                 650                 655

Asp Pro Leu Met Arg Arg Ala Ala Lys Thr Val Asn Phe Gly Val Leu
            660                 665                 670

Tyr Gly Met Ser Ala His Arg Leu Ser Gln Glu Leu Ala Ile Pro Tyr
        675                 680                 685

Glu Glu Ala Val Ala Phe Ile Glu Arg Tyr Phe Gln Ser Phe Pro Lys
    690                 695                 700

Val Arg Ala Trp Ile Glu Lys Thr Leu Glu Glu Gly Arg Lys Arg Gly
705                 710                 715                 720

Tyr Val Glu Thr Leu Phe Gly Arg Arg Tyr Val Pro Asp Leu Asn
                725                 730                 735

Ala Arg Val Lys Ser Val Arg Glu Ala Ala Glu Arg Met Ala Phe Asn
            740                 745                 750

Met Pro Val Gln Gly Thr Ala Ala Asp Leu Met Lys Leu Ala Met Val
        755                 760                 765

Lys Leu Phe Pro His Leu Arg Glu Met Gly Ala Arg Met Leu Leu Gln
770                 775                 780

Val His Asp Glu Leu Leu Leu Glu Ala Pro Gln Ala Arg Ala Glu Glu
785                 790                 795                 800

Val Ala Ala Leu Ala Lys Glu Ala Met Glu Lys Ala Tyr Pro Leu Ala
                805                 810                 815

Val Pro Leu Glu Val Glu Val Gly Ile Gly Glu Asp Trp Leu Ser Ala
            820                 825                 830

<210> SEQ ID NO 83
<211> LENGTH: 892
<212> TYPE: PRT
<213> ORGANISM: Thermosipho africanus
<220> FEATURE:
<223> OTHER INFORMATION: DNA polymerase

<400> SEQUENCE: 83

Met Gly Lys Met Phe Leu Phe Asp Gly Thr Gly Leu Val Tyr Arg Ala
1               5                   10                  15

Phe Tyr Ala Ile Asp Gln Ser Leu Gln Thr Ser Ser Gly Leu His Thr
                20                  25                  30

Asn Ala Val Tyr Gly Leu Thr Lys Met Leu Ile Lys Phe Leu Lys Glu
            35                  40                  45

His Ile Ser Ile Gly Lys Asp Ala Cys Val Phe Val Leu Asp Ser Lys
        50                  55                  60

Gly Gly Ser Lys Lys Arg Lys Asp Ile Leu Glu Thr Tyr Lys Ala Asn
65                  70                  75                  80

-continued

```
Arg Pro Ser Thr Pro Asp Leu Leu Leu Glu Gln Ile Pro Tyr Val Glu
                85                  90                  95

Glu Leu Val Asp Ala Leu Gly Ile Lys Val Leu Lys Ile Glu Gly Phe
            100                 105                 110

Glu Ala Asp Asp Ile Ile Ala Thr Leu Ser Lys Lys Phe Glu Ser Asp
            115                 120                 125

Phe Glu Lys Val Asn Ile Ile Thr Gly Asp Lys Asp Leu Leu Gln Leu
130                 135                 140

Val Ser Asp Lys Val Phe Val Trp Arg Val Glu Arg Gly Ile Thr Asp
145                 150                 155                 160

Leu Val Leu Tyr Asp Arg Asn Lys Val Ile Glu Lys Tyr Gly Ile Tyr
                165                 170                 175

Pro Glu Gln Phe Lys Asp Tyr Leu Ser Leu Val Gly Asp Gln Ile Asp
            180                 185                 190

Asn Ile Pro Gly Val Lys Gly Ile Gly Lys Lys Thr Ala Val Ser Leu
            195                 200                 205

Leu Lys Lys Tyr Asn Ser Leu Glu Asn Val Leu Lys Asn Ile Asn Leu
210                 215                 220

Leu Thr Glu Lys Leu Arg Arg Leu Leu Glu Asp Ser Lys Glu Asp Leu
225                 230                 235                 240

Gln Lys Ser Ile Glu Leu Val Glu Leu Ile Tyr Asp Val Pro Met Asp
                245                 250                 255

Val Glu Lys Asp Glu Ile Ile Tyr Arg Gly Tyr Asn Pro Asp Lys Leu
            260                 265                 270

Leu Lys Val Leu Lys Lys Tyr Glu Phe Ser Ser Ile Ile Lys Glu Leu
            275                 280                 285

Asn Leu Gln Glu Lys Leu Glu Lys Glu Tyr Ile Leu Val Asp Asn Glu
290                 295                 300

Asp Lys Leu Lys Lys Leu Ala Glu Glu Ile Glu Lys Tyr Lys Thr Phe
305                 310                 315                 320

Ser Ile Asp Thr Glu Thr Thr Ser Leu Asp Pro Phe Glu Ala Lys Leu
                325                 330                 335

Val Gly Ile Ser Ile Ser Thr Met Glu Gly Lys Ala Tyr Tyr Ile Pro
            340                 345                 350

Val Ser His Phe Gly Ala Lys Asn Ile Ser Lys Ser Leu Ile Asp Lys
            355                 360                 365

Phe Leu Lys Gln Ile Leu Gln Glu Lys Asp Tyr Asn Ile Val Gly Gln
370                 375                 380

Asn Leu Lys Phe Asp Tyr Glu Ile Phe Lys Ser Met Gly Phe Ser Pro
385                 390                 395                 400

Asn Val Pro His Phe Asp Thr Met Ile Ala Ala Tyr Leu Leu Asn Pro
                405                 410                 415

Asp Glu Lys Arg Phe Asn Leu Glu Glu Leu Ser Leu Lys Tyr Leu Gly
            420                 425                 430

Tyr Lys Met Ile Ser Phe Asp Glu Leu Val Asn Glu Asn Val Pro Leu
            435                 440                 445

Phe Gly Asn Asp Phe Ser Tyr Val Pro Leu Glu Arg Ala Val Glu Tyr
450                 455                 460

Ser Cys Glu Asp Ala Asp Val Thr Tyr Arg Ile Phe Arg Lys Leu Gly
465                 470                 475                 480
```

```
Arg Lys Ile Tyr Glu Asn Glu Met Glu Lys Leu Phe Tyr Glu Ile Glu
            485                 490                 495

Met Pro Leu Ile Asp Val Leu Ser Glu Met Glu Leu Asn Gly Val Tyr
        500                 505                 510

Phe Asp Glu Glu Tyr Leu Lys Glu Leu Ser Lys Lys Tyr Gln Glu Lys
        515                 520                 525

Met Asp Gly Ile Lys Glu Lys Val Phe Glu Ile Ala Gly Glu Thr Phe
    530                 535                 540

Asn Leu Asn Ser Ser Thr Gln Val Ala Tyr Ile Leu Phe Glu Lys Leu
545                 550                 555                 560

Asn Ile Ala Pro Tyr Lys Lys Thr Ala Thr Gly Lys Phe Ser Thr Asn
                565                 570                 575

Ala Glu Val Leu Glu Glu Leu Ser Lys Glu His Glu Ile Ala Lys Leu
            580                 585                 590

Leu Leu Glu Tyr Arg Lys Tyr Gln Lys Leu Lys Ser Thr Tyr Ile Asp
        595                 600                 605

Ser Ile Pro Leu Ser Ile Asn Arg Lys Thr Asn Arg Val His Thr Thr
    610                 615                 620

Phe His Gln Thr Gly Thr Ser Thr Gly Arg Leu Ser Ser Ser Asn Pro
625                 630                 635                 640

Asn Leu Gln Asn Leu Pro Thr Arg Ser Glu Glu Gly Lys Glu Ile Arg
                645                 650                 655

Lys Ala Val Arg Pro Gln Arg Gln Asp Trp Trp Ile Leu Gly Ala Asp
            660                 665                 670

Tyr Ser Gln Ile Glu Leu Arg Val Leu Ala His Val Ser Lys Asp Glu
        675                 680                 685

Asn Leu Leu Lys Ala Phe Lys Glu Asp Leu Asp Ile His Thr Ile Thr
    690                 695                 700

Ala Ala Lys Ile Phe Gly Val Ser Glu Met Phe Val Ser Glu Gln Met
705                 710                 715                 720

Arg Arg Val Gly Lys Met Val Asn Phe Ala Ile Ile Tyr Gly Val Ser
                725                 730                 735

Pro Tyr Gly Leu Ser Lys Arg Ile Gly Leu Ser Val Ser Glu Thr Lys
            740                 745                 750

Lys Ile Ile Asp Asn Tyr Phe Arg Tyr Tyr Lys Gly Val Phe Glu Tyr
        755                 760                 765

Leu Lys Arg Met Lys Asp Glu Ala Arg Lys Lys Gly Tyr Val Thr Thr
    770                 775                 780

Leu Phe Gly Arg Arg Arg Tyr Ile Pro Gln Leu Arg Ser Lys Asn Gly
785                 790                 795                 800

Asn Arg Val Gln Glu Gly Glu Arg Ile Ala Val Asn Thr Pro Ile Gln
                805                 810                 815

Gly Thr Ala Ala Asp Ile Ile Lys Ile Ala Met Ile Asn Ile His Asn
            820                 825                 830

Arg Leu Lys Lys Glu Asn Leu Arg Ser Lys Met Ile Leu Gln Val His
        835                 840                 845

Asp Glu Leu Val Phe Glu Val Pro Asp Asn Glu Leu Glu Ile Val Lys
    850                 855                 860

Asp Leu Val Arg Asp Glu Met Glu Asn Ala Val Lys Leu Asp Val Pro
865                 870                 875                 880

Leu Lys Val Asp Val Tyr Tyr Gly Lys Glu Trp Glu
                885                 890
```

<210> SEQ ID NO 84
<211> LENGTH: 834
<212> TYPE: PRT
<213> ORGANISM: Thermus caldophilus
<220> FEATURE:
<223> OTHER INFORMATION: DNA polymerase

<400> SEQUENCE: 84

```
Met Glu Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Tyr Glu Ala Asp Asp Val Leu Ala Thr Leu Ala Lys
        115                 120                 125

Asn Pro Glu Lys Glu Gly Tyr Glu Val Arg Ile Leu Thr Ala Asp Arg
    130                 135                 140

Asp Leu Asp Gln Leu Val Ser Asp Arg Val Ala Val Leu His Pro Glu
145                 150                 155                 160

Gly His Leu Ile Thr Pro Glu Trp Leu Trp Gln Lys Tyr Gly Leu Lys
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Leu Leu Lys Asn Leu Asp Arg
    210                 215                 220

Val Lys Pro Glu Asn Val Arg Glu Lys Ile Lys Ala His Leu Glu Asp
225                 230                 235                 240

Leu Arg Leu Ser Leu Glu Leu Ser Arg Val Arg Thr Asp Leu Pro Leu
                245                 250                 255

Glu Val Asp Leu Ala Gln Gly Arg Glu Pro Asp Arg Glu Gly Leu Arg
            260                 265                 270

Ala Phe Leu Glu Arg Leu Glu Phe Gly Ser Leu Leu His Glu Phe Gly
        275                 280                 285

Leu Leu Glu Ala Pro Ala Pro Leu Glu Glu Ala Pro Trp Pro Pro Pro
    290                 295                 300

Glu Gly Ala Phe Val Gly Phe Val Leu Ser Arg Pro Glu Pro Met Trp
305                 310                 315                 320

Ala Glu Leu Lys Ala Leu Ala Ala Cys Arg Asp Gly Arg Val His Arg
                325                 330                 335

Ala Ala Asp Pro Leu Ala Gly Leu Lys Asp Leu Lys Glu Val Arg Gly
            340                 345                 350

Leu Leu Ala Lys Asp Leu Ala Val Leu Ala Ser Arg Glu Gly Leu Asp
        355                 360                 365
```

```
Leu Val Pro Gly Asp Asp Pro Met Leu Leu Ala Tyr Leu Leu Asp Pro
    370             375                 380

Ser Asn Thr Thr Pro Glu Gly Val Ala Arg Arg Tyr Gly Gly Glu Trp
385                 390                 395                 400

Thr Glu Asp Ala Ala His Arg Ala Leu Leu Ser Glu Arg Leu His Arg
                405                 410                 415

Asn Leu Leu Lys Arg Leu Gln Gly Glu Lys Leu Leu Trp Leu Tyr
                420                 425                 430

His Glu Val Glu Lys Pro Leu Ser Arg Val Leu Ala His Met Glu Ala
            435                 440                 445

Thr Gly Val Arg Leu Asp Val Ala Tyr Leu Gln Ala Leu Ser Leu Glu
    450                 455                 460

Leu Ala Glu Glu Ile Arg Arg Leu Glu Glu Val Phe Arg Leu Ala
465                 470                 475                 480

Gly His Pro Phe Asn Leu Asn Ser Arg Asp Gln Leu Glu Arg Val Leu
                485                 490                 495

Phe Asp Glu Leu Arg Leu Pro Ala Leu Gly Lys Thr Gln Lys Thr Gly
                500                 505                 510

Lys Arg Ser Thr Ser Ala Ala Val Leu Glu Ala Leu Arg Glu Ala His
                515                 520                 525

Pro Ile Val Glu Lys Ile Leu Gln His Arg Glu Leu Thr Lys Leu Lys
    530                 535                 540

Asn Thr Tyr Val Asp Pro Leu Pro Ser Leu Val His Pro Asn Thr Gly
545                 550                 555                 560

Arg Leu His Thr Arg Phe Asn Gln Thr Ala Thr Ala Thr Gly Arg Leu
                565                 570                 575

Ser Ser Ser Asp Pro Asn Leu Gln Asn Ile Pro Val Arg Thr Pro Leu
                580                 585                 590

Gly Gln Arg Ile Arg Arg Ala Phe Val Ala Glu Ala Gly Trp Ala Leu
            595                 600                 605

Val Ala Leu Asp Tyr Ser Gln Ile Glu Leu Arg Val Leu Ala His Leu
    610                 615                 620

Ser Gly Asp Glu Asn Leu Ile Arg Val Phe Gln Glu Gly Lys Asp Ile
625                 630                 635                 640

His Thr Gln Thr Ala Ser Trp Met Phe Gly Val Pro Pro Glu Ala Val
                645                 650                 655

Asp Pro Leu Met Arg Arg Ala Ala Lys Thr Val Asn Phe Gly Val Leu
                660                 665                 670

Tyr Gly Met Ser Ala His Arg Leu Ser Gln Glu Leu Ala Ile Pro Tyr
            675                 680                 685

Glu Glu Ala Val Ala Phe Ile Glu Arg Tyr Phe Gln Ser Phe Pro Lys
    690                 695                 700

Val Arg Ala Trp Ile Glu Lys Thr Leu Glu Glu Gly Arg Lys Arg Gly
705                 710                 715                 720

Tyr Val Glu Thr Leu Phe Gly Arg Arg Tyr Val Pro Asp Leu Asn
                725                 730                 735

Ala Arg Val Lys Ser Val Arg Glu Ala Ala Glu Arg Met Ala Phe Asn
                740                 745                 750

Met Pro Val Gln Gly Thr Ala Ala Asp Leu Met Lys Leu Ala Met Val
            755                 760                 765

Lys Leu Phe Pro Arg Leu Arg Glu Met Gly Ala Arg Met Leu Leu Gln
770                 775                 780
```

-continued

```
Val His Asp Glu Leu Leu Leu Glu Ala Pro Gln Ala Gly Ala Glu Glu
785                 790                 795                 800

Val Ala Ala Leu Ala Lys Glu Ala Met Glu Lys Ala Tyr Pro Leu Ala
                805                 810                 815

Val Pro Leu Glu Val Glu Val Gly Met Gly Glu Asp Trp Leu Ser Ala
            820                 825                 830

Lys Gly

<210> SEQ ID NO 85
<211> LENGTH: 893
<212> TYPE: PRT
<213> ORGANISM: Thermotoga neapolitana
<220> FEATURE:
<223> OTHER INFORMATION: DNA polymerase

<400> SEQUENCE: 85

Met Ala Arg Leu Phe Leu Phe Asp Gly Thr Ala Leu Ala Tyr Arg Ala
1               5                   10                  15

Tyr Tyr Ala Leu Asp Arg Ser Leu Ser Thr Ser Thr Gly Ile Pro Thr
            20                  25                  30

Asn Ala Val Tyr Gly Val Ala Arg Met Leu Val Lys Phe Ile Lys Glu
        35                  40                  45

His Ile Ile Pro Glu Lys Asp Tyr Ala Ala Val Ala Phe Asp Lys Lys
    50                  55                  60

Ala Ala Thr Phe Arg His Lys Leu Leu Val Ser Asp Lys Ala Gln Arg
65                  70                  75                  80

Pro Lys Thr Pro Ala Leu Leu Val Gln Gln Leu Pro Tyr Ile Lys Arg
                85                  90                  95

Leu Ile Glu Ala Leu Gly Phe Lys Val Leu Glu Leu Glu Gly Tyr Glu
            100                 105                 110

Ala Asp Asp Ile Ile Ala Thr Leu Ala Val Arg Ala Ala Arg Phe Leu
        115                 120                 125

Met Arg Phe Ser Leu Ile Thr Gly Asp Lys Asp Met Leu Gln Leu Val
    130                 135                 140

Asn Glu Lys Ile Lys Val Trp Arg Ile Val Lys Gly Ile Ser Asp Leu
145                 150                 155                 160

Glu Leu Tyr Asp Ser Lys Lys Val Lys Glu Arg Tyr Gly Val Glu Pro
                165                 170                 175

His Gln Ile Pro Asp Leu Leu Ala Leu Thr Gly Asp Asp Ile Asp Asn
            180                 185                 190

Ile Pro Gly Val Thr Gly Ile Gly Glu Lys Thr Ala Val Gln Leu Leu
        195                 200                 205

Gly Lys Tyr Arg Asn Leu Glu Tyr Ile Leu Glu His Ala Arg Glu Leu
    210                 215                 220

Pro Gln Arg Val Arg Lys Ala Leu Leu Arg Asp Arg Glu Val Ala Ile
225                 230                 235                 240

Leu Ser Lys Lys Leu Ala Thr Leu Val Thr Asn Ala Pro Val Glu Val
                245                 250                 255

Asp Trp Glu Glu Met Lys Tyr Arg Gly Tyr Asp Lys Arg Lys Leu Leu
            260                 265                 270

Pro Ile Leu Lys Glu Leu Glu Phe Ala Ser Ile Met Lys Glu Leu Gln
        275                 280                 285

Leu Tyr Glu Glu Ala Glu Pro Thr Gly Tyr Glu Ile Val Lys Asp His
    290                 295                 300
```

```
Lys Thr Phe Glu Asp Leu Ile Glu Lys Leu Lys Glu Val Pro Ser Phe
305                 310                 315                 320

Ala Leu Asp Leu Glu Thr Ser Ser Leu Asp Pro Phe Asn Cys Glu Ile
            325                 330                 335

Val Gly Ile Ser Val Ser Phe Lys Pro Lys Thr Ala Tyr Tyr Ile Pro
            340                 345                 350

Leu His His Arg Asn Ala His Asn Leu Asp Glu Thr Leu Val Leu Ser
            355                 360                 365

Lys Leu Lys Glu Ile Leu Glu Asp Pro Ser Ser Lys Ile Val Gly Gln
    370                 375                 380

Asn Leu Lys Tyr Asp Tyr Lys Val Leu Met Val Lys Gly Ile Ser Pro
385                 390                 395                 400

Val Tyr Pro His Phe Asp Thr Met Ile Ala Ala Tyr Leu Leu Glu Pro
                405                 410                 415

Asn Glu Lys Lys Phe Asn Leu Glu Asp Leu Ser Leu Lys Phe Leu Gly
                420                 425                 430

Tyr Lys Met Thr Ser Tyr Gln Glu Leu Met Ser Phe Ser Ser Pro Leu
            435                 440                 445

Phe Gly Phe Ser Phe Ala Asp Val Pro Val Asp Lys Ala Ala Glu Tyr
    450                 455                 460

Ser Cys Glu Asp Ala Asp Ile Thr Tyr Arg Leu Tyr Lys Ile Leu Ser
465                 470                 475                 480

Met Lys Leu His Glu Ala Glu Leu Glu Asn Val Phe Tyr Arg Ile Glu
                485                 490                 495

Met Pro Leu Val Asn Val Leu Ala Arg Met Glu Phe Asn Trp Val Tyr
            500                 505                 510

Val Asp Thr Glu Phe Leu Lys Lys Leu Ser Glu Glu Tyr Gly Lys Lys
            515                 520                 525

Leu Glu Glu Leu Ala Glu Lys Ile Tyr Gln Ile Ala Gly Glu Pro Phe
    530                 535                 540

Asn Ile Asn Ser Pro Lys Gln Val Ser Asn Ile Leu Phe Glu Lys Leu
545                 550                 555                 560

Gly Ile Lys Pro Arg Gly Lys Thr Thr Lys Thr Gly Asp Tyr Ser Thr
                565                 570                 575

Arg Ile Glu Val Leu Glu Glu Ile Ala Asn Glu His Glu Ile Val Pro
            580                 585                 590

Leu Ile Leu Glu Phe Arg Lys Ile Leu Lys Leu Lys Ser Thr Tyr Ile
            595                 600                 605

Asp Thr Leu Pro Lys Leu Val Asn Pro Lys Thr Gly Arg Phe His Ala
    610                 615                 620

Ser Phe His Gln Thr Gly Thr Ala Thr Gly Arg Leu Ser Ser Ser Asp
625                 630                 635                 640

Pro Asn Leu Gln Asn Leu Pro Thr Lys Ser Glu Glu Gly Lys Glu Ile
                645                 650                 655

Arg Lys Ala Ile Val Pro Gln Asp Pro Asp Trp Trp Ile Val Ser Ala
                660                 665                 670

Asp Tyr Ser Gln Ile Glu Leu Arg Ile Leu Ala His Leu Ser Gly Asp
            675                 680                 685

Glu Asn Leu Val Lys Ala Phe Glu Gly Ile Asp Val His Thr Leu
    690                 695                 700

Thr Ala Ser Arg Ile Tyr Asn Val Lys Pro Glu Glu Val Asn Glu Glu
705                 710                 715                 720
```

```
Met Arg Arg Val Gly Lys Met Val Asn Phe Ser Ile Ile Tyr Gly Val
            725             730             735

Thr Pro Tyr Gly Leu Ser Val Arg Leu Gly Ile Pro Val Lys Glu Ala
            740             745             750

Glu Lys Met Ile Ile Ser Tyr Phe Thr Leu Tyr Pro Lys Val Arg Ser
            755             760             765

Tyr Ile Gln Gln Val Val Ala Glu Ala Lys Glu Lys Gly Tyr Val Arg
            770             775             780

Thr Leu Phe Gly Arg Lys Arg Asp Ile Pro Gln Leu Met Ala Arg Asp
785             790             795             800

Lys Asn Thr Gln Ser Glu Gly Glu Arg Ile Ala Ile Asn Thr Pro Ile
            805             810             815

Gln Gly Thr Ala Ala Asp Ile Ile Lys Leu Ala Met Ile Asp Ile Asp
            820             825             830

Glu Glu Leu Arg Lys Arg Asn Met Lys Ser Arg Met Ile Ile Gln Val
            835             840             845

His Asp Glu Leu Val Phe Glu Val Pro Asp Glu Glu Lys Glu Glu Leu
    850             855             860

Val Asp Leu Val Lys Asn Lys Met Thr Asn Val Val Lys Leu Ser Val
865             870             875             880

Pro Leu Glu Val Asp Ile Ser Ile Gly Lys Ser Trp Ser
            885             890
```

DNA POLYMERASES AND RELATED METHODS

CROSS-REFERENCE TO RELATED APPLICATIONS

This application is a divisional of U.S. application Ser. No. 14/601,168, filed on Jan. 20, 2015, now U.S. Pat. No. 9,738,876, which is a divisional of U.S. application Ser. No. 11/873,896, filed on Oct. 17, 2007, now U.S. Pat. No. 8,962,293, which claims the benefit of priority to U.S. Provisional Application No. 60/852,882, filed on Oct. 18, 2006, the entire contents of each of which are hereby incorporated by reference in their entirety.

REFERENCE TO A "SEQUENCE LISTING," A TABLE, OR A COMPUTER PROGRAM LISTING APPENDIX SUBMITTED AS AN ASCII TEXT FILE

The Sequence Listing written in file-501-1.TXT, created on Jan. 12, 2011, 156,000 bytes, machine format IBM-PC, MS-Windows operating system, is hereby incorporated by reference in its entirety for all purposes.

FIELD OF INVENTION

The present invention lies in the field of DNA polymerases and their use in various applications, including nucleic acid primer extension and amplification.

BACKGROUND OF THE INVENTION

DNA polymerases are responsible for the replication and maintenance of the genome, a role that is central to accurately transmitting genetic information from generation to generation. DNA polymerases function in cells as the enzymes responsible for the synthesis of DNA. They polymerize deoxyribonucleoside triphosphates in the presence of a metal activator, such as $Mg^{2+}$, in an order dictated by the DNA template or polynucleotide template that is copied. In vivo, DNA polymerases participate in a spectrum of DNA synthetic processes including DNA replication, DNA repair, recombination, and gene amplification. During each DNA synthetic process, the DNA template is copied once or at most a few times to produce identical replicas. In contrast, in vitro, DNA replication can be repeated many times such as, for example, during polymerase chain reaction (see, e.g., U.S. Pat. No. 4,683,202 to Mullis).

In the initial studies with polymerase chain reaction (PCR), the DNA polymerase was added at the start of each round of DNA replication (see U.S. Pat. No. 4,683,202, supra). Subsequently, it was determined that thermostable DNA polymerases could be obtained from bacteria that grow at elevated temperatures, and that these enzymes need to be added only once (see U.S. Pat. No. 4,889,818 to Gelfand and U.S. Pat. No. 4,965,188 to Mullis). At the elevated temperatures used during PCR, these enzymes are not irreversibly inactivated. As a result, one can carry out repetitive cycles of polymerase chain reactions without adding fresh enzymes at the start of each synthetic addition process. DNA polymerases, particularly thermostable polymerases, are the key to a large number of techniques in recombinant DNA studies and in medical diagnosis of disease. For diagnostic applications in particular, a target nucleic acid sequence may be only a small portion of the DNA or RNA in question, so it may be difficult to detect the presence of a target nucleic acid sequence without amplification. Due to the importance of DNA polymerases in biotechnology and medicine, it would be highly advantageous to generate DNA polymerase mutants having desired enzymatic properties such as, for example, improved primer extension rates, reverse transcription efficiency, or amplification ability.

The overall folding pattern of polymerases resembles the human right hand and contains three distinct subdomains of palm, fingers, and thumb. (See Beese et al., *Science* 260: 352-355, 1993); Patel et al., *Biochemistry* 34:5351-5363, 1995). While the structure of the fingers and thumb subdomains vary greatly between polymerases that differ in size and in cellular functions, the catalytic palm subdomains are all superimposable. For example, motif A, which interacts with the incoming dNTP and stabilizes the transition state during chemical catalysis, is superimposable with a mean deviation of about one Å amongst mammalian pol α and prokaryotic pol I family DNA polymerases (Wang et al., *Cell* 89:1087-1099, 1997). Motif A begins structurally at an antiparallel β-strand containing predominantly hydrophobic residues and continues to an α-helix. The primary amino acid sequence of DNA polymerase active sites is exceptionally conserved. In the case of motif A, for example, the sequence DYSQIELR (SEQ ID NO:22) is retained in polymerases from organisms separated by many millions years of evolution, including, e.g., *Thermus aquaticus, Chlamydia trachomatis*, and *Escherichia coli*. Taken together, these observations indicate that polymerases function by similar catalytic mechanisms.

In addition to being well-conserved, the active site of DNA polymerases has also been shown to be relatively mutable, capable of accommodating certain amino acid substitutions without reducing DNA polymerase activity significantly. (See, e.g., U.S. Pat. No. 6,602,695 to Patel et al.) Such mutant DNA polymerases can offer various selective advantages in, e.g., diagnostic and research applications comprising nucleic acid synthesis reactions. Thus, there is a need in the art for identification of amino acid positions amenable to mutation to yield improved polymerase activity, including, for example, improved extension rates, reverse transcription efficiency, or amplification ability. The present invention, as set forth herein, meets these and other needs.

BRIEF SUMMARY OF THE INVENTION

The present invention provides DNA polymerases having improved enzyme activity relative to the corresponding unmodified polymerase and which are useful in a variety of nucleic acid synthesis applications. In some embodiments, the polymerase comprises an amino acid sequence having at least one of the following motifs in the polymerase domain:
a) $X_{a1}$-$X_{a2}$-$X_{a3}$-$X_{a4}$-R-$X_{a6}$-$X_{a7}$-$X_{a8}$-K-L-$X_{a11}$-$X_{a12}$-T-Y-$X_{a15}$-$X_{a16}$ (SEQ ID NO:1);
  wherein $X_{a1}$ is I or L;
  $X_{a2}$ is L or Q;
  $X_{a3}$ is Q, H or E;
  $X_{a4}$ is Y, H or F;
  $X_{a6}$ is E, Q or K;
  $X_{a7}$ is I, L or Y;
  $X_{a8}$ is an amino acid other than Q, T, M, G or L;
  $X_{a11}$ is K or Q;
  $X_{a12}$ is S or N;
  $X_{a15}$ is I or V; and
  $X_{a16}$ is E or D;
b) T-G-R-L-S-S-$X_{b7}$-$X_{b8}$-P-N-L-Q-N (SEQ ID NO:2); wherein
  $X_{b7}$ is S or T; and
  $X_{b8}$ is an amino acid other than D, E or N; and
c) $X_{c1}$-$X_{c2}$-$X_{c3}$-$X_{c4}$-$X_{c5}$-$X_{c6}$-$X_{c7}$-D-Y-S-Q-I-E-L-R (SEQ ID NO:3); wherein
  $X_{c1}$ is G, N, or D;
  $X_{c2}$ is W or H;
  $X_{c3}$ is W, A, L, or V;

$X_{c4}$ is an amino acid other than I or L;

$X_{c5}$ is V, F or L;

$X_{c6}$ is an amino acid other than S, A, V, or G; and $X_{c7}$ is A or L, wherein the polymerase has an improved nucleic acid extension rate and/or an improved reverse transcription efficiency relative to an otherwise identical polymerase wherein $X_{a8}$ is an amino acid selected from Q, T, M, G or L; $X_{b8}$ is an amino acid selected from D, E or N and/or $X_{c6}$ is an amino acid selected from S, A, V, or G (i.e., a reference polymerase). In some embodiments of the reference polymerase (e.g., Z05 or CS5/CS6), $X_{a8}$ is Q, T, M, G or L, $X_{b8}$ is D, E or N, $X_{c4}$ is I or L, and $X_{c6}$ is S, A, V, or G (SEQ ID NOS:23 and 24). In some embodiments of the reference polymerase, $X_{b8}$ is D, E or N (SEQ ID NOS:25 and 26).

With respect to motif a) $X_{a1}$-$X_{a2}$-$X_{a3}$-$X_{a4}$-R-$X_{a6}$-$X_{a7}$-$X_{a8}$-K-L-$X_{a11}$-$X_{a12}$-T-Y-$X_{a15}$-$X_{a16}$ (SEQ ID NO:1), in some embodiments, $X_{a8}$ is a D- or L-amino acid selected from the group consisting of: A, C, D, E, F, H, I, K, N, P, R, S, V, W, Y (SEQ ID NO:27), and analogs thereof. In some embodiments, $X_{a8}$ is an amino acid selected from the group consisting of: R, K and N (SEQ ID NO:28). In some embodiments, $X_{a8}$ is Arginine (R) (SEQ ID NO:29).

With respect to motif b) T-G-R-L-S-S-$X_{b7}$-$X_{b8}$-P-N-L-Q-N (SEQ ID NO:2), in some embodiments, $X_{b8}$ is D- or L-amino acid selected from the group consisting of: A, C, F, G, H, I, K, L, M, P, Q, R, S, T, V, W, Y (SEQ ID NO:30), and analogs thereof. In some embodiments, $X_{b8}$ is an amino acid selected from the group consisting of: G, A, S, T, R, K, Q, L, V and I (SEQ ID NO:31). In some embodiments, $X_{b8}$ is an amino acid selected from the group consisting of: G, T, R, K and L (SEQ ID NO:32).

With respect to motif c) $X_{c1}$-$X_{c2}$-$X_{c3}$-$X_{c4}$-$X_{c5}$-$X_{c6}$-$X_{c7}$-D-Y-S-Q-I-E-L-R (SEQ ID NO:3), in some embodiments, $X_{c4}$ is a D- or L-amino acid selected from the group consisting of: A, C, D, E, F, G, H, K, M, N, P, Q, R, S, T, V, W, Y (SEQ ID NO:33), and analogs thereof. In some embodiments, $X_{c4}$ is an amino acid selected from the group consisting of F and Y (SEQ ID NO:34). In some embodiments, $X_{c4}$ is phenylalanine (F) (SEQ ID NO:35). In some embodiments, $X_{c6}$ is an amino acid selected from the group consisting of C, D, E, F, H, I, K, L, M, N, P, Q, R, T, W and Y (SEQ ID NO:36). In some embodiments, $X_{c6}$ is an amino acid selected from the group consisting of F and Y (SEQ ID NO:37). In some embodiments, $X_{c6}$ is phenylalanine (F) (SEQ ID NO:38).

In some embodiments, the improved polymerases (e.g., Z05 or CS5/CS6) that comprise at least one of Arginine (R) at position $X_{a8}$; Glycine (G) at position $X_{b8}$; Phenylalanine (F) at position $X_{c4}$; and/or Phenylalanine (F) at position $X_{c6}$ (SEQ ID NOS:39-68).

In some embodiments, the DNA polymerases of the invention are modified versions of an unmodified polymerase. In its unmodified form, the polymerase includes an amino acid sequence having the following motifs in the polymerase domain:

$X_{a1}$-$X_{a2}$-$X_{a3}$-$X_{a4}$-R-$X_{a6}$-$X_{a7}$-$X_{a8}$-K-L-$X_{a11}$-$X_{a12}$-T-Y-$X_{a15}$-$X_{a16}$ (SEQ ID NO:69); wherein $X_{a1}$ is I or L; $X_{a2}$ is L or Q; $X_{a3}$ is Q, H or E; $X_{a4}$ is Y, H or F; $X_{a6}$ is E, Q or K; $X_{a7}$ is I, L or Y; $X_{a8}$ is Q, T, M, G or L; $X_{a11}$ is K or Q; $X_{a12}$ is S or N; $X_{a15}$ is I or V; and $X_{a16}$ is E or D;

T-G-R-L-S-S-$X_{b7}$-$X_{b8}$-P-N-L-Q-N (SEQ ID NO:70); wherein $X_{b7}$ is S or T; and $X_{b8}$ is D, E or N; and $X_{c1}$-$X_{c2}$-$X_{c3}$-$X_{c4}$-$X_{c5}$-$X_{c6}$-$X_{c7}$-D-Y-S-Q-I-E-L-R (SEQ ID NO:71); wherein $X_{c1}$ is G, N or D; $X_{c2}$ is W or H; $X_{c3}$ is W, A, L or V; $X_{c4}$ is I or L; $X_{c5}$ is V, F or L; $X_{c6}$ is S, A, V or G; and $X_{c7}$ is A or L.

Various DNA polymerases are amenable to mutation according to the present invention. Particularly suitable are thermostable polymerases, including wild-type or naturally occurring thermostable polymerases from various species of thermophilic bacteria, as well as thermostable polymerases derived from such wild-type or naturally occurring enzymes by amino acid substitution, insertion, or deletion, or other modification. Exemplary unmodified forms of polymerase include, e.g., CS5, CS6 or Z05 DNA polymerase, or a functional DNA polymerase having at least 90%, 91%, 92%, 93%, 94%, 95%, 96%, 97%, 98% or 99% sequence identity thereto. Other unmodified polymerases include, e.g., DNA polymerases from any of the following species of thermophilic bacteria (or a functional DNA polymerase having at least 90%, 91%, 92%, 93%, 94%, 95%, 96%, 97%, 98% or 99% sequence identity to such a polymerase): *Thermotoga maritima; Thermus aquaticus; Thermus thermophilus; Thermus flavus; Thermus filiformis; Thermus* sp. sps17; *Thermus* sp. Z05; *Thermotoga neopolitana; Thermosipho africanus; Thermus caldophilus* or *Bacillus caldotenax*. Suitable polymerases also include those having reverse transcriptase (RT) activity and/or the ability to incorporate unconventional nucleotides, such as ribonucleotides or other 2'-modified nucleotides.

In some embodiments, the unmodified form of the polymerase comprises a chimeric polymerase. In one embodiment, for example, the unmodified form of the chimeric polymerase is CS5 DNA polymerase (SEQ ID NO:18), CS6 DNA polymerase (SEQ ID NO:19), or a polymerase having at least 90%, 91%, 92%, 93%, 94%, 95%, 96%, 97%, 98% or 99% sequence identity to the CS5 DNA polymerase or the CS6 DNA polymerase. In specific variations, the unmodified form of the chimeric polymerase includes one or more amino acid substitutions relative to SEQ ID NO:18 or SEQ ID NO:19 that are selected from G46E, L329A, and E678G. For example, the unmodified form of the mutant or improved polymerase can be G46E CS5; G46E L329A CS5; G46E E678G CS5; or G46E L329A E678G CS5. In exemplary embodiments, these unmodified forms are substituted to provide a mutant polymerase including one or more amino acid substitutions selected from S671F, D640G, Q601R, and I669F. For example, the mutant or improved DNA polymerase can be any one of the following: G46E S671F CS5; G46E D640G CS5; G46E Q601R CS5; G46E I669F CS5; G46E D640G S671F CS5; G46E L329A S671F CS5; G46E L329A D640G CS5; G46E L329A Q601R CS5; G46E L329A I669F CS5; G46E L329A D640G S671F CS5; G46E S671F E678G CS5; G46E D640G E678G CS5; G46E Q601R E678G CS5; G46E I669F E678G CS5; G46E L329A S671F E678G CS5; G46E L329A D640G E678G CS5; G46E L329A Q601R E678G CS5; G46E L329A Q601R D640G I669F S671F E678G CS5; G46E L329A I669F E678G CS5; or the like.

In some embodiments, the polymerase is a CS5 polymerase (SEQ ID NO:15), a CS6 polymerase (SEQ ID NO:16) or a Z05 polymerase (SEQ ID NO:6), wherein $X_{b8}$ is an amino acid selected from the group consisting of: G, T, R, K and L. For example, the CS5 or CS6 polymerase can be selected from the following: D640G, D640T, D640R, D640K and D640L. The Z05 polymerase can be selected from the group consisting of: D580G, D580T, D580R, D580K and D580L.

The mutant or improved polymerase can include other, non-substitutional modifications. One such modification is a thermally reversible covalent modification that inactivates the enzyme, but which is reversed to activate the enzyme upon incubation at an elevated temperature, such as a temperature typically used for primer extension. In one embodiment, the mutant or improved polymerase comprising the thermally reversible covalent modification is produced by a reaction, carried out at alkaline pH at a temperature that is less than about 25° C., of a mixture of a thermostable DNA polymerase and a dicarboxylic acid anhydride having one of the following formulas I or II:

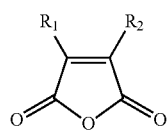

(I)

wherein $R_1$ and $R_2$ are hydrogen or organic radicals, which may be linked; or

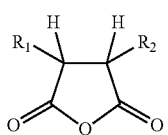

(II)

wherein $R_1$ and $R_2$ are organic radicals, which may linked, and the hydrogens are cis. In a specific variation of such an enzyme, the unmodified form of the polymerase is G64E CS5.

In some embodiments, the extension rate is determined using a single-stranded DNA as a template (e.g, M13mp18, HIV), primed with an appropriate primer (e.g., a polynucleotide of the nucleic acid sequence 5'-GGGAAGGGC-GATCGGTGCGGGCCTCTTCGC-3' (SEQ ID NO:72)), and detecting formation of double-stranded DNA by measuring the incorporation of a fluorophore at regular time intervals (e.g., every 5, 10, 15, 20, 30 or 60 seconds), as described herein. The extension rate of a polymerase of the invention can be compared to the extension rate of a reference polymerase (e.g., a naturally occurring or unmodified polymerase), over a preselected unit of time, as described herein.

In various other aspects, the present invention provides a recombinant nucleic acid encoding a mutant or improved DNA polymerase as described herein, a vector comprising the recombinant nucleic acid, and a host cell transformed with the vector. In certain embodiments, the vector is an expression vector. Host cells comprising such expression vectors are useful in methods of the invention for producing the mutant or improved polymerase by culturing the host cells under conditions suitable for expression of the recombinant nucleic acid. The polymerases of the invention may be contained in reaction mixtures and/or kits. The embodiments of the recombinant nucleic acids, host cells, vectors, expression vectors, reaction mixtures and kits are as described above and herein.

In yet another aspect, a method for conducting primer extension is provided. The method generally includes contacting a mutant or improved DNA polymerase of the invention with a primer, a polynucleotide template, and free nucleotides under conditions suitable for extension of the primer, thereby producing an extended primer. The polynucleotide template can be, for example, an RNA or DNA template. The free nucleotides can include unconventional nucleotides such as, e.g., ribonucleotides and/or labeled nucleotides. Further, the primer and/or template can include one or more nucleotide analogs. In some variations, the primer extension method is a method for polynucleotide amplification that includes contacting the mutant or improved DNA polymerase with a primer pair, the polynucleotide template, and the free nucleotides under conditions suitable for amplification of the polynucleotide.

The present invention also provides a kit useful in such a primer extension method. Generally, the kit includes at least one container providing a mutant or improved DNA polymerase as described herein. In certain embodiments, the kit further includes one or more additional containers providing one or more additional reagents. For example, in specific variations, the one or more additional containers provide free nucleotides; a buffer suitable for primer extension; and/or a primer hybridizable, under primer extension conditions, to a predetermined polynucleotide template.

Further provided are reaction mixtures comprising the polymerases of the invention. The reactions mixtures can also contain a template nucleic acid (DNA and/or RNA), one or more primer or probe polynucleotides, free nucleotides (including, e.g., deoxyribonucleotides, ribonucleotides, labeled nucleotides, unconventional nucleotides), buffers, salts, labels (e.g., fluorophores).

DEFINITIONS

Unless defined otherwise, all technical and scientific terms used herein have the same meaning as commonly understood by one of ordinary skill in the art to which this invention pertains. Although essentially any methods and materials similar to those described herein can be used in the practice or testing of the present invention, only exemplary methods and materials are described. For purposes of the present invention, the following terms are defined below.

The terms "a," "an," and "the" include plural referents, unless the context clearly indicates otherwise.

An "amino acid" refers to any monomer unit that can be incorporated into a peptide, polypeptide, or protein. As used herein, the term "amino acid" includes the following twenty natural or genetically encoded alpha-amino acids: alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), lysine (Lys or K), methionine (Met or M), phenylalanine (Phe or F), proline (Pro or P), serine (Ser or S), threonine (Thr or T), tryptophan (Trp or W), tyrosine (Tyr or Y), and valine (Val or V). The structures of these twenty natural amino acids are shown in, e.g., Stryer et al., *Biochemistry*, 5$^{th}$ ed., Freeman and Company (2002), which is incorporated by reference. Additional amino acids, such as selenocysteine and pyrrolysine, can also be genetically coded for (Stadtman (1996) "Selenocysteine," *Annu Rev Biochem.* 65:83-100 and Ibba et al. (2002) "Genetic code: introducing pyrrolysine," *Curr Biol.* 12(13):R464-R466, which are both incorporated by reference). The term "amino acid" also includes unnatural amino acids, modified amino acids (e.g., having modified side chains and/or backbones), and amino acid analogs. See, e.g., Zhang et al. (2004) "Selective incorporation of 5-hydroxytryptophan into proteins in mammalian cells," *Proc. Natl. Acad. Sci. U.S.A.* 101(24):8882-8887, Anderson et al. (2004) "An expanded genetic code with a functional quadruplet codon" *Proc. Natl. Acad. Sci. U.S.A.* 101(20):7566-7571, Ikeda et al. (2003) "Synthesis of a novel histidine analogue and its efficient incorporation into a protein in vivo," *Protein Eng. Des. Sel.* 16(9):699-706, Chin et al. (2003) "An Expanded Eukaryotic Genetic Code," *Science* 301(5635):964-967, James et al. (2001) "Kinetic characterization of ribonuclease S mutants containing photoisomerizable phenylazophenylalanine residues," *Protein Eng. Des. Sel.* 14(12):983-991, Kohrer et al. (2001) "Import of amber and ochre suppressor tRNAs into mammalian cells: A general approach to site-specific insertion of amino acid analogues into proteins," *Proc. Natl. Acad. Sci. U.S.A.* 98(25): 14310-14315, Bacher et al. (2001) "Selection and Characterization of *Escherichia coli* Variants Capable of Growth on an Otherwise Toxic Tryptophan Analogue," *J. Bacteriol.* 183(18):5414-5425, Hamano-Takaku et al. (2000) "A Mutant *Escherichia coli* Tyrosyl-tRNA Synthetase Utilizes the Unnatural Amino Acid Azatyrosine More Efficiently than Tyrosine," *J. Biol. Chem.* 275(51): 40324-40328, and Budisa et al. (2001) "Proteins with {beta}-(thienopyrrolyl)alanines as alternative chromophores and pharmaceutically active amino acids," *Protein Sci.* 10(7):1281-1292, which are each incorporated by reference.

To further illustrate, an amino acid is typically an organic acid that includes a substituted or unsubstituted amino group, a substituted or unsubstituted carboxy group, and one or more side chains or groups, or analogs of any of these groups. Exemplary side chains include, e.g., thiol, seleno, sulfonyl, alkyl, aryl, acyl, keto, azido, hydroxyl, hydrazine, cyano, halo, hydrazide, alkenyl, alkynl, ether, borate, boronate, phospho, phosphono, phosphine, heterocyclic, enone, imine, aldehyde, ester, thioacid, hydroxylamine, or any combination of these groups. Other representative amino acids include, but are not limited to, amino acids comprising photoactivatable cross-linkers, metal binding amino acids, spin-labeled amino acids, fluorescent amino acids, metal-containing amino acids, amino acids with novel functional groups, amino acids that covalently or noncovalently interact with other molecules, photocaged and/or photoisomerizable amino acids, radioactive amino acids, amino acids comprising biotin or a biotin analog, glycosylated amino acids, other carbohydrate modified amino acids, amino acids comprising polyethylene glycol or polyether, heavy atom substituted amino acids, chemically cleavable and/or photocleavable amino acids, carbon-linked sugar-containing amino acids, redox-active amino acids, amino thioacid containing amino acids, and amino acids comprising one or more toxic moieties.

The term "mutant," in the context of DNA polymerases of the present invention, means a polypeptide, typically recombinant, that comprises one or more amino acid substitutions relative to a corresponding, functional DNA polymerase.

The term "unmodified form," in the context of a mutant polymerase, is a term used herein for purposes of defining a mutant DNA polymerase of the present invention: the term "unmodified form" refers to a functional DNA polymerase that has the amino acid sequence of the mutant polymerase except at one or more amino acid position(s) specified as characterizing the mutant polymerase. Thus, reference to a mutant DNA polymerase in terms of (a) its unmodified form and (b) one or more specified amino acid substitutions means that, with the exception of the specified amino acid substitution(s), the mutant polymerase otherwise has an amino acid sequence identical to the unmodified form in the specified motif. The polymerase may contain additional mutations to provide desired functionality, e.g., improved incorporation of dideoxyribonucleotides, ribonucleotides, ribonucleotide analogs, dye-labeled nucleotides, modulating 5'-nuclease activity, modulating 3'-nuclease (or proofreading) activity, or the like. Accordingly, in carrying out the present invention as described herein, the unmodified form of a DNA polymerase is predetermined. The unmodified form of a DNA polymerase can be, for example, a wild-type and/or a naturally occurring DNA polymerase, or a DNA polymerase that has already been intentionally modified. An unmodified form of the polymerase is preferably a thermostable DNA polymerases, such as DNA polymerases from various thermophilic bacteria, as well as functional variants thereof having substantial sequence identity to a wild-type or naturally occurring thermostable polymerase Such variants can include, for example, chimeric DNA polymerases such as, for example, the chimeric DNA polymerases described in U.S. Pat. No. 6,228,628 and U.S. Application Publication No. 2004/0005599, which are incorporated by reference herein in their entirety. In certain embodiments, the unmodified form of a polymerase has reverse transcriptase (RT) activity.

The term "thermostable polymerase," refers to an enzyme that is stable to heat, is heat resistant, and retains sufficient activity to effect subsequent primer extension reactions and does not become irreversibly denatured (inactivated) when subjected to the elevated temperatures for the time necessary to effect denaturation of double-stranded nucleic acids. The heating conditions necessary for nucleic acid denaturation are well known in the art and are exemplified in, e.g., U.S. Pat. Nos. 4,683,202, 4,683,195, and 4,965,188, which are incorporated herein by reference. As used herein, a thermostable polymerase is suitable for use in a temperature cycling reaction such as the polymerase chain reaction ("PCR"). Irreversible denaturation for purposes herein refers to permanent and complete loss of enzymatic activity. For a thermostable polymerase, enzymatic activity refers to the catalysis of the combination of the nucleotides in the proper manner to form primer extension products that are complementary to a template nucleic acid strand. Thermostable DNA polymerases from thermophilic bacteria include, e.g., DNA polymerases from *Thermotoga maritima, Thermus aquaticus, Thermus thermophilus, Thermus flavus, Thermus filiformis, Thermus* species sps17, *Thermus* species Z05, *Thermus caldophilus, Bacillus caldotenax, Thermotoga neopolitana*, and *Thermosipho africanus*.

As used herein, a "chimeric" protein refers to a protein whose amino acid sequence represents a fusion product of subsequences of the amino acid sequences from at least two distinct proteins. A chimeric protein typically is not produced by direct manipulation of amino acid sequences, but, rather, is expressed from a "chimeric" gene that encodes the chimeric amino acid sequence. In certain embodiments, for example, an unmodified form of a mutant DNA polymerase of the present invention is a chimeric protein that consists of an amino-terminal (N-terminal) region derived from a *Thermus* species DNA polymerase and a carboxy-terminal (C-terminal) region derived from Tma DNA polymerase. The N-terminal region refers to a region extending from the N-terminus (amino acid position 1) to an internal amino acid. Similarly, the C-terminal region refers to a region extending from an internal amino acid to the C-terminus.

In the context of mutant DNA polymerases, "correspondence" to another sequence (e.g., regions, fragments, nucleotide or amino acid positions, or the like) is based on the convention of numbering according to nucleotide or amino acid position number and then aligning the sequences in a manner that maximizes the percentage of sequence identity. Because not all positions within a given "corresponding region" need be identical, non-matching positions within a corresponding region may be regarded as "corresponding positions." Accordingly, as used herein, referral to an "amino acid position corresponding to amino acid position [X]" of a specified DNA polymerase represents referral to a collection of equivalent positions in other recognized DNA polymerases and structural homologues and families. In typical embodiments of the present invention, "correspondence" of amino acid positions are determined with respect to a region of the polymerase comprising one or more motifs of SEQ ID NO:1, SEQ ID NO:2, and SEQ ID NO:3, as discussed further herein.

"Recombinant," as used herein, refers to an amino acid sequence or a nucleotide sequence that has been intentionally modified by recombinant methods. By the term "recombinant nucleic acid" herein is meant a nucleic acid, originally formed in vitro, in general, by the manipulation of a nucleic acid by endonucleases, in a form not normally found in nature. Thus an isolated, mutant DNA polymerase nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. A "recombinant protein" is a protein made using recombinant techniques, i.e., through the expression of a recombinant nucleic acid as depicted above. A recombinant protein is typically distinguished from naturally occurring protein by at least one or more characteristics.

A nucleic acid is "operably linked" when it is placed into a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation.

The term "host cell" refers to both single-cellular prokaryote and eukaryote organisms (e.g., bacteria, yeast, and actinomycetes) and single cells from higher order plants or animals when being grown in cell culture.

The term "vector" refers to a piece of DNA, typically double-stranded, which may have inserted into it a piece of foreign DNA. The vector or may be, for example, of plasmid origin. Vectors contain "replicon" polynucleotide sequences that facilitate the autonomous replication of the vector in a host cell. Foreign DNA is defined as heterologous DNA, which is DNA not naturally found in the host cell, which, for example, replicates the vector molecule, encodes a selectable or screenable marker, or encodes a transgene. The vector is used to transport the foreign or heterologous DNA into a suitable host cell. Once in the host cell, the vector can replicate independently of or coincidental with the host chromosomal DNA, and several copies of the vector and its inserted DNA can be generated. In addition, the vector can also contain the necessary elements that permit transcription of the inserted DNA into an mRNA molecule or otherwise cause replication of the inserted DNA into multiple copies of RNA. Some expression vectors additionally contain sequence elements adjacent to the inserted DNA that increase the half-life of the expressed mRNA and/or allow translation of the mRNA into a protein molecule. Many molecules of mRNA and polypeptide encoded by the inserted DNA can thus be rapidly synthesized.

The term "nucleotide," in addition to referring to the naturally occurring ribonucleotide or deoxyribonucleotide monomers, shall herein be understood to refer to related structural variants thereof, including derivatives and analogs, that are functionally equivalent with respect to the particular context in which the nucleotide is being used (e.g., hybridization to a complementary base), unless the context clearly indicates otherwise.

The term "nucleic acid" or "polynucleotide" refers to a polymer that can be corresponded to a ribose nucleic acid (RNA) or deoxyribose nucleic acid (DNA) polymer, or an analog thereof. This includes polymers of nucleotides such as RNA and DNA, as well as synthetic forms, modified (e.g., chemically or biochemically modified) forms thereof, and mixed polymers (e.g., including both RNA and DNA subunits). Exemplary modifications include methylation, substitution of one or more of the naturally occurring nucleotides with an analog, internucleotide modifications such as uncharged linkages (e.g., methyl phosphonates, phosphotriesters, phosphoamidates, carbamates, and the like), pendent moieties (e.g., polypeptides), intercalators (e.g., acridine, psoralen, and the like), chelators, alkylators, and modified linkages (e.g., alpha anomeric nucleic acids and the like). Also included are synthetic molecules that mimic polynucleotides in their ability to bind to a designated sequence via hydrogen bonding and other chemical interactions. Typically, the nucleotide monomers are linked via phosphodiester bonds, although synthetic forms of nucleic acids can comprise other linkages (e.g., peptide nucleic acids as described in Nielsen et al. (*Science* 254:1497-1500, 1991). A nucleic acid can be or can include, e.g., a chromosome or chromosomal segment, a vector (e.g., an expression vector), an expression cassette, a naked DNA or RNA polymer, the product of a polymerase chain reaction (PCR), an oligonucleotide, a probe, and a primer. A nucleic acid can be, e.g., single-stranded, double-stranded, or triple-stranded and is not limited to any particular length. Unless otherwise indicated, a particular nucleic acid sequence optionally comprises or encodes complementary sequences, in addition to any sequence explicitly indicated.

The term "oligonucleotide" refers to a nucleic acid that includes at least two nucleic acid monomer units (e.g., nucleotides). An oligonucleotide typically includes from about six to about 175 nucleic acid monomer units, more typically from about eight to about 100 nucleic acid monomer units, and still more typically from about 10 to about 50 nucleic acid monomer units (e.g., about 15, about 20, about 25, about 30, about 35, or more nucleic acid monomer units). The exact size of an oligonucleotide will depend on many factors, including the ultimate function or use of the oligonucleotide. Oligonucleotides are optionally prepared by any suitable method, including, but not limited to, isolation of an existing or natural sequence, DNA replication or amplification, reverse transcription, cloning and restriction digestion of appropriate sequences, or direct chemical synthesis by a method such as the phosphotriester method of Narang et al. (*Meth. Enzymol.* 68:90-99, 1979); the phosphodiester method of Brown et al. (*Meth. Enzymol.* 68:109-151, 1979); the diethylphosphoramidite method of Beaucage et al. (*Tetrahedron Lett.* 22:1859-1862, 1981); the triester method of Matteucci et al. (*J. Am. Chem. Soc.* 103:3185-3191, 1981); automated synthesis methods; or the solid support method of U.S. Pat. No. 4,458,066, entitled "PROCESS FOR PREPARING POLYNUCLEOTIDES," issued Jul. 3, 1984 to Caruthers et al., or other methods known to those skilled in the art. All of these references are incorporated by reference.

The term "primer" as used herein refers to a polynucleotide capable of acting as a point of initiation of template-directed nucleic acid synthesis when placed under conditions in which primer extension is initiated (e.g., under conditions comprising the presence of requisite nucleoside triphosphates (as dictated by the template that is copied) and a polymerase in an appropriate buffer and at a suitable temperature or cycle(s) of temperatures (e.g., as in a polymerase chain reaction)). To further illustrate, primers can also be used in a variety of other oligonucleotide-mediated synthesis processes, including as initiators of de novo RNA synthesis and in vitro transcription-related processes (e.g., nucleic acid sequence-based amplification (NASBA), transcription mediated amplification (TMA), etc.). A primer is typically a single-stranded oligonucleotide (e.g., oligodeoxyribonucleotide). The appropriate length of a primer depends on the intended use of the primer but typically ranges from 6 to 40 nucleotides, more typically from 15 to 35 nucleotides. Short primer molecules generally require cooler temperatures to form sufficiently stable hybrid complexes with the template. A primer need not reflect the exact sequence of the template but must be sufficiently complementary to hybridize with a template for primer elongation to occur. In certain embodiments, the term "primer pair" means a set of primers including a 5' sense primer (sometimes called "forward") that hybridizes with the complement of the 5' end of the nucleic acid sequence to be amplified and a 3' antisense primer (sometimes called "reverse") that hybridizes with the 3' end of the sequence to be amplified (e.g., if the target sequence is expressed as RNA or is an RNA). A primer can be labeled, if desired, by incorporating a label detectable by spectroscopic, photochemical, biochemical, immunochemical, or chemical means. For example, useful labels include $^{32}$P, fluorescent dyes, electron-dense reagents, enzymes (as commonly used in ELISA assays), biotin, or haptens and proteins for which antisera or monoclonal antibodies are available.

The term "conventional" or "natural" when referring to nucleic acid bases, nucleoside triphosphates, or nucleotides refers to those which occur naturally in the polynucleotide being described (i.e., for DNA these are dATP, dGTP, dCTP and dTTP). Additionally, dITP, and 7-deaza-dGTP are frequently utilized in place of dGTP and 7-deaza-dATP can be utilized in place of dATP in in vitro DNA synthesis reactions, such as sequencing. Collectively, these may be referred to as dNTPs.

The term "unconventional" or "modified" when referring to a nucleic acid base, nucleoside, or nucleotide includes modification, derivations, or analogues of conventional bases, nucleosides, or nucleotides that naturally occur in a particular polynucleotide. Certain unconventional nucleotides are modified at the 2' position of the ribose sugar in comparison to conventional dNTPs. Thus, although for RNA the naturally occurring nucleotides are ribonucleotides (i.e., ATP, GTP, CTP, UTP, collectively rNTPs), because these nucleotides have a hydroxyl group at the 2' position of the sugar, which, by comparison is absent in dNTPs, as used herein, ribonucleotides are unconventional nucleotides as substrates for DNA polymerases. As used herein, unconventional nucleotides include, but are not limited to, compounds used as terminators for nucleic acid sequencing. Exemplary terminator compounds include but are not limited to those compounds that have a 2',3' dideoxy structure and are referred to as dideoxynucleoside triphosphates. The dideoxynucleoside triphosphates ddATP, ddTTP, ddCTP and ddGTP are referred to collectively as ddNTPs. Additional examples of terminator compounds include 2'-PO$_4$ analogs of ribonucleotides (see, e.g., U.S. Application Publication Nos. 2005/0037991 and 2005/0037398, which are both incorporated by reference). Other unconventional nucleotides include phosphorothioate dNTPs ([[α]-S]dNTPs), 5'-[α]-borano-dNTPs, [α]-methyl-phosphonate dNTPs, and ribonucleoside triphosphates (rNTPs). Unconventional bases may be labeled with radioactive isotopes such as $^{32}$P, $^{33}$P, or $^{35}$S; fluorescent labels; chemiluminescent labels; bioluminescent labels; hapten labels such as biotin; or enzyme labels such as streptavidin or avidin. Fluorescent labels may include dyes that are negatively charged, such as dyes of the fluorescein family, or dyes that are neutral in charge, such as dyes of the rhodamine family, or dyes that are positively charged, such as dyes of the cyanine family. Dyes of the fluorescein family include, e.g., FAM, HEX, TET, JOE, NAN and ZOE. Dyes of the rhodamine family include Texas Red, ROX, R110, R6G, and TAMRA. Various dyes or nucleotides labeled with FAM, HEX, TET, JOE, NAN, ZOE, ROX, R110, R6G, Texas Red and TAMRA are marketed by Perkin-Elmer (Boston, Mass.), Applied Biosystems (Foster City, Calif.), or Invitrogen/Molecular Probes (Eugene, Oreg.). Dyes of the cyanine family include Cy2, Cy3, Cy5, and Cy7 and are marketed by GE Healthcare UK Limited (Amersham Place, Little Chalfont, Buckinghamshire, England).

As used herein, "percentage of sequence identity" is determined by comparing two optimally aligned sequences over a comparison window, wherein the portion of the sequence in the comparison window can comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of nucleotides or amino acid residues that are the same (e.g., 60% identity, optionally 65%, 70%, 75%, 80%, 85%, 90%, or 95% identity over a specified region), when compared and aligned for maximum correspondence over a comparison window, or designated region as measured using one of the following sequence comparison algorithms or by manual alignment and visual inspection. Sequences are "substantially identical" to each other if they are at least 20%, at least 25%, at least 30%, at least 35%, at least 40%, at least 45%, at least 50%, or at least 55% identical. These definitions also refer to the complement of a test sequence. Optionally, the identity exists over a region that is at least about 50 nucleotides in length, or more typically over a region that is 100 to 500 or 1000 or more nucleotides in length.

The terms "similarity" or "percent similarity," in the context of two or more polypeptide sequences, refer to two or more sequences or subsequences that have a specified percentage of amino acid residues that are either the same or similar as defined by a conservative amino acid substitutions (e.g., 60% similarity, optionally 65%, 70%, 75%, 80%, 85%, 90%, or 95% similar over a specified region), when compared and aligned for maximum correspondence over a comparison window, or designated region as measured using one of the following sequence comparison algorithms or by manual alignment and visual inspection. Sequences are "substantially similar" to each other if they are at least 20%, at least 25%, at least 30%, at least 35%, at least 40%, at least 45%, at least 50%, or at least 55% similar to each other. Optionally, this similarly exists over a region that is at least about 50 amino acids in length, or more typically over a region that is at least about 100 to 500 or 1000 or more amino acids in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are commonly used, or alternative parameters can be designated. The sequence comparison algorithm then calculates the percent sequence identities or similarities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, for example, by the local homology algorithm of Smith and Waterman (*Adv. Appl. Math.* 2:482, 1970), by the homology alignment algorithm of Needleman and Wunsch (*J. Mol. Biol.* 48:443, 1970), by the search for similarity method of Pearson and Lipman (*Proc. Natl. Acad. Sci. USA* 85:2444, 1988), by computerized implementations of these algorithms (e.g., GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng and Doolittle (*J. Mol. Evol.* 35:351-360, 1987). The method used is similar to the method described by Higgins and Sharp (*CABIOS* 5:151-153, 1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package (e.g., version 7.0 (Devereaux et al., *Nuc. Acids Res.* 12:387-95, 1984) or later).

Another example of an algorithm that is suitable for determining percent sequence identity and sequence similarity are the BLAST and BLAST 2.0 algorithms, which are described in Altschul et al. (*Nuc. Acids Res.* 25:3389-402, 1977), and Altschul et al. (*J. Mol. Biol.* 215:403-10, 1990), respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff, *Proc. Natl. Acad. Sci. USA* 89:10915, 1989) alignments (B) of 50, expectation (E) of 10, M=5, N=−4, and a comparison of both strands.

The BLAST algorithm also performs a statistical analysis of the similarity between two sequences (see, e.g., Karlin and Altschul, *Proc. Natl. Acad. Sci. USA* 90:5873-87, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, typically less than about 0.01, and more typically less than about 0.001.

The term "nucleic acid extension rate" refers the rate at which a biocatalyst (e.g., an enzyme, such as a polymerase, ligase, or the like) extends a nucleic acid (e.g., a primer or other oligonucleotide) in a template-dependent or template-independent manner by attaching (e.g., covalently) one or more nucleotides to the nucleic acid. To illustrate, certain mutant DNA polymerases described herein have improved nucleic acid extension rates relative to unmodified forms of these DNA polymerases, such that they can extend primers at higher rates than these unmodified forms under a given set of reaction conditions.

The term "reverse transcription efficiency" refers to the fraction of RNA molecules that are reverse transcribed as cDNA in a given reverse transcription reaction. In certain embodiments, the mutant DNA polymerases of the invention have improved reverse transcription efficiencies relative to unmodified forms of these DNA polymerases. That is, these mutant DNA polymerases reverse transcribe a higher fraction of RNA templates than their unmodified forms under a particular set of reaction conditions.

BRIEF DESCRIPTION OF THE DRAWINGS

FIG. 1 depicts an amino acid sequence alignment of a region from the polymerase domain of exemplary thermostable DNA polymerases from various species of thermophilic bacteria: *Thermus thermophilus* (Tth) (SEQ ID NO:4), *Thermus caldophilus* (Tca) (SEQ ID NO:5), *Thermus* species Z05 (Z05) (SEQ ID NO:6), *Thermus aquaticus* (Taq) (SEQ ID NO:7), *Thermus flavus* (Tfl) (SEQ ID NO:8), *Thermus filiformis* (Tfi) (SEQ ID NO:9), *Thermus* species sps17 (Sps17) (SEQ ID NO:10), *Thermotoga maritima* (Tma) (SEQ ID NO:11), *Thermotoga neapolitana* (Tne) (SEQ ID NO:12), *Thermosipho africanus* (Taf) (SEQ ID NO:13), and *Bacillus caldotenax* (Bca) (SEQ ID NO:14). The amino acid sequence alignment also includes a region from the polymerase domain of representative chimeric thermostable DNA polymerases, namely, CS5 (SEQ ID NO:15) and CS6 (SEQ ID NO:16). In addition, a sequence (Cons) (SEQ ID NO:17) showing consensus amino acid residues among these exemplary sequences is also included. Further, the polypeptide regions shown comprise the amino acid motifs XXXXRXXXKLXXTYXX (SEQ ID NO:1), TGRLSSXXPNLQN (SEQ ID NO:2), and XXXXXXXDYSQIELR (SEQ ID NO:3), the variable positions of which are further defined herein. These motifs are highlighted in bold type for each polymerase sequence. Amino acid positions amenable to mutation in accordance with the present invention are indicated with an asterisk (*). Gaps in the alignments are indicated with a dot (.).

FIG. 2A presents the amino acid sequence of the chimeric thermostable DNA polymerase CS5 (SEQ ID NO:18).

FIG. 2B presents a nucleic acid sequence encoding the chimeric thermostable DNA polymerase CS5 (SEQ ID NO:20).

FIG. 3A presents the amino acid sequence of the chimeric thermostable DNA polymerase CS6 (SEQ ID NO:19).

FIG. 3B presents a nucleic acid sequence encoding the chimeric thermostable DNA polymerase CS6 (SEQ ID NO:21).

FIGS. 13A and 13B are photographs of agarose gels that illustrate the ability of certain enzymes described herein to make full length amplicon under the various conditions involving ribonucleotides. As labeled on the photographs, the enzymes tested were GQDSE, CS6-GQDSE, GLQDSE, GDSE, GLDSE, GLDE, GE (G46E CSSR), and a 4:1 mixture of GL and GLE (GL CS5/GLE), where G=G46E, L=L329A, Q=Q601R, D=D640G, S=S671F, and E=E678G. All of the enzymes were CS5 enzymes aside from the one denoted CS6-GQDSE.

FIG. 14A is a plot of delta Cts (y-axis) for the enzymes described with respect to FIGS. 13A and 13B against various rATP conditions tested (y-axis), while FIG. 14B is a plot of % rNTP incorporation (y-axis) for the enzymes described with respect to FIGS. 13A and 13B against various rNTP conditions tested (y-axis).

FIG. 16A is a plot of delta Cts (y-axis) for the enzymes (x-axis) described with respect to FIGS. 15A and 15B for various rCTP conditions tested (legend), while FIG. 16B is a plot of delta Cts (y-axis) for those enzymes (x-axis) for various biotin labeled rCTP conditions tested (legend).

FIG. 17 is a bar graph that shows the effect of enzyme concentration on threshold cycle (Ct) values in pyrophosphorolysis activated polymerization (PAP) reactions utilizing a G46E L329A E678G (GLE) CS5 DNA polymerase. The y-axis represents Ct value, while the x-axis represents the enzyme concentration (nM). The legend that accompanies the plot shows the number of copies of the template nucleic acid corresponding to each trace in the graph (no copies of the template nucleic acid (no temp), 1e$^4$ copies of the template nucleic acid (1E4/rxn), 1e$^5$ copies of the template nucleic acid (1E5/rxn), and 1e$^6$ copies of the template nucleic acid (1E6/rxn)).

FIG. 18 is a bar graph that shows the effect of enzyme concentration on threshold cycle (Ct) values in pyrophosphorolysis activated polymerization (PAP) reactions utilizing a G46E L329A D640G S671F E678G (GLDSE) CS5 DNA polymerase. The y-axis represents Ct value, while the x-axis represents the enzyme concentration (nM). The legend that accompanies the plot shows the number of copies of the template nucleic acid corresponding to each trace in the graph (no copies of the template nucleic acid (no temp), 1e$^4$ copies of the template nucleic acid (1E4/rxn), 1e$^5$ copies of the template nucleic acid (1E5/rxn), and 1e$^6$ copies of the template nucleic acid (1E6/rxn)).

DETAILED DESCRIPTION OF THE INVENTION

Figure 4:
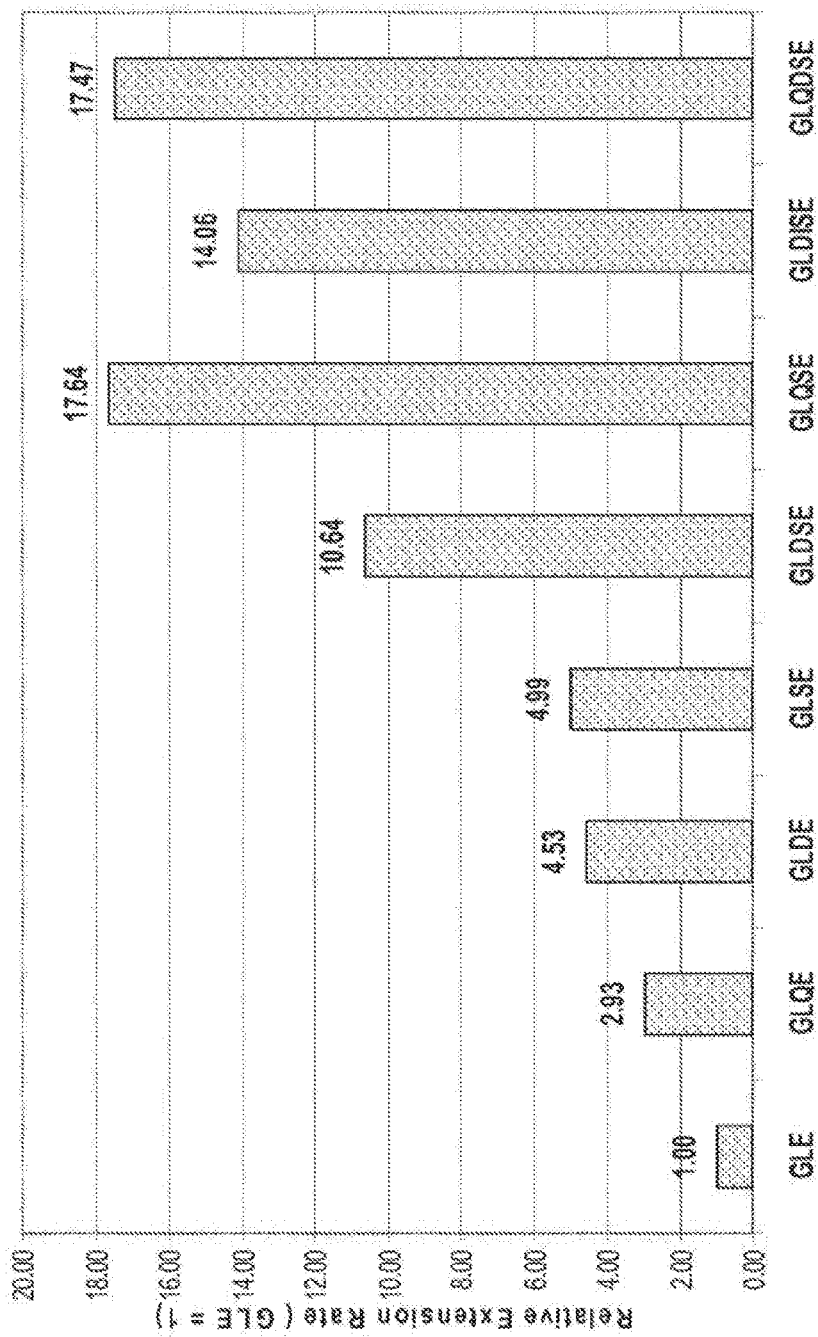
FIG. 4 is a bar graph that shows the normalized extension rates of various mutants of a G46E L329A E678G (GLE) CS5 DNA polymerase. The y-axis represents the relative extension rates, while the x-axis represents the DNA polymerases having specified point mutations (G=G46E, L=L329A, Q=Q601R, D=D640G, I=I669F, S=S671F, and E=E678G). The extension rate values obtained for the mutant polymerases are normalized relative to the value obtained for the GLE CS5 DNA polymerase, which is set to 1.00.

The present invention provides novel mutant DNA polymerases in which one or more amino acids in the polymerase domain have been mutated relative to a functional DNA polymerase. The mutant DNA polymerases of the invention are active enzymes having improved rates of nucleotide incorporation relative to the unmodified form of the polymerase and, in certain embodiments, concomitant increases in reverse transcriptase activity and/or amplification ability. The mutant DNA polymerases may be used at lower concentrations for superior or equivalent performance as the parent enzymes. In certain embodiments, the mutant DNA polymerases described herein have improved thermostability relative to parent enzymes. The mutant DNA polymerases are therefore useful in a variety of applications involving primer extension as well as reverse transcription or amplification of polynucleotide templates, including, for example, applications in recombinant DNA studies and medical diagnosis of disease.

Unmodified forms of DNA polymerases amenable to mutation in accordance with the present invention are those having a functional polymerase domain comprising the following amino acid motifs:

(a) Xaa-Xaa-Xaa-Xaa-Arg-Xaa-Xaa-Xaa-Lys-Leu-Xaa-Xaa-Thr-Tyr-Xaa-Asp (also referred to herein in the one-letter code as $X_{a1}$-$X_{a2}$-$X_{a3}$-$X_{a4}$-R-$X_{a6}$-$X_{a7}$-$X_{a8}$-K-L-$X_{a11}$-$X_{a12}$-T-Y-$X_{a15}$-$X_{a16}$ (SEQ ID NO:1)); wherein $X_{a1}$ is Ile (I) or Leu (L);
$X_{a2}$ is Gln (Q) or Leu (L);
$X_{a3}$ is Gln (Q), His (H) or Glu (E);
$X_{a4}$ is Tyr (Y), His (H), or Phe (F);
$X_{a6}$ is Glu (E), Gln (Q) or Lys (K);
$X_{a7}$ is Ile (I), Leu (L) or Tyr (Y);
$X_{a8}$ is Gln (Q), Thr (T), Met (M), Gly (G) or Leu (L);
$X_{a11}$ is Lys (K) or Gln (Q);

$X_{a12}$ is Ser (S) or Asn (N);
$X_{a15}$ is Ile (I) or Val (V); and
$X_{a16}$ is Glu (E) or Asp (D);
(b) Thr-Gly-Arg-Leu-Ser-Ser-Xaa-Xaa-Pro-Asn-Leu-Gln-Asn (also referred to herein in the one-letter code as T-G-R-L-S-S-$X_{b7}$-$X_{b8}$-P-N-L-Q-N (SEQ ID NO:2));
wherein
$X_{b7}$ is Ser (S) or Thr (T);
$X_{b8}$ is Asp (D), Glu (E) or Asn (N); and
(c) Xaa-Xaa-Xaa-Xaa-Xaa-Xaa-Xaa-Asp-Tyr-Ser-Gln-Ile-Glu-Leu-Arg (also referred to herein in the one-letter code as $X_{c1}$-$X_{c2}$-$X_{c3}$-$X_{c4}$-$X_{c5}$-$X_{c6}$-$X_{c7}$-D-Y-S-Q-I-E-L-R (SEQ ID NO:3); wherein
$X_{c1}$ is Gly (G), Asn (N), or Asp (D);
$X_{c2}$ is Trp (W) or His (H);
$X_{c3}$ is Trp (W), Ala (A), Leu (L) or Val (V);
$X_{c4}$ is Ile (I) or Leu (L);
$X_{c5}$ is Val (V), Phe (F) or Leu (L);
$X_{c6}$ is Ser (S), Ala (A), Val (V) or Gly (G); and
$X_{c7}$ is Ala (A) or Leu (L).

Figure 1:
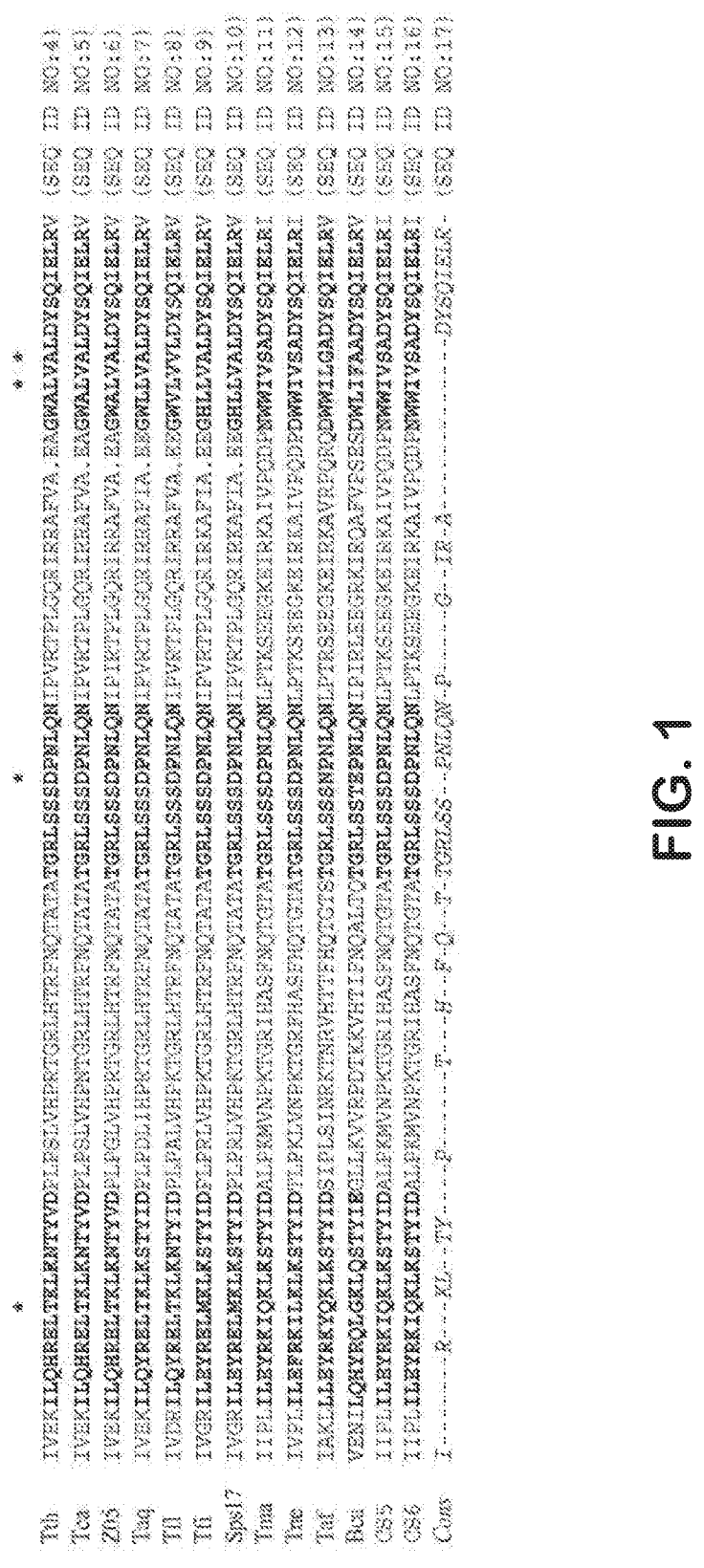

These motifs are present within a region of about 100 amino acids in the active site of many Family A type DNA-dependent DNA polymerases, particularly thermostable DNA polymerases from thermophilic bacteria. For example, FIG. 1 shows an amino acid sequence alignment of a region from the polymerase domain of DNA polymerases from several species of thermophilic bacteria: *Thermotoga maritima, Thermus aquaticus, Thermus thermophilus, Thermus flavus, Thermus filiformis, Thermus* sp. sps17, *Thermus* sp. Z05, *Thermotoga neopolitana, Thermosipho africanus, Bacillus caldotenax* and *Thermus caldophilus*. The amino acid sequence alignment shown in FIG. 1 also includes a region from the polymerase domain of representative chimeric thermostable DNA polymerases. As shown, each of the motifs of SEQ ID NOS:1, 2, and 3 is present in each of these polymerases, indicating a conserved function for these regions of the active site.

Accordingly, in some embodiments, the unmodified form of the DNA polymerase is a wild-type or a naturally occurring DNA polymerase, such as, for example, a polymerase from any of the species of thermophilic bacteria listed above. In one variation, the unmodified polymerase is from a species of the genus *Thermus*. In other embodiments of the invention, the unmodified polymerase is from a thermophilic species other than *Thermus*. The full nucleic acid and amino acid sequence for numerous thermostable DNA polymerases are available. The sequences each of *Thermus aquaticus* (Taq) (SEQ ID NO:78), *Thermus thermophilus* (Tth) (SEQ ID NO:79), *Thermus* species Z05 (SEQ ID NO:82), *Thermus* species sps17 (SEQ ID NO:81), *Thermotoga maritima* (Tma) (SEQ ID NO:77), and *Thermosipho africanus* (Taf) (SEQ ID NO:83) polymerase have been published in PCT International Patent Publication No. WO 92/06200, which is incorporated herein by reference. The sequence for the DNA polymerase from *Thermus flavus* (SEQ ID NO:80) has been published in Akhmetzjanov and Vakhitov (Nucleic Acids Research 20:5839, 1992), which is incorporated herein by reference. The sequence of the thermostable DNA polymerase from *Thermus caldophilus* (SEQ ID NO:84) is found in EMBL/GenBank Accession No. U62584. The sequence of the thermostable DNA polymerase from *Thermus filiformis* can be recovered from ATCC Deposit No. 42380 using, e.g., the methods provided in U.S. Pat. No. 4,889,818, as well as the sequence information provided in Table 1. The sequence of the *Thermotoga neapolitana* DNA polymerase (SEQ ID NO:85) is from GeneSeq Patent Data Base Accession No. R98144 and PCT WO 97/09451, each incorporated herein by reference. The sequence of the thermostable DNA polymerase from *Bacillus caldotenax* is described in, e.g., Uemori et al. (J Biochem (Tokyo) 113(3):401-410, 1993; see also, Swiss-Prot database Accession No. Q04957 and Gen-Bank Accession Nos. D12982 and BAA02361), which are each incorporated by reference. Examples of unmodified forms of DNA polymerases that can be modified as described herein are also described in, e.g., U.S. Pat. No. 6,228,628, entitled "Mutant chimeric DNA polymerase" issued May 8, 2001 to Gelfand et al.; U.S. Pat. No. 6,346,379, entitled "Thermostable DNA polymerases incorporating nucleoside triphosphates labeled with fluorescein family dyes" issued Feb. 12, 2002 to Gelfand et al.; U.S. Pat. No. 7,030,220, entitled "Thermostable enzyme promoting the fidelity of thermostable DNA polymerases—for improvement of nucleic acid synthesis and amplification in vitro" issued Apr. 18, 2006 to Ankenbauer et al.; U.S. Pat. No. 6,881,559, entitled "Mutant B-type DNA polymerases exhibiting improved performance in PCR" issued Apr. 19, 2005 to Sobek et al.; U.S. Pat. No. 6,794,177, entitled "Modified DNA-polymerase from carboxydothermus hydrogenoformans and its use for coupled reverse transcription and polymerase chain reaction" issued Sep. 21, 2004 to Markau et al.; U.S. Pat. No. 6,468,775, entitled "Thermostable DNA polymerase from carboxydothermus hydrogenoformans" issued Oct. 22, 2002 to Ankenbauer et al.; and U.S. Pat. Appl. Nos. 20040005599, entitled "Thermostable or thermoactive DNA polymerase molecules with attenuated 3'-5' exonuclease activity" filed Mar. 26, 2003 by Schoenbrunner et al.; 20020012970, entitled "High temperature reverse transcription using mutant DNA polymerases" filed Mar. 30, 2001 by Smith et al.; 20060078928, entitled "Thermostable enzyme promoting the fidelity of thermostable DNA polymerases—for improvement of nucleic acid synthesis and amplification in vitro" filed Sep. 29, 2005 by Ankenbauer et al.; 20040115639, entitled "Reversibly modified thermostable enzymes for DNA synthesis and amplification in vitro" filed Dec. 11, 2002 by Sobek et al., which are each incorporated by reference.

Also amenable to the mutations described herein are functional DNA polymerases that have been previously modified (e.g., by amino acid substitution, addition, or deletion), provided that the previously modified polymerase retains the amino acid motifs of SEQ ID NOS:1, 2, and 3. Thus, suitable unmodified DNA polymerases also include functional variants of wild-type or naturally occurring polymerases. Such variants typically will have substantial sequence identity or similarity to the wild-type or naturally occurring polymerase, typically at least 80% sequence identity and more typically at least 90%, 91%, 92%, 93%, 94%, 95%, 96%, 97%, 98% or 99% sequence identity. In certain embodiments, the unmodified DNA polymerase has reverse transcriptase (RT) activity and/or the ability to incorporate ribonucleotides or other 2'-modified nucleotides.

Suitable polymerases also include, for example, certain chimeric DNA polymerases comprising polypeptide regions from two or more enzymes. Examples of such chimeric DNA polymerases are described in, e.g., U.S. Pat. No. 6,228,628, which is incorporated by reference herein in its entirety. Particularly suitable are chimeric CS-family DNA polymerases, which include the CS5 (SEQ ID NO:18) and CS6 (SEQ ID NO:19) polymerases and variants thereof having substantial sequence identity or similarity to SEQ ID NO:18 or SEQ ID NO:19 (typically at least 80% sequence identity and more typically at least 90%, 91%, 92%, 93%, 94%, 95%, 96%, 97%, 98% or 99% sequence identity). The CS5 and CS6 DNA polymerases are chimeric enzymes derived from *Thermus* sp. Z05 and *Thermotoga maritima* (Tma) DNA polymerases. They comprise the N-terminal 5'-nuclease domain of the *Thermus* enzyme and the C-terminal 3'-5' exonuclease and the polymerase domains of the Tma enzyme. These enzymes have efficient reverse transcriptase activity, can extend nucleotide analog-containing primers, and can incorporate alpha-phosphorothioate dNTPs, dUTP, dITP, and also fluorescein- and cyanine-dye family labeled dNTPs. The CS5 and CS6 polymerases are also efficient $Mg^{2+}$-activated PCR enzymes. Nucleic acid sequences encoding CS5 and CS6 polymerases are provided in FIGS. 2B and 3B, respectively. CS5 and CS6 chimeric polymerases are further described in, e.g., U.S. Pat. Application Publication No. 2004/0005599, which is incorporated by reference herein in its entirety.

In some embodiments, the unmodified form of the DNA polymerase is a polymerase that has been previously modified, typically by recombinant means, to confer some selective advantage. Such modifications include, for example, the amino acid substitutions G46E, L329A, and/or E678G in CS5 DNA polymerase, CS6 DNA polymerase, or corresponding mutation(s) in other polymerases. Accordingly, in specific variations, the unmodified form of the DNA polymerase is one of the following (each having the amino acid sequence of SEQ ID NO:18 or SEQ ID NO:19 except for the designated substitution(s)): G46E; G46E L329A; G46E E678G; or G46E L329A E678G. The E678G substitution, for example, allows for the incorporation of ribonucleotides and other 2'-modified nucleotides, but this mutation also appears to result in an impaired ability to extend primed templates. In certain embodiments, the mutations according to the present invention, which result in a faster extension rate of the mutant polymerase, ameliorate this particular feature of the E678G mutation.

The mutant DNA polymerases of the present invention comprise one or more amino acid substitutions in the active site relative to the unmodified polymerase. In some embodiments, the amino acid substitution(s) are at at least one of the following amino acid positions:

position $X_{a8}$ of the motif set forth in SEQ ID NO:1;
position $X_{b8}$ of the motif set forth in SEQ ID NO:2;
position $X_{c4}$ of the motif set forth in SEQ ID NO:3; and
position $X_{c6}$ of the motif set forth in SEQ ID NO:3.

Amino acid substitution at one or more of these positions confers improved nucleotide-incorporating activity, yielding a mutant DNA polymerase with an improved (faster) nucleic acid extension rate relative to the unmodified polymerase. In addition, amino acid substitution at one or more of these positions confers increased 3'-5' exonuclease (proofreading) activity relative to the unmodified polymerase. While not intending to be limited to any particular theory, the present inventors believe that the improved nucleic acid extension rate of the mutant polymerases of the invention is a consequence of tighter binding to a template, i.e., less frequent dissociation from the template, resulting in a higher "processivity" enzyme. These features permit using lower concentrations of the mutant polymerase in, e.g., primer extension reactions relative to reactions involving the unmodified DNA polymerase. Thus, at a sufficiently high enzyme concentration, the extension rate of the unmodified polymerase (i.e., lacking the specific mutations that are the subject of the invention) could conceivably approach that of the mutant enzyme. The mutant polymerases also appear to perform much better than the unmodified forms at high ionic strength. However, at a sufficiently high enzyme concentration, the performance of the unmodified polymerase at low ionic strength would approach that of the mutant polymerase.

Because the unmodified forms of DNA polymerase are unique, the amino acid position corresponding to each of $X_{a8}$, $X_{b8}$, $X_{c4}$, and $X_{c6}$ is typically distinct for each mutant polymerase. Amino acid and nucleic acid sequence alignment programs are readily available (see, e.g., those referred to supra) and, given the particular motifs identified herein, serve to assist in the identification of the exact amino acids (and corresponding codons) for modification in accordance with the present invention. The positions corresponding to each of $X_{a8}$, $X_{b8}$, $X_{c4}$, and $X_{c6}$ are shown in Table 1 for representative chimeric thermostable DNA polymerases and thermostable DNA polymerases from exemplary thermophilic species.

TABLE 1

Amino Acid Positions Corresponding to Motif Positions $X_{a8}$, $X_{b8}$, $X_{c4}$, and $X_{c6}$ in Exemplary Thermostable Polymerases.

| Organism or Chimeric Sequence Consensus | Amino Acid Position | | | |
|---|---|---|---|---|
| | $X_{a8}$ | $X_{b8}$ | $X_{c4}$ | $X_{c6}$ |
| T. thermophilus | 541 | 580 | 608 | 610 |
| T. caldophilus | 541 | 580 | 608 | 610 |
| T. sp. Z05 | 541 | 580 | 608 | 610 |
| T. aquaticus | 539 | 578 | 606 | 608 |
| T. flavus | 538 | 577 | 605 | 607 |
| T. filiformis | 537 | 576 | 604 | 606 |
| T. sp. sps17 | 537 | 576 | 604 | 606 |
| T. maritima | 601 | 640 | 669 | 671 |
| T. neapolitana | 601 | 640 | 669 | 671 |
| T. africanus | 600 | 639 | 668 | 670 |
| B. caldotenax | 582 | 621 | 650 | 652 |
| CS5 | 601 | 640 | 669 | 671 |
| CS6 | 601 | 640 | 669 | 671 |

In some embodiments, the amino acid substitutions are single amino acid substitutions. The mutant polymerase can, e.g., comprise any one of the amino acid substitutions at position $X_{a8}$, $X_{b8}$, $X_{c4}$, or $X_{c6}$ separately. Alternatively, the mutant polymerase comprises any one of various combinations of substitutions at two, three, or all four of these positions. For example, in one embodiment, the mutant DNA polymerase of the invention comprises amino acid substitutions at each of positions $X_{b8}$ and $X_{c6}$. Typically, the amino acid at position $X_{a8}$, $X_{b8}$, $X_{c4}$, or $X_{c6}$ is substituted with an amino acid that does not correspond to the respective motif as set forth in SEQ ID NO:1, SEQ ID NO:2, or SEQ ID NO:3. Thus, typically, the amino acid at position $X_{a8}$, if substituted, is not Q, T, M, G or L; the amino acid at position $X_{b8}$, if substituted, is not D, E or N; the amino acid at position $X_{c4}$, if substituted, is not I or L; and/or the amino acid at position $X_{c6}$, if substituted, is not S, A, V or G. In certain embodiments, amino acid substitutions include Arginine (R) at position $X_{a8}$, Glycine (G) at position $X_{b8}$, Phenylalanine (F) at position $X_{c4}$, and/or Phenylalanine (F) at position $X_{c6}$. Other suitable amino acid substitution(s) at one or more of the identified sites can be determined using, e.g., known methods of site-directed mutagenesis and determination of primer extension performance in assays described further herein or otherwise known to persons of skill in the art.

As previously discussed, in some embodiments, the mutant DNA polymerase of the present invention is derived from CS5 DNA polymerase (SEQ ID NO:18), CS6 DNA polymerase (SEQ ID NO:19), or a variant of those polymerases (e.g., G46E; G46E L329A; G46E E678G; G46E L329A E678G; or the like). As referred to above, in CS5 DNA polymerase or CS6 DNA polymerase, position $X_{a8}$ corresponds to Glutamine (Q) at position 601; position $X_{b8}$ corresponds to Aspartate (D) at position 640; position $X_{c4}$ corresponds to Isoleucine (I) at position 669; and position $X_{c6}$ corresponds to Serine (S) at position 671. Thus, in certain variations of the invention, the mutant polymerase comprises at least one amino acid substitution, relative to a CS5 DNA polymerase or a CS6 DNA polymerase, at S671, D640, Q601, and/or I669. Exemplary CS5 DNA polymerase and CS6 DNA polymerase mutants include those comprising the amino acid substitution(s) S671F, D640G, Q601R, and/or I669F. In some embodiments, the mutant CS5 polymerase or mutant CS6 polymerase comprises, e.g., amino acid substitutions at both D640 and S671 (e.g., D640G and S671F). Other, exemplary CS5 DNA polymerase and CS6 DNA polymerase mutants include the following (each having the amino acid sequence of SEQ ID NO:18 or SEQ ID NO:19 except for the designated substitutions):

G46E S671F;
G46E D640G;
G46E Q601R;
G46E I669F;
G46E D640G S671F;
G46E L329A S671F;
G46E L329A D640G;
G46E L329A Q601R;
G46E L329A I669F;
G46E L329A D640G S671F;
G46E S671F E678G;
G46E D640G E678G;
G46E Q601R E678G;
G46E I669F E678G;
G46E D640G S671F E678G;
G46E Q601R D640G S671F E678G;
G46E Q601R D640G S671F I669F E678G;
G46E L329A S671F E678G;
G46E L329A D640G E678G;
G46E L329A Q601R E678G;
G46E L329A I669F E678G;
G46E L329A D640G S671F E678G; and
G46E L329A Q601R D640G S671F E678G.

In addition to mutation of the motifs of SEQ ID NOS:1, 2, and/or 3 as described herein, the mutant DNA polymerases of the present invention can also include other, non-substitutional modification(s). Such modifications can include, for example, covalent modifications known in the art to confer an additional advantage in applications comprising primer extension. For example, in certain embodiments, the mutant DNA polymerase further includes a thermally reversible covalent modification. In these embodiments, a modifier group is covalently attached to the protein, resulting in a loss of all, or nearly all, of the enzyme activity. The modifier group is chosen so that the modification is reversed by incubation at an elevated temperature. DNA polymerases comprising such thermally reversible modifications are particularly suitable for hot-start applications, such as, e.g., various hot-start PCR techniques. Thermally reversible modifier reagents amenable to use in accordance with the mutant DNA polymerases of the present invention are described in, for example, U.S. Pat. No. 5,773,258 to Birch et al., which is incorporated by reference herein. Exemplary modifications include, e.g., reversible blocking of lysine residues by chemical modification of the e-amino group of lysine residues (see Birch et al., supra). In certain variations, the thermally reversible covalent modification includes covalent attachment, to the e-amino group of lysine residues, of a dicarboxylic anhydride as described in Birch et al., supra.

For example, particularly suitable mutant polymerases comprising a thermally reversible covalent modification are produced by a reaction, carried out at alkaline pH at a temperature which is less than about 25° C., of a mixture of a thermostable enzyme and a dicarboxylic acid anhydride having a general formula as set forth in the following formula I:

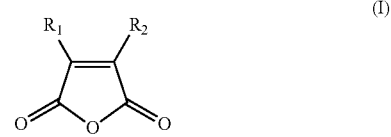

where $R_1$ and $R_2$ are hydrogen or organic radicals, which may be linked; or having the following formula II:

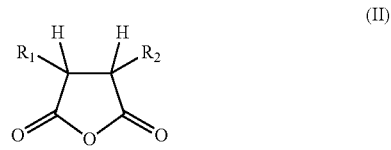

where $R_1$ and $R_2$ are organic radicals, which may linked, and the hydrogens are cis, essentially as described in Birch et al, supra. In specific embodiments comprising a thermally reversible covalent modification, the unmodified form of the polymerase is G64E CS5 DNA polymerase.

The mutant DNA polymerases of the present invention can be constructed by mutating the DNA sequences that encode the corresponding unmodified polymerase (e.g., a wild-type polymerase or a corresponding variant from which the mutant polymerase of the invention is derived), such as by using techniques commonly referred to as site-directed mutagenesis. Nucleic acid molecules encoding the unmodified form of the polymerase can be mutated by a variety of polymerase chain reaction (PCR) techniques well-known to one of ordinary skill in the art. (See, e.g., *PCR Strategies* (M. A. Innis, D. H. Gelfand, and J. J. Sninsky eds., 1995, Academic Press, San Diego, Calif.) at Chapter 14; *PCR Protocols: A Guide to Methods and Applications* (M. A. Innis, D. H. Gelfand, J. J. Sninsky, and T. J. White eds., Academic Press, N Y, 1990).

By way of non-limiting example, the two primer system, utilized in the Transformer Site-Directed Mutagenesis kit from Clontech, may be employed for introducing site-directed mutants into a polynucleotide encoding an unmodified form of the polymerase. Following denaturation of the target plasmid in this system, two primers are simultaneously annealed to the plasmid; one of these primers contains the desired site-directed mutation, the other contains a mutation at another point in the plasmid resulting in elimination of a restriction site. Second strand synthesis is then carried out, tightly linking these two mutations, and the resulting plasmids are transformed into a mutS strain of *E. coli*. Plasmid DNA is isolated from the transformed bacteria, restricted with the relevant restriction enzyme (thereby linearizing the unmutated plasmids), and then retransformed into *E. coli*. This system allows for generation of mutations directly in an expression plasmid, without the necessity of subcloning or generation of single-stranded phagemids. The tight linkage of the two mutations and the subsequent linearization of unmutated plasmids result in high mutation efficiency and allow minimal screening. Following synthesis of the initial restriction site primer, this method requires the use of only one new primer type per mutation site. Rather than prepare each positional mutant separately, a set of "designed degenerate" oligonucleotide primers can be synthesized in order to introduce all of the desired mutations at a given site simultaneously. Transformants can be screened by sequencing the plasmid DNA through the mutagenized region to identify and sort mutant clones. Each mutant DNA can then be restricted and analyzed by electrophoresis, such as for example, on a Mutation Detection Enhancement gel (Mallinckrodt Baker, Inc., Phillipsburg, N.J.) to confirm that no other alterations in the sequence have occurred (by band shift comparison to the unmutagenized control). Alternatively, the entire DNA region can be sequenced to confirm that no additional mutational events have occurred outside of the targeted region.

Verified mutant duplexes in pET (or other) overexpression vectors can be employed to transform *E. coli* such as, e.g., strain *E. coli* BL21 (DE3) pLysS, for high level production of the mutant protein, and purification by standard protocols. The method of FAB-MS mapping, for example, can be employed to rapidly check the fidelity of mutant expression. This technique provides for sequencing segments throughout the whole protein and provides the necessary confidence in the sequence assignment. In a mapping experiment of this type, protein is digested with a protease (the choice will depend on the specific region to be modified since this segment is of prime interest and the remaining map should be identical to the map of unmutagenized protein). The set of cleavage fragments is fractionated by, for example, microbore HPLC (reversed phase or ion exchange, again depending on the specific region to be modified) to provide several peptides in each fraction, and the molecular weights of the peptides are determined by standard methods, such as FAB-MS. The determined mass of each fragment are then compared to the molecular weights of peptides expected from the digestion of the predicted sequence, and the correctness of the sequence quickly ascertained. Since this mutagenesis approach to protein modification is directed, sequencing of the altered peptide should not be necessary if the MS data agrees with prediction. If necessary to verify a changed residue, CAD-tandem MS/MS can be employed to sequence the peptides of the mixture in question, or the target peptide can be purified for subtractive Edman degradation or carboxypeptidase Y digestion depending on the location of the modification.

Mutant DNA polymerases with more than one amino acid substituted can be generated in various ways. In the case of amino acids located close together in the polypeptide chain (as with amino acids $X_{c4}$ and $X_{c6}$ of the motif set forth in SEQ ID NO:3), they may be mutated simultaneously using one oligonucleotide that codes for all of the desired amino acid substitutions. If however, the amino acids are located some distance from each other (separated by more than ten amino acids, for example) it is more difficult to generate a single oligonucleotide that encodes all of the desired changes. Instead, one of two alternative methods may be employed. In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. An alternative method involves two or more rounds of mutagenesis to produce the desired mutant. The first round is as described for the single mutants: DNA encoding the unmodified polymerase is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on. Alternatively, the multi-site mutagenesis method of Seyfang & Jin (*Anal. Biochem.* 324:285-291. 2004) may be utilized.

Accordingly, also provided are recombinant nucleic acids encoding any of the mutant DNA polymerases of the present invention. Using a nucleic acid of the present invention, encoding a mutant DNA polymerase, a variety of vectors can be made. Any vector containing replicon and control sequences that are derived from a species compatible with the host cell can be used in the practice of the invention. Generally, expression vectors include transcriptional and translational regulatory nucleic acid regions operably linked to the nucleic acid encoding the mutant DNA polymerase. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. In addition, the vector may contain a Positive Retroregulatory Element (PRE) to enhance the half-life of the transcribed mRNA (see Gelfand et al. U.S. Pat. No. 4,666,848). The transcriptional and translational regulatory nucleic acid regions will generally be appropriate to the host cell used to express the polymerase. Numerous types of appropriate expression vectors, and suitable regulatory sequences are known in the art for a variety of host cells. In general, the transcriptional and translational regulatory sequences may include, e.g., promoter sequences, ribosomal binding sites, transcriptional start and stop sequences, translational start and stop sequences, and enhancer or activator sequences. In typical embodiments, the regulatory sequences include a promoter and transcriptional start and stop sequences. Vectors also typically include a polylinker region containing several restriction sites for insertion of foreign DNA. In certain embodiments, "fusion flags" are used to facilitate purification and, if desired, subsequent removal of tag/flag sequence, e.g., "His-Tag". However, these are generally unnecessary when purifying an thermoactive and/or thermostable protein from a mesophilic host (e.g., *E. coli*) where a "heat-step" may be employed. The construction of suitable vectors containing DNA encoding replication sequences, regulatory sequences, phenotypic selection genes, and the mutant polymerase of interest are prepared using standard recombinant DNA procedures. Isolated plasmids, viral vectors, and DNA fragments are cleaved, tailored, and ligated together in a specific order to generate the desired vectors, as is well-known in the art (see, e.g., Sambrook et al., *Molecular Cloning: A Laboratory Manual* (Cold Spring Harbor Laboratory Press, New York, N.Y., 2nd ed. 1989)).

In certain embodiments, the expression vector contains a selectable marker gene to allow the selection of transformed host cells. Selection genes are well known in the art and will vary with the host cell used. Suitable selection genes can include, for example, genes coding for ampicillin and/or tetracycline resistance, which enables cells transformed with these vectors to grow in the presence of these antibiotics.

In one aspect of the present invention, a nucleic acid encoding a mutant DNA polymerase is introduced into a cell, either alone or in combination with a vector. By "introduced into" or grammatical equivalents herein is meant that the nucleic acids enter the cells in a manner suitable for subsequent integration, amplification, and/or expression of the nucleic acid. The method of introduction is largely dictated by the targeted cell type. Exemplary methods include $CaPO_4$ precipitation, liposome fusion, LIPOFECTIN®, electroporation, viral infection, and the like.

Prokaryotes are typically used as host cells for the initial cloning steps of the present invention. They are particularly useful for rapid production of large amounts of DNA, for production of single-stranded DNA templates used for site-directed mutagenesis, for screening many mutants simultaneously, and for DNA sequencing of the mutants generated. Suitable prokaryotic host cells include *E. coli* K12 strain 94 (ATCC No. 31,446), *E. coli* strain W3110 (ATCC No. 27,325), *E. coli* K12 strain DG116 (ATCC No. 53,606), *E. coli* X1776 (ATCC No. 31,537), and *E. coli* B; however many other strains of *E. coli*, such as HB101, JM101, NM522, NM538, NM539, and many other species and genera of prokaryotes including bacilli such as *Bacillus subtilis*, other enterobacteriaceae such as *Salmonella typhimurium* or *Serratia marcesans*, and various *Pseudomonas* species can all be used as hosts. Prokaryotic host cells or other host cells with rigid cell walls are typically transformed using the calcium chloride method as described in section 1.82 of Sambrook et al., supra. Alternatively, electroporation can be used for transformation of these cells. Prokaryote transformation techniques are set forth in, for example Dower, in *Genetic Engineering, Principles and Methods* 12:275-296 (Plenum Publishing Corp., 1990); Hanahan et al., *Meth. Enzymol.*, 204:63, 1991. Plasmids typically used for transformation of *E. coli* include pBR322, pUCI8, pUCI9, pUCI18, pUC119, and Bluescript M13, all of which are described in sections 1.12-1.20 of Sambrook et al., supra. However, many other suitable vectors are available as well.

The mutant DNA polymerases of the present invention are typically produced by culturing a host cell transformed with an expression vector containing a nucleic acid encoding the mutant DNA polymerase, under the appropriate conditions to induce or cause expression of the mutant DNA polymerase. Methods of culturing transformed host cells under conditions suitable for protein expression are well-known in the art (see, e.g., Sambrook et al., supra). Suitable host cells for production of the mutant polymerases from lambda pL promotor-containing plasmid vectors include *E. coli* strain DG116 (ATCC No. 53606) (see U.S. Pat. No. 5,079,352 and Lawyer, F. C. et al., *PCR Methods and Applications* 2:275-87, 1993, which are both incorporated herein by reference). Following expression, the mutant polymerase can be harvested and isolated. Methods for purifying the thermostable DNA polymerase are described in, for example, Lawyer et al., supra.

Once purified, the ability of the mutant DNA polymerases to extend primed templates can be tested in any of various known assays for measuring nucleotide incorporation. For example, in the presence of primed template molecules (e.g., M13 DNA, etc.), an appropriate buffer, a complete set of dNTPs (e.g., dATP, dCTP, dGTP, and dTTP), and metal ion, DNA polymerases will extend the primers, converting single-stranded DNA (ssDNA) to double-stranded DNA (dsDNA). This conversion can be detected and quantified by, e.g., adding a dsDNA-binding dye, such as SYBR Green I. Using a kinetic thermocycler (see, Watson, et al. *Anal. Biochem.* 329:58-67, 2004, and also available from, e.g., Applied Biosystems, Stratagene, and BioRad), digital images of reaction plates can be taken (e.g., at 10-30 second intervals), thereby allowing the progress of the reactions to be followed. The amount of fluorescence detected can be readily converted to extension rates. Using such routine assays, extension rates of the mutants relative to the unmodified forms of polymerase can be determined.

The mutant DNA polymerases of the present invention may be used for any purpose in which such enzyme activity is necessary or desired. Accordingly, in another aspect of the invention, methods of primer extension using the mutant polymerases are provided. Conditions suitable for primer extension are known in the art. (See, e.g., Sambrook et al., supra. See also Ausubel et al., *Short Protocols in Molecular Biology* (4th ed., John Wiley & Sons 1999). Generally, a primer is annealed, i.e., hybridized, to a target nucleic acid to form a primer-template complex. The primer-template complex is contacted with the mutant DNA polymerase and free nucleotides in a suitable environment to permit the addition of one or more nucleotides to the 3' end of the primer, thereby producing an extended primer complementary to the target nucleic acid. The primer can include, e.g., one or more nucleotide analog(s). In addition, the free nucleotides can be conventional nucleotides, unconventional nucleotides (e.g., ribonucleotides or labeled nucleotides), or a mixture thereof. In some variations, the primer extension reaction comprises amplification of a target nucleic acid. Conditions suitable for nucleic acid amplification using a DNA polymerase and a primer pair are also known in the art (e.g., PCR amplification methods). (See, e.g., Sambrook et al., supra; Ausubel et al., supra; *PCR Applications: Protocols for Functional Genomics* (Innis et al. eds., Academic Press 1999). In other, non-mutually exclusive embodiments, the primer extension reaction comprises reverse transcription of an RNA template (e.g., RT-PCR). Use of the present mutant polymerases, which provide an improved extension rate, allow for, e.g., the ability to perform such primer extension reactions with relatively short incubation times, decreased enzyme concentrations, and/or increased product yield.

In yet other embodiments, the mutant polymerases are used for primer extension in the context of DNA sequencing, DNA labeling, or labeling of primer extension products. For example, DNA sequencing by the Sanger dideoxynucleotide method (Sanger et al., *Proc. Natl. Acad. Sci. USA* 74: 5463, 1977) is improved by the present invention for polymerases capable of incorporating unconventional, chain-terminating nucleotides. Advances in the basic Sanger et al. method have provided novel vectors (Yanisch-Perron et al., *Gene* 33:103-119, 1985) and base analogues (Mills et al., *Proc. Natl. Acad. Sci. USA* 76:2232-2235, 1979; and Barr et al., *Biotechniques* 4:428-432, 1986). In general, DNA sequencing requires template-dependent primer extension in the presence of chain-terminating base analogs, resulting in a distribution of partial fragments that are subsequently separated by size. The basic dideoxy sequencing procedure involves (i) annealing an oligonucleotide primer, optionally labeled, to a template; (ii) extending the primer with DNA polymerase in four separate reactions, each containing a mixture of unlabeled dNTPs and a limiting amount of one chain terminating agent such as a ddNTP, optionally labeled; and (iii) resolving the four sets of reaction products on a high-resolution denaturing polyacrylamide/urea gel. The reaction products can be detected in the gel by autoradiography or by fluorescence detection, depending on the label used, and the image can be examined to infer the nucleotide sequence. These methods utilize DNA polymerase such as the Klenow fragment of E. coli Pol I or a modified T7 DNA polymerase.

The availability of thermostable polymerases, such as Taq DNA polymerase, resulted in improved methods for sequencing with thermostable DNA polymerase (see Innis et al., Proc. Natl. Acad. Sci. USA 85:9436, 1988) and modifications thereof referred to as "cycle sequencing" (Murray, Nuc Acids Res. 17:8889, 1989). Accordingly, mutant thermostable polymerases of the present invention can be used in conjunction with such methods. As an alternative to basic dideoxy sequencing, cycle sequencing is a linear, asymmetric amplification of target sequences complementary to the template sequence in the presence of chain terminators. A single cycle produces a family of extension products of all possible lengths. Following denaturation of the extension reaction product from the DNA template, multiple cycles of primer annealing and primer extension occur in the presence of terminators such as ddNTPs. Cycle sequencing requires less template DNA than conventional chain-termination sequencing. Thermostable DNA polymerases have several advantages in cycle sequencing; they tolerate the stringent annealing temperatures which are required for specific hybridization of primer to nucleic acid targets as well as tolerating the multiple cycles of high temperature denaturation which occur in each cycle, e.g., 90-95° C. For this reason, AMPLITAQ® DNA Polymerase and its derivatives and descendants, e.g., AmpliTaq CS DNA Polymerase and AmpliTaq FS DNA Polymerase have been included in Taq cycle sequencing kits commercialized by companies such as Perkin-Elmer (Norwalk, Conn.) and Applied Biosystems (Foster City, Calif.).

Variations of chain termination sequencing methods include dye-primer sequencing and dye-terminator sequencing. In dye-primer sequencing, the ddNTP terminators are unlabeled, and a labeled primer is utilized to detect extension products (Smith et al., Nature 32:674-679, 1986). In dye-terminator DNA sequencing, a DNA polymerase is used to incorporate dNTPs and fluorescently labeled ddNTPs onto the end of a DNA primer (Lee et al., Nuc. Acids. Res. 20:2471, 1992). This process offers the advantage of not having to synthesize dye labeled primers. Furthermore, dye-terminator reactions are more convenient in that all four reactions can be performed in the same tube.

Both dye-primer and dye-terminator methods may be automated using an automated sequencing instrument produced by Applied Biosystems (Foster City, Calif.) (U.S. Pat. No. 5,171,534, which is herein incorporated by reference). When using the instrument, the completed sequencing reaction mixture is fractionated on a denaturing polyacrylamide gel or capillaries mounted in the instrument. A laser at the bottom of the instrument detects the fluorescent products as they are electrophoresed according to size through the gel.

Two types of fluorescent dyes are commonly used to label the terminators used for dye-terminator sequencing-negatively charged and zwitterionic fluorescent dyes. Negatively charged fluorescent dyes include those of the fluorescein and BODIPY families. BODIPY dyes (4,4-difluoro-4-bora-3a, 4a-diaza-s-indacene) are described in International Patent Publication WO 97/00967, which is incorporated herein by reference. Zwitterionic fluorescent dyes include those of the rhodamine family. Commercially available cycle sequencing kits use terminators labeled with rhodamine derivatives. However, the rhodamine-labeled terminators are rather costly and the product must be separated from unincorporated dye-ddNTPs before loading on the gel since they co-migrate with the sequencing products. Rhodamine dye family terminators seem to stabilize hairpin structures in GC-rich regions, which causes the products to migrate anomalously. This requires the use of dITP, which relaxes the secondary structure but also affects the efficiency of incorporation of terminator.

In contrast, fluorescein-labeled terminators eliminate the separation step prior to gel loading since they have a greater net negative charge and migrate faster than the sequencing products. In addition, fluorescein-labeled sequencing products have better electrophoretic migration than sequencing products labeled with rhodamine. Although wild-type Taq DNA polymerase does not efficiently incorporate terminators labeled with fluorescein family dyes, this can now be accomplished efficiently by use of the modified enzymes as described in U.S. Patent Application Publication No. 2002/0142333, which is incorporated by reference herein in its entirety. Accordingly, modifications as described in US 2002/0142333 can be used in the context of the present invention to produce fluorescein-family-dye-incorporating thermostable polymerases having improved primer extension rates. For example, in certain embodiments, the unmodified DNA polymerase in accordance with the present invention is a modified thermostable polymerase as described in US 2002/0142333 and having the motifs set forth in SEQ ID NOS:1, 2, and 3.

Other exemplary nucleic acid sequencing formats in which the mutant DNA polymerases of the invention can be used include those involving terminator compounds that include 2'-$PO_4$ analogs of ribonucleotides (see, e.g., U.S. Application Publication Nos. 2005/0037991, 2005/0037398, 2007/0219361 and 2007/0154914, which are each incorporated by reference). The mutant DNA polymerases described herein generally improve these sequencing methods, e.g., by reducing the time necessary for the cycled extension reactions and/or by reducing the amount or concentration of enzyme that is utilized for satisfactory performance.

In another aspect of the present invention, kits are provided for use in primer extension methods described herein. Typically, the kit is compartmentalized for ease of use and contains at least one container providing a mutant DNA polymerase in accordance with the present invention. One or more additional containers providing additional reagent(s) can also be included. Such additional containers can include any reagents or other elements recognized by the skilled artisan for use in primer extension procedures in accordance with the methods described above, including reagents for use in, e.g., nucleic acid amplification procedures (e.g., PCR, RT-PCR), DNA sequencing procedures, or DNA labeling procedures. For example, in certain embodiments, the kit further includes a container providing a 5' sense primer hybridizable, under primer extension conditions, to a predetermined polynucleotide template, or a primer pair comprising the 5' sense primer and a corresponding 3' antisense primer. In other, non-mutually exclusive variations, the kit includes one or more containers providing free nucleotides (conventional and/or unconventional). In specific embodiments, the kit includes alpha-phophorothioate dNTPs, dUTP, dITP, and/or labeled dNTPs such as, e.g., fluorescein- or cyanin-dye family dNTPs. In still other, non-mutually exclusive embodiments, the kit includes one or more containers providing a buffer suitable for a primer extension reaction.

EXAMPLES

It is understood that the examples and embodiments described herein are for illustrative purposes only and are not intended to limit the scope of the claimed invention. It is also understood that various modifications or changes in light the examples and embodiments described herein will be suggested to persons skilled in the art and are to be included within the spirit and purview of this application and scope of the appended claims.

Example I: Identification and Characterization of Mutant DNA Polymerases with Improved Enzyme Activity Mutations in CS family polymerases were identified that provide, e.g., improved ability to extend primed DNA templates in the presence of free nucleotides. In brief, the steps in this screening process included library generation, expression and partial purification of the mutant enzymes, screening of the enzymes for the desired property, DNA sequencing, clonal purification, and further characterization of selected candidate mutants, and generation, purification, and characterization of combinations of the mutations from the selected mutants. Each of these steps is described further below.

The mutations identified by this process include S671F, D640G, Q601R, and I669F, either separately or in various combinations. These mutations were placed in several CS-family polymerases, including G46E CS5, G46E L329A CS5, G46E E678G CS5, and G46E L329A E678G CS5. Some of these mutant polymerases are listed in Table 2. Other exemplary mutant polymerases that have been made include CS6 G46E Q601R D640G S671F E678G DNA polymerase and certain *Thermus* sp. Z05 DNA polymerase mutants. The resulting mutant polymerases were characterized by analyzing their performance in a series of Kinetic Thermal Cycling (KTC) experiments.

TABLE 2

Exemplary CS5 DNA Polymerase Mutants

| | |
|---|---|
| G46E D640G | G46E S671F E678G |
| G46E S671F | G46E D640G S671F E678G |
| G46E Q601R D640G | G46E Q601R D640G S671F E678G |
| G46E D640G S671F | G46E L329A Q601R E678G |
| G46E Q601R D640G S671F | G46E L329A D640G E678G |
| G46E L329A D640G | G46E L329A S671F E678G |
| G46E L329A Q601R D640G S671F | G46E L329A Q601R S671F E678G |
| G46E L329A S671F | G46E L329A D640G S671F E678G |
| G46E L329A Q601R D640G | G46E L329A Q601R D640G S671F E678G |
| G46E L329A D640G S671F | G46E L329A D640G I669F S671F E678G |
| L329A D640G | L329A Q601R E678G |
| L329A D640G S671F | L329A S671F E678G |
| L329A Q601R D640G S671F | S671F |
| L329A S671F | D640G S671F |
| D640G | Q601R D640G S671F |

The identified mutations, S671F, D640G, Q601R, and I669F, resulted in, e.g., an improved ability to extend primed templates. In the particular context of the E678G mutation, which allows for the incorporation of ribonucleotides and other 2'-modified nucleotides, but which also results in an impaired ability to extend primed templates, the S671F, D640G, Q601R, and I669F mutations ameliorated this property of impaired primer extension ability. The identified mutations, particularly S671F alone and S671F plus D640G, also showed improved efficiency of reverse transcription when placed in G46E CS5 and G46E L329A CS5 DNA polymerases. Additional features of the mutant DNA polymerases of the invention are described further below.

Clonal Library Generation:

A nucleic acid encoding the polymerase domain of CS5 E678G DNA polymerase was subjected to error-prone (mutagenic) PCR between Bgl II and Hind III restriction sites of a plasmid including this nucleic acid sequence. PCR was performed using a range of $Mg^{+2}$ concentrations from 1.8-3.5 mM, in order to generate libraries with a corresponding range of mutation rates. Buffer conditions were: 50 mM Bicine pH 8.2, 115 mM KOAc, 8% w/v glycerol, 0.2 mM each dNTPs, and 0.2×SYBR Green I. A GeneAmp® AccuRT Hot Start PCR enzyme was used at 0.15 U/μl. Starting with $5 \times 10^5$ copies of linearized CS5 E678G plasmid DNA/reaction volume of 50 μl, 30 cycles of amplification were performed, using an annealing temperature of 60° C. for 15 seconds, an extension temperature of 72° C. for 45 seconds, and a denaturation temperature of 95° C. for 15 seconds.

The resulting amplicon was purified over a Qiaquick spin column (Qiagen, Inc., Valencia, Calif., USA) and cut with Bgl II and Hind III, then re-purified. A vector plasmid, a modification of G46E L329A CS5 carrying a large deletion in the polymerase domain between the BglII and HindIII sites, was prepared by cutting with the same two restriction enzymes and treating with calf intestinal phosphatase (CIP). The cut vector and the mutated insert were mixed at different ratios and treated with T4 ligase overnight at 15° C. The ligations were purified and transformed into an *E. coli* host strain by electroporation.

Aliquots of the expressed cultures were plated on ampicillin-selective medium in order to determine the number of unique transformants in each transformation. Transformations with the most unique transformants at each mutagenesis rate were stored at −70 to −80° C. in the presence of glycerol as a cryo-protectant.

Each library was then spread on large format ampicillin-selective agar plates. Individual colonies were transferred to 384-well plates containing 2× Luria broth with ampicillin and 10% w/v glycerol using an automated colony picker (QPix2, Genetix Ltd). These plates were incubated overnight at 30° C. to allow the cultures to grow, then stored at −70 to −80° C. The glycerol added to the 2× Luria broth was low enough to permit culture growth and yet high enough to provide cryo-protection. Several thousand colonies at several mutagenesis ($Mg^{+2}$) levels were prepared in this way for later use.

Extract Library Preparation Part 1—Fermentation:

From the clonal libraries described above, a corresponding library of partially purified extracts suitable for screening purposes was prepared. The first step of this process was to make small-scale expression cultures of each clone. These cultures were grown in 96-well format; therefore there were 4 expression culture plates for each 384-well library plate. One μl was transferred from each well of the clonal library plate to a well of a 96 well seed plate, containing 150 μl of Medium A (see Table 3 below). This seed plate was shaken overnight at 1150 rpm at 30° C., in an iEMS plate incubater/shaker (ThermoElectron). These seed cultures were then used to inoculate the same medium, this time inoculating 10 μl into 300 μl Medium A in large format 96 well plates (Nunc #267334). These plates were incubated overnight at 37° C. The expression plasmid contained transcriptional control elements, which allow for expression at 37° C. but not at 30°

C. After overnight incubation, the cultures expressed the clone protein at typically 1-10% of total cell protein. The cells from these cultures were harvested by centrifugation. These cells were either frozen (−20° C.) or processed immediately, as described below.

TABLE 3

Medium A (Filter-sterilized prior to use)

| Component | Concentration |
|---|---|
| MgSO$_4$•7H$_2$O | 0.2 g/L |
| Citric acid•H$_2$O | 2 g/L |
| K$_2$HPO$_4$ | 10 g/L |
| NaNH$_4$PO$_4$•4H$_2$O | 3.5 g/L |
| MgSO$_4$ | 2 mM |
| Casamino acids | 2.5 g/L |
| Glucose | 2 g/L |
| Thiamine•HCl | 10 mg/L |
| Ampicillin | 100 mg/L |

Extract Library Preparation Part 2—Extraction:

Cell pellets from the fermentation step were resuspended in 30 µl Lysis buffer (Table 4 below) and transferred to 384-well thermocycler plates. Note that the buffer contained lysozyme to assist in cell lysis, and two nucleases to remove both RNA and DNA from the extract. The plates were subjected to three rounds of freeze-thaw (−70° C. freeze, 37° C. thaw, not less than 15 minutes per step) to lyse the cells. Ammonium sulfate was added (5 µl of a 0.75M solution) and the plates incubated at 75° C. for 15 minutes in order to precipitate and inactivate contaminating proteins, including the exogenously added nucleases. The plates were centrifuged at 3000×g for 15 minutes and the supernatants transferred to a fresh 384-well thermocycler plate. These extract plates were frozen at −20° C. for later use in screens. Each well contained about 0.5-3 µM of the mutant library polymerase enzyme.

TABLE 4

Lysis Buffer

| Component | Concentration or Percentage |
|---|---|
| Tris pH 8.0 | 20 mM |
| EDTA | 1 mM |
| MgCl$_2$ | 5 mM |
| TLCK | 1 mM |
| Leupeptin | 1 µg/ml |
| Pefabloc | 0.5 mg/ml |
| Tween 20 | 0.5% v/v |
| Lysozyme (from powder) | 2 mg/ml |
| RNase | 0.025 mg/ml |
| DNase I | 0.075 Units/µl |

Screening Extract Libraries for Improved Extension Rate:

M13mp18 single-stranded DNA (M13; GenBank Accession No. X02513), primed with an oligonucleotide having the following sequence:

(SEQ ID NO: 72)
5'-GGGAAGGGCGATCGGTGCGGGCCTCTTCGC-3' was used as the template molecule in the extension assay screen. 0.5-1.0 µl of extract was added to 10-20 µl reaction master mix containing 0.5-1 nM primed M13 template in 384-well PCR plates. Extension of the primed template was monitored every 10-30 seconds in a modified kinetic thermal cycler using a CCD camera (see, Watson, supra). A typical reaction master mix is listed below. Master mixes invariably included metal ion, usually magnesium at 1-4 mM, a mixture of all four dNTPs or dNTP analogs, buffer components to control the pH and the ionic strength, typically 25 mM Tricine pH 8.3/35 mM KOAc, and SYBR Green I at 0.6× (Molecular Probes), which allowed for the fluorescent detection of primer strand extension. In order to distinguish extension-derived fluorescence from background fluorescence, parallel wells were included in the experiment in which primer strand extension was prevented, for example, by adding a metal chelator such as EDTA, or leaving out the nucleotides from the reaction master mix.

In order to find mutant enzymes that have improved nucleic acid extension rates in the presence of ribonucleotides, extension reactions were run in the presence and absence of ribonucleotides and the resulting rates of extension were compared, using the methods described above. Adding a high level of ribonucleotide (for example, a 50:50 mix of rATP and dATP) reduced the rate of extension of the parental enzyme, G46E L329A E678G CS5. Mutant extracts that exhibited a reduced level of inhibition by ribonucleotides were identified in this screen. Primary screening was done on the scale of thousands of extracts. The top several percent of these were chosen for re-screening. Culture wells corresponding to the top extracts were sampled to fresh growth medium and re-grown to produce a new culture plate containing all of the top producers, as well as a number of parental cultures to be used for comparison. These culture plates were then fed into the same screening process, to get more data on the candidate mutants. Following this secondary screening round, a relatively small number of extracts still appeared to consistently display improved extension rate relative to the parental clone. These clones were chosen for further testing. They were first streaked on selective agar plates to ensure clonal purity, then the DNA sequence of the mutated region of the polymerase gene was sequenced to determine the mutation(s) that were present in any single clone. In parallel with this work, enough mutant enzyme was produced in shake flask culture for the concentration to be determined by gel-based densitometry, after partial purification in a manner similar to that used to prepare the primary extracts. These quantified extracts were compared to parental enzyme in the conditions used in the screen, but at equal protein concentration. This final screen ensured that the differences observed were not simply protein concentration effects.

Following this final round of screening, four clones still appeared to have improved extension rates in the presence of ribonucleotides. The sequences of these four clones were determined to code for the following amino acid changes relative to the parental strain:

clone 1: S553T D640G D664G E830A
clone 2: S671F
clone 3: F557L I669F
clone 4: Q601R Y739C V749A In the case of clone 2, it was clear that the S671F mutation must have been responsible for the observed phenotype, since it was the only amino acid mutation in the clone. For the other three clones, it was initially impossible to tell which mutation, or combination of mutations, was responsible for the observed phenotype. Therefore, the individual mutations were separated from one another, by combining DNA from the mutant plasmid with the parental plasmid using restriction fragment swaps. This is easily effected in cases where a vector-unique restriction site exists between mutations to be separated. For clone 1, such sites exist between all four of the mutations, accordingly it was possible to prepare plasmids containing each mutation individually as well as other plasmids carrying any 2 or 3 of the 4 original mutations. For clone 4, there was no such site between Y739C and V749A, but there was a site between Q601R and Y739C. Therefore it was possible to prepare plasmid DNA encoding a polymerase carrying just the Q601R mutation, and another plasmid carrying the Y739C/V749A combination.

These new plasmids were transformed into the *E. coli* host, and polymerase protein was expressed, purified to homogeneity, and quantified. These resulting new mutant enzymes were compared to the parental types and to the original mutant enzymes under the conditions of the original screen. It was clear from this data that the mutation D640G was solely responsible for the improved phenotype of mutant clone 1, that the mutation I669F was responsible for the improvements in mutant clone 3, and that the mutation Q601R was responsible for the improvements in mutant clone 4.

These active mutations were then combined with one another, and moved into different CS-type backbones (see, e.g., Table 2, above), again using restriction fragment swaps to create the desired expression plasmid, then transforming the plasmid into the *E. coli* host, and finally expressing, purifying to homogeneity, and quantifying the mutant polymerase, as described above. These new combination mutants were tested for the ability to extend primed M13 DNA in the presence of ribonucleotides. Interestingly, it was found that combining the mutations D640G, S671F, and Q601R resulted in an increase in extension rate relative to clones carrying only a single mutation. The double combination mutants tested, including D640G S671F and Q601R S671F, also showed improved extension rates relative to strains carrying only a single mutation. Moreover, the combination mutants also demonstrated improved rates of extension on primed M13 DNA when only dNTPs were present, when compared to the parental type, and furthermore it was observed that the degree of improvement relative to the parental type was greatest when the extension rate experiment was performed at low enzyme concentration or relatively high salt concentration. These observations were repeated when the combination mutations were moved into a genetic backbone that did not include the riboincorporating mutation E678G. Surprisingly, even in the E678 background, the individual mutant enzymes and the combination mutant enzymes were even "faster" than their corresponding E678 "parents." These and other characteristics of the mutant polymerases of the invention are further illustrated in the examples provided below.

Example II: Properties of Mutants of G46E L329A E678G CS5 DNA Polymerase Under Varied Salt Concentrations The nucleic acid extension rates of various mutants of G46E L329A E678G CS5 DNA polymerase were determined in the presence of 90% riboadenosine triphosphate (ribo ATP or rATP). The reaction mixture contained 25 mM Tricine pH 8.3, 20 mM (FIG. 4) or 60 mM (FIG. 5) KOAc, 3 mM MgCl$_2$, 2.5% v/v Storage Buffer (50% v/v glycerol, 100 mM KCl, 20 mM Tris pH 8.0, 0.1 mM EDTA, 1 mM DTT, 0.5% Tween 20), 1% DMSO, 1×SYBR Green I, 0.5 nM primed M13, and 5 nM enzyme. To this, nucleotides were added to a final concentration of 0.1 mM dGTP, 0.1 mM dTTP, and 0.1 mM dCTP, 0.01 mM dATP, and 0.09 mM ribo ATP. Parallel reactions containing no nucleotides were also set up. All reactions were run in quadruplicate in 20 µl volume in 384 well thermocycler plates. The extension of primed M13 template was monitored by fluorescence in a kinetic thermocycler set at 64° C., taking readings every 10 seconds. Replicate identical reactions were averaged and the parallel minus nucleotide reactions subtracted. Extension rate was estimated by linear regression analysis of the resulting data.

Figure 5:
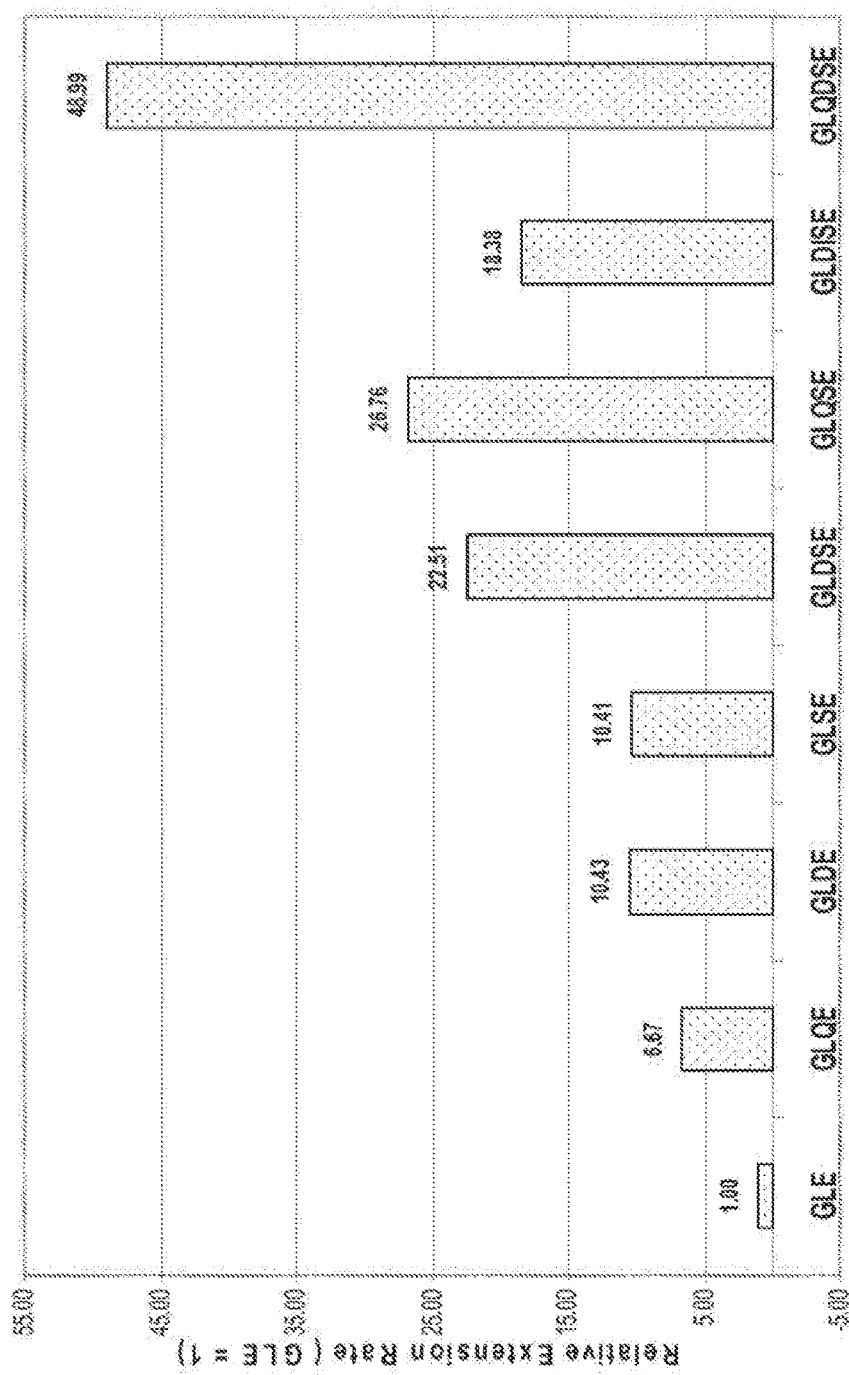
FIG. 5 is a bar graph that shows the normalized extension rates of various mutants of a G46E L329A E678G (GLE) CS5 DNA polymerase. The y-axis represents the relative extension rates, while the x-axis represents the DNA polymerases having specified point mutations (G=G46E, L=L329A, Q=Q601R, D=D640G, I=I669F, S=S671F, and E=E678G). The extension rate values obtained for the mutant polymerases are normalized relative to the value obtained for the GLE CS5 DNA polymerase, which is set to 1.00.

As indicated above, FIGS. 4 and 5 show results obtained from these analyses. For example, FIGS. 4 and 5 illustrate that improved nucleic acid extension rates result from various mutants described herein, when ribonucleotides are present in reaction mixtures and incorporated on a DNA template. As further shown, for example, when certain mutations are combined in a single mutant enzyme, even further extension rate improvements are observed.

Example III: Properties of Mutants of G46E L329A CS5 DNA Polymerase Under Varied Salt Concentrations The nucleic acid extension rate of various mutants of G46E L329A CS5 DNA polymerase, as well as *Thermus* sp. Z05 DNA polymerase and its truncate, delta Z05 DNA polymerase (see, e.g., U.S. Pat. No. 5,455,170, entitled "MUTATED THERMOSTABLE NUCLEIC ACID POLYMERASE ENZYME FROM *THERMUS* SPECIES Z05" issued Oct. 3, 1995 to Abramson et al. and U.S. Pat. No. 5,674,738, entitled "DNA ENCODING THERMOSTABLE NUCLEIC ACID POLYMERASE ENZYME FROM *THERMUS* SPECIES Z05" issued Oct. 7, 1997 to Abramson et al., which are both incorporated by reference), was determined. The reaction mixture contained 25 mM Tricine pH 8.3, 0 mM (FIG. 6) or 60 mM (FIG. 7) KOAc, 3 mM MgCl$_2$, 2.5% v/v Storage Buffer (50% v/v glycerol, 100 mM KCl, 20 mM Tris pH 8.0, 0.1 mM EDTA, 1 mM DTT, 0.5% Tween 20), 1% DMSO, 1×SYBR Green I, 0.5 nM primed M13, and 5 nM enzyme. To this, nucleotides were added to a final concentration of 0.1 mM dGTP, 0.1 mM dTTP, and 0.1 mM dCTP, and 0.1 mM dATP. Parallel reactions containing no nucleotides were also set up. All reactions were run in quadruplicate in 20 µl volume in 384 well thermocycler plates. The extension of primed M13 template was monitored by fluorescence in a kinetic thermocycler set at 64° C., taking readings every 10 seconds. Replicate identical reactions were averaged and the parallel minus nucleotide reactions subtracted. Extension rate was estimated by linear regression analysis of the resulting data.

Figure 6:
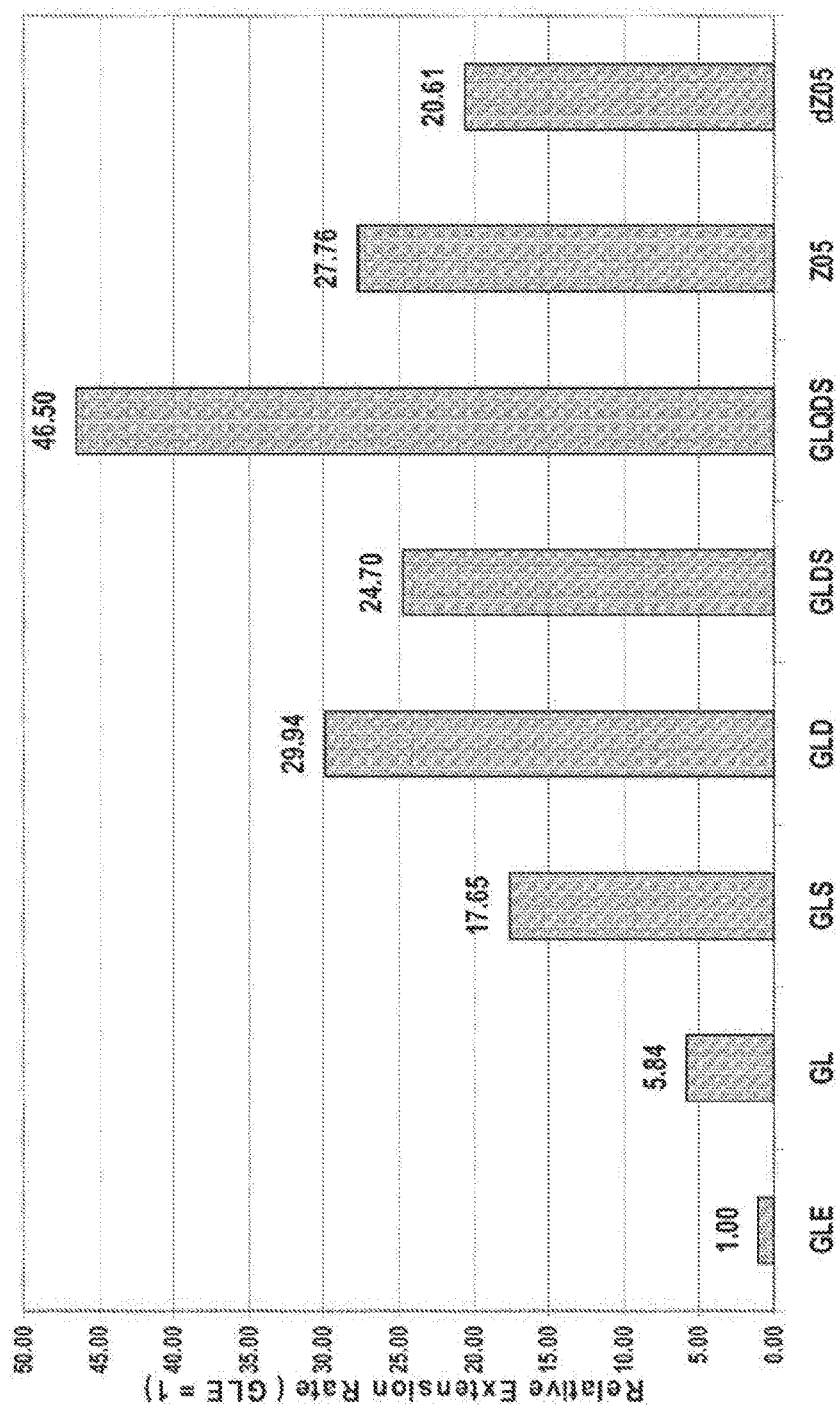
FIG. 6 is a bar graph that shows the normalized extension rates of a Z05 DNA polymerase, a ΔZ05 DNA (dZ05 in FIG. 6) polymerase (see, e.g., U.S. Pat. No. 5,455,170, entitled "MUTATED THERMOSTABLE NUCLEIC ACID POLYMERASE ENZYME FROM *THERMUS* SPECIES Z05" issued Oct. 3, 1995 to Abramson et al. and U.S. Pat. No. 5,674,738, entitled "DNA ENCODING THERMOSTABLE NUCLEIC ACID POLYMERASE ENZYME FROM *THERMUS* SPECIES Z05" issued Oct. 7, 1997 to Abramson et al., which are both incorporated by reference), and various mutants of a G46E L329A (GL) CS5 DNA polymerase. The y-axis represents the relative extension rates, while the x-axis represents the DNA polymerases having specified point mutations (G=G46E, L=L329A, Q=Q601R, D=D640G, I=I669F, S=S671F, and E=E678G). The extension rate values obtained for the mutant polymerases are normalized relative to the value obtained for a GLE CS5 DNA polymerase, which is set to 1.00.
Figure 7:
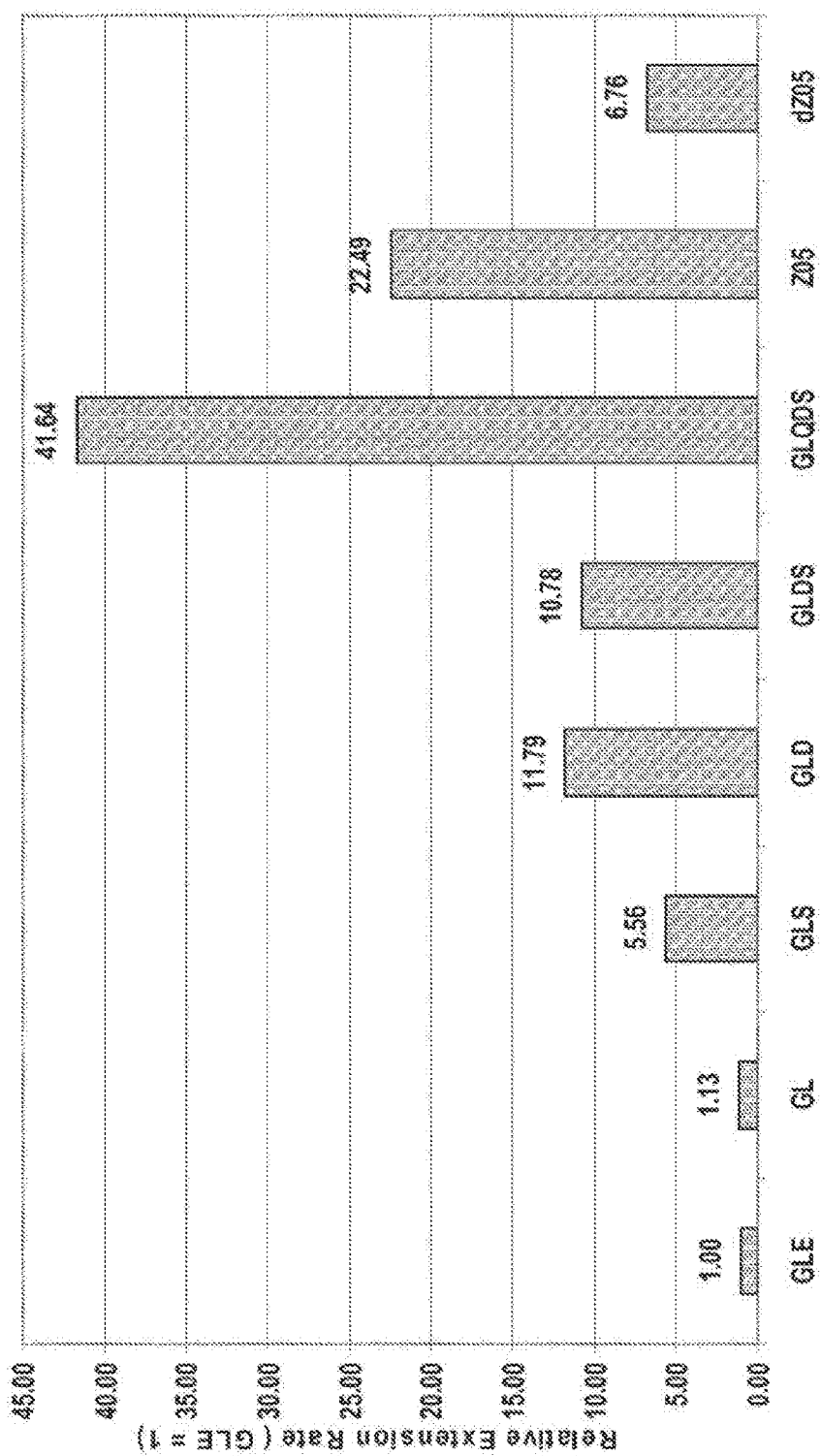
FIG. 7 is a bar graph that shows the normalized extension rates of a Z05 DNA polymerase, a ΔZ05 (dZ05 in FIG. 7) DNA polymerase, and various mutants of a G46E L329A (GL) CS5 DNA polymerase. The y-axis represents the relative extension rates, while the x-axis represents the DNA polymerases having specified point mutations (G=G46E, L=L329A, Q=Q601R, D=D640G, I=I669F, S=S671F, and E=E678G). The extension rate values obtained for the mutant polymerases are normalized relative to the value obtained for a GLE CS5 DNA polymerase, which is set to 1.00.

The data shown in FIGS. 6 and 7 illustrate, e.g., that certain mutations described herein result in improved nucleic acid extension rates even when ribonucleotides are not present in the reaction mixtures, and even in a genetic backbone that does not include the ribonucleotide-incorporation mutation, E678G. As further shown, for example, this rate improvement is even greater when the mutations are combined in a single mutant enzyme.

Example IV: Effect of Salt Concentration on the Extension Rates of Various Mutant CS5 DNA Polymerases The nucleic acid extension rate of various mutants of G46E L329A CS5 DNA polymerase, as well as *Thermus* sp. Z05 DNA polymerase and its truncate, delta Z05 DNA polymerase, was determined. The reaction mixture contained 25 mM Tricine pH 8.3, 0-100 mM KOAc, 3 mM MgCl$_2$, 2.5% v/v Storage Buffer (50% v/v glycerol, 100 mM KCl, 20 mM Tris pH 8.0, 0.1 mM EDTA, 1 mM DTT, 0.5%

Figure 8:
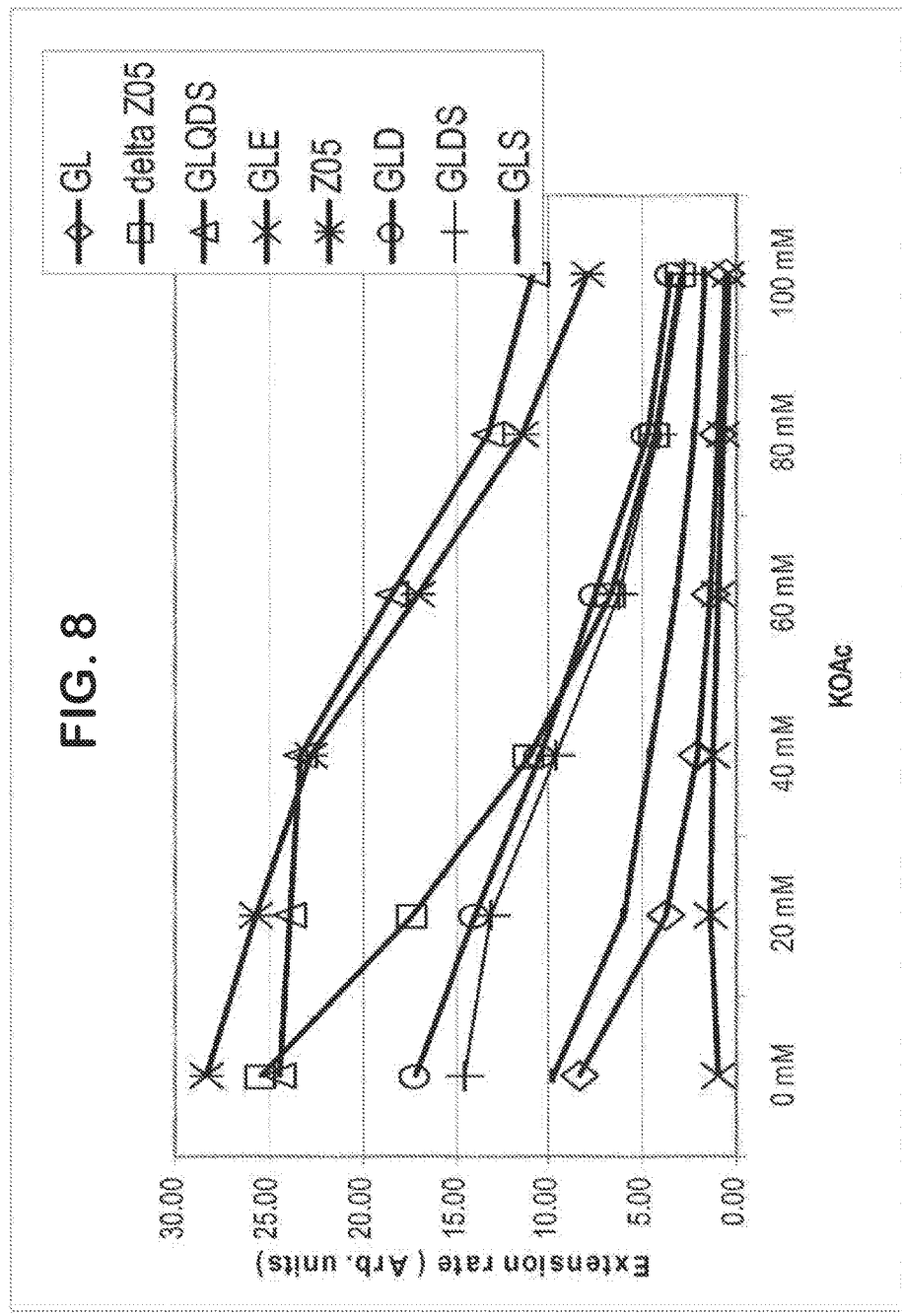
FIG. 8 is a plot that shows the extension rates of different DNA polymerases under varied salt (KOAc) concentrations. The y-axis represents the extension rates (Arbitrary Units), while the x-axis represents KOAc concentration (mM). The legend that accompanies the plot shows the DNA polymerase corresponding to each trace in the plot. In particular, delta Z05 refers to A Z05 DNA polymerase and Z05 refers to Z05 DNA polymerase, while the other enzymes indicated refer to mutant CS5 DNA polymerases having specified point mutations (G=G46E, L=L329A, Q=Q601R, D=D640G, S=S671F, and E=E678G).
Figure 9:
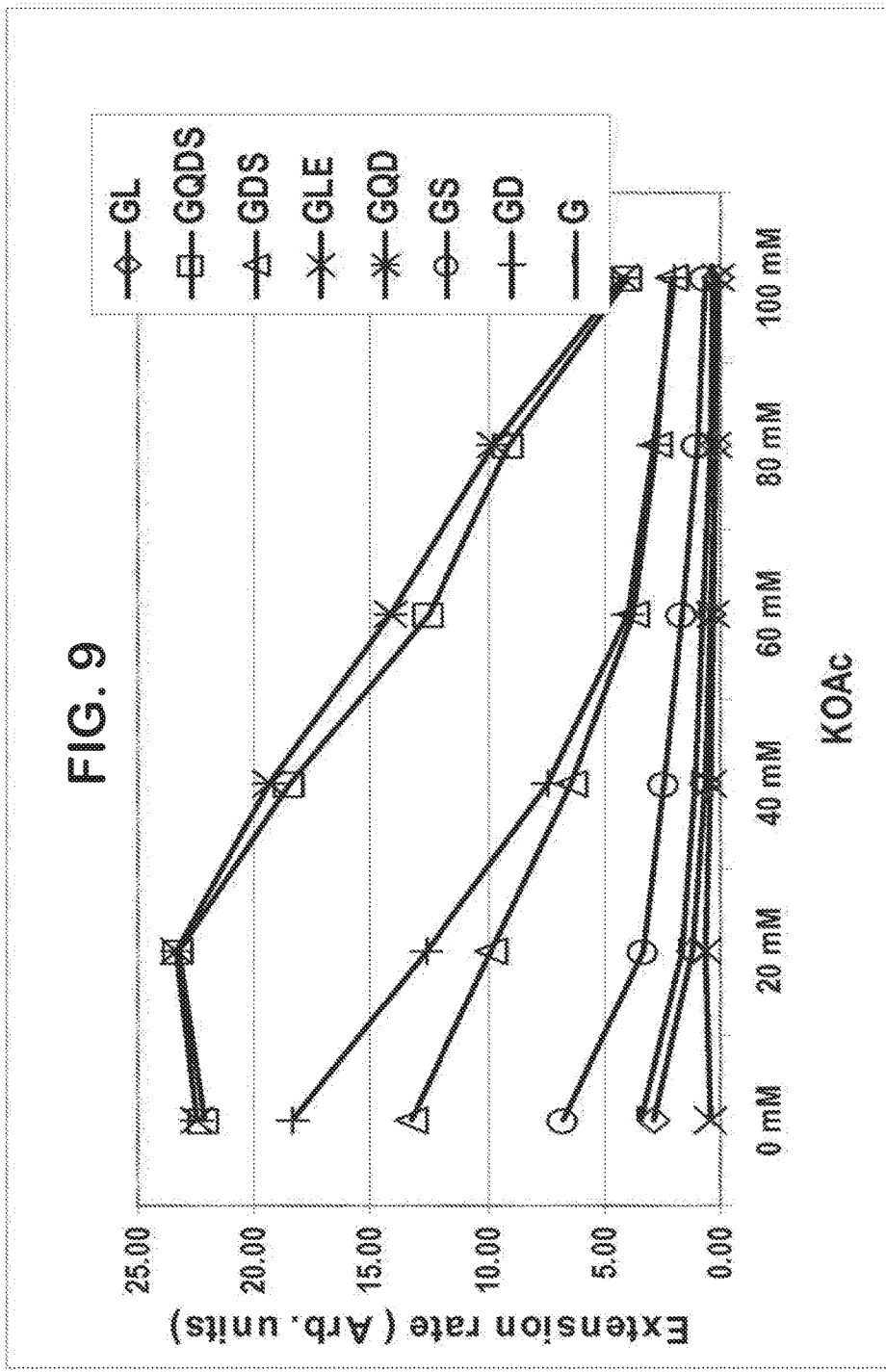
FIG. 9 is a plot that shows the extension rates of different DNA polymerases under varied salt (KOAc) concentrations. The y-axis represents the extension rates (Arbitrary Units), while the x-axis represents KOAc concentration (mM). The legend that accompanies the plot shows the DNA polymerase corresponding to each trace in the plot. In particular, the other enzymes indicated refer to mutant CS5 DNA polymerases having specified point mutations (G=G46E, L=L329A, Q=Q601R, D=D640G, S=S671F, and E=E678G).

Tween 20), 1% DMSO, 1×SYBR Green I, 0.5 nM primed M13, and 25 nM (FIG. 8) or 5 nM (FIG. 9) enzyme. To this, nucleotides were added to a final concentration of 0.1 mM dGTP, 0.1 mM dTTP, and 0.1 mM dCTP, and 0.1 mM dATP. Parallel reactions containing no nucleotides were also set up. All reactions were run in quadruplicate in 20 µl volume in 384 well thermocycler plates. The extension of primed M13 template was monitored by fluorescence in a kinetic thermocycler set at 64° C., taking readings every 10 seconds. Replicate identical reactions were averaged and the parallel minus nucleotide reactions subtracted. Extension rate was estimated by linear regression analysis of the resulting data.

The data shown in FIGS. 6 and 7 illustrate, among other properties, e.g., that the increased nucleic acid extension rates conferred by the certain mutants described herein are maintained over a wide range of salt and enzyme concentrations, and also that the mutations confer an extension rate increase in a genetic background that includes full proofreading activity.

Example V: Use of Various Mutant CS5 DNA Polymerases in RT-PCR $Mg^{2+}$-Based RT:

The mutations Q601R, D640G, and S671F, separately and in combination, were evaluated for their effect on PCR and RT-PCR efficiency in the presence of $Mg^{+2}$. The reactions all contained the following components: 50 mM Tricine pH 8.0, 2.5 mM Mg(OAc)$_2$, 6% v/v Storage Buffer (50% v/v glycerol, 100 mM KCl, 20 mM Tris pH 8.0, 0.1 mM EDTA, 1 mM DTT, 0.2% Tween 20), 0.2×SYBR Green I, 0.02 units/µl UNG, 0.2 mM each dATP, dCTP, and dGTP, 0.3 mM dUTP, 0.03 mM dTTP, and 200 nM of each primer, wherein the primers comprise a 2'-amino-C at the 3'-end at the 3'-end.

Enzymes were used at their pre-determined concentration and KOAc optima. These are given in Table 5.

TABLE 5

| Polymerase | Pol (nM) | KOAc (mM) | Polymerase | Pol (nM) | KOAc (mM) |
|---|---|---|---|---|---|
| G | 236 | 25 | GL | 236 | 25 |
| GD | 59 | 50 | GLD | 59 | 50 |
| GS | 118 | 25 | GLS | 118 | 25 |
| GDS | 23.6 | 25 | GLDS | 23.6 | 25 |
| GQDS | 23.6 | 100 | GLQDS | 23.6 | 100 |

Figure 10:
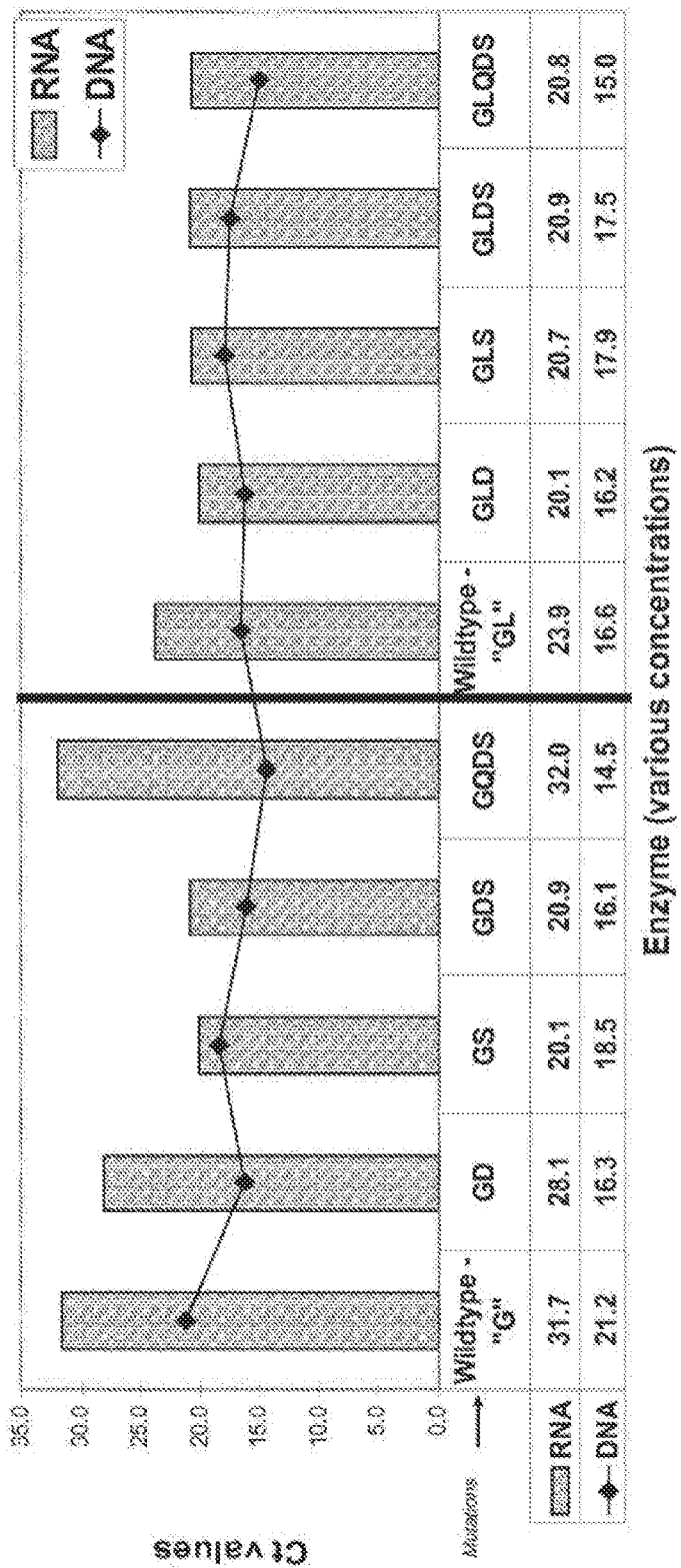
FIG. 10 is a bar graph that shows the threshold cycle (Ct) values obtained for various mutant CS5 DNA polymerases in RT-PCRs. The y-axis represents the Ct values, while the x-axis represents the DNA polymerases having specified point mutations (G=G46E, L=L329A, Q=Q601R, D=D640G, and S=S671F).
Figure 11:
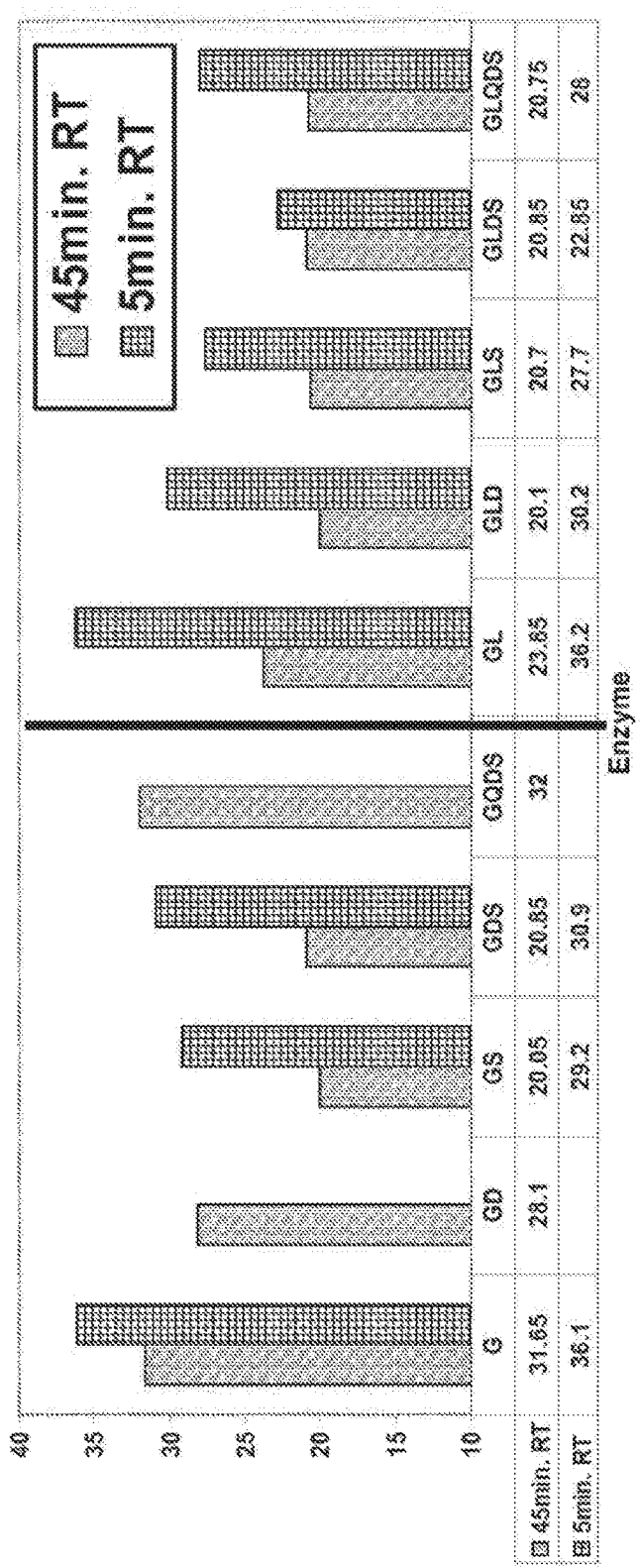
FIG. 11 is a bar graph that shows the threshold cycle (Ct) values obtained for various mutant CS5 DNA polymerases in $Mg^{+2}$-activated RT-PCRs having varied RT incubation times. The y-axis represents the Ct values, while the x-axis represents the DNA polymerases having specified point mutations (G=G46E, L=L329A, Q=Q601R, D=D640G, and S=S671F).

Each enzyme was tested with both 10$^6$ copies/50 µl reaction DNA template (pAW109 plasmid DNA) and 10$^6$ copies/50 µl reaction RNA template (pAW109 transcript). Reactions were run in a kinetic thermocycler (ABI 5700 thermalcycler). The thermocycling parameters were: 50° C. for 2 minutes; 65° C. for 45 minutes; 93° C. for 1 minute; then 40 cycles of: 93° C. for 15 seconds; and 65° C. for 30 seconds. Fluorescence data was analyzed to determine Ct values (emergence of fluorescence over baseline) (FIG. 10). More specifically, the data shown in FIG. 10 (see also, FIG. 11) illustrates, among other properties, e.g., that the mutations described herein, either singly or in combination, improve the efficiency of the $Mg^{2+}$-activated reverse transcription activity of the mutant enzyme relative to the corresponding parent or non-mutant enzyme. For example, the GLDS enzyme performed well, e.g., when the time allowed for reverse transcription was decreased to 5 minutes, as shown in FIG. 11 (referred to additionally below).

$Mg^{2+}$-Based RT with Reduced RT Time:

The mutations Q601R, D640G, and S671F, separately and in combination, were evaluated for their effect on RT-PCR efficiency in the presence of $Mg^{+2}$, using either 45 minute or 5 minute RT time. The reactions all contained the following components: 50 mM Tricine pH 8.0, 2.5 mM Mg(OAc)$_2$, 6% v/v Storage Buffer (50% v/v glycerol, 100 mM KCl, 20 mM Tris pH 8.0, 0.1 mM EDTA, 1 mM DTT, 0.2% Tween 20), 1% DMSO, 0.2×SYBR Green I, 0.02 units/µl UNG, 0.2 mM each dATP, dCTP, and dGTP, 0.3 mM dUTP, 0.03 mM dTTP, and 200 nM of each primer, wherein the primers comprise a 2'-amino-C at the 3'-end.

Enzymes were used at their pre-determined concentration and KOAc optima. These are given in the following Tables 6 and 7:

TABLE 6

45 minute RT Time:

| Polymerase | Pol (nM) | KOAc (mM) | Polymerase | Pol (nM) | KOAc (mM) |
|---|---|---|---|---|---|
| G | 236 | 25 | GL | 236 | 25 |
| GD | 59 | 50 | GLD | 59 | 50 |
| GS | 118 | 25 | GLS | 118 | 25 |
| GDS | 23.6 | 25 | GLDS | 23.6 | 25 |
| GQDS | 23.6 | 100 | GLQDS | 23.6 | 100 |

TABLE 7

5 minute RT time:

| Polymerase | Pol (nM) | KOAc (mM) | Polymerase | Pol (nM) | KOAc (mM) |
|---|---|---|---|---|---|
| G | 118 | 25 | GL | 236 | 55 |
| GD | ~ | ~ | GLD | 94.4 | 50 |
| GS | 118 | 25 | GLS | 118 | 25 |
| GDS | 23.6 | 25 | GLDS | 106.2 | 50 |
| GQDS | ~ | ~ | GLQDS | 23.6 | 100 |

~ denotes condition that was not done

Each enzyme was tested with 10$^6$ copies/50 µl reaction RNA template (pAW109 transcript). Reactions were run in a kinetic thermocycler (ABI5700). The thermocycling parameters were: 50° C. for 2 minutes; 65° C. for 5 minutes or 45 minutes; 93° C. for 1 minute; then 40 cycles of: 93° C. for 15 seconds; and 65° C. for 30 seconds. Fluorescence data was analyzed to determine Ct values (emergence of fluorescence over baseline) (FIG. 11).

$Mn^{2+}$-Based RT with Reduced RT Time:

The mutations Q601R, D640G, and S671F, separately and in combination, were evaluated for their effect on RT-PCR efficiency in the presence of $Mn^{+2}$, using either 45 minute or 5 minute RT time. The reactions all contained the following components: 50 mM Tricine pH 8.0, 1 mM Mn(OAc)$_2$, 6% v/v Storage Buffer (50% v/v glycerol, 100 mM KCl, 20 mM Tris pH 8.0, 0.1 mM EDTA, 1 mM DTT, 0.2% Tween 20), 1% DMSO, 0.2×SYBR Green I, 0.02 units/µl UNG, 0.2 mM each dATP, dCTP, and dGTP, 0.3 mM dUTP, 0.03 mM dTTP, and 200 nM of each primer, wherein the primers comprise a 2'-amino-C at the 3'-end.

Enzymes were used at their pre-determined concentration/KOAc optima. These are given in the following Tables 8 and 9:

TABLE 8

45 minute RT Time:

| Polymerase | Pol (nM) | KOAc (mM) | Polymerase | Pol (nM) | KOAc (mM) |
|---|---|---|---|---|---|
| G | 236 | 55 | GL | 236 | 55 |
| GD | ~ | ~ | GLD | 59 | 55 |

TABLE 8-continued 45 minute RT Time:

| Polymerase | Pol (nM) | KOAc (mM) | Polymerase | Pol (nM) | KOAc (mM) |
|---|---|---|---|---|---|
| GS | 118 | 55 | GLS | 118 | 55 |
| GDS | 23.6 | 55 | GLDS | 23.6 | 70 |
| GQDS | 23.6 | 100 | GLQDS | 23.6 | 100 |

TABLE 9

5 minute RT time:

| Polymerase | Pol (nM) | KOAc (mM) | Polymerase | Pol (nM) | KOAc (mM) |
|---|---|---|---|---|---|
| G | ~ | ~ | GL | 354 | 68 |
| GD | ~ | ~ | GLD | ~ | ~ |
| GS | ~ | ~ | GLS | 59 | 55 |
| GDS | ~ | ~ | GLDS | 23.6 | 70 |
| GQDS | 59 | 100 | GLQDS | 11.8 | 100 |

~ denotes condition that was not done

Figure 12:
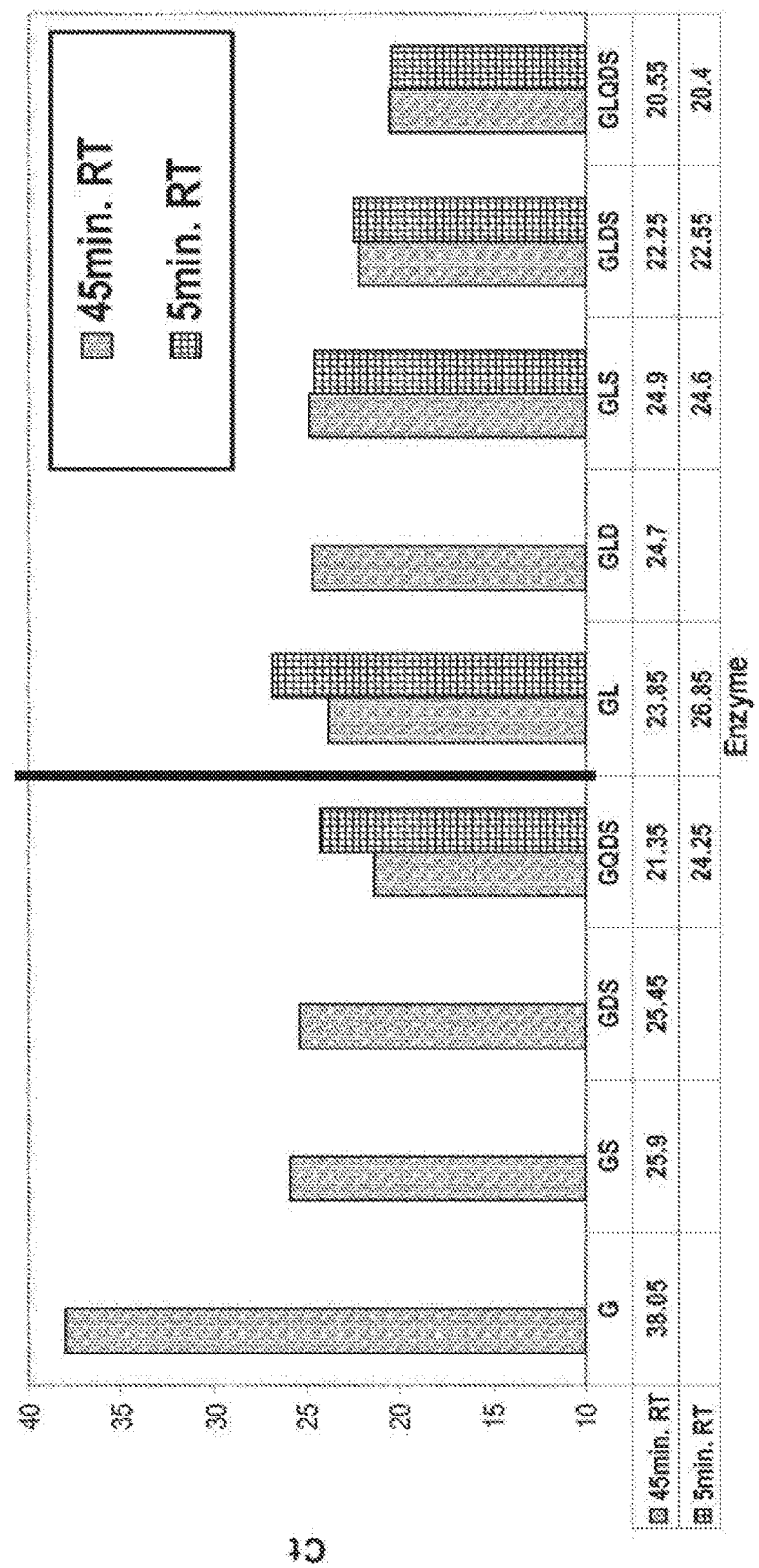
FIG. 12 is a bar graph that shows the Ct values obtained for various mutant CS5 DNA polymerases in $Mn^{+2}$-activated RT-PCRs having varied RT incubation times. The y-axis represents the Ct values, while the x-axis represents the DNA polymerases having specified point mutations (G=G46E, L=L329A, Q=Q601R, D=D640G, and S=S671F).

Each enzyme was tested with $10^5$ copies/50 µl reaction RNA template (pAW109 transcript). Reactions were run in a kinetic thermocycler (ABI5700). The thermocycling parameters were: 50° C. for 2 minutes; 65° C. for 5 minutes or 45 minutes; 93° C. for 1 minute; then 40 cycles of: 93° C. for 15 seconds; and 65° C. for 30 seconds. Fluorescence data was analyzed to determine Ct values (emergence of fluorescence over baseline) (FIG. 12). More specifically, the data shown in FIG. 12 illustrates, among other properties, e.g., that improved $Mn^{2+}$-activated reverse transcription efficiency results from certain of the mutations described herein, either singly or in combination, and that this improvement is enhanced when the time allowed for reverse transcription is decreased.

Example VI: Fragmentation Using Low-Level Ribonucleoside Triphosphate Incorporation It is sometimes useful to fragment a PCR product, for example when analyzing the product in a hybridization-based assay. Fragmentation can be easily accomplished by treating with alkali and heat, if ribonucleotides have been incorporated into the PCR product. For such applications relatively low level ribo-substitution will suffice to achieve fragments of optimal length. The ability of various mutant DNA polymerases to generate ribo-substituted PCR product of length 1 kb was demonstrated in the following example.

The reaction mixture was composed of 100 mM Tricine pH 8.3, 75 mM KOAc, 5% v/v glycerol, 2.5 mM Mg(OAc)$_2$, 50 nM enzyme, 0.1% v/v DMSO, and 2.5% v/v enzyme storage buffer (50% v/v glycerol, 100 mM KCl, 20 mM Tris pH 8.0, 0.1 mM EDTA, 1 mM DTT, 0.5% Tween 20). Various mixtures of dNTPs and rNTPS were tested. In all cases, the sum of rATP and dATP was 200 µM, as was the sum of dCTP and rCTP, and dGTP and rGTP. The sum of dTTP and rTTP was 40 µM and the sum of dUTP and rUTP was 360 µM. In this analysis either all four rNTPS were added together, up to 10% of the total (see, "rNTP Series" in FIGS. 13A and 13B (% rNTP indicated above the relevant lane in the gel)), or rATP alone was added, up to 50% of the total (see, "rATP Series" in FIGS. 13A and 13B (% rATP indicated above the relevant lane in the gel)). Enzymes tested were GQDSE, CS6-GQDSE, GLQDSE, GDSE, GLDSE, GLDE, GE, and a 4:1 mixture of GL and GLE (G=G46E, L=L329A, Q=Q601R, D=D640G, S=S671F, and E=E678G).

This reaction mix included primers used to generate a 1 kb product from an M13 template. The primers were used at 200 nM each, wherein the primers comprise a 2'-amino-C at the 3'-end. M13 DNA was added to $10^6$ copies per 100 µl reaction.

Reactions were run in an ABI 9700 thermocycler. The thermocycling parameters were: 50° C. for 15 seconds; 92° C. for 1 minute; then 30 cycles of: 92° C. for 15 seconds; followed by an extension step of 62° C. for 4 minutes. The ability to make full length amplicon under the various conditions tested was determined by agarose gel electrophoresis, loading 5 µl of each reaction per lane on a 2% egel-48 (Invitrogen) (FIGS. 13A and 13B). More specifically, these figures show, e.g., that certain mutant enzymes described herein are able to produce full-length (1 kb) amplicons at higher levels of ribonucleotides present in the reaction mixtures than the corresponding parental or non-mutant G46E CSSR enzyme. For example, the mixture of GL CS5 and GLE enzymes made amplicon at the highest level of ribonucleotide assayed in this example, but because GL CS5 polymerase cannot incorporate ribonucleotides, these amplicons contained a relatively low level of ribonucleotides incorporated in the amplicon.

These amplicons were then fragmented as follows: 2 µl amplicon was diluted 27.5× in 0.3N NaOH and 20 mM EDTA, then heated at 98° C. for 10 minutes. The fragmented amplicon was neutralized by adding 2.5 µl 6 N HCl. To determine the degree of fragmentation achieved, the copy number of an internal fragment of the amplicon was compared before and after fragmentation, using quantitative PCR without UNG. The cycle delay observed due to fragmentation is an indication of the degree of fragmentation (and of ribonucleotide incorporation). Increased ribonucleotide incorporation leads to increased Ct delay. For this amplification, the reaction mixture was composed of 100 mM Tricine pH 8.3, 50 mM KOAc, 5% v/v glycerol, 2.5 mM Mg(OAc)$_2$, 20 nM GQDS, 0.5% DMSO, 0.1×SYBR Green I, 2.5% v/v enzyme storage buffer (50% v/v glycerol, 100 mM KCl, 20 mM Tris pH 8.0, 0.1 mM EDTA, 1 mM DTT, 0.5% Tween 20), 200 µM each dCTP, dGTP, and dATP, 360 µM dUTP, and 40 µM dTTP. This reaction mix was used to generate a 340 bp product from the fragmented and unfragmented amplicons, diluting these templates a further 10,000-fold from the dilution used for fragmentation. The primer sequences were used at 200 nM each, wherein the primers comprise a 2'-amino-C at the 3'-end.

Reactions were run in 384-well plates, 20 µl per reaction in a kinetic thermocycler. The thermocycling parameters were: 50° C. for 15 seconds; 92° C. for 1 minute; then 46 cycles of: 92° C. for 15 seconds; followed by an extension step of 62° C. for 1 minute. Threshold Cts were determined and corresponding fragmented and unfragmented Cts were compared, thus generating a delta Ct for each enzyme/rNTP condition tested. In this example, the greater the amount of incorporated NTP (reflecting an improved ability to incorporate NTPs in the presence of dNTPs), the greater will be the delta Ct or Ct delay after alkali-induced fragmentation. These are shown in FIGS. 14A and 14B. The data show, e.g., that the mutant enzymes of the invention are superior in the incorporation of ATP or NTP in generating PCR products that have increased extents of ribonucleotide substitution. Compare any of the illustrated enzymes to the parental blend "GL/GLE" or to "C5R". Increased fragmentation derives from increased ribonucleotide incorporation and an improved ability to incorporate a limiting concentration of ribonucleotides in the presence deoxynucleotides.

Hybridization assays frequently involve attaching biotin to the molecule being detected. It is therefore useful to incorporate biotin into PCR product. If biotin is attached to ribonucleotide, each fragment (except the 3' most distal fragment, which is usually complementary to the other primer and therefore uninformative) will carry a single biotin moiety, which will result in equal signal generation by each fragment.

The ability of various enzymes to incorporate ribonucleotides linked to a biotin into PCR product was determined, as described below. The reaction mixture was composed of 100 mM Tricine pH 8.3, 75 mM KOAc, 5% v/v glycerol, 2.5 mM Mg(OAc)$_2$, 50 nM enzyme, 0.1% DMSO, 2.5% v/v enzyme storage buffer (50% v/v glycerol, 100 mM KCl, 20 mM Tris pH 8.0, 0.1 mM EDTA, 1 mM DTT, 0.5% Tween 20), 200 µM each dCTP+ analogs, dGTP, and dATP, 360 µM dUTP, and 40 µM dTTP. rCTP up to 40% of the total or biotin-LC-rCTP up to 50% of the total were tested. Enzymes (CS5 polymerases) tested were GE, GQDSE, GDSE, and a 4:1 blend of GL and GLE (G=G46E, L=L329A, Q=Q601R, D=D640G, S=S671F, and E=E678G).

Figure 15A:
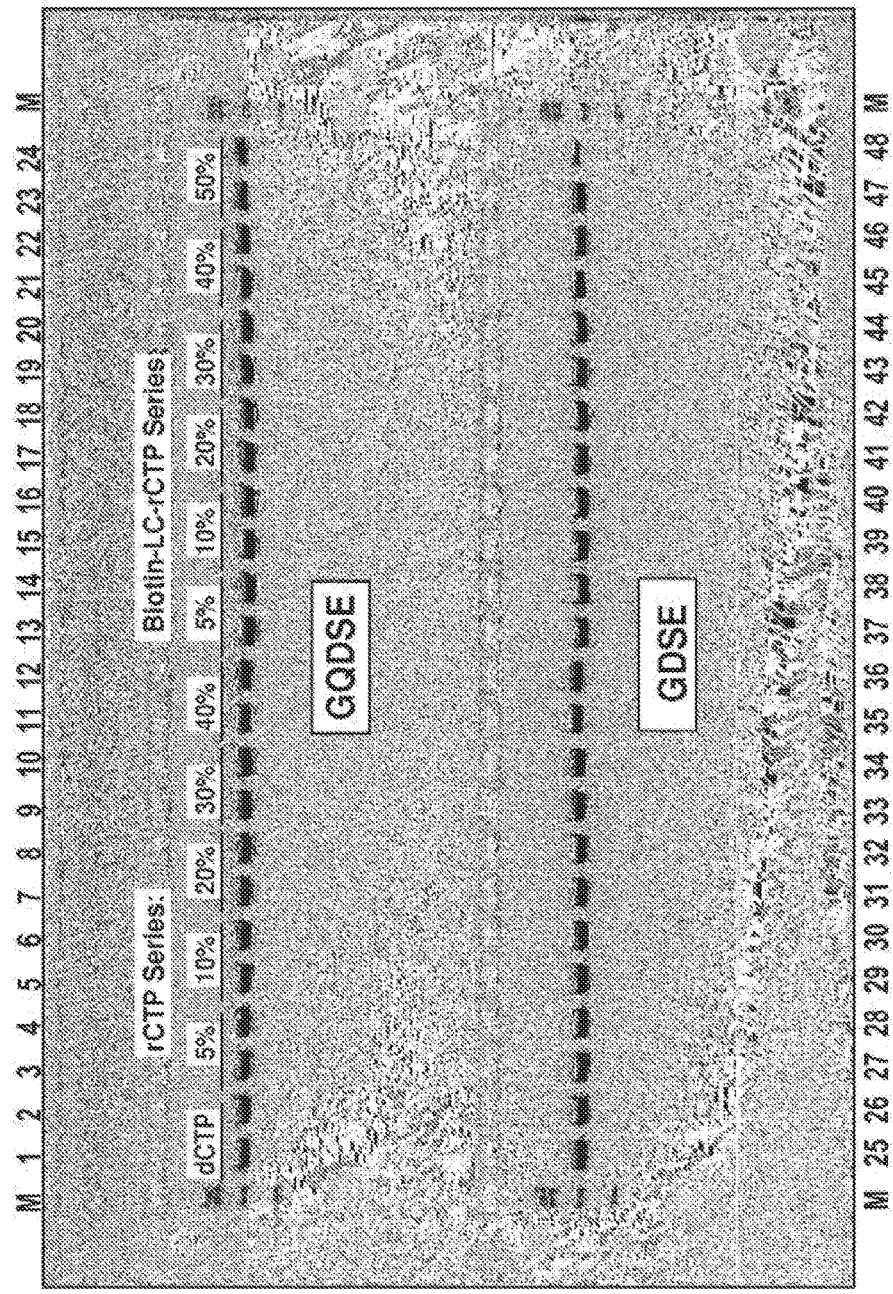
FIGS. 15A and 15B are photographs of agarose gels that illustrate the ability of certain enzymes described herein to make full length amplicon under the various conditions involving biotinylated ribonucleotides. As labeled on the photographs, the CS5 enzymes tested were GQDSE, GDSE, GE (G46E CSSR), and a 4:1 mixture of GL and GLE (GL/GLE Blend (4:1)), where G=G46E, L=L329A, Q=Q601R, D=D640G, S=S671F, and E=E678G.
Figure 15B:
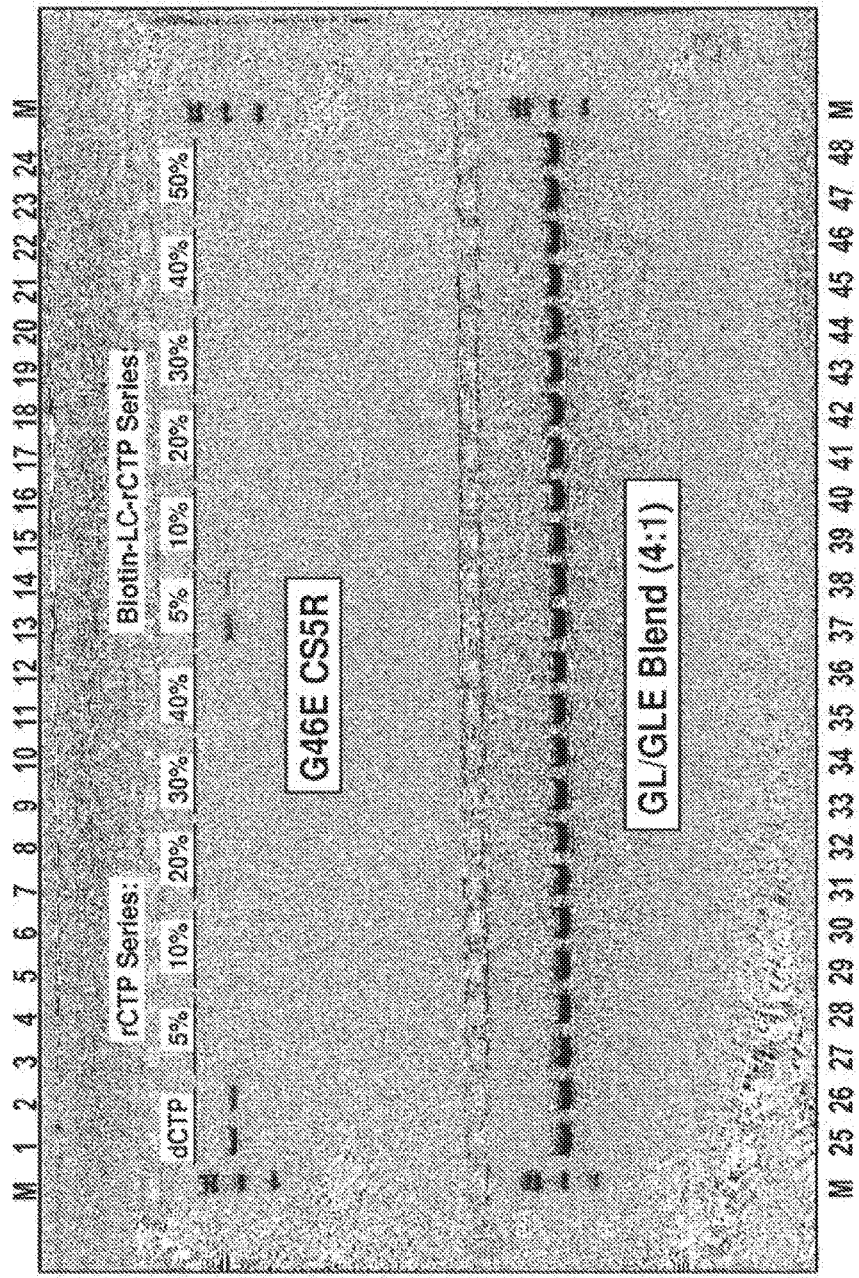

This reaction mix was used to generate a 1 kb product from an M13 template, using primer sequences comprising a 2'-amino-C at 200 nM each. M13 DNA was added to 5×10$^5$ copies per 50 µl reaction. Reactions were run in an ABI 9700 thermocycler. The thermocycling parameters were: 50° C. for 15 seconds; 92° C. for 1 minute; then 30 cycles of: 92° C. for 15 seconds; followed by an extension step of 62° C. for 4 minutes. The ability to make full length amplicon under the various conditions tested was determined by agarose gel electrophoresis, loading 5 µl of each reaction per lane on a 2% egel-48 (Invitrogen) (FIGS. 15A and 15B). More specifically, FIGS. 15A and 15B show, e.g., that mutants GQDSE and GDSE are both able to produce amplicon in higher levels of rCTP and biotinylated rCTP than can the corresponding parental or non-mutant G46E CSSR enzyme. Further while the GL/GLE blend can produce amplicon, this amplicon will have a low level of either rCTP or biotinylated rCTP incorporation, because the GL enzyme cannot incorporate these compounds.

These amplicons were then fragmented as follows: 2 µl amplicon was diluted 27.5× in 0.3N NaOH and 20 mM EDTA, then heated at 98° C. for 10 minutes. The fragmented amplicon was neutralized by adding 2.5 µl 6 N HCl. To determine the degree of fragmentation achieved, the copy number of an internal fragment of the amplicon was compared before and after fragmentation, using quantitative PCR without UNG. The cycle delay observed due to fragmentation is an indication of the degree of fragmentation (and of ribonucleotide incorporation). Thus, increased ribonucleotide incorporation leads to an increased Ct delay. For this amplification, the reaction mixture was composed of 100 mM Tricine pH 8.3, 50 mM KOAc, 5% v/v glycerol, 2.5 mM Mg(OAc)$_2$, 20 nM GQDS, 0.5% DMSO, 0.1×SYBR Green I, 2.5% v/v enzyme storage buffer (50% v/v glycerol, 100 mM KCl, 20 mM Tris pH 8.0, 0.1 mM EDTA, 1 mM DTT, 0.5% Tween 20), 200 µM each dCTP, dGTP, and dATP, 360 µM dUTP, and 40 µM dTTP. This reaction mix was used to generate a 340 bp product from the fragmented and unfragmented amplicons, diluting these templates a further 10,000-fold from the dilution used for fragmentation. The primer sequences were used at 200 nM each, wherein each primer comprised a 2'-amino-C.

Reactions were run in 384-well plates, 20 µl per reaction in a kinetic thermocycler. The thermocycling parameters were: 50° C. for 15 seconds; 92° C. for 1 minute; then 46 cycles of: 92° C. for 15 seconds; followed by an extension step of 62° C. for 1 minute. Threshold Cts were determined and corresponding fragmented and unfragmented Cts were compared, generating a delta Ct for each enzyme/rNTP condition tested. These are shown in FIGS. 16A and 16B. More specifically, FIGS. 16A and 16B illustrate, e.g., that an increase in the degree of fragmentation can be achieved by the mutant enzymes when using either rCTP or biotinylated rCTP, because they are able to produce amplicon with a higher level of ribonucleotide incorporation than the corresponding parental enzymes.

Example VII: Pyrophosphorolysis Activated Polymerization

The abilities of G46E L329A E678G CS5 DNA polymerase and G46E L329A D640 S671F E678G CS5 DNA polymerase to perform pyrophosphorolysis activated polymerization ("PAP") were compared. The reaction buffer was comprised of 100 mM Tricine pH 8.0, 2.5-50 mM G46E L329A E678G CS5 DNA polymerase or 2.5-50 mM G46E L329A D640G S671F E678G CS5 DNA polymerase, 50 nM KOAc, 10% v/v glycerol, 0.04 U/µl UNG, 4 mM Mg(OAc)$_2$, 1% DMSO, 0.2×SYBR Green I, 2.5% v/v enzyme storage buffer (50% v/v glycerol, 100 mM KCl, 20 mM Tris pH 8.0, 0.1 mM EDTA, 1 mM DTT, 0.5% Tween 20), 0.2 mM each dATP, dCTP, and dGTP, and 0.4 mM dUTP, and 100 µM pyrophosphate. M13 template and enzyme were cross-titrated. M13 concentrations used were 0, 10$^4$, 10$^5$, and 10$^6$ copies per 20 µl reaction. Enzyme concentrations used were 2.5 nM, 5 nM, 10 nM, 15 nM, 20 nM, 25 nM, 35 nM, and 50 nM. Reactions were set up in triplicate in a 384-well thermocycler, using the following cycling parameters: 50° C. for 2 minutes; 90° C. for 1 minute; then 46 cycles of: 90° C. for 15 seconds followed by an extension temperature of 62° C. for 60 seconds.

One of the primers comprised a 2'-amino-C at the 3'-end and the other primer comprised a 2'-PO$_4$-A (i.e., a 2'-terminator nucleotide) at the 3'-end. These primers, added to the reaction mix at 0.1 µM each, will result in a 348 bp product from M13 template. However, the 2'-PO$_4$-A residue at the 3'-end of the second primer effectively acts as a terminator. In order to serve as a primer, it must be activated by pyrophosphorolytic removal of the terminal residue.

Fluorescence data was analyzed to determine elbow values (C(t)) (emergence of fluorescence over baseline). C(t) values for G46E L329A E678G CS5 DNA polymerase are shown in FIG. 17. C(t) values for G46E L329A D640G S671F E678G CS5 DNA polymerase are shown in FIG. 18. Further, FIGS. 17 and 18 show, e.g., that using the mutant enzyme results in more efficient PAP-PCR at lower enzyme concentrations than the corresponding non-mutant or parental enzyme. By gel analysis, the amplicon in the no template reactions in this example was specific product that likely arose from environmental M13.

Example VIII: Effect of Selected Mutations on the Extension Rate of *Thermus* Sp. Z05 DNA Polymerase Several of the mutations isolated by the screen described in Example I were transferred to *Thermus* sp. Z05 DNA polymerase (see, e.g., U.S. Pat. No. 5,455,170, entitled "MUTATED THERMOSTABLE NUCLEIC ACID POLY- MERASE ENZYME FROM *THERMUS* SPECIES Z05" issued Oct. 3, 1995 to Abramson et al. and U.S. Pat. No. 5,674,738, entitled "DNA ENCODING THERMOSTABLE NUCLEIC ACID POLYMERASE ENZYME FROM *THERMUS* SPECIES Z05" issued Oct. 7, 1997 to Abramson et al., which are both incorporated by reference). First, the amino acid position corresponding to the mutations were determined by using the alignment shown in FIG. 1. These were named as follows: "Q"=T541R; "D"=D580G; and "S"=A610F. These mutations were introduced into a plasmid encoding Z05 DNA polymerase by using the method known as overlap extension PCR (see, e.g., Higuchi, R. in PCR Protocols: A Guide to Methods and Applications, ed. Innis, Gelfand, Sninsky and White, Academic Press, 1990, and Silver et. al., "Site-specific Mutagenesis Using the Polymerase Chain Reaction", in "PCR Strategies", ed. Innis, Gelfand, and Sninsky, Academic Press, 1995, which is incorporated by reference). In this method, two amplicons are first generated, one upstream and one downstream of the site to be mutagenized, with the mutation being introduced in one of the primers of each reaction. These amplification products are then combined and re-amplified using the outside, non-mutagenic primers. The resulting amplicon includes the introduced mutation and also is designed to span vector-unique restriction sites, which can then be used to clone the amplicon into the vector plasmid DNA. Diagnostic restriction sites may also be introduced into the mutagenic primers as needed, in order to facilitate selection of the desired mutation from the resulting clones, which may include a mixture of mutants and wild-type clones. This procedure may introduce undesired mutations caused by low fidelity PCR, and hence it is necessary to sequence the resulting clones to confirm that only the desired mutations were created. Once the mutations were confirmed, they were combined with each other or with the previously isolated E683R mutation (ES112) (see, U.S. Pat. Appl. No. 20020012970, entitled "High temperature reverse transcription using mutant DNA polymerases" filed Mar. 30, 2001 by Smith et al., which is incorporated by reference) by restriction fragment swaps, as described previously.

Figure 19:
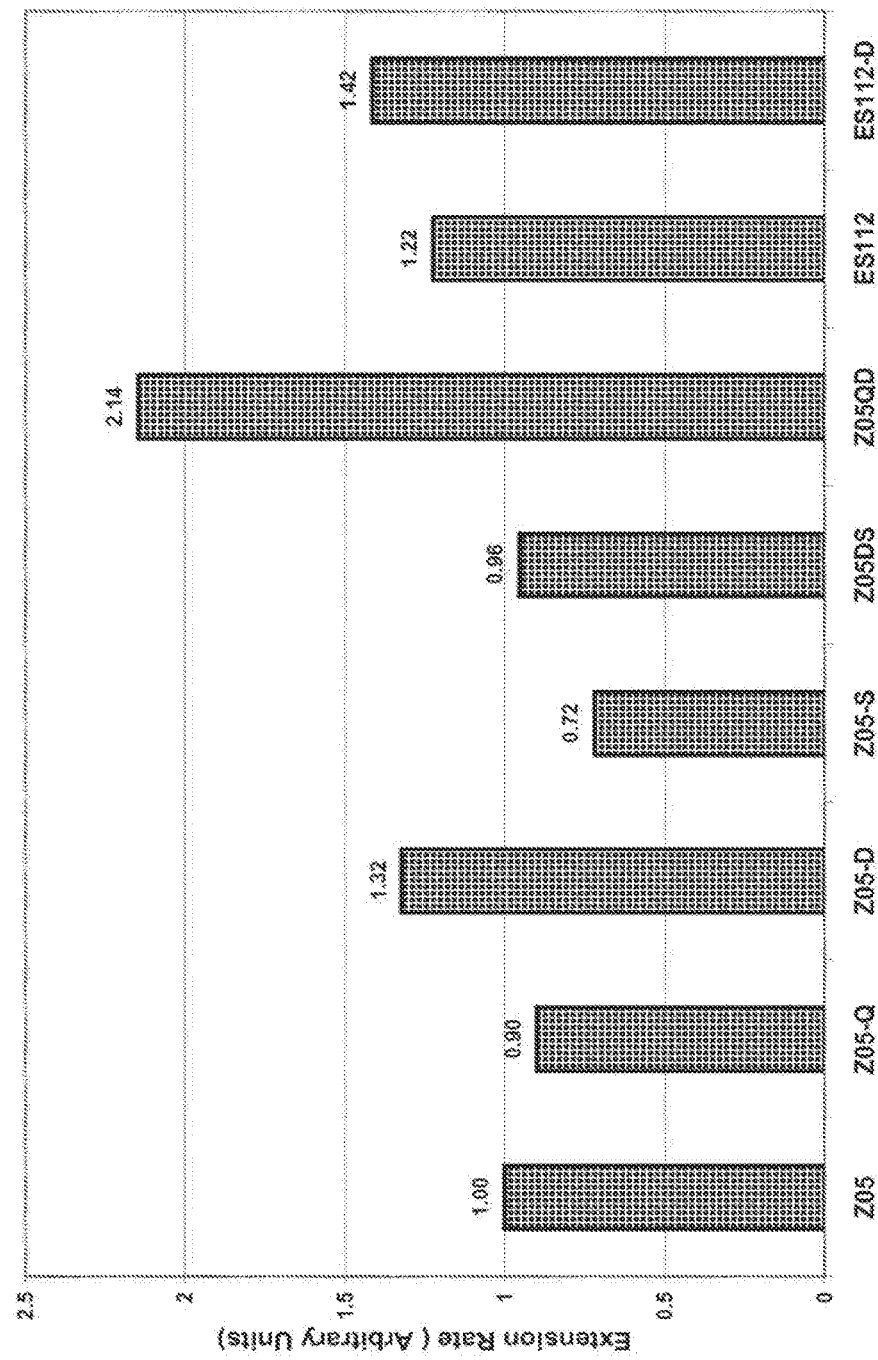
FIG. 19 is a bar graph that shows the normalized extension rates of various mutants of a *Thermus* sp. Z05 DNA polymerase. The y-axis represents the relative extension rates, while the x-axis represents *Thermus* sp. Z05 DNA polymerase (Z05) and various Z05 DNA polymerases having specified point mutations (Q=T541R, D=D580G, and S=A610F). The x-axis represents also represents ES112 (E683R Z05 DNA polymerase; see, U.S. Pat. Appl. No. 20020012970, entitled "High temperature reverse transcription using mutant DNA polymerases" filed Mar. 30, 2001 by Smith et al., which is incorporated by reference) and ES112-D (D580G E683R Z05 DNA polymerase). The extension rate values obtained for the mutant polymerases are normalized relative to the value obtained for the Z05 DNA polymerase, which is set to 1.00.

Expression plasmids created in this way were used to make purified protein of the various mutants, as described earlier in Example I. The nucleic acid extension rate of the various mutants was then determined. The reaction mixture contained 25 mM Tricine pH 8.3, 100 mM KOAc, 3 mM MgCl$_2$, 2.5% v/v Storage Buffer (50% v/v glycerol, 100 mM KCl, 20 mM Tris pH 8.0, 0.1 mM EDTA, 1 mM DTT, 0.5% Tween 20), 1% DMSO, 1×SYBR Green I, 0.5 nM primed M13, and 5 nM enzyme. To this, nucleotides were added to a final concentration of 0.1 mM dGTP, 0.1 mM dTTP, and 0.1 mM dCTP, and 0.1 mM dATP. Parallel reactions containing no nucleotides were also set up. All reactions were run in quadruplicate in 20 µl volume in 384 well thermocycler plates. The extension of primed M13 template was monitored by fluorescence in a kinetic thermocycler set at 64° C., taking readings every 10 seconds. Identical reactions were averaged and the parallel minus nucleotide reactions subtracted. Extension rate (see, FIG. 19) was estimated by linear regression analysis of the resulting data. This data indicates, e.g., that in some cases the mutations described herein also have beneficial effects in the context of a non-chimeric *Thermus* DNA polymerase.

Example IX: HIV DNA Template Titrations

Figure 20:
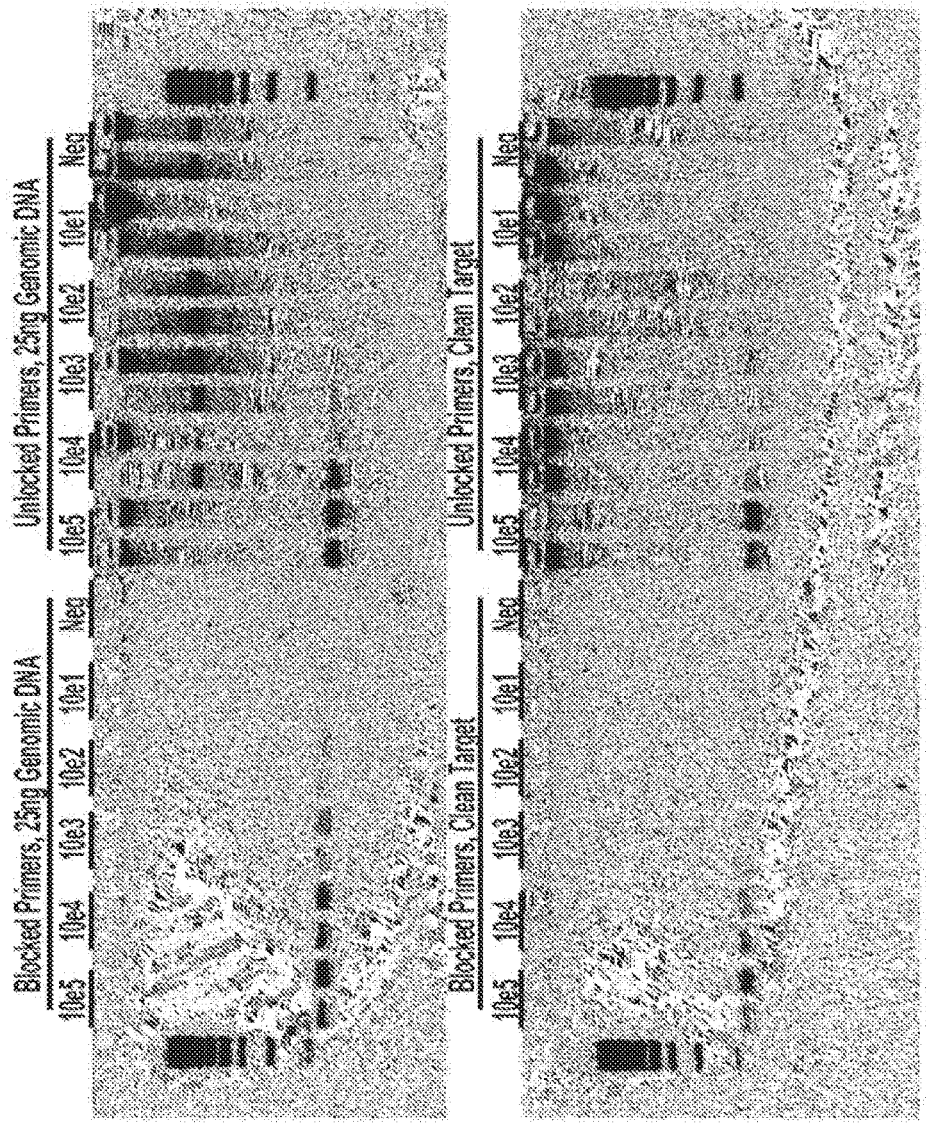
FIG. 20 is a photograph of a gel that shows the detection of PCR products from an analysis that involved PAP-related HIV DNA template titrations.

PAP-related HIV DNA template titrations were performed with and without the presence of genomic DNA. FIG. 20 is a photograph of a gel that shows the detection of the PCR products under the varied reaction conditions utilized in this analysis. This data illustrates, e.g., the improved amplification specificity and sensitivity that can be achieved using the blocked primers relative to reactions not using those primers.

More specifically, the reactions were performed using an ABI 5700 Sequence Detection System with the following temperature profile:
50° C. 2 minutes
93° C. 1 minutes
93° C., 15 seconds→52° C., 4 minutes×4 cycles
90° C., 15 seconds→55° C., 4 minutes×56 cycles
The following reaction conditions were common to all reactions:

| Master Mix Components | conc. |
|---|---|
| Tricine (pH 8.0) | 100 mM |
| dATP | 200 µM |
| dCTP | 200 µM |
| dGTP | 200 µM |
| dTTP | 30 µM |
| dUTP | 300 µM |
| Primer 3 or Primer 1 | 200 nM |
| Primer 4 or Primer 2 | 200 nM |
| KOAc | 110 mM |
| SYBR Green I | 0.2X |
| NaPPi | 225 µM |
| Mg(OAc)$_2$ | 2.5 mM |
| Tth Storage Buffer (0.2% Tween) | 6% v/v |
| GLQDSE CS5 DNA polymerase | 10 nM |

Note, that "GLQDSE CS5 DNA polymerase" refers to a G46E L329A Q601R D640G S671F E678G CS5 DNA polymerase. Note further, that the "Tth Storage Buffer" included 0.2% Tween 20, 20 mM Tris pH8.0, 0.1 mM EDTA, 100 mM KCl, 1 mM DTT, and 50% v/v glycerol. In addition, each reaction volume was brought to 50 µl with diethylpyrocarbonate (DEPC) treated water.

The varied reaction components included unblocked primers (see, the reactions denoted "unblocked primers" in FIG. 20) and primers blocked with a 2'-Phosphate-U (i.e., a 2'-terminator nucleotide comprising a phosphate group at the 2' position) (see, the reactions denoted "blocked primers" in FIG. 20). The reactions also either included (see, the reactions denoted "25 ng Genomic DNA" in FIG. 20) or lacked (see, the reactions denoted "Clean Target" in FIG. 20) 25 ng of human genomic DNA added to the mixtures. As further shown in FIG. 20, the reactions also included 10$^5$, 10$^4$, 10$^3$, 10$^2$, or 10$^1$ copies of linearized plasmid DNA, which included the target nucleic acid, diluted in 1 µl HIV Specimen Diluent (10 mM Tris, 0.1 mM EDTA, 20 µg/mL Poly A, and 0.09% NaN$_3$) or 1 µl HIV Specimen Diluent in "Neg" reactions. The indicated primer pairs amplified a 170 base pair product from the plasmid DNA.

Figure 21:
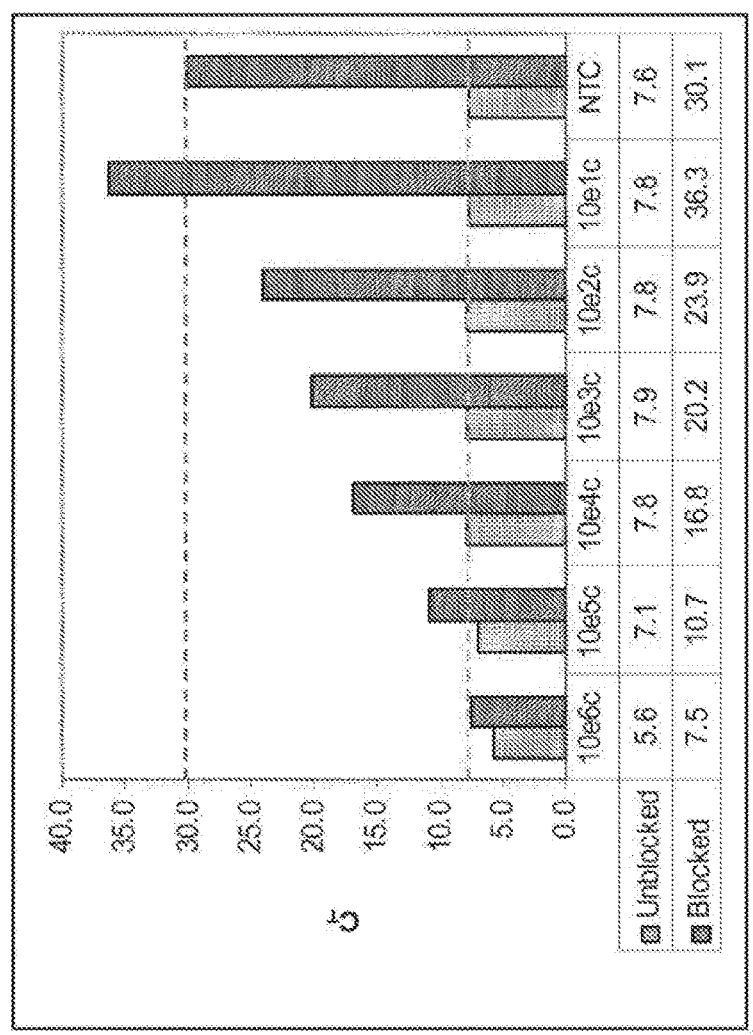
FIG. 21 is a graph that shows threshold cycle ($C_T$) values observed for various mutant K-Ras plasmid template copy numbers utilized in amplifications that involved blocked or unblocked primers.

Example X: Amplification of Mutant K-Ras Plasmid Template in a Background of Wild-Type K-Ras Plasmid Template Amplifications involving various copy numbers of mutant K-Ras plasmid template in a background of wild-type K-Ras plasmid template and comparing blocked and unblocked primers were performed. FIG. 21 is a graph that shows threshold cycle (C$_T$) values (y-axis) observed for the various mutant K-Ras plasmid template copy numbers (x-axis) utilized in these reactions. FIG. 21 further illustrates, e.g., the improved discrimination that can be achieved using the blocked primers described herein.

The reactions were performed using an ABI 5700 Sequence Detection System with the following temperature profile:
50° C. 2 minutes
93° C. 1 minute
92° C., 15 seconds→65° C., 2 minutes×60 cycles The following reaction conditions were common to all reactions:

| Master Mix Components | conc. |
|---|---|
| Tricine (pH 8.0) | 100 mM |
| dATP | 200 µM |
| dCTP | 200 µM |
| dGTP | 200 µM |
| dTTP | 30 µM |
| dUTP | 300 µM |
| Primer 7 or Primer 5 | 200 nM |
| Primer 8 or Primer 6 | 200 nM |
| SYBR Green I | 0.1X |
| NaPPi | 225 µM |
| Mg(OAc)$_2$ | 2.5 mM |
| Ung | 2U |
| Tth Storage Buffer (0.2% Tween) | 6% v/v |
| GDSE CS5 DNA polymerase | 5 nM |
| Linearized Wild-Type Plasmid DNA | $10^6$ copies |

Note, that "GDSE CS5 DNA polymerase" refers to a G46E D640G S671F E678G CS5 DNA polymerase. In addition, each reaction volume was brought to 50 µl with DEPC treated water.

The varied reaction components included unblocked primers (see, the reactions denoted "unblocked" in FIG. 21) and primers blocked with a 2'-Phosphate-C or a 2'-Phosphate-A (i.e., 2'-terminator nucleotides comprising phosphate groups at 2' positions). In addition, $10^6$, $10^5$, $10^4$, $10^3$, $10^2$, $10^1$ or 0 copies (NTC reactions) (10e6c, 10e5c, 10e4c, 10e3c, 10e2c, 10e1c, and NTC, respectively, in FIG. 21) of linearized mutant K-Ras plasmid DNA were added to the reactions. The relevant subsequences of the mutant plasmid DNA were perfectly matched to both the blocked and unblocked primer sets. Further, the mutant K-Ras plasmid DNA was diluted in 1 µl HIV Specimen Diluent (see, above) or 1 µl HIV Specimen Diluent (see, above) in "NTC" reactions. Additionally, $10^6$ copies of linearized wild-type K-Ras plasmid DNA were present in all reactions. The wild-type K-Ras plasmid DNA was identical in sequence to mutant plasmid DNA except that it creates a C:C mismatch with the ultimate 3' base (dC) in primers 5 and 7. Both blocked and unblocked primer pairs created a 92 base pair amplicon on the mutant linearized plasmid template.

Figure 22:
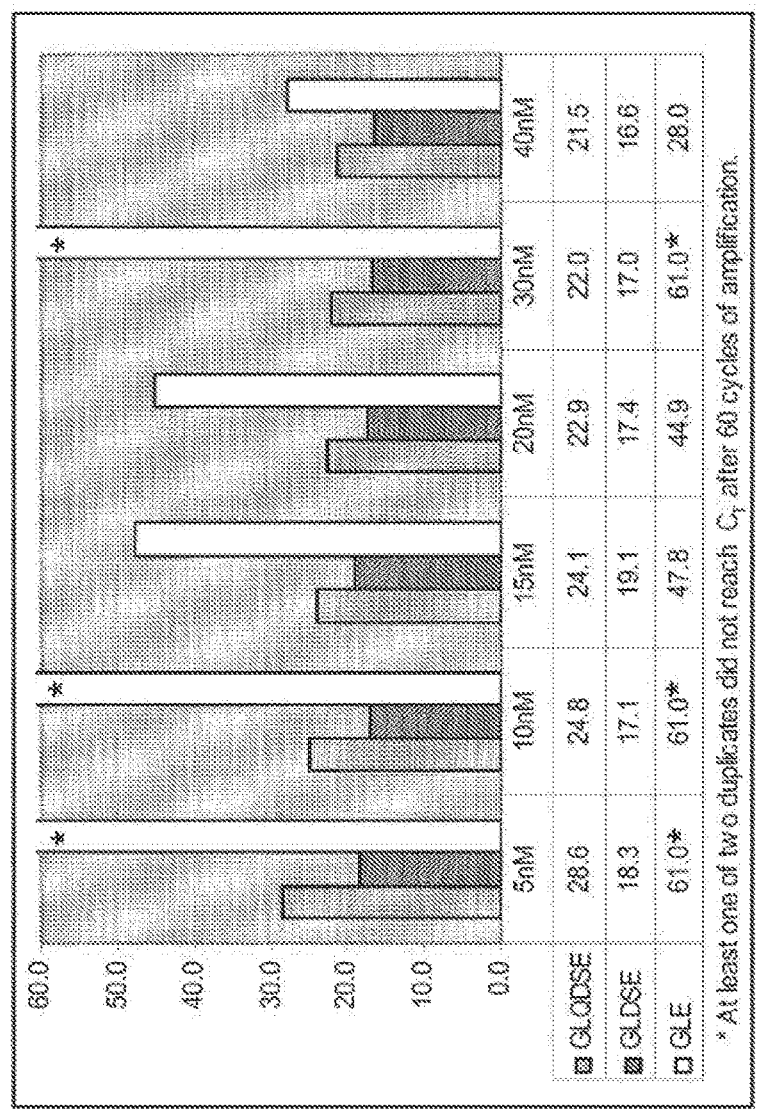
FIG. 22 is a graph that shows threshold cycle ($C_T$) values observed for various enzymes and enzyme concentrations utilized in amplifications that involved a K-Ras plasmid template.

Example XI: Amplification of K-Ras Plasmid Template with Various Enzymes at Varied Concentrations Amplifications involving K-Ras plasmid template with various enzymes at varied concentrations were performed. FIG. 22 is a graph that shows threshold cycle ($C_T$) values (y-axis) observed for the various enzymes and concentrations (x-axis) utilized in these reactions. These data show, e.g., the improved PAP amplification efficiencies that can be achieved using certain enzymes described herein.

The reactions were performed using an ABI 5700 Sequence Detection System with the following temperature profile:
50° C. 2 minutes
93° C. 1 minute
92° C., 15 seconds→60° C., 2 minutes×60 cycles The following reaction conditions were common to all reactions:

| Master Mix Components | conc. |
|---|---|
| Tricine (pH 8.0) | 100 mM |
| dATP | 200 µM |
| dCTP | 200 µM |
| dGTP | 200 µM |
| dTTP | 30 µM |
| dUTP | 300 µM |
| Primer 9 | 200 nM |
| Primer 10 | 200 nM |
| SYBR Green I | 0.1X |
| NaPPi | 225 µM |
| Mg(OAc)$_2$ | 2.5 mM |
| Ung | 2U |
| Tth Storage Buffer (0.2% Tween) | 6% v/v |
| Linearized K-Ras Plasmid DNA | $10^4$ copies |

The reaction components included primers blocked with a 2'-Phosphate-U or a 2'-Phosphate-A (i.e., 2'-terminator nucleotides comprising phosphate groups at 2' positions). The primer pairs created a 92 base pair amplicon on the linearized K-Ras plasmid template. In addition, each reaction volume was brought to 50 µl with diethylpyrocarbonate (DEPC) treated water.

The polymerase concentration and KOAc concentrations were optimized for each individual polymerase as follows:

| Polymerase | Polymerase Conc. (nM) | KOAc (mM) |
|---|---|---|
| GLQDSE | 5, 10, 15, 20, 30, or 40 nM | 110 |
| GLDSE | 5, 10, 15, 20, 30, or 40 nM | 25 |
| GLE | 5, 10, 15, 20, 30, or 40 nM | 25 |

Note, that "GLQDSE" refers to a G46E L329A Q601R D640G S671F E678G CS5 DNA polymerase, "GLDSE" refers to a G46E L329A D640G S671F E678G CS5 DNA polymerase, and "GLE" refers to a G46E E678G CS5 DNA polymerase.

Figure 23:
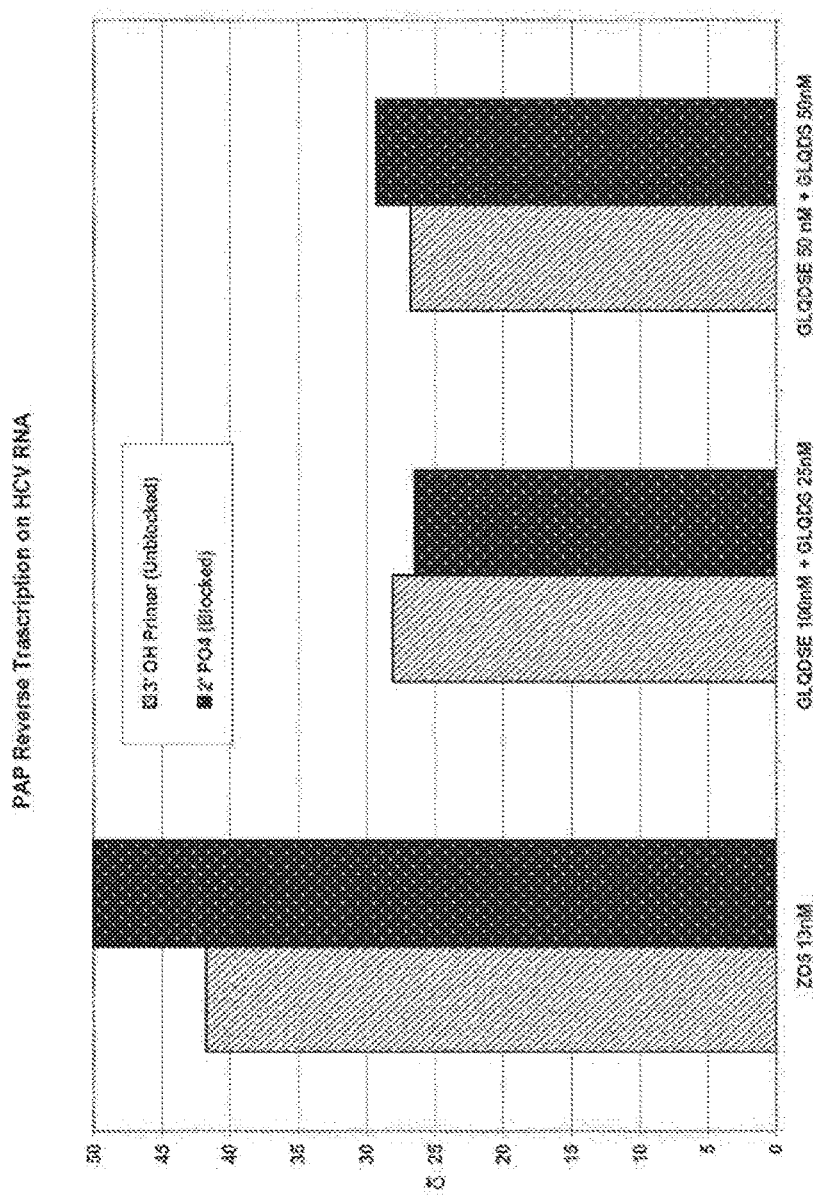
FIG. 23 is a bar graph that shows data for PAP reverse transcription reactions on HCV RNA in which products of the cDNA reaction were measured using a quantitative PCR assay specific for the HCV cDNA. The y-axis represents Ct value, while the x-axis represents the Units of enzyme utilized in the reactions. As indicated, the enzymes used in these reactions were Z05 DNA polymerase (Z05) or blends of G46E L329A Q601R D640G S671F E678G (GLQDSE) and G46E L329A Q601R D640G S671F (GLQDS) CS5 DNA polymerases.

Example XII: Hepatitis C Virus (HCV) RNA to cDNA Reverse Transcription (RT) Comparing Unblocked and Blocked RT Primers The extension of an unblocked HCV RT primer was compared to the extension of a blocked primer on an HCV RNA template in reverse transcription reactions. These RT comparisons were performed using various polymerases. To illustrate, FIG. 23 is a graph that shows threshold cycle (Ct) values (y-axis) observed for the various enzymes (x-axis) utilized in these reactions in which the cDNA was measured using real-time PCR involving 5'-nuclease probes.

The following reaction conditions were common to all RT reactions:

| RT Mix Component | Concentration |
|---|---|
| Tricine pH 8.0 | 100 mM |
| KOAc | 100 mM |
| DMSO | 4% (v/v) |
| Primer 1 or 2 | 200 nM |
| dATP | 200 µM |
| dCTP | 200 µM |
| dGTP | 200 µM |
| dTTP | 30 µM |

| RT Mix Component | Concentration |
|---|---|
| dUTP | 300 µM |
| UNG | 0.2 Unit |
| Mn(OAc)₂ | 1 mM |
| PPi | 175 uM |

The varied reaction components included a 3'-OH unblocked primer (see, the reactions denoted "3' OH Primer (Unblocked)" in FIG. 23) and a primer blocked with a 2'-Phosphate-A or a 2'-monophosphate-3'-hydroxyl adenosine nucleotide (i.e., 2' terminator nucleotide comprising a phosphate group at the 2' position) (see, the reactions denoted "2' PO4 (Blocked)" in FIG. 23). Further, the following polymerase conditions were compared in the cDNA reactions (see, FIG. 23):

Z05 DNA polymerase (13 nM)
GLQDSE CS5 DNA polymerase (100 nM) combined with GLQDS CS5 DNA polymerase (25 nM)
GLQDSE CS5 DNA polymerase (50 nM) combined with GLQDS CS5 DNA polymerase (50 nM
where "GLQDSE CS5 DNA polymerase" refers to a G46E L329A Q601R D640G S671F E678G CS5 DNA polymerase and "GLQDS CS5 DNA polymerase" refers to a G46E L329A Q601R D640G S671F CS5 DNA polymerase. In addition, each reaction was brought to 20 µl with diethylpyrocarbonate (DEPC) treated water.

The RT reactions were incubated at 60° C. for 60 minutes in an ABI 9600 Thermal Cycler. After the RT incubation, RT reactions were diluted 100-fold in DEPC treated water. The presence of cDNA was confirmed and quantitated by 5' nuclease probe-based real-time HCV PCR reactions designed to specifically measure the HCV cDNA products of the RT reactions. These reactions were performed using an ABI Prism 7700 Sequence Detector with the following temperature profile:

50° C. 2 minutes
95° C. 15 seconds→60° C. 1 minutes×50 cycles.

Example XIII: Bidirectional Pap for BRAF Mutation Detection

Figure 24:
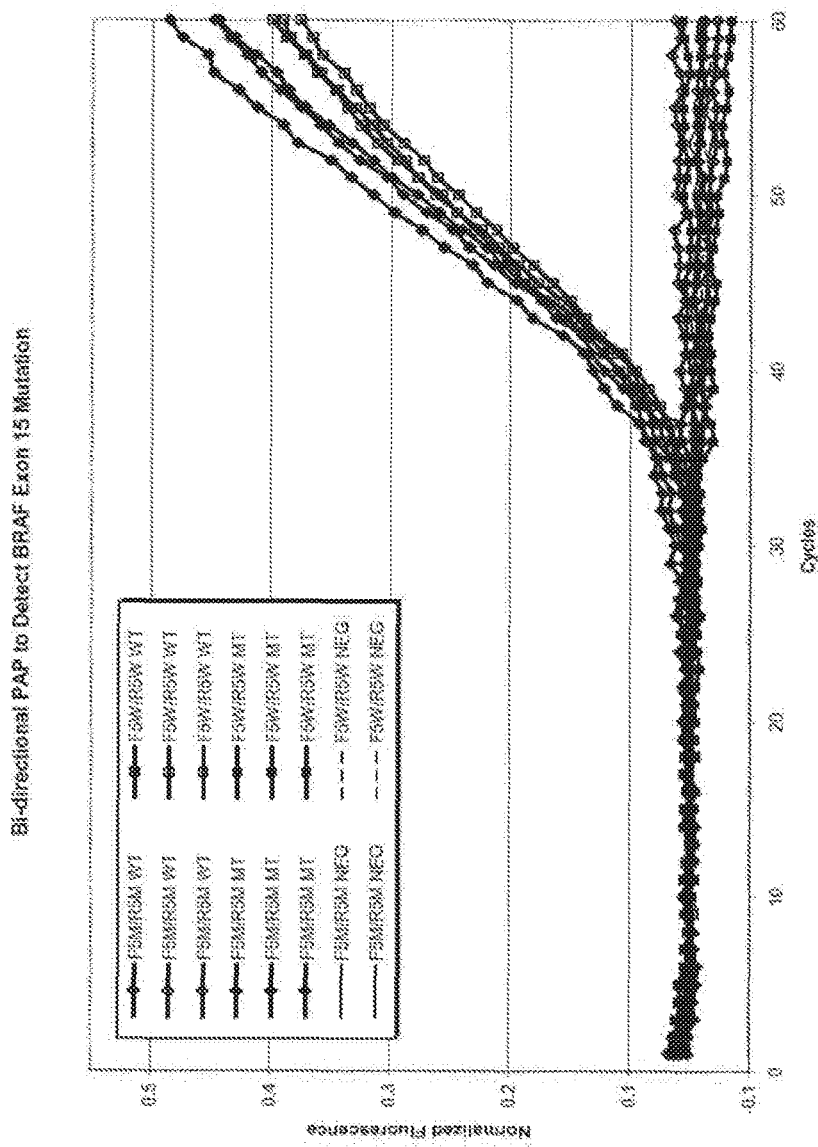
FIG. 24 shows PCR growth curves of BRAF oncogene amplifications that were generated when bidirectional PAP was performed. The x-axis shows normalized, accumulated fluorescence and the y-axis shows cycles of PAP PCR amplification.

FIG. 24 shows PCR growth curves of BRAF oncogene amplifications that were generated when bidirectional PAP was performed. The x-axis shows normalized, accumulated fluorescence and the y-axis shows cycles of PAP PCR amplification. More specifically, these data were produced when mutation-specific amplification of the T→A mutation responsible for the V599E codon change in the BRAF oncogene (see, Brose et al. (2002) *Cancer Res* 62:6997-7000, which is incorporated by reference) was performed using 2'-terminator blocked primers that overlap at their 3'-terminal nucleotide at the precise position of the mutation. When primers specific to wild-type sequence were reacted to wild-type target or mutant target, only wild-type target was detected. Conversely, when primers specific to mutant sequence were reacted to wild-type target or mutant target, only mutant target was detected.

The following reaction conditions were common to all RT reactions:

| Component | Concentration |
|---|---|
| Tricine pH 8.0 | 100 mM |
| KOAc | 100 mM |
| Glycerol | 3.5% v/v |

| Component | Concentration |
|---|---|
| Primer F5W or F5M | 200 nM |
| Primer R5W or R5M | 200 nM |
| dATP | 200 µM |
| dCTP | 200 µM |
| dGTP | 200 µM |
| dTTP | 30 µM |
| dUTP | 300 µM |
| UNG | 1 Unit |
| PPi | 175 uM |
| GLQDSE | 15 nM |
| SYBR I/carboxyrhodamine | 1/100,000 (0.1x) |
| Mg(OAc)₂ | 3.0 mM | where "GLQDSE" refers to a G46E L329A Q601R D640G S671F E678G CS5 DNA polymerase.

The varied reaction components included the wild-type BRAF primers blocked with a 2'-Phosphate-A; a 2'-monophosphate-3'-hydroxyl adenosine nucleotide; a 2'-Phosphate-U; or a 2'-monophosphate-3'-hydroxyl uridine nucleotide (i.e., 2' terminator nucleotides comprising a phosphate group at the 2' position) (labeled "F5W/R5W" in FIG. 24).

In addition, each reaction was brought to 50 µl with DEPC treated water. Wild-type reactions (labeled "WT" in FIG. 24) contained linearized DNA plasmid of the BRAF wild-type sequence and mutant reactions (labeled "MT" in FIG. 24) contained linearized DNA plasmid of the BRAF mutant sequence. Negative reactions (labeled "NEG" in FIG. 24) contained HIV specimen diluent (10 mM Tris, 0.1 mM EDTA, 20 µg/mL Poly A, and 0.09% NaN₃) with no DNA. Combinations of the primers in PCR produced a 50 bp amplicon. Further, the reactions were performed using an ABI Prism 7700 Sequence Detector with the following temperature profile:

50° C. 1 minutes
93° C. 1 minutes
90° C. 15 seconds
60° C. 150 seconds→×60 Cycles.

Example XIV: Detection of Fluorescent PAP Release Product

This prophetic example illustrates a real-time monitoring protocol that involves PAP activation in which a blocked primer leads to the production of detectable signal as that primer is activated and extended.

Construction of a 3' Terminated, Dual-Labeled Oligonucleotide Primer:

The primer QX below is a DNA oligonucleotide that includes a quenching dye molecule, Black Hole Quencher® (BHQ) (Biosearch Technologies, Inc.) attached to the thirteenth nucleotide (A) from the 3' terminus.

An oligonucleotide primer of the QX is mixed in solution with a complimentary oligonucleotide R1 (see, below) such that they form a hybrid duplex. This duplex is further mixed with the reagents in the Table 10 provided below which notably include a fluorescein-labeled deoxyriboadenine tetraphosphate (i.e., a fluorescein-labeled 2'-terminator nucleotide) and DNA polymerase capable of incorporating such labeled tetraphosphate. See, U.S. patent application Ser. No. 10/879,494, entitled "SYNTHESIS AND COMPOSITIONS OF 2'-TERMINATOR NUCLEOTIDES", filed Jun. 28, 2004 and Ser. No. 10/879,493, entitled "2'-TERMINATOR NUCLEOTIDE-RELATED METHODS AND SYSTEMS," filed Jun. 28, 2004, which are both incorporated by reference. Incubation of the mixture at a temperature of 60° C.

for, e.g., one hour could causes the 3' terminus of the sequence QX to be extended one nucleotide in a template directed manner, resulting in at least a portion of the QX oligonucleotides being extended at their 3' ends with the fluorescein-labeled deoxyriboadenine 2'-phosphate nucleotides, represented below as Primer $QX^{FAM}$.

TABLE 10

| Mix Component | Concentration |
|---|---|
| Tricine pH 8.3 | 50 mM |
| KOAc | 100 mM |
| Glycerol | 8% (w/v) |
| Primer QX | 10 µM |
| Oligonucleotide R1 | 15 µM |
| Fluorescein dA4P | 15 µM |
| G46E L329A E678G CS5 DNA polymerase | 50 nM |
| Mg(OAc)$_2$ | 2.5 mM |

The newly elongated Primer $QX^{FAM}$ are purified from the mixture above using any number of purification methods known to persons of skill in the art. An example of such a method capable of purifying Primer $QX^{FAM}$ from the mixture is High Performance Liquid Chromatography (HPLC). HPLC purification parameters are selected such that the preparation of Primer $QX^{FAM}$ is substantially free of non-extended Primer QX and fluorescein-labeled adenine tetraphosphates. Dual HPLC (Reverse Phase and Anion Exchange HPLC) is known as a method for purifying such molecules.

Once purified, molecules such as Primer $QX^{FAM}$ which contain a BHQ quenching molecule and a fluorescein molecule on the same oligonucleotide generally exhibit a suppressed fluorescein signal due to energy absorbance by the BHQ2 "quencher" molecule.

Optionally, Primer $QX^{FAM}$ is synthesized chemically as described in, e.g., U.S. Patent Publication No. 2007/0219361.

The sequences referred to in this example are as follows:

(SEQ ID NO: 73)
Primer QX    5'-GCAAGCACCCTATCA$^Q$GGCAGTACCACA-3'

(Where Q represents the presence of a BHQ molecule)

(SEQ ID NO: 74)
R1    3'-PCGTTCGTGGGATAGTCCGTCATGGTGTT-5'

(Where P represents 3' phosphate)

(SEQ ID NO: 75)
Primer QXFAM 5'-GCAAGCACCCTATCA$^Q$GGCAGTACCACA$^F$-3'

(Where Q represents the presence of a BHQ molecule, and F represents a fluorescein-labeled 2' phosphate adenine)

(SEQ ID NO: 76)
Primer HC2    5'-GCAGAAAGCGTCTAGCCATGGCTTA-3'.

Use of the Primer in PCR.

A Primer $QX^{FAM}$ is combined with the reagents in Table 11.

TABLE 11

| Component | Concentration |
|---|---|
| Tricine pH 8.0 | 100 mM |
| KOAc | 100 mM |
| Glycerol | 3.5% (v/v) |
| DMSO | 5% (v/v) |
| Primer $QX^{FAM}$ | 150 nM |
| Primer HC2 | 150 nM |
| dATP | 200 µM |
| dCTP | 200 µM |
| dGTP | 200 µM |
| dTTP | 30 µM |
| dUTP | 300 µM |
| UNG | 1 Unit |
| PPi | 175 µM |
| GLQDSE | 15 nM |
| Target sequence | $10^6$ copies |
| Mg(OAc)$_2$ | 3.0 mM |

In addition each reaction is brought to 50 µl with DEPC treated water. Some reactions contain a target sequence which serves as a substrate for PCR amplification, while others contain no target. For example, the target can be a DNA sequence identical to the 5'UTR region of the HCV genome. Combinations of these primers in PCR are expected to produce an approximately 244 bp amplicon.

The reactions can be performed using an ABI Prism 7700 Sequence Detector with the following temperature profile:
50° C. 1 minute
93° C. 1 minute
90° C. 15 seconds
60° C. 150"→×60 Cycles For such a PCR to progress, PAP activation of the fluorescein-terminated Primer $QX^{FAM}$ is necessary, and would result in the removal of the fluorescein-labeled deoxyadenine tetraphosphate molecule. Such a release is expected to result in an increase in fluorescent signal at approximately 520 nm wavelength. With monitoring of signal at approximately 520 nm wavelength as the PCR progresses, one would expect to observe an increase in fluorescence in those reactions containing target nucleic acid while observing no increased fluorescence in reactions that do not contain target.

Example XV: Effect D580K, D580L, D580R and D580T Mutations on the Extension Rate Z05 DNA Polymerase The effect of various substitutions at the D580 position on the nucleic acid extension rate of Z05 DNA polymerase was determined. First, the mutations were created in Z05 DNA polymerase, utilizing the technique of overlap PCR, and the mutant enzymes purified and quantified, as described previously. The extension rate on primed M13 (single-stranded DNA) template was determined, using both $Mg^{+2}$ and $Mn^{+2}$ as the metal co-factor, by monitoring the increase in SYBR Green I florescence, as described in Example II above, and elsewhere. In this example, the reaction mixture contained 50 mM Tricine pH 8.3, 40 mM KOAc, 1 mM Mn(OAc)$_2$ or 2.5 mM Mg(OAc)$_2$, 1.25% v/v Storage Buffer (50% v/v glycerol, 100 mM KCl, 20 mM Tris pH 8.0, 0.1 mM EDTA, 1 mM DTT, 0.5% Tween 20), 1% DMSO, 0.6×SYBR Green I, 1.0 nM primed M13, and or 5 nM enzyme. To this, nucleotides were added to a final concentration of 0.2 mM dGTP, 0.2 mM dTTP, and 0.2 mM dCTP, and 0.2 mM dATP. Parallel reactions containing no nucleotides were also set up. All reactions were run in quadruplicate in 20 µl volume in 384 well thermocycler plates. The extension of primed M13 template was monitored by fluorescence in a kinetic thermocycler set at 64° C., taking readings every 15 seconds. Replicate identical reactions were averaged and the parallel minus nucleotide reactions subtracted. Extension rate was estimated by linear regression analysis of the resulting data. Results are shown in Table 12 below:

TABLE 12

Extension Rate of D580X Mutants of Z05.
(Based on Change in Fluorescence, arbitrary units)

|  | Z05 | Z05-D | Z05-580K | Z05-580L | Z05-580R | Z05-580T |
|---|---|---|---|---|---|---|
| 1 mM Mn | 35.27 | 119.81 | 185.25 | 87.31 | 171.56 | 153.46 |
| 2.5 mM Mg | 127.94 | 216.59 | 258.69 | 176.59 | 237.58 | 238.33 |

The data indicate that all 5 amino acid substitutions at position 580 of Z05 DNA polymerase result in faster extension rate under the conditions tested.

Example XVI

Use of Various Mutant Z05 DNA Polymerases in RT-PCR $Mn^{2+}$-Based RT:

The mutations D580G, D580K, and D580R were evaluated for their effect on RT-PCR efficiency in the presence of $Mn^{+2}$. The reactions all contained the following components: 55 mM Tricine pH 8.3, 4% v/v glycerol, 5% v/v DMSO, 110 mM KOAc, 2.7 mM $Mn(OAc)_2$, 3.6% v/v Storage Buffer (50% v/v glycerol, 100 mM KCl, 20 mM Tris pH 8.0, 0.1 mM EDTA, 1 mM DTT, 0.2% Tween 20), 0.04 units/µl UNG, 0.45 mM each dATP, dCTP, dUTP, dGTP; 750 nM of each primer, wherein each primer comprised a t-butyl benzyl dA at the 3'-end; and 150 nM of a TaqMan probe, labeled with a cyclohexyl-FAM, a black hole quencher (BHQ-2), a 3'-Phosphate. Together, the two primers generate a 241 bp amplicon on the HCV-1B transcript. $10^5$ copies of RNA transcript HCV-1B was added to each 100 µl reaction.

Parallel reactions with no transcript were also set up. Each enzyme was added to a final concentration of 27 nM. Reactions were run in a Roche LC480 kinetic thermocycler. The thermocycling conditions were: 5 minutes at 50° C. ("UNG" step); 2, 5, or 30 minutes at 66° C. ("RT" step); 2 cycles of 95° C. for 15 seconds followed by 58° C. for 50 seconds; and 50 cycles of 91° C. for 15 seconds followed by 58° C. for 50 seconds.

Table 13 shows the Ct values obtained from the FAM signal increase due to cleavage of the TaqMan probe:

TABLE 13

| RT time | Z05 | Z05 D580G | Z05 D580R | Z05 D580K |
|---|---|---|---|---|
| 30 min. RT | 23.6 | 22.8 | 23.2 | 23.1 |
| 5 min. RT | 27.9 | 23.4 | 23.3 | 23.2 |
| 2 min. RT | 31.3 | 23.5 | 23.3 | 23.1 |

The results indicate these three mutations at position D580 allow for a much shorter RT time while maintaining equivalent RT efficiency.

$Mg^{2+}$-Based RT:

The mutations D580G and D580K, were compared to ES112 (Z05 E683R) for their ability to perform RT-PCR in the presence of $Mg^{+2}$. The parental enzyme, Z05 DNA polymerase, is known to perform $Mg^{+2}$-based RT-PCR with greatly delayed Ct values relative to ES112, and was not re-tested in this study. The conditions used were identical to those described immediately above, except that the KOAc was changed to 50 mM, the $Mn(OAc)_2$ was replaced with 2 mM $Mg(OAC)_2$, and the enzyme concentration was reduced to 10 nM. Thermocycling conditions were identical, except that only the 30 minute RT time was tested.

Table 14 shows the Ct values obtained from the FAM signal increase due to cleavage of the TaqMan probe:

TABLE 14

| RT time | ES112 | Z05 D580G | Z05 D580K |
|---|---|---|---|
| 30 min. RT | 30.9 | 31.5 | 25.1 |

The results indicate the D580G mutant performs $Mg^{+2}$-based RT PCR with roughly the same efficiency as does ES112, and that the D580K mutant results in significantly a earlier Ct value, indicative of a much higher RT efficiency under these conditions.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A recombinant nucleic acid encoding a DNA polymerase comprising a motif in the polymerase domain comprising T-G-R-L-S-S-$X_{b7}$-$X_{b8}$-P-N-L-Q-N(SEQ ID NO:2); wherein $X_{b7}$ is S or T; and $X_{b8}$ is an amino acid selected from the group consisting of: G, T, R, K and L;

wherein the DNA polymerase has at least 95% sequence identity to the amino acid sequence of SEQ ID NO:82;

wherein the polymerase has an increased nucleic acid extension rate and/or an increased reverse transcription efficiency relative to an otherwise identical DNA polymerase wherein $X_{b8}$ is an amino acid selected from D, E or N.

2. An expression vector comprising the recombinant nucleic acid of claim 1.

3. A host cell comprising the expression vector of claim 2.

4. A method of producing a DNA polymerase, said method comprising:

culturing the host cell of claim 3 under conditions suitable for expression of the nucleic acid encoding the DNA polymerase.

* * * * *